United States Patent
Shekdar et al.

(10) Patent No.: US 9,347,934 B2
(45) Date of Patent: May 24, 2016

(54) ASSAYS FOR IDENTIFYING COMPOUNDS THAT MODULATE BITTER TASTE

(71) Applicants: CHROMOCELL CORPORATION, North Brunswick, NJ (US); KRAFT FOODS GROUP BRANDS LLC, Northfield, IL (US)

(72) Inventors: Kambiz Shekdar, New York, NY (US); Purvi Manoj Shah, Bridgewater, NJ (US); Joseph Gunnet, Flemington, NJ (US); Jane V. Leland, Wilmette, IL (US); Peter H. Brown, Glenview, IL (US); Louise Slade, Morris Plains, NJ (US)

(73) Assignees: Chromocell Corporation, North Brunswick, NJ (US); Kraft Foods Group Brands LLC, Northfield, IL (US)

( * ) Notice: Subject to any disclaimer, the term of this patent is extended or adjusted under 35 U.S.C. 154(b) by 0 days.

(21) Appl. No.: 14/352,620

(22) PCT Filed: Oct. 22, 2012

(86) PCT No.: PCT/US2012/061400
§ 371 (c)(1),
(2) Date: Apr. 17, 2014

(87) PCT Pub. No.: WO2013/059836
PCT Pub. Date: Apr. 25, 2013

(65) Prior Publication Data
US 2014/0248639 A1 Sep. 4, 2014

Related U.S. Application Data

(60) Provisional application No. 61/549,693, filed on Oct. 20, 2011.

(51) Int. Cl.
*G01N 33/50* (2006.01)
*G01N 33/74* (2006.01)

(52) U.S. Cl.
CPC ........ *G01N 33/5044* (2013.01); *G01N 33/5041* (2013.01); *G01N 33/74* (2013.01); *G01N 2333/726* (2013.01)

(58) Field of Classification Search
None
See application file for complete search history.

(56) References Cited

U.S. PATENT DOCUMENTS

| | | | |
|---|---|---|---|
| 5,853,792 A | 12/1998 | Zolotov et al. | |
| 2008/0003344 A1* | 1/2008 | Jensen et al. | 426/629 |
| 2008/0038739 A1 | 2/2008 | Li et al. | |
| 2008/0167286 A1* | 7/2008 | Gopalakrishnan et al. | 514/210.16 |
| 2010/0129833 A1* | 5/2010 | Brune et al. | 435/7.21 |

FOREIGN PATENT DOCUMENTS

| | | |
|---|---|---|
| CN | 1341632 A | 3/2002 |
| CN | 101583717 A | 11/2009 |
| CN | 101828111 A | 9/2010 |
| WO | WO-0038536 A2 | 7/2000 |
| WO | WO-2004029087 | 4/2004 |
| WO | WO-2006053771 A2 | 5/2006 |
| WO | WO-2007002026 A2 | 1/2007 |
| WO | WO-2008057470 | 5/2008 |
| WO | WO-2008119195 A1 | 10/2008 |
| WO | WO-2008119196 | 10/2008 |
| WO | WO-2008119197 | 10/2008 |
| WO | WO-2008128730 A2 | 10/2008 |
| WO | WO-2009015504 | 2/2009 |
| WO | WO-2010088633 | 8/2010 |
| WO | WO-2010099983 A1 | 9/2010 |
| WO | WO-2013022947 | 2/2013 |

OTHER PUBLICATIONS

Bachmanov et al., Taste Receptor Genes, 2007, 27:389-414.*
Behrens et al., Structural Requirements for Bitter Taste Receptor Activation, AChemS 2009 Annual Meeting, Sarasota, FL, Poster P141, Apr. 22-26, 2009.
Brockhoff et al., "Structural Requirements of Bitter Taste Receptor Activation," PNAS, 107(24): 11110-11115 (2010).
Kim et al., "Positional cloning of the human quantitative trait locus underlying taste sensitivity to phenylthiocarbamide," Science, 299(5610):1221-1225 (2003).
Kuhn et al., "Bitter taste receptors for saccharin and acesulfame K," Journal of Neuroscience, 24(45):10260-10265 (2004).

(Continued)

*Primary Examiner* — John Ulm
(74) *Attorney, Agent, or Firm* — Ropes & Gray LLP; Karen Mangasarian; Brian M. Gummow

(57) ABSTRACT

The present invention is based on applicants' discovery, disclosed herein, of agonists for the TAS2R receptors TAS2R1, TAS2R4, TAS2R9, TAS2R13, TAS2R14, TAS2R16, TAS2R44, TAS2R46, and TAS2R60. The assignment of agonists to these receptors makes assays for identifying compounds that modulate bitter taste possible. For example, the present invention provides methods of identifying compounds that inhibit the bitter taste due to these agonists. The present invention also provides methods of identifying compounds that selectively inhibit the bitter taste due to these agonists. The present invention further provides methods of identifying compounds that mimic the bitter taste due these agonists. The present invention also provides methods of identifying compounds that enhance the bitter taste due to these agonists.

21 Claims, 7 Drawing Sheets

(56) References Cited

OTHER PUBLICATIONS

Slack et al., "Modulation of bitter taste perception by a small molecule hTAS2R antagonist," Currently Biology, 20(12):1104-1109 (2010).
Slack et al., "Inhibition of Bitter Taste Receptors," AChemS 2009 Annual Meeting, Sarasota, FL, Poster P195, Apr. 22-26, 2009.
Winnig et al., "Saccharin: Artificial Sweetener, Bitter Tastant, and Sweet Taste Inhibitor," Sweetness and Sweeteners, Chapter 16, pp. 230-240 Chapter DOI: 10.1021/bk-2008-0979.ch016 ACS Symposium Series, vol. 979 http://pubs.acs.org/doi/abs/10.1021/bk-2008-0979.ch016.
Behrens et al., "Bitter taste receptors and human bitter taste perception," CMLS Cellular and Molecular Life Sciences, Birkhauser Verlag, Heidelberg, DE 6(13):1501-1509 (2006).

* cited by examiner

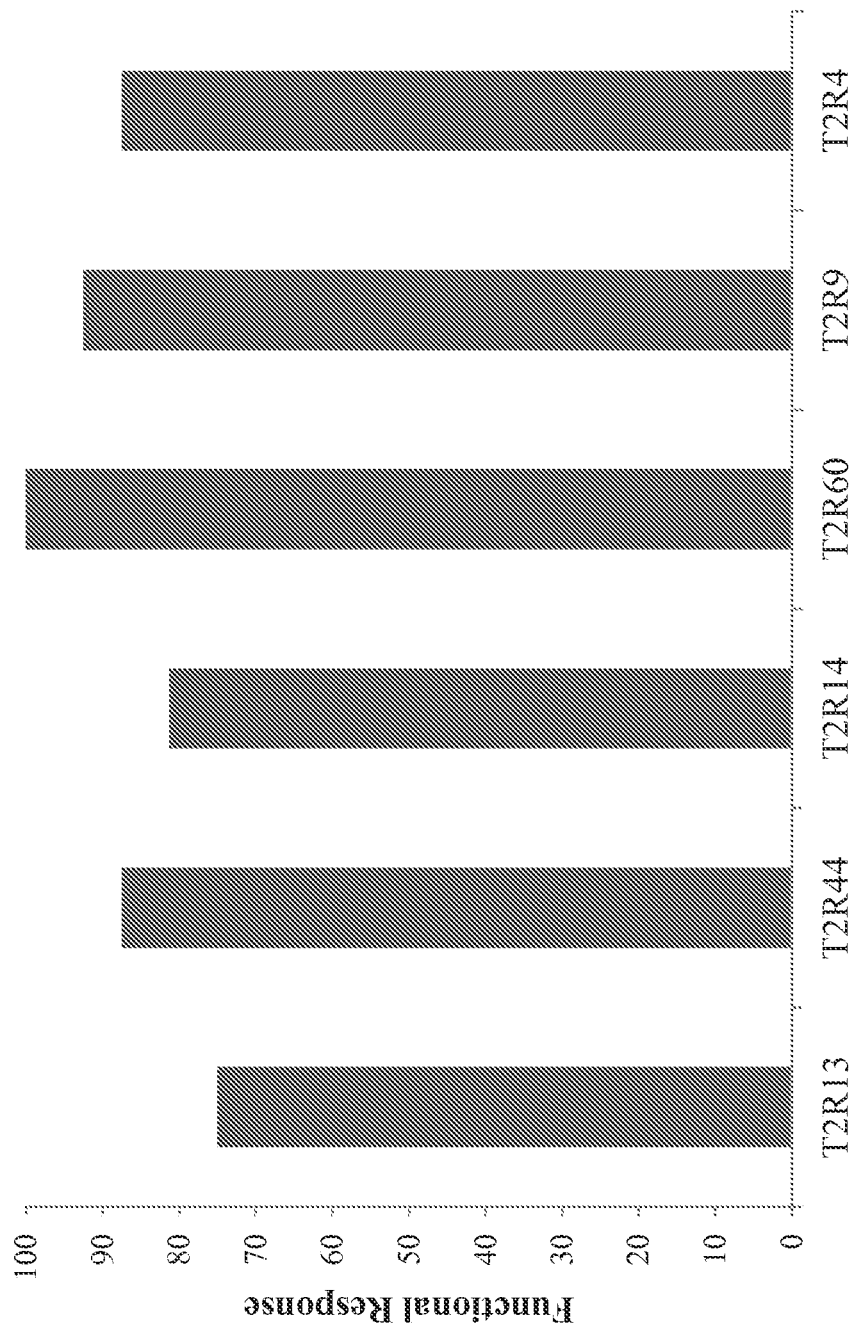

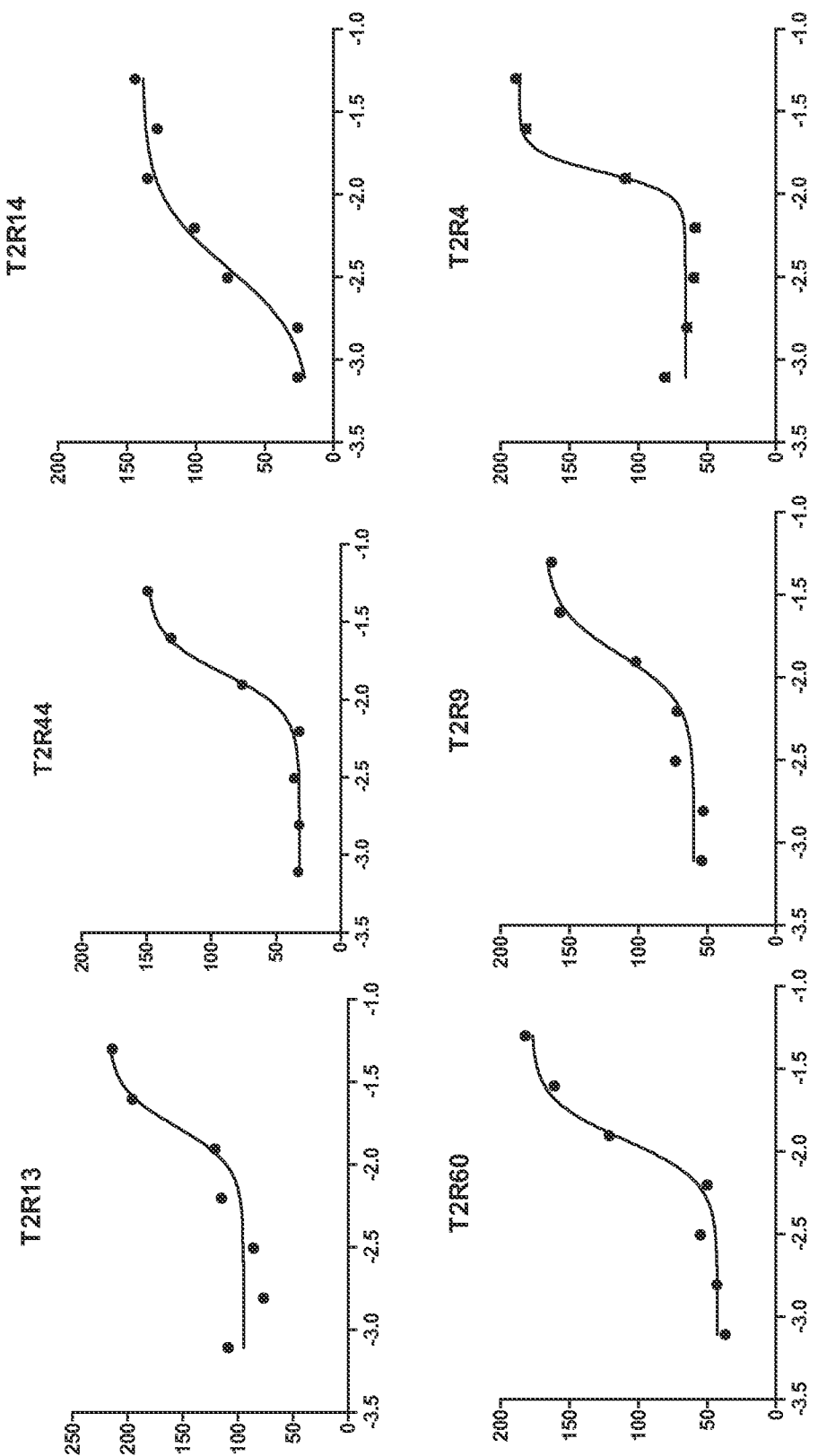

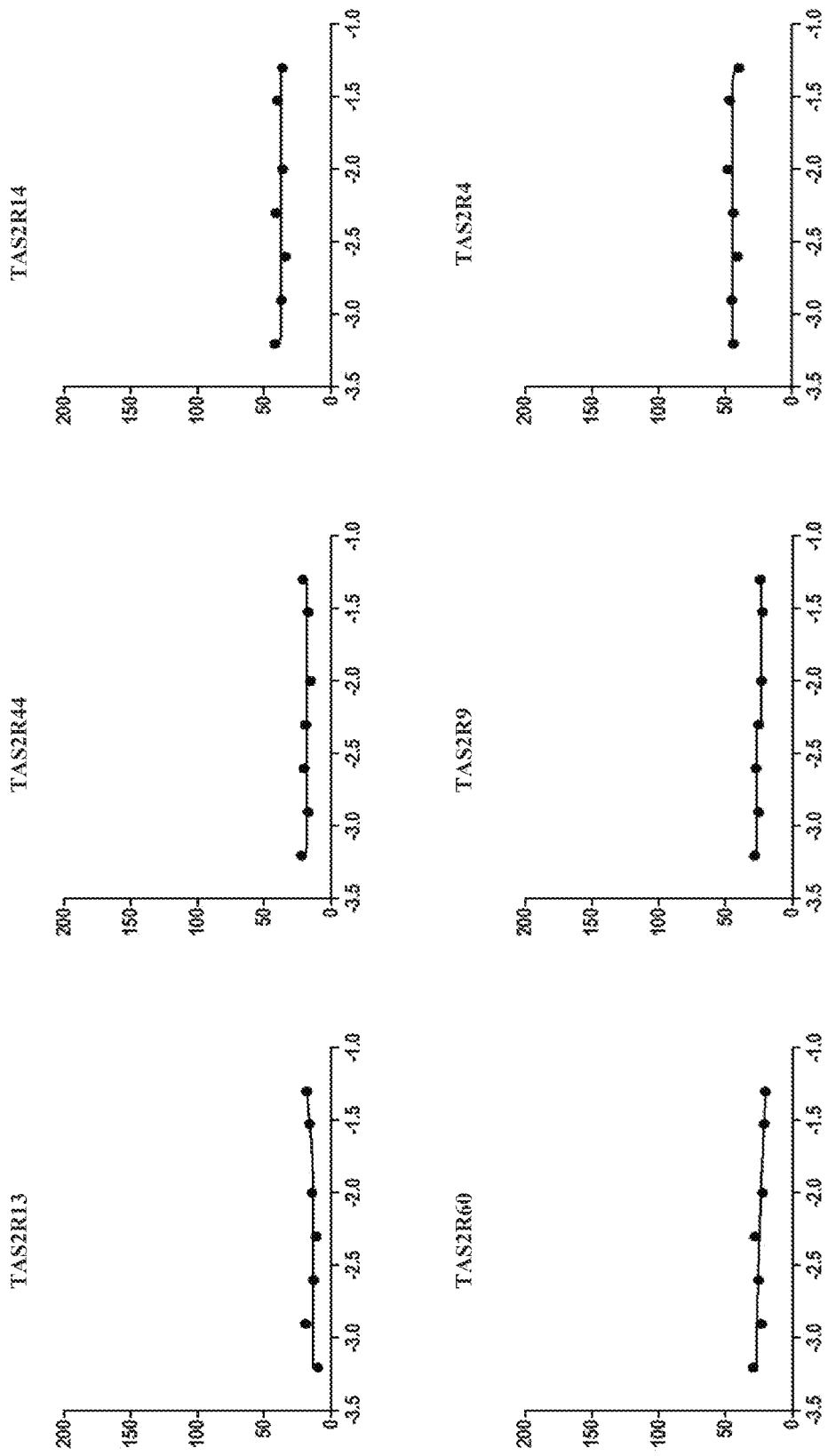

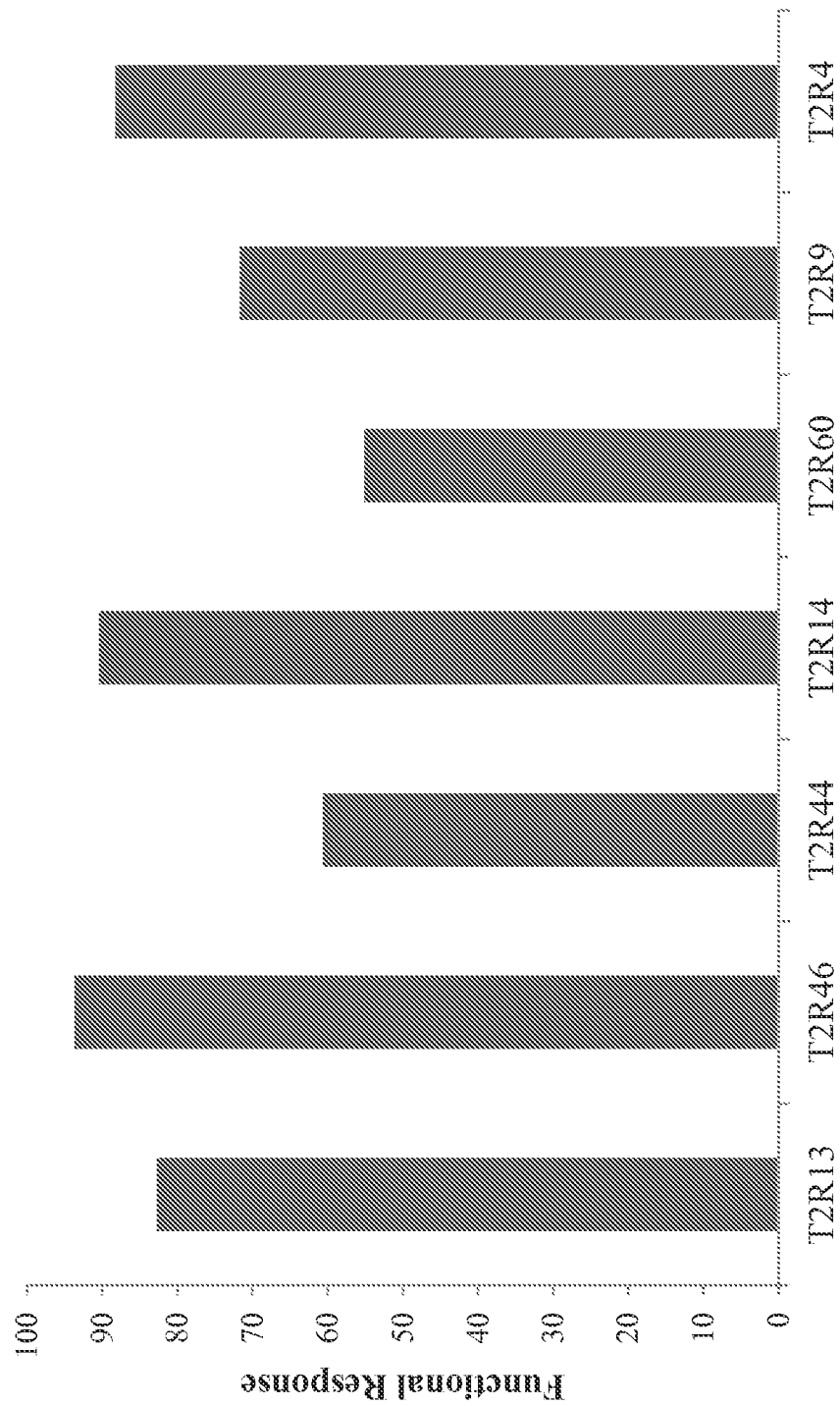

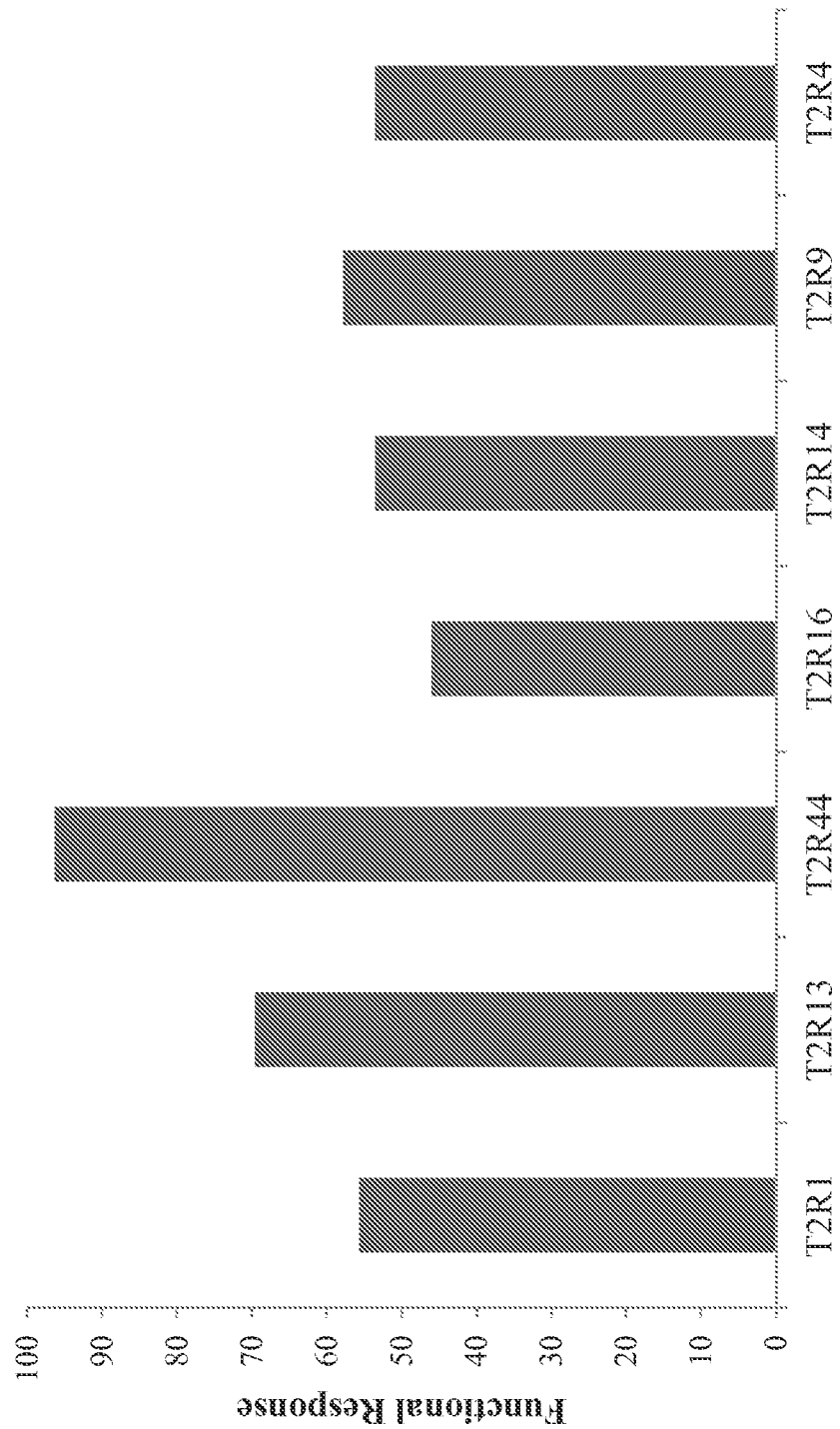

Figure 6

| | T2R1 | T2R8 | T2R13 | T2R7 | T2R3 | T2R43 | T2R38 | T2R45 | T2R46 | T2R30 | T2R5 | T2R44 | T2R55 | T2R16 | T2R14 | T2R10 | T2R48 | T2R41 | T2R40 | T2R60 | T2R49 | T2R43 | T2R47 | T2R39 | T2R9 | T2R4 |
|---|---|---|---|---|---|---|---|---|---|---|---|---|---|---|---|---|---|---|---|---|---|---|---|---|---|---|
| KCl | | ✓ | | | | | | | | | ✓ | | | ✓ | | | | | ✓ | | | | ✓ | ✓ | ✓ |
| K-lactate | | ✓ | | | | | ✓ | | | ✓ | | | ✓ | | | | | ✓ | | | | ✓ | ✓ | ✓ |
| Acesulfame-K | ✓ | ✓ | | | | | | | | | ✓ | | ✓ | ✓ | | | | | ✓ | | | | ✓ | ✓ | ✓ |

SEQUENCE LISTING

<160> NUMBER OF SEQ ID NOS: 54

<210> SEQ ID NO 1
<211> LENGTH: 374
<212> TYPE: PRT
<213> ORGANISM: Homo sapiens

<400> SEQUENCE: 1

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

```
Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
                195                 200                 205

Val Gly Gly Gln Lys Ser Glu Arg Lys Lys Trp Ile His Cys Phe Glu
        210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
        355                 360                 365

Asp Glu Ile Asn Leu Leu
        370

<210> SEQ ID NO 2
<211> LENGTH: 900
<212> TYPE: DNA
<213> ORGANISM: Homo sapiens

<400> SEQUENCE: 2
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttcttcatag aattcatcat gttctctgcg     240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaattttc      480 tcccaaaatg ccacaattca aaagaagat acactggcta cagattttt ctcttttgtt      540 gctgagttct cagtgccatt gcttatcttc cttttgctg ttttgctctt gattttctct      600
```

```
ctggggaggc acacccggca aatgagaaac acagtggccg gcagcagggt tcctggcagg      660
ggtgcaccca tcagcgcgtt gctgtctatc ctgtccttcc tgatcctcta cttctcccac      720
tgcatgataa agttttttct ctcttctcta agtttcaca tcagaaggtt catctttctg       780
ttcttcatcc ttgtgattgg tgtataccct tctggacact ctctcatctt aattttagga     840
aatcctaaat tgaaacaaaa tgcaaaaaag ttcctcctcc acagtaagtg ctgtcagtga     900
```

<210> SEQ ID NO 3
<211> LENGTH: 951
<212> TYPE: DNA
<213> ORGANISM: Homo sapiens

<400> SEQUENCE: 3

```
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct tgaggatcat tctgctgtgt     180
attatcttga ctgatagttt tttaatagaa ttctctccca acacacatga ttcagggata     240
ataatgcaaa ttattgatgt ttcctggaca tttacaaacc atctgagcat ttggcttgcc     300
acctgtcttg gtgtcctcta ctgcctgaaa atcgccagtt tctctcaccc cacattcctc     360
tggctcaagt ggagagtttc tagggtgatg gtatggatgc tgttgggtgc actgctctta    420
tcctgtggta gtaccgcatc tctgatcaat gagtttaagc tctattctgt ctttagggga    480
attgaggcca ccaggaatgt gactgaacac ttcagaaaga gaggagtga gtattatctg     540 atccatgttc ttgggactct gtggtacctg cctcccttaa ttgtgtccct ggcctcctac    600
tctttgctca tcttctccct ggggaggcac acacggcaga tgctgcaaaa tgggacaagc     660
tccagagatc caaccactga ggcccacaag agggccatca gaatcatcct tccttcttc      720 tttctcttct tactttactt tcttgctttc ttaattgcat catttggtaa tttcctacca     780
aaaaccaaga tggctaagat gattggtgaa gtaatgacaa tgttttatcc tgctggccac    840
tcatttattc tcattctggg gaacagtaag ctgaagcaga catttgtagt gatgctccgg    900
tgtgagtctg gtcatctgaa gcctggatcc aagggaccca ttttctctta g             951
```

<210> SEQ ID NO 4
<211> LENGTH: 900
<212> TYPE: DNA
<213> ORGANISM: Homo sapiens

<400> SEQUENCE: 4

```
atgcttcggt tattctattt ctctgctatt attgcctcag ttatttttaaa ttttgtagga    60 atcattatga atctgtttat tacagtggtc aattgcaaaa cttgggtcaa aagcccataga   120 atctcctctt ctgataggat tctgttcagc ctgggcatca ccaggtttct tatgctggga    180
ctatttctgg tgaacaccat ctacttcgtc tcttcaaata cggaaaggtc agtctacctg   240
tctgcttttt ttgtgttgtg tttcatgttt ttggactcga gcagtgtctg gtttgtgacc   300
ttgctcaata tcttgtactg tgtgaagatt actaacttcc aacactcagt gtttctcctg    360
ctgaagcgga atatctcccc aaagatcccc aggctgctgc tggcctgtgt gctgattttct    420 gctttcacca cttgcctgta catcacgctt agccaggcat cacctttttcc tgaacttgtg    480 actacgagaa ataacacatc atttaatatc agtgagggca tcttgtcttt agtggttct    540 ttggtcttga gctcatctct ccagttcatc attaatgtga cttctgcttc cttgctaata   600
```

| | |
|---|---|
| cactccttga ggagacatat acagaagatg cagaaaaatg ccactggttt ctggaatccc | 660 |
| cagacggaag ctcatgtagg tgctatgaag ctgatggtct atttcctcat cctctacatt | 720 |
| ccatattcag ttgctaccct ggtccagtat ctccccttt atgcagggat ggatatgggg | 780 |
| accaaatcca tttgtctgat ttttgccacc ctttactctc caggacattc tgttctcatt | 840 |
| attatcacac atcctaaact gaaaacaaca gcaaagaaga ttctttgttt caaaaaatag | 900 |

<210> SEQ ID NO 5
<211> LENGTH: 900
<212> TYPE: DNA
<213> ORGANISM: Homo sapiens

<400> SEQUENCE: 5

| | |
|---|---|
| atgctgagcg ctggcctagg actgctgatg ctggtggcag tggttgaatt tctcatcggt | 60 |
| ttaattggaa atggaagcct ggtggtctgg agttttagag aatggatcag aaaattcaac | 120 |
| tggtcctcat ataacctcat tatcctgggc ctggctggct gccgatttct cctgcagtgg | 180 |
| ctgatcattt tggacttaag cttgtttcca cttttccaga gcagccgttg gcttcgctat | 240 |
| cttagtatct tctgggtcct ggtaagccag gccagcttat ggtttgccac cttcctcagt | 300 |
| gtcttctatt gcaagaagat cacgaccttc gatcgcccgg cctacttgtg gctgaagcag | 360 |
| agggcctata acctgagtct ctggtgcctt ctgggctact ttataatcaa tttgttactt | 420 |
| acagtccaaa ttggcttaac attctatcat cctccccaag aaacagcag cattcggtat | 480 |
| cccttttgaaa gctggcagta cctgtatgca tttcagctca attcaggaag ttatttgcct | 540 |
| ttagtggtgt ttcttgtttc ctctgggatg ctgattgtct ctttgtatac acaccacaag | 600 |
| aagatgaagg tccattcagc tggtaggagg gatgtccggg ccaaggctca catcactgcg | 660 |
| ctgaagtcct tgggctgctt cctcttactt cacctggttt atatcatggc cagccccttc | 720 |
| tccatcacct ccaagactta tcctcctgat ctcaccagtg tcttcatctg ggagacactc | 780 |
| atggcagcct atccttctct tcattctctc atattgatca tggggattcc tagggtgaag | 840 |
| cagacttgtc agaagatcct gtggaagaca gtgtgtgctc ggagatgctg ggcccatga | 900 |

<210> SEQ ID NO 6
<211> LENGTH: 957
<212> TYPE: DNA
<213> ORGANISM: Homo sapiens

<400> SEQUENCE: 6

| | |
|---|---|
| atggcagata aagtgcagac tactttattg ttcttagcag ttggagagtt ttcagtgggg | 60 |
| atcttaggga atgcattcat tggattggta aactgcatgg attgggtcaa gaagaggaaa | 120 |
| attgcctcca ttgatttaat cctcacaagt ctggccatat ccagaatttg tctattgtgc | 180 |
| gtaatactat tagattgttt tatattggtg ctatatccag atgtctatgc cactggtaaa | 240 |
| gaaatgagaa tcattgactt cctctggaca ctaaccaatc atttaagtat ctggtttgca | 300 |
| acctgcctca gcatttacta tttcttcaag ataggtaatt tctttcaccc acttttcctc | 360 |
| tggatgaagt ggagaattga cagggtgatt tcctggattc tactggggtg cgtggttctc | 420 |
| tctgtgttta ttagccttcc agccactgag aatttgaacg ctgatttcag gttttgtgtg | 480 |
| aaggcaaaga ggaaaacaaa cttaacttgg agttgcagag taaataaaac tcaacatgct | 540 |
| tctaccaagt tatttctcaa cctggcaacg ctgctcccct tttgtgtgtg cctaatgtcc | 600 |
| ttttttcctct tgatcctctc cctgcgggaga catatcaggc gaatgcagct cagtgccaca | 660 |
| gggtgcagag accccagcac agaagcccat gtgagagccc tgaaagctgt catttccttc | 720 |

| | |
|---|---|
| cttctcctct ttattgccta ctatttgtcc tttctcattg ccacctccag ctactttatg | 780 |
| ccagagacgg aattagctgt gattttggt gagtccatag ctctaatcta cccctcaagt | 840 |
| cattcattta tcctaatact ggggaacaat aaattaagac atgcatctct aaaggtgatt | 900 |
| tggaaagtaa tgtctattct aaaaggaaga aaattccaac aacataaaca aatctga | 957 |

<210> SEQ ID NO 7
<211> LENGTH: 930
<212> TYPE: DNA
<213> ORGANISM: Homo sapiens

<400> SEQUENCE: 7

| | |
|---|---|
| atgttcagtc ctgcagataa catctttata atcctaataa ctggagaatt catactagga | 60 |
| atattgggga atggatacat tgcactagtc aactggattg actggattaa gaagaaaaag | 120 |
| atttccacag ttgactacat ccttaccaat ttagttatcg ccagaatttg tttgatcagt | 180 |
| gtaatggttg taaatggcat tgtaatagta ctgaacccag atgtttatac aaaaaataaa | 240 |
| caacagatag tcattttac cttctggaca tttgccaact acttaaatat gtggattacc | 300 |
| acctgcctta atgtcttcta ttttctgaag atagccagtt cctctcatcc acttttctc | 360 |
| tggctgaagt ggaaaattga tatggtggtg cactggatcc tgctgggatg ctttgccatt | 420 |
| tccttgttgg tcagccttat agcagcaata gtactgagtt gtgattatag gtttcatgca | 480 |
| attgccaaac ataaaagaaa cattactgaa atgttccatg tgagtaaaat accatacttt | 540 |
| gaacccttga ctctctttaa cctgtttgca attgtcccat ttattgtgtc actgatatca | 600 |
| ttttcctttt tagtaagatc tttatggaga cataccaagc aaataaaact ctatgctacc | 660 |
| ggcagtagag accccagcac agaagttcat gtgagagcca ttaaaactat gacttcattt | 720 |
| atcttctttt ttttcctata ctatatttct tctattttga tgacctttag ctatcttatg | 780 |
| acaaaataca agttagctgt ggagtttgga gagattgcag caattctcta cccttgggt | 840 |
| cactcactta ttttaattgt tttaaataat aaactgaggc agacatttgt cagaatgctg | 900 |
| acatgtagaa aaattgcctg catgatatga | 930 |

<210> SEQ ID NO 8
<211> LENGTH: 939
<212> TYPE: DNA
<213> ORGANISM: Homo sapiens

<400> SEQUENCE: 8

| | |
|---|---|
| atgccaagtg caatagaggc aatatatatt atttttaattg ctggtgaatt gaccataggg | 60 |
| atttggggaa atggattcat tgtactagtt aactgcattg actggctcaa agaagagat | 120 |
| atttccttga ttgacatcat cctgatcagc ttggccatct ccagaatctg tctgctgtgt | 180 |
| gtaatatcat tagatggctt ctttatgctg ctctttccag gtacatatgg caatagcgtg | 240 |
| ctagtaagca ttgtgaatgt tgtctggaca tttgccaata attcaagtct ctggtttact | 300 |
| tcttgcctca gtatcttcta tttactcaag atagccaata tatcgcaccc atttttcttc | 360 |
| tggctgaagc taaagatcaa caaggtcatg cttgcgattc ttctggggtc ctttcttatc | 420 |
| tctttaatta ttagtgttcc aaagaatgat gatatgtggt atcacctttt caaagtcagt | 480 |
| catgaagaaa acattacttg gaaattcaaa gtgagtaaaa ttccaggtac tttcaaacag | 540 |
| ttaaccctga acctggggt gatggttccc tttatccttt gcctgatctc atttttcttg | 600 |
| ttacttttct ccctagttag acacaccaag cagattcgac tgcatgctac agggttcaga | 660 |

```
gaccccagta cagaggccca catgagggcc ataaaggcag tgatcatctt tctgctcctc    720
ctcatcgtgt actacccagt ctttcttgtt atgacctcta gcgctctgat tcctcaggga    780
aaattagtgt tgatgattgg tgacatagta actgtcattt tcccatcaag ccattcattc    840
attctaatta tgggaaatag caagttgagg gaagcttttc tgaagatgtt aagatttgtg    900
aagtgtttcc ttagaagaag aaagccttt gttccatag                            939
```

<210> SEQ ID NO 9
<211> LENGTH: 924
<212> TYPE: DNA
<213> ORGANISM: Homo sapiens

<400> SEQUENCE: 9

```
atgctacgtg tagtggaagg catcttcatt tttgttgtag ttagtgagtc agtgtttggg     60
gttttgggga atggatttat tggacttgta aactgcattg actgtgccaa gaataagtta    120
tctacgattg gctttattct caccggctta gctatttcaa gaattttct gatatggata     180 ataattacag atggatttat acagatattc tctccaaata tatgcctc cggtaaccta      240 attgaatata ttagttactt tgggtaatt ggtaatcaat caagtatgtg gtttgccacc    300
agcctcagca tcttctattt cctgaagata gcaaattttt ccaactacat atttctctgg    360
ttgaagagca gaacaaatat ggttcttccc ttcatgatag tattcttact tatttcatcg    420
ttacttaatt tgcatacat tgcgaagatt cttaatgatt ataaaatgaa gaatgacaca    480
gtctgggatc tcaacatgta taaaagtgaa tactttatta aacagatttt gctaaatctg    540
ggagtcattt tcttctttac actatcccta attacatgta ttttttttaat catttcccctt    600 tggagacaca acaggcagat gcaatcaaat gtgacaggat tgagagactc caacacagaa    660
gctcatgtga aggcaatgaa agttttgata tctttcatca tcctcttat cttgtatttt     720 ataggcatgg ccatagaaat atcatgtttt actgtgcgag aaaacaaact gctgcttatg    780
tttggaatga caaccacagc catctatccc tggggtcact catttatctt aattctagga    840
aacagcaagc taaagcaagc ctctttgagg gtactgcagc aattgaagtg ctgtgagaaa    900
aggaaaaatc tcagagtcac atag                                           924
```

<210> SEQ ID NO 10
<211> LENGTH: 912
<212> TYPE: DNA
<213> ORGANISM: Homo sapiens

<400> SEQUENCE: 10

```
atggaaagtg ccctgccgag tatcttcact cttgtaataa ttgcagaatt cataattggg     60
aatttgagca atggatttat agtactgatc aactgcattg actgggtcag taaagagag     120 ctgtcctcag tcgataaact cctcattatc ttggcaatct ccagaattgg gctgatctgg    180
gaaatattag taagttggtt tttagctctg cattatctag ccatatttgt gtctggaaca    240
ggattaagaa ttatgatttt tagctggata gtttctaatc acttcaatct ctggcttgct    300
acaatcttca gcatctttta tttgctcaaa atagcgagtt tctctagccc tgcttttctc    360
tatttgaagt ggagagtaaa caaagtgatt ctgatgatac tgctaggaac cttggtcttc    420 ttattttaa atctgataca aataaacatg catataaaag actggctgga ccgatatgaa    480
agaaacacaa cttggaattt cagtatgagt gactttgaaa catttcagt gtcggtcaaa    540 ttcactatga ctatgttcag tctaacacca tttactgtgg ccttcatctc ttttctcctg    600
ttaattttct ccctgcagaa acatctccag aaaatgcaac tcaattacaa aggacacaga    660
```

```
gaccccagga ccaaggtcca tacaaatgcc ttgaaaattg tgatctcatt cctttattc      720 tatgctagtt tctttctatg tgttctcata tcatggattt ctgagctgta tcagaacaca      780
gtgatctaca tgctttgtga gacgattgga gtcttctctc cttcaagcca ctcctttctt      840
ctgattctag gaaacgctaa gttaagacag gcctttcttt tggtggcagc taaggtatgg      900
gctaaacgat ga                                                           912
```

<210> SEQ ID NO 11
<211> LENGTH: 954
<212> TYPE: DNA
<213> ORGANISM: Homo sapiens

<400> SEQUENCE: 11

```
atgggtggtg tcataaagag catatttaca ttcgttttaa ttgtggaatt tataattgga       60
aatttaggaa atagtttcat agcactggtg aactgtattg actgggtcaa gggaagaaag      120
atctcttcgg ttgatcggat cctcactgct ttggcaatct ctcgaattag cctggtttgg      180
ttaatattcg gaagctggtg tgtgtctgtg ttttccccag ctttatttgc cactgaaaaa      240
atgttcagaa tgcttactaa tatctggaca gtgatcaatc attttagtgt ctggttagct      300
acaggcctcg gtactttta ttttctcaag atagccaatt tttctaactc tattttctc       360 tacctaaagt ggagggttaa aaaggtggtt tggtgctgc ttcttgtgac ttcggtcttc      420 ttgttttaa atattgcact gataaacatc catataaatg ccagtatcaa tggatacaga      480
agaaacaaga cttgcagttc tgattcaagt aactttacac gattttccag tcttattgta      540
ttaaccagca ctgtgttcat tttcatatccc tttactttgt ccctggcaat gtttcttctc      600
ctcatcttct ccatgtggaa acatcgcaag aagatgcagc acactgtcaa atatatccgga     660 gacgccagca ccaaagccca cagaggagtt aaaagtgtga tcactttctt cctactctat      720 gccatttct ctctgtcttt ttcatatca gtttggacct ctgaaaggtt ggaggaaaat       780
ctaattattc ttttcccaggt gatgggaatg gcttatcctt catgtcactc atgtgttctg      840
attcttggaa acaagaagct gagacaggcc tctctgtcag tgctactgtg gctgaggtac      900
atgttcaaag atggggagcc ctcaggtcac aaagaattta gagaatcatc ttga            954
```

<210> SEQ ID NO 12
<211> LENGTH: 876
<212> TYPE: DNA
<213> ORGANISM: Homo sapiens

<400> SEQUENCE: 12

```
atgataccca tccaactcac tgtcttcttc atgatcatct atgtgcttga gtccttgaca       60
attattgtgc agagcagcct aattgttgca gtgctgggca gagaatggct gcaagtcaga      120
aggctgatgc ctgtggacat gattctcatc agcctgggca tctctcgctt ctgtctacag      180
tgggcatcaa tgctgaacaa ttttttgctcc tattttaatt tgaattatgt actttgcaac      240
ttaacaatca cctgggaatt ttttaatatc cttacattct ggttaaacag cttgcttacc      300
gtgttctact gcatcaaggt ctcttctttc acccatcaca tctttctctg gctgaggtgg      360 agaatttga ggttgtttcc ctggatatta ctgggttctc tgatgattac ttgtgtaaca       420
atcatccctt cagctattgg gaattacatt caaattcagt tactcaccat ggagcatcta      480
ccaagaaaca gcactgtaac tgacaaactt gaaaatttc atcagtatca gttccaggct      540
catacagttg cattggttat tcctttcatc ctgttcctgg cctccaccat ctttctcatg      600
```

| | |
|---|---|
| gcatcactga ccaagcagat acaacatcat agcactggtc actgcaatcc aagcatgaaa | 660 |
| gcgcgcttca ctgccctgag gtcccttgcc gtcttattta ttgtgtttac ctcttacttt | 720 |
| ctaaccatac tcatcaccat tataggtact ctatttgata agagatgttg gttatgggtc | 780 |
| tgggaagctt ttgtctatgc tttcatctta atgcattcca cttcactgat gctgagcagc | 840 |
| cctacgttga aaggattct aaagggaaag tgctag | 876 |

<210> SEQ ID NO 13
<211> LENGTH: 1002
<212> TYPE: DNA
<213> ORGANISM: Homo sapiens

<400> SEQUENCE: 13

| | |
|---|---|
| atgttgactc taactcgcat ccgcactgtg tcctatgaag tcaggagtac atttctgttc | 60 |
| atttcagtcc tggagtttgc agtggggttt ctgaccaatg ccttcgtttt cttggtgaat | 120 |
| ttttgggatg tagtgaagag gcaggcactg agcaacagtg attgtgtgct gctgtgtctc | 180 |
| agcatcagcc ggcttttcct gcatggactg ctgttcctga gtgctatcca gcttacccac | 240 |
| ttccagaagt tgagtgaacc actgaaccac agctaccaag ccatcatcat gctatggatg | 300 |
| attgcaaacc aagccaacct ctggcttgct gcctgcctca gctgcttta ctgctccaag | 360 |
| ctcatccgtt tctctcacac cttcctgatc tgcttggcaa gctgggtctc caggaagatc | 420 |
| tcccagatgc tcctgggtat tattctttgc tcctgcatct gcactgtcct ctgtgtttgg | 480 |
| tgcttttta gcagacctca cttcacagtc acaactgtgc tattcatgaa taacaataca | 540 |
| aggctcaact ggcagattaa agatctcaat ttatttatt cctttctctt ctgctatctg | 600 |
| tggtctgtgc ctcctttcct attgtttctg gtttcttctg ggatgctgac tgtctccctg | 660 |
| ggaaggcaca tgaggacaat gaaggtctat accagaaact ctcgtgaccc cagcctggag | 720 |
| gcccacatta agccctcaa gtctcttgtc tcctttttct gcttctttgt gatatcatcc | 780 |
| tgtgctgcct tcatctctgt gccccctactg attctgtggc gcgacaaaat agggtgatg | 840 |
| gtttgtgttg ggataatggc agcttgtccc tctgggcatg cagccatcct gatctcaggc | 900 |
| aatgccaagt tgaggagagc tgtgatgacc attctgctct gggctcagag cagcctgaag | 960 |
| gtaagagccg accacaaggc agattcccgg acactgtgct ga | 1002 |

<210> SEQ ID NO 14
<211> LENGTH: 1014
<212> TYPE: DNA
<213> ORGANISM: Homo sapiens

<400> SEQUENCE: 14

| | |
|---|---|
| atgctaggga gatgttttcc tccagacacc aaagagaagc aacagctcag aatgactaaa | 60 |
| ctctgcgatc ctgcagaaag tgaattgtcg ccatttctca tcaccttaat tttagcagtt | 120 |
| ttacttgctg aatacctcat tggtatcatt gcaaatggtt tcatcatggc tatacatgca | 180 |
| gctgaatggg ttcaaaataa ggcagtttcc acaagtggca ggatcctggt tttcctgagt | 240 |
| gtatccagaa tagctctcca aagcctcatg atgttagaaa ttaccatcag ctcaacctcc | 300 |
| ctaagttttt attctgaaga cgctgtatat tatgcattca aaataagttt tatattctta | 360 |
| aattttgta gcctgtggtt tgctgcctgg ctcagtttct tctactttgt gaagattgcc | 420 |
| aatttctcct accccctttt cctcaaactg aggtggagaa ttactggatt gatacccctgg | 480 |
| cttctgtggc tgtccgtgtt tatttccttc agtcacagca tgttctgcat caacatctgc | 540 |
| actgtgtatt gtaacaattc tttccctatc cactcctcca actccactaa gaaaacatac | 600 |

| | |
|---|---|
| ttgtctgaga tcaatgtggt cggtctggct ttttctttta acctggggat tgtgactcct | 660 |
| ctgatcatgt tcatcctgac agccaccctg ctgatcctct ctctcaagag acacacccta | 720 |
| cacatgggaa gcaatgccac agggtccaac gacccagca tggaggctca catgggggcc | 780 |
| atcaaagcta tcagctactt tctcattctc tacattttca atgcagttgc tctgttttatc | 840 |
| tacctgtcca acatgtttga catcaacagt ctgtggaata atttgtgcca gatcatcatg | 900 |
| gctgcctacc ctgccagcca ctcaattcta ctgattcaag ataaccctgg gctgagaaga | 960 |
| gcctggagcg gcttcagctt cgacttcatc tttacccaaa agagtggact ctga | 1014 |

<210> SEQ ID NO 15
<211> LENGTH: 972
<212> TYPE: DNA
<213> ORGANISM: Homo sapiens

<400> SEQUENCE: 15

| | |
|---|---|
| atggcaacgg tgaacacaga tgccacagat aaagacatat ccaagttcaa ggtcaccttc | 60 |
| actttggtgg tctccggaat agagtgcatc actggcatcc ttgggagtgg cttcatcacg | 120 |
| gccatctatg gggctgagtg ggccaggggc aaaacactcc ccactggtga ccgcattatg | 180 |
| ttgatgctga gcttttccag gctcttgcta cagatttgga tgatgctgga gaacattttc | 240 |
| agtctgctat tccgaattgt ttataaccaa aactcagtgt atatcctctt caaagtcatc | 300 |
| actgtctttc tgaaccattc caatctctgg tttgctgcct ggctcaaagt cttctattgt | 360 |
| cttagaattg caaacttcaa tcatccttg ttcttcctga tgaagaggaa aatcatagtg | 420 |
| ctgatgcctt ggcttctcag gctgtcagtg ttggtttcct taagcttcag ctttcctctc | 480 |
| tcgagagatg tcttcaatgt gtatgtgaat agctccattc ctatcccctc ctccaactcc | 540 |
| acggagaaga agtacttctc tgagaccaat atggtcaacc tggtattttt ctataacatg | 600 |
| gggatcttcg ttcctctgat catgttcatc ctggcagcca ccctgctgat cctctctctc | 660 |
| aagagacaca ccctacacat gggaagcaat gccacagggt ccagggaccc cagcatgaag | 720 |
| gctcacatag ggccatcaa agccaccagc tactttctca tcctctacat tttcaatgca | 780 |
| attgctctat ttcttccac gtccaacatc tttgacactt acagttcctg gaatattttg | 840 |
| tgcaagatca tcatggctgc ctaccctgcc ggccactcag tacaactgat cttgggcaac | 900 |
| cctgggctga agagcctg gaagcggttt cagcaccaag ttcctcttta cctaaaaggg | 960 |
| cagactctgt ga | 972 |

<210> SEQ ID NO 16
<211> LENGTH: 924
<212> TYPE: DNA
<213> ORGANISM: Homo sapiens

<400> SEQUENCE: 16

| | |
|---|---|
| atgcaagcag cactgacggc cttcttcgtg ttgctctttta gcctgctgag tcttctgggg | 60 |
| attgcagcga atggcttcat tgtgctggtg ctgggcaggg agtggctgcg atatggcagg | 120 |
| ttgctgccct tggatatgat cctcattagc ttgggtgcct cccgcttctg cctgcagttg | 180 |
| gttgggacgg tgcacaactt ctactactct gcccagaagg tcgagtactc tgggggtctc | 240 |
| ggccgacagt tcttccatct acactggcac ttcctgaact cagccacctt ctggttttgc | 300 |
| agctggctca gtgtcctgtt ctgtgtgaag attgctaaca tcacacactc caccttcctg | 360 |
| tggctgaagt ggaggttccc agggtgggtg cctggctcc tgttgggctc tgtcctgatc | 420 |

```
tccttcatca taaccctgct gttttttttgg gtgaactacc ctgtatatca agaatttta      480 attagaaaat tttctgggaa catgacctac aagtggaata caaggataga aacatactat      540
ttcccatccc tgaaactggt catctggtca attccttttt ctgttttct ggtctcaatt       600 atgctgctga ttaattctct gaggaggcat actcagagaa tgcagcacaa cgggcacagc      660
ctgcaggacc ccagcaccca ggctcacacc agagctctga agtccctcat ctccttcctc      720
attctttatg ctctgtcctt tctgtccctg atcattgatg ccgcaaaatt tatctccatg      780
cagaacgact tttactggcc atggcaaatt gcagtctacc tgtgcatatc tgtccatccc      840
ttcatcctca tcttcagcaa cctcaagctt cgaagcgtgt tctcacagct cctgttgttg      900 gcaagggct tctgggtggc ctga                                              924

<210> SEQ ID NO 17
<211> LENGTH: 930
<212> TYPE: DNA
<213> ORGANISM: Homo sapiens

<400> SEQUENCE: 17
atgataactt ttctgcccat cattttttcc agtctggtag tggttacatt tgttattgga       60
aattttgcta atggcttcat agcactggta aattccattg agtggttcaa gagacaaaag      120
atctcctttg ctgaccaaat tctcactgct ctggcggtct ccagagttgg tttgctctgg      180
gtattattat taaactggta ttcaactgtg ttgaatccag cttttaatag tgtagaagta      240
agaactactg cttataatat ctgggcagtg atcaaccatt tcagcaactg gcttgctact      300
accctcagca tatttatt gctcaagatt gccaatttct ccaactttat ttttcttcac        360
ttaaagagga gagttaagag tgtcattctg gtgatgttgt tggggccttt gctatttttg      420
gcttgtcatc tttttgtgat aaacatgaat gagattgtgc ggacaaaaga atttgaagga      480
aacatgactt ggaagatcaa attgaagagt gcaatgtact tttcaaatat gactgtaacc      540
atggtagcaa acttagtacc cttcactctg acccctactat cttttatgct gttaatctgt      600
tctttgtgta acatctcaa gaagatgcag ctccatggta aaggatctca agatcccagc       660
accaaggtcc acataaaagc tttgcaaact gtgatctcct tcctcttgtt atgtgccatt      720
tactttctgt ccataatgat atcagttttgg agttttggaa gtctggaaaa caaacctgtc    780
ttcatgttct gcaaagctat tagattcagc tatccttcaa tccacccatt catcctgatt     840
tggggaaaca agaagctaaa gcagacttt cttcagtttt tttggcaaat gaggtactgg     900
gtgaaaggag agaagacttc atctccatga                                       930

<210> SEQ ID NO 18
<211> LENGTH: 930
<212> TYPE: DNA
<213> ORGANISM: Homo sapiens

<400> SEQUENCE: 18
atgacaactt ttatacccat catttttttcc agtgtggtag tggttctatt tgttattgga      60
aattttgcta atggcttcat agcattggta aattccattg agcgggtcaa gagacaaaag     120
atctcttttg ctgaccagat tctcactgct ctggcggtct ccagagttgg tttgctctgg     180
gtattattat taaattggta ttcaactgtg tttaatccag cttttttatag tgtagaagta    240 agaactactg cttataatgt ctgggcagta accggccatt tcagcaactg gcttgctact    300
agcctcagca tatttatt gctcaagatt gccaatttct ccaaccttat ttttcttcac       360
ttaaagagga gagttaagag tgtcattctg gtgatgctgt tggggccttt actatttttg     420
```

```
gcttgtcaac tttttgtgat aaacatgaaa gagattgtac ggacaaaaga atatgaagga    480
aacttgactt ggaagatcaa attgaggagt gcagtgtacc tttcagatgc gactgtaacc    540
acgctaggaa acttagtgcc cttcactctg accctgctat gttttttgct gttaatctgt    600
tctctgtgta aacatctcaa gaagatgcag ctccatggta aaggatctca agatcccagc    660
accaaggtcc acataaaagc tttgcaaact gtgatctttt tcctcttgtt atgtgccgtt    720
tactttctgt ccataatgat atcagtttgg agttttggga gtctggaaaa caaacctgtc    780
ttcatgttct gcaaagctat tagattcagc tatccttcaa tccacccatt catcctgatt    840
tggggaaaca agaagctaaa gcagactttt ctttcagttt gcggcaagt gaggtactgg     900 gtgaaaggag agaagccttc atctccatga                                     930
```

<210> SEQ ID NO 19
<211> LENGTH: 900
<212> TYPE: DNA
<213> ORGANISM: Homo sapiens

<400> SEQUENCE: 19

```
atgataactt ttctgcccat catatttttcc attctagtag tggttacatt tgttattgga    60
aattttgcta atggcttcat agcgttggta aattccaccg agtgggtgaa gagacaaaag   120
atctcctttg ctgaccaaat tgtcactgct ctggcggtct ccagagttgg tttgctctgg   180
gtgttattat taaattggta ttcaactgtg ttgaatccag ctttttgtag tgtagaatta   240
agaactactg cttataatat ctgggcagta accggccatt tcagcaactg gcctgctact   300
agcctcagca tattttatttt gctcaagatt gccaatttct ccaaccttat ttttcttcgc   360
ttaaagagga gagttaagag tgtcattctg gtgatgctgt ggggcctttt gctattttttg   420 gcttgtcatc ttttttgtggt aaacatgaat cagattgtat ggacaaaaga atatgaagga   480
aacatgactt ggaagatcaa attgaggcgt gcaatgtacc tttcagatac gactgtaacc   540
atgctagcaa acttagtacc ctttactgta acctgatat cttttctgct gttagtctgt    600
tctctgtgta aacatctcaa gaagatgcac ctccatggca aaggatctca agatcccagt   660
accaaggtcc acataaaagt tttgcaaact gtgatctcct tcctcttgtt atgtgccatt   720
tactttgtgt ctgtaataat atcagtttgg agttttaaga atctggaaaa caaacctgtc   780
ttcatgttct gccaagctat tggattcagc tgttcttcag cccacccgtt catcctgatt   840
tggggaaaca agaagctaaa gcagacttat cttttcagttt gtgggcaaat gaggtactga   900
```

<210> SEQ ID NO 20
<211> LENGTH: 900
<212> TYPE: DNA
<213> ORGANISM: Homo sapiens

<400> SEQUENCE: 20

```
atgataactt ttctgcccat cattttttcc attctaatag tggttacatt tgtgattgga    60
aattttgcta atggcttcat agcattggta aattccattg agtggtttaa gagacaaaag   120 atctctttttg ctgaccaaat tctcactgct ctggcagtct ccagagttgg tttactctgg   180
gtattagtat taaattggta tgcaactgag ttgaatccag cttttttaacag tatagaagta   240 agaattactg cttacaatgt ctgggcagta atcaaccatt tcagcaactg gcttgctact   300
agcctcagca tattttatttt gctcaagatt gccaatttct ccaaccttat ttttcttcac   360
ttaaagagga gagttaagag tgttgttctg gtgatactat ggggcctttt gctattttttg   420
```

```
gtttgtcatc tttttgtgat aaacatgaat cagattatat ggacaaaaga atatgaagga      480
aacatgactt ggaagatcaa actgaggagt gcaatgtacc tttcaaatac aacggtaacc      540
atcctagcaa acttagttcc cttcactctg accctgatat cttttctgct gttaatctgt      600
tctctgtgta aacatctcaa aaagatgcag ctccatggca aaggatctca agatcccagc      660
atgaaggtcc ataaaaagc tttgcaaact gtgacctcct tcctcttgtt atgtgccatt       720
tactttctgt ccataatcat gtcagtttgg agttttgaga gtctggaaaa caaacctgtc      780
ttcatgttct gcgaagctat tgcattcagc tatccttcaa cccacccatt catcctgatt      840
tggggaaaca agaagctaaa gcagacttt cttcagtttt gtggcaaat gaggtactga       900
```

<210> SEQ ID NO 21
<211> LENGTH: 960
<212> TYPE: DNA
<213> ORGANISM: Homo sapiens

<400> SEQUENCE: 21

```
atgataactt ttctgcccat cattttttcc attctaatag tggttatatt tgttattgga       60
aattttgcta atggcttcat agcattggta aattccattg agtgggtcaa gagacaaaag      120
atctcctttg ttgaccaaat tctcactgct ctggcggtct ccagagttgg tttgctctgg      180
gtgttattac tacattggta tgcaactcag ttgaatccag ctttttatag tgtagaagta      240
agaattactg cttataatgt ctgggcagta accaaccatt tcagcagctg gcttgctact      300
agcctcagca tgttttattt gctcaggatt gccaatttct ccaaccttat ttttcttcgc      360
ataaagagga gagttaagag tgttgttctg gtgatactgt tggggccttt gctatttttg      420
gtttgtcatc tttttgtgat aaacatggat gagactgtat ggacaaaaga atatgaagga      480
aacgtgactt ggaagatcaa attgaggagt gcaatgtacc attcaaatat gactctaacc      540
atgctagcaa actttgtacc cctcactctg accctgatat cttttctgct gttaatctgt      600
tctctgtgta aacatctcaa gaagatgcag ctccatggca aaggatctca agatcccagc      660
accaaggtcc ataaaaagc tttgcaaact gtgacctcct ttcttctgtt atgtgccatt       720
tactttctgt ccatgatcat atcagttgt aattttggga ggctggaaaa gcaacctgtc       780
ttcatgttct gccaagctat tatattcagc tatccttcaa cccacccatt catcctgatt      840
ttgggaaaca agaagctaaa gcagattttt ctttcagttt tgcggcatgt gaggtactgg      900
gtgaaagaca gaagccttcg tctccataga ttcacaagag gggcattgtg tgtcttctga     960
```

<210> SEQ ID NO 22
<211> LENGTH: 900
<212> TYPE: DNA
<213> ORGANISM: Homo sapiens

<400> SEQUENCE: 22

```
atgatgtgtt ttctgctcat catttcatca attctggtag tgtttgcatt tgttcttgga       60
aatgttgcca atggcttcat agccctagta aatgtcattg actgggttaa cacacgaaag      120
atctcctcag ctgagcaaat tctcactgct ctggtggtct ccagaattgg tttactctgg      180
gtcatgttat tcctttggta tgcaactgtg tttaattctg ctttatatgg tttagaagta      240
agaattgttg cttctaatgc ctgggctgta acgaaccatt tcagcatgtg gcttgctgct      300
agcctcagca tattttgttt gctcaagatt gccaatttct ccaaccttat ttctctccac      360
ctaaagaaga gaattaagag tgttgttctg gtgatactgt tggggccctt ggtatttctg      420
atttgtaatc ttgctgtgat aaccatggat gagagagtgt ggacaaaaga atatgaagga      480
```

| | |
|---|---|
| aatgtgactt ggaagatcaa attgaggaat gcaatacacc tttcaagctt gactgtaact | 540 |
| actctagcaa acctcatacc ctttactctg agcctaatat gttttctgct gttaatctgt | 600 |
| tctctttgta aacatctcaa gaagatgcgg ctccatagca aaggatctca agatcccagc | 660 |
| accaaggtcc atataaaagc tttgcaaact gtgacctcct tcctcatgtt atttgccatt | 720 |
| tactttctgt gtataatcac atcaacttgg aatcttagga cacagcagag caaacttgta | 780 |
| ctcctgcttt gccaaactgt tgcaatcatg tatccttcat tccactcatt catcctgatt | 840 |
| atgggaagta ggaagctaaa acagacctt ctttcagttt tgtggcagat gacacgctga | 900 |

```
<210> SEQ ID NO 23
<211> LENGTH: 930
<212> TYPE: DNA
<213> ORGANISM: Homo sapiens

<400> SEQUENCE: 23
```

| | |
|---|---|
| atgatgagtt ttctacacat tgttttttcc attctagtag tggttgcatt tattcttgga | 60 |
| aattttgcca atggctttat agcactgata aatttcattg cctgggtcaa gagacaaaag | 120 |
| atctcctcag ctgatcaaat tattgctgct ctggcagtct ccagagttgg tttgctctgg | 180 |
| gtaatattat tacattggta ttcaactgtg ttgaatccaa cttcatctaa tttaaaagta | 240 |
| ataatttta tttctaatgc ctgggcagta accaatcatt tcagcatctg gcttgctact | 300 |
| agcctcagca tattttattt gctcaagatc gtcaatttct ccagacttat ttttcatcac | 360 |
| ttaaaaagga aggctaagag tgtagttctg gtgatagtgt tggggtcttt gttcttttg | 420 |
| gtttgtcacc ttgtgatgaa acacacgtat ataaatgtgt ggacagaaga atgtgaagga | 480 |
| aacgtaactt ggaagatcaa actgaggaat gcaatgcacc tttccaactt gactgtagcc | 540 |
| atgctagcaa acttgatacc attcactctg accctgatat cttttctgct gttaatctac | 600 |
| tctctgtgta aacatctgaa gaagatgcag ctccatggca aaggatctca agatcccagc | 660 |
| accaagatcc acataaaagc tctgcaaact gtgacctcct tcctcatatt acttgccatt | 720 |
| tactttctgt gtctaatcat atcgttttgg aatttttaaga tgcgaccaaa agaaattgtc | 780 |
| ttaatgcttt gccaagcttt tggaatcata tatccatcat tccactcatt cattctgatt | 840 |
| tgggggaaca agacgctaaa gcagaccttt cttcagttt tgtggcaggt gacttgctgg | 900 |
| gcaaaaggac agaaccagtc aactccatag | 930 |

```
<210> SEQ ID NO 24
<211> LENGTH: 900
<212> TYPE: DNA
<213> ORGANISM: Homo sapiens

<400> SEQUENCE: 24
```

| | |
|---|---|
| atgataactt ttctatacat ttttttttca attctaataa tggttttatt tgttctcgga | 60 |
| aactttgcca atggcttcat agcactggta aatttcattg actgggtgaa gagaaaaag | 120 |
| atctcctcag ctgaccaaat tctcactgct ctggcggtct ccagaattgg tttgctctgg | 180 |
| gcattattat taaattggta tttaactgtg ttgaatccag cttttttatag tgtagaatta | 240 |
| agaattactt cctataatgc ctgggttgta accaaccatt tcagcatgtg gcttgctgct | 300 |
| aacctcagca tattttattt gctcaagatt gccaatttct ccaaccttct ttttcttcat | 360 |
| ttaaagagga gagttaggag tgtcattctg gtgatactgt tggggacttt gatattttg | 420 |
| gtttgtcatc ttcttgtggc aaacatggat gagagtatgt gggcagaaga atatgaagga | 480 |

| | |
|---|---|
| aacatgactg ggaagatgaa attgaggaat acagtacatc tttcatattt gactgtaact | 540 |
| accctatgga gcttcatacc ctttactctg tccctgatat cttttctgat gctaatctgt | 600 |
| tctctgtgta aacatctcaa gaagatgcag ctccatggag aaggatcgca agatctcagc | 660 |
| accaaggtcc acataaaagc tttgcaaact ctgatctcct tcctcttgtt atgtgccatt | 720 |
| ttctttctat tcctaatcgt ttcggtttgg agtcctagga ggctgcggaa tgacccggtt | 780 |
| gtcatggtta gcaaggctgt tggaaacata tatcttgcat tcgactcatt catcctaatt | 840 |
| tggagaacca agaagctaaa acacaccttt cttttgattt tgtgtcagat taggtgctga | 900 |

```
<210> SEQ ID NO 25
<211> LENGTH: 945
<212> TYPE: DNA
<213> ORGANISM: Homo sapiens

<400> SEQUENCE: 25
```

| | |
|---|---|
| atggccaccg aattggacaa aatctttctg attctggcaa tagcagaatt catcatcagc | 60 |
| atgctgggga atgtgttcat tggactggta aactgctctg aagggatcaa gaaccaaaag | 120 |
| gtcttctcag ctgacttcat cctcacctgc ttggctatct ccacaattgg acaactgttg | 180 |
| gtgatactgt ttgattcatt tctagtggga cttgcttcac atttatatac cacatataga | 240 |
| ctaggaaaaa ctgttattat gctttggcac atgactaatc acttgacaac ctggcttgcc | 300 |
| acctgcctaa gcattttcta tttctttaag atagcccact tcccccactc cttttcctc | 360 |
| tggctgaggt ggaggatgaa cggaatgatt gttatgcttc ttatattgtc tttgttctta | 420 |
| ctgattttg acagtttagt gctagaaata tttattgata tctcactcaa tataatagat | 480 |
| aaaagtaatc tgactttata tttagatgaa agtaaaactc tctttgataa actctctatt | 540 |
| ttaaaaactc ttctcagctt gaccagtttt atccccttt ctctgtccct gacctccttg | 600 |
| ctttttttat ttctgtccctt ggtgagacat actagaaatt tgaagctcag ttccttgggc | 660 |
| tctagagact ccagcacaga ggcccatagg agggccatga aaatggtgat gtcttttcctt | 720 |
| ttcctcttca tagttcattt ttttttcctta caagtggcca attggatatt tttatgttg | 780 |
| tggaacaaca agtacataaa gtttgtcatg ttagccttaa atgcctttcc ctcgtgccac | 840 |
| tcatttattc tcattctggg aaacagcaag ctgcgacaga cagctgtgag gctactgtgg | 900 |
| catcttagga actatacaaa aacaccaaat gctttacctt tgtga | 945 |

```
<210> SEQ ID NO 26
<211> LENGTH: 957
<212> TYPE: DNA
<213> ORGANISM: Homo sapiens

<400> SEQUENCE: 26
```

| | |
|---|---|
| atgaatggag accacatggt tctaggatct tcggtgactg acaagaaggc catcatcttg | 60 |
| gttaccattt tactccttt acgcctggta gcaatagcag gcaatggctt catcactgct | 120 |
| gctctgggcg tggagtgggt gctacggaga atgttgttgc cttgtgataa gttattggtt | 180 |
| agcctagggg cctctcgctt ctgtctgcag tcagtggtaa tgggtaagac catttatgtt | 240 |
| ttcttgcatc cgatggcctt cccatacaac cctgtactgc agtttctagc tttccagtgg | 300 |
| gacttcctga atgctgccac cttatggtcc tctacctggc tcagtgtctt ctattgtgtg | 360 |
| aaaattgcta ccttcacccca ccctgtcttc ttctggctaa agcacaagtt gtctgggtgg | 420 |
| ctaccatgga tgctcttcag ctctgtaggg ctctccagct tcaccaccat tctattttc | 480 |
| ataggcaacc acagaatgta tcagaactat ttaaggaacc atctacaacc ttggaatgtc | 540 |

```
actggcgata gcatacggag ctactgtgag aaattctatc tcttccctct aaaaatgatt      600
acttggacaa tgcccactgc tgtcttttc atttgcatga ttttgctcat cacatctctg       660
ggaagacaca ggaagaaggc tctccttaca acctcaggat tccgagagcc cagtgtgcag      720
gcacacataa aggctctgct ggctctcctc tcttttgcca tgctcttcat ctcatatttc      780
ctgtcactgg tgttcagtgc tgcaggtatt tttccacctc tggactttaa attctgggtg     840
tgggagtcag tgatttatct gtgtgcagca gttcacccca tcattctgct cttcagcaac     900
tgcaggctga gagctgtgct gaagagtcgt cgttcctcaa ggtgtgggac accttga        957
```

<210> SEQ ID NO 27
<211> LENGTH: 1125
<212> TYPE: DNA
<213> ORGANISM: Homo sapiens

<400> SEQUENCE: 27

```
atggcccggt ccctgacttg gggctgctgt ccctggtgcc tgacagagga ggagaagact      60
gccgccagaa tcgaccagga gatcaacagg attttgttgg aacagaaaaa acaagagcgc     120
gaggaattga aactcctgct gttggggcct ggtgagagcg ggaagagtac gttcatcaag     180
cagatgcgca tcattcacgg tgtgggctac tcggaggagg accgcagagc cttccggctg     240
ctcatctacc agaacatctt cgtctccatg caggccatga tagatgcgat ggaccggctg     300
cagatcccct tcagcaggcc tgacagcaag cagcacgcca gcctagtgat gacccaggac     360
ccctataaag tgagcacatt cgagaagcca tatgcagtgg ccatgcagta cctgtggcgg     420
gacgcgggca tccgtgcatg ctacgagcga aggcgtgaat tccaccttct ggactccgcg     480
gtgtattacc tgtcacacct ggagcgcata tcagaggaca gctacatccc cactgcgcaa     540
gacgtgctgc gcagtcgcat gcccaccaca ggcatcaatg agtactgctt ctccgtgaag     600
aaaaccaaac tgcgcatcgt ggatgttggt ggccagaggt cagagcgtag gaaatggatt     660
cactgtttcg agaacgtgat tgccctcatc tacctggcct ccctgagcga gtatgaccag     720
tgcctagagg agaacgatca ggagaaccgc atggaggaga gtctcgctct gttcagcacg     780
atcctagagc tgccctggtt caagagcacc tcggtcatcc tcttcctcaa caagacggac     840
atcctggaag ataagattca cacctcccac ctggccacat acttccccag cttccaggga     900 cccccggcgag acgcagaggc cgccaagagc ttcatcttgg acatgtatgc gcgcgtgtac     960
gcgagctgcg cagagcccca ggacggtggc aggaaaggct cccgcgcgcg ccgcttcttc    1020
gcacacttca cctgtgccac ggacacgcaa agcgtccgca gcgtgttcaa ggacgtgcgg    1080
gactcggtgc tggcccggta cctggacgag atcaacctgc tgtga                   1125
```

<210> SEQ ID NO 28
<211> LENGTH: 299
<212> TYPE: PRT
<213> ORGANISM: Homo sapiens

<400> SEQUENCE: 28

```
Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Val Asn Gly
                20                  25                  30

Ile Asp Leu Ile Lys His Arg Lys Met Ala Pro Leu Asp Leu Leu Leu
            35                  40                  45

Ser Cys Leu Ala Val Ser Arg Ile Phe Leu Gln Leu Phe Ile Phe Tyr
```

```
                50                  55                  60
Val Asn Val Ile Val Ile Phe Phe Ile Glu Phe Ile Met Cys Ser Ala
 65                  70                  75                  80

Asn Cys Ala Ile Leu Leu Phe Ile Asn Glu Leu Glu Leu Trp Leu Ala
                 85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
            115                 120                 125

Met Ile Leu Gly Ser Leu Leu Tyr Val Ser Met Ile Cys Val Phe His
        130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
290                 295
```

<210> SEQ ID NO 29
<211> LENGTH: 316
<212> TYPE: PRT
<213> ORGANISM: Homo sapiens

<400> SEQUENCE: 29

```
Met Met Gly Leu Thr Glu Gly Val Phe Leu Ile Leu Ser Gly Thr Gln
 1               5                  10                  15

Phe Thr Leu Gly Ile Leu Val Asn Cys Phe Ile Glu Leu Val Asn Gly
             20                  25                  30

Ser Ser Trp Phe Lys Thr Lys Arg Met Ser Leu Ser Asp Phe Ile Ile
         35                  40                  45

Thr Thr Leu Ala Leu Leu Arg Ile Ile Leu Leu Cys Ile Ile Leu Thr
     50                  55                  60

Asp Ser Phe Leu Ile Glu Phe Ser Pro Asn Thr His Asp Ser Gly Ile
 65                  70                  75                  80

Ile Met Gln Ile Ile Asp Val Ser Trp Thr Phe Thr Asn His Leu Ser
                 85                  90                  95

Ile Trp Leu Ala Thr Cys Leu Gly Val Leu Tyr Cys Leu Lys Ile Ala
            100                 105                 110

Ser Phe His Pro Thr Phe Leu Trp Leu Lys Trp Arg Val Ser Arg
            115                 120                 125
```

```
Val Met Val Trp Met Leu Leu Gly Ala Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
                245                 250                 255

Asn Phe Leu Pro Lys Thr Lys Met Ala Lys Met Ile Gly Glu Val Met
                260                 265                 270

Thr Met Phe Tyr Pro Ala Gly His Ser Phe Ile Leu Ile Leu Gly Asn
            275                 280                 285

Ser Lys Leu Lys Gln Thr Phe Val Val Met Leu Arg Cys Glu Ser Gly
        290                 295                 300

His Leu Lys Pro Gly Ser Lys Gly Pro Ile Phe Ser
305                 310                 315

<210> SEQ ID NO 30
<211> LENGTH: 299
<212> TYPE: PRT
<213> ORGANISM: Homo sapiens

<400> SEQUENCE: 30

Met Leu Arg Leu Phe Tyr Phe Ser Ala Ile Ala Ser Val Ile Leu
1               5                   10                  15

Asn Phe Val Gly Ile Ile Met Asn Leu Phe Ile Thr Val Val Asn Cys
                20                  25                  30

Lys Thr Trp Val Lys Ser His Arg Ile Ser Ser Ser Asp Arg Ile Leu
            35                  40                  45

Phe Ser Leu Gly Ile Thr Arg Phe Leu Met Leu Gly Leu Phe Leu Val
        50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
                100                 105                 110

Phe Gln His Ser Val Phe Leu Leu Leu Lys Arg Asn Ile Ser Pro Lys
            115                 120                 125

Ile Pro Arg Leu Leu Leu Ala Cys Val Leu Ile Ser Ala Phe Thr Thr
130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190
```

```
Val Thr Ser Ala Ser Leu Leu Ile His Ser Leu Arg Arg His Ile Gln
            195                 200                 205

Lys Met Gln Lys Asn Ala Thr Gly Phe Trp Asn Pro Gln Thr Glu Ala
    210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
            245                 250                 255

Met Asp Met Gly Thr Lys Ser Ile Cys Leu Ile Phe Ala Thr Leu Tyr
            260                 265                 270

Ser Pro Gly His Ser Val Leu Ile Ile Ile Thr His Pro Lys Leu Lys
            275                 280                 285

Thr Thr Ala Lys Lys Ile Leu Cys Phe Lys Lys
            290                 295
```

<210> SEQ ID NO 31
<211> LENGTH: 299
<212> TYPE: PRT
<213> ORGANISM: Homo sapiens

<400> SEQUENCE: 31

```
Met Leu Ser Ala Gly Leu Gly Leu Leu Met Leu Val Ala Val Val Glu
1               5                   10                  15

Phe Leu Ile Gly Leu Ile Gly Asn Gly Ser Leu Val Val Trp Ser Phe
                20                  25                  30

Arg Glu Trp Ile Arg Lys Phe Asn Trp Ser Ser Tyr Asn Leu Ile Ile
            35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Val Ser Gln Ala Ser Leu Trp Phe Ala
                85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
    115                 120                 125

Cys Leu Leu Gly Tyr Phe Ile Ile Asn Leu Leu Leu Thr Val Gln Ile
130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
    195                 200                 205

Arg Arg Asp Val Arg Ala Lys Ala His Ile Thr Ala Leu Lys Ser Leu
210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
```

```
                         260                 265                 270
Ile Met Gly Ile Pro Arg Val Lys Gln Thr Cys Gln Lys Ile Leu Trp
                275                 280                 285
Lys Thr Val Cys Ala Arg Arg Cys Trp Gly Pro
            290                 295

<210> SEQ ID NO 32
<211> LENGTH: 318
<212> TYPE: PRT
<213> ORGANISM: Homo sapiens

<400> SEQUENCE: 32

Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Arg Lys Ile Ala Ser Ile Asp Leu Ile Leu
            35                  40                  45

Thr Ser Leu Ala Ile Ser Arg Ile Cys Leu Leu Cys Val Ile Leu Leu
50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
            115                 120                 125

Val Ile Ser Trp Ile Leu Leu Gly Cys Val Val Leu Ser Val Phe Ile
130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
            195                 200                 205

Arg Arg His Ile Arg Arg Met Gln Leu Ser Ala Thr Gly Cys Arg Asp
210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
            275                 280                 285

Asn Asn Lys Leu Arg His Ala Ser Leu Lys Val Ile Trp Lys Val Met
            290                 295                 300

Ser Ile Leu Lys Gly Arg Lys Phe Gln Gln His Lys Gln Ile
305                 310                 315

<210> SEQ ID NO 33
<211> LENGTH: 309
```

<212> TYPE: PRT
<213> ORGANISM: Homo sapiens

<400> SEQUENCE: 33

```
Met Phe Ser Pro Ala Asp Asn Ile Phe Ile Ile Leu Ile Thr Gly Glu
1               5                   10                  15

Phe Ile Leu Gly Ile Leu Gly Asn Gly Tyr Ile Ala Leu Val Asn Trp
                20                  25                  30

Ile Asp Trp Ile Lys Lys Lys Ile Ser Thr Val Asp Tyr Ile Leu
            35                  40                  45

Thr Asn Leu Val Ile Ala Arg Ile Cys Leu Ile Ser Val Met Val Val
        50                  55                  60

Asn Gly Ile Val Ile Val Leu Asn Pro Asp Val Tyr Thr Lys Asn Lys
65                  70                  75                  80

Gln Gln Ile Val Ile Phe Thr Phe Trp Thr Phe Ala Asn Tyr Leu Asn
                85                  90                  95

Met Trp Ile Thr Thr Cys Leu Asn Val Phe Tyr Phe Leu Lys Ile Ala
                100                 105                 110

Ser Ser Ser His Pro Leu Phe Leu Trp Leu Lys Trp Lys Ile Asp Met
            115                 120                 125

Val Val His Trp Ile Leu Leu Gly Cys Phe Ala Ile Ser Leu Leu Val
130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
            195                 200                 205

Trp Arg His Thr Lys Gln Ile Lys Leu Tyr Ala Thr Gly Ser Arg Asp
        210                 215                 220

Pro Ser Thr Glu Val His Val Arg Ala Ile Lys Thr Met Thr Ser Phe
225                 230                 235                 240

Ile Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
            260                 265                 270

Ala Ala Ile Leu Tyr Pro Leu Gly His Ser Leu Ile Leu Ile Val Leu
            275                 280                 285

Asn Asn Lys Leu Arg Gln Thr Phe Val Arg Met Leu Thr Cys Arg Lys
290                 295                 300

Ile Ala Cys Met Ile
305
```

<210> SEQ ID NO 34
<211> LENGTH: 312
<212> TYPE: PRT
<213> ORGANISM: Homo sapiens

<400> SEQUENCE: 34

```
Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
                20                  25                  30
```

```
Ile Asp Trp Leu Lys Arg Arg Asp Ile Ser Leu Ile Asp Ile Ile Leu
            35                  40                  45

Ile Ser Leu Ala Ile Ser Arg Ile Cys Leu Leu Cys Val Ile Ser Leu
 50                  55                  60

Asp Gly Phe Phe Met Leu Leu Phe Pro Gly Thr Tyr Gly Asn Ser Val
 65                  70                  75                  80

Leu Val Ser Ile Val Asn Val Val Trp Thr Phe Ala Asn Asn Ser Ser
                 85                  90                  95

Leu Trp Phe Thr Ser Cys Leu Ser Ile Phe Tyr Leu Leu Lys Ile Ala
               100                 105                 110

Asn Ile Ser His Pro Phe Phe Phe Trp Leu Lys Leu Lys Ile Asn Lys
               115                 120                 125

Val Met Leu Ala Ile Leu Leu Gly Ser Phe Leu Ile Ser Leu Ile Ile
 130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
               165                 170                 175

Thr Phe Lys Gln Leu Thr Leu Asn Leu Gly Val Met Val Pro Phe Ile
               180                 185                 190

Leu Cys Leu Ile Ser Phe Phe Leu Leu Phe Ser Leu Val Arg His
               195                 200                 205

Thr Lys Gln Ile Arg Leu His Ala Thr Gly Phe Arg Asp Pro Ser Thr
               210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
               245                 250                 255

Ile Pro Gln Gly Lys Leu Val Leu Met Ile Gly Asp Ile Val Thr Val
               260                 265                 270

Ile Phe Pro Ser Ser His Ser Phe Ile Leu Ile Met Gly Asn Ser Lys
               275                 280                 285

Leu Arg Glu Ala Phe Leu Lys Met Leu Arg Phe Val Lys Cys Phe Leu
290                 295                 300

Arg Arg Arg Lys Pro Phe Val Pro
305                 310

<210> SEQ ID NO 35
<211> LENGTH: 300
<212> TYPE: PRT
<213> ORGANISM: Homo sapiens

<400> SEQUENCE: 35

Met Leu Arg Val Val Glu Gly Ile Phe Ile Phe Val Val Ser Glu
  1                   5                  10                  15

Ser Val Phe Gly Val Leu Gly Asn Gly Phe Ile Gly Leu Val Asn Cys
                 20                  25                  30

Ile Asp Cys Ala Lys Asn Lys Leu Ser Thr Ile Gly Phe Ile Leu Thr
                 35                  40                  45

Gly Leu Ala Ile Ser Arg Ile Phe Leu Ile Trp Ile Ile Thr Asp
 50                  55                  60

Gly Phe Ile Gln Ile Phe Ser Pro Asn Ile Tyr Ala Ser Gly Asn Leu
 65                  70                  75                  80

Ile Glu Tyr Ile Ser Tyr Phe Trp Val Ile Gly Asn Gln Ser Ser Met
                 85                  90                  95
```

```
Trp Phe Ala Thr Ser Leu Ser Ile Phe Tyr Phe Leu Lys Ile Ala Asn
                100                 105                 110

Phe Ser Asn Tyr Ile Phe Leu Trp Leu Lys Ser Arg Thr Asn Met Val
            115                 120                 125

Leu Pro Phe Met Ile Val Phe Leu Leu Ile Ser Ser Leu Leu Asn Phe
        130                 135                 140

Ala Tyr Ile Ala Lys Ile Leu Asn Asp Tyr Lys Met Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Thr Leu Ser Leu Ile Thr
            180                 185                 190

Cys Ile Phe Leu Ile Ile Ser Leu Trp Arg His Asn Arg Gln Met Gln
195                 200                 205

Ser Asn Val Thr Gly Leu Arg Asp Ser Asn Thr Glu Ala His Val Lys
    210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
                260                 265                 270

His Ser Phe Ile Leu Ile Leu Gly Asn Ser Lys Leu Lys Gln Ala Ser
            275                 280                 285

Leu Arg Val Leu Gln Gln Leu Lys Cys Cys Glu Lys
        290                 295                 300

<210> SEQ ID NO 36
<211> LENGTH: 300
<212> TYPE: PRT
<213> ORGANISM: Homo sapiens

<400> SEQUENCE: 36

Met Glu Ser Ala Leu Pro Ser Ile Phe Thr Leu Val Ile Ile Ala Glu
1               5                   10                  15

Phe Ile Ile Gly Asn Leu Ser Asn Gly Phe Ile Val Leu Ile Asn Cys
                20                  25                  30

Ile Asp Trp Val Ser Lys Arg Glu Leu Ser Ser Val Asp Lys Leu Leu
            35                  40                  45

Ile Ile Leu Ala Ile Ser Arg Ile Gly Leu Ile Trp Glu Ile Leu Val
    50                  55                  60

Ser Trp Phe Leu Ala Leu His Tyr Leu Ala Ile Phe Val Ser Gly Thr
65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
                100                 105                 110

Ser Phe Ser Ser Pro Ala Phe Leu Tyr Leu Lys Trp Arg Val Asn Lys
            115                 120                 125

Val Ile Leu Met Ile Leu Leu Gly Thr Leu Val Phe Leu Phe Leu Asn
        130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
```

```
            165                 170                 175
Val Ser Val Lys Phe Thr Met Thr Met Phe Ser Leu Thr Pro Phe Thr
            180                 185                 190

Val Ala Phe Ile Ser Phe Leu Leu Ile Phe Ser Leu Gln Lys His
        195                 200                 205

Leu Gln Lys Met Gln Leu Asn Tyr Lys Gly His Arg Asp Pro Arg Thr
    210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Asn Thr Val Ile Tyr Met Leu Cys Glu Thr Ile Gly Val Phe
            260                 265                 270

Ser Pro Ser Ser His Ser Phe Leu Leu Ile Leu Gly Asn Ala Lys Leu
        275                 280                 285

Arg Gln Ala Phe Leu Leu Val Ala Ala Lys Val Trp
    290                 295                 300

<210> SEQ ID NO 37
<211> LENGTH: 317
<212> TYPE: PRT
<213> ORGANISM: Homo sapiens

<400> SEQUENCE: 37

Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
                20                  25                  30

Ile Asp Trp Val Lys Gly Arg Lys Ile Ser Ser Val Asp Arg Ile Leu
            35                  40                  45

Thr Ala Leu Ala Ile Ser Arg Ile Ser Leu Val Trp Leu Ile Phe Gly
        50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
                100                 105                 110

Asn Phe Ser Asn Ser Ile Phe Leu Tyr Leu Lys Trp Arg Val Lys Lys
            115                 120                 125

Val Val Leu Val Leu Leu Val Thr Ser Val Phe Leu Phe Leu Asn
        130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Val Phe Ile Phe Ile Pro Phe Thr
            180                 185                 190

Leu Ser Leu Ala Met Phe Leu Leu Ile Phe Ser Met Trp Lys His
        195                 200                 205

Arg Lys Lys Met Gln His Thr Val Lys Ile Ser Gly Asp Ala Ser Thr
    210                 215                 220

Lys Ala His Arg Gly Val Lys Ser Val Ile Thr Phe Phe Leu Leu Tyr
225                 230                 235                 240
```

```
Ala Ile Phe Ser Leu Ser Phe Ile Ser Val Trp Thr Ser Glu Arg
            245                 250                 255

Leu Glu Glu Asn Leu Ile Ile Leu Ser Gln Val Met Gly Met Ala Tyr
        260                 265                 270

Pro Ser Cys His Ser Cys Val Leu Ile Leu Gly Asn Lys Lys Leu Arg
            275                 280                 285

Gln Ala Ser Leu Ser Val Leu Leu Trp Leu Arg Tyr Met Phe Lys Asp
    290                 295                 300

Gly Glu Pro Ser Gly His Lys Glu Phe Arg Glu Ser Ser
305                 310                 315

<210> SEQ ID NO 38
<211> LENGTH: 291
<212> TYPE: PRT
<213> ORGANISM: Homo sapiens

<400> SEQUENCE: 38

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Ile Leu Phe Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290
```

```
<210> SEQ ID NO 39
<211> LENGTH: 333
<212> TYPE: PRT
<213> ORGANISM: Homo sapiens

<400> SEQUENCE: 39

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Ala Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 40
<211> LENGTH: 338
<212> TYPE: PRT
<213> ORGANISM: Homo sapiens

<400> SEQUENCE: 40
```

```
Met Leu Gly Arg Cys Phe Pro Pro Asp Thr Lys Glu Lys Gln Gln Leu
1               5                   10                  15

Arg Met Thr Lys Leu Cys Asp Pro Ala Glu Ser Glu Leu Ser Pro Phe
            20                  25                  30

Leu Ile Thr Leu Ile Leu Ala Val Leu Leu Ala Glu Tyr Leu Ile Gly
        35                  40                  45

Ile Ile Ala Asn Gly Phe Ile Met Ala Ile His Ala Ala Glu Trp Val
50                      55                  60

Gln Asn Lys Ala Val Ser Thr Ser Gly Arg Ile Leu Val Phe Leu Ser
65                      70                  75                  80

Val Ser Arg Ile Ala Leu Gln Ser Leu Met Met Leu Glu Ile Thr Ile
                85                  90                  95

Ser Ser Thr Ser Leu Ser Phe Tyr Ser Glu Asp Ala Val Tyr Tyr Ala
            100                 105                 110

Phe Lys Ile Ser Phe Ile Phe Leu Asn Phe Cys Ser Leu Trp Phe Ala
        115                 120                 125

Ala Trp Leu Ser Phe Phe Tyr Phe Val Lys Ile Ala Asn Phe Ser Tyr
130                     135                 140

Pro Leu Phe Leu Lys Leu Arg Trp Arg Ile Thr Gly Leu Ile Pro Trp
145                 150                 155                 160

Leu Leu Trp Leu Ser Val Phe Ile Ser Phe Ser His Ser Met Phe Cys
                165                 170                 175

Ile Asn Ile Cys Thr Val Tyr Cys Asn Asn Ser Phe Pro Ile His Ser
            180                 185                 190

Ser Asn Ser Thr Lys Lys Thr Tyr Leu Ser Glu Ile Asn Val Val Gly
        195                 200                 205

Leu Ala Phe Phe Phe Asn Leu Gly Ile Val Thr Pro Leu Ile Met Phe
210                 215                 220

Ile Leu Thr Ala Thr Leu Leu Ile Leu Ser Leu Lys Arg His Thr Leu
225                 230                 235                 240

His Met Gly Ser Asn Ala Thr Gly Ser Asn Asp Pro Ser Met Glu Ala
                245                 250                 255

His Met Gly Ala Ile Lys Ala Ile Ser Tyr Phe Leu Ile Leu Tyr Ile
            260                 265                 270

Phe Asn Ala Val Ala Leu Phe Ile Tyr Leu Ser Asn Met Phe Asp Ile
        275                 280                 285

Asn Ser Leu Trp Asn Asn Leu Cys Gln Ile Ile Met Ala Ala Tyr Pro
290                 295                 300

Ala Ser His Ser Ile Leu Leu Ile Gln Asp Asn Pro Gly Leu Arg Arg
305                 310                 315                 320

Ala Trp Lys Arg Leu Gln Leu Arg Leu His Leu Tyr Pro Lys Glu Trp
                325                 330                 335

Thr Leu

<210> SEQ ID NO 41
<211> LENGTH: 323
<212> TYPE: PRT
<213> ORGANISM: Homo sapiens

<400> SEQUENCE: 41

Met Ala Thr Val Asn Thr Asp Ala Thr Asp Lys Asp Ile Ser Lys Phe
1               5                   10                  15

Lys Val Thr Phe Thr Leu Val Val Ser Gly Ile Glu Cys Ile Thr Gly
            20                  25                  30
```

```
Ile Leu Gly Ser Gly Phe Ile Thr Ala Ile Tyr Gly Ala Glu Trp Ala
            35                  40                  45

Arg Gly Lys Thr Leu Pro Thr Gly Asp Arg Ile Met Leu Met Leu Ser
 50                  55                  60

Phe Ser Arg Leu Leu Leu Gln Ile Trp Met Met Leu Glu Asn Ile Phe
 65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
               100                 105                 110

Ala Trp Leu Lys Val Phe Tyr Cys Leu Arg Ile Ala Asn Phe Asn His
               115                 120                 125

Pro Leu Phe Phe Leu Met Lys Arg Lys Ile Ile Val Leu Met Pro Trp
           130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
               180                 185                 190

Asn Leu Val Phe Phe Tyr Asn Met Gly Ile Phe Val Pro Leu Ile Met
               195                 200                 205

Phe Ile Leu Ala Ala Thr Leu Leu Ile Leu Ser Leu Lys Arg His Thr
           210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
               260                 265                 270

Thr Tyr Ser Ser Trp Asn Ile Leu Cys Lys Ile Ile Met Ala Ala Tyr
           275                 280                 285

Pro Ala Gly His Ser Val Gln Leu Ile Leu Gly Asn Pro Gly Leu Arg
           290                 295                 300

Arg Ala Trp Lys Arg Phe Gln His Gln Val Pro Leu Tyr Leu Lys Gly
305                 310                 315                 320

Gln Thr Leu

<210> SEQ ID NO 42
<211> LENGTH: 307
<212> TYPE: PRT
<213> ORGANISM: Homo sapiens

<400> SEQUENCE: 42

Met Gln Ala Ala Leu Thr Ala Phe Phe Val Leu Leu Phe Ser Leu Leu
  1               5                  10                  15

Ser Leu Leu Gly Ile Ala Ala Asn Gly Phe Ile Val Leu Val Leu Gly
                 20                  25                  30

Arg Glu Trp Leu Arg Tyr Gly Arg Leu Leu Pro Leu Asp Met Ile Leu
             35                  40                  45

Ile Ser Leu Gly Ala Ser Arg Phe Cys Leu Gln Leu Val Gly Thr Val
         50                  55                  60

His Asn Phe Tyr Tyr Ser Ala Gln Lys Val Glu Tyr Ser Gly Gly Leu
 65                  70                  75                  80
```

```
Gly Arg Gln Phe Phe His Leu His Trp His Phe Leu Asn Ser Ala Thr
                85                  90                  95

Phe Trp Phe Cys Ser Trp Leu Ser Val Leu Phe Cys Val Lys Ile Ala
            100                 105                 110

Asn Ile Thr His Ser Thr Phe Leu Trp Leu Lys Trp Arg Phe Leu Gly
        115                 120                 125

Trp Val Pro Trp Leu Leu Leu Gly Ser Val Leu Ile Ser Phe Ile Ile
130                 135                 140

Thr Leu Leu Phe Phe Trp Val Asn Tyr Pro Val Tyr Gln Glu Phe Leu
145                 150                 155                 160

Ile Arg Lys Phe Ser Gly Asn Met Thr Tyr Lys Trp Asn Thr Arg Ile
                165                 170                 175

Glu Thr Tyr Tyr Phe Pro Ser Leu Lys Leu Val Ile Trp Ser Ile Pro
            180                 185                 190

Phe Ser Val Phe Leu Val Ser Ile Met Leu Leu Ile Asn Ser Leu Arg
        195                 200                 205

Arg His Thr Gln Arg Met Gln His Asn Gly His Ser Leu Gln Asp Pro
    210                 215                 220

Ser Thr Gln Ala His Thr Arg Ala Leu Lys Ser Leu Ile Ser Phe Leu
225                 230                 235                 240

Ile Leu Tyr Ala Leu Ser Phe Leu Ser Leu Ile Ile Asp Ala Ala Lys
                245                 250                 255

Phe Ile Ser Met Gln Asn Asp Phe Tyr Trp Pro Trp Gln Ile Ala Val
            260                 265                 270

Tyr Leu Cys Ile Ser Val His Pro Phe Ile Leu Ile Phe Ser Asn Leu
        275                 280                 285

Lys Leu Arg Ser Val Phe Ser Gln Leu Leu Leu Ala Arg Gly Phe
    290                 295                 300

Trp Val Ala
305

<210> SEQ ID NO 43
<211> LENGTH: 309
<212> TYPE: PRT
<213> ORGANISM: Homo sapiens

<400> SEQUENCE: 43

Met Ile Thr Phe Leu Pro Ile Ile Phe Ser Ser Leu Val Val Val Thr
1               5                   10                  15

Phe Val Ile Gly Asn Phe Ala Asn Gly Phe Ile Ala Leu Val Asn Ser
            20                  25                  30

Ile Glu Ser Phe Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Arg Val Lys Ser Val
        115                 120                 125

Ile Leu Val Met Leu Leu Gly Pro Leu Leu Phe Leu Ala Cys His Leu
```

```
            130                 135                 140
Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu Arg Gly Lys Gly Ser Gln Asp Pro Ser Thr Lys Val His
    210                 215                 220

Ile Lys Ala Leu Gln Thr Val Ile Ser Phe Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Met Arg Tyr Trp Val Lys Gly Glu
    290                 295                 300

Lys Thr Ser Ser Pro
305

<210> SEQ ID NO 44
<211> LENGTH: 300
<212> TYPE: PRT
<213> ORGANISM: Homo sapiens

<400> SEQUENCE: 44

Met Thr Thr Phe Ile Pro Ile Ile Phe Ser Ser Val Val Val Val Leu
1               5                   10                  15

Phe Val Ile Gly Asn Phe Ala Asn Gly Phe Ile Ala Leu Val Asn Ser
                20                  25                  30

Ile Glu Arg Val Lys Arg Gln Lys Ile Ser Phe Ala Asp Gln Ile Leu
            35                  40                  45

Thr Ala Leu Ala Val Ser Arg Val Gly Leu Leu Trp Val Leu Leu Leu
        50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Tyr Glu Gly
145                 150                 155                 160

Asn Met Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
            180                 185                 190
```

```
Leu Cys Phe Leu Leu Leu Ile Cys Ser Leu Cys Lys His Leu Lys Lys
            195                 200                 205

Met Gln Leu His Gly Lys Gly Ser Gln Asp Pro Ser Thr Lys Val His
        210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Leu Arg Gln Val Arg Tyr Trp
        290                 295                 300

<210> SEQ ID NO 45
<211> LENGTH: 299
<212> TYPE: PRT
<213> ORGANISM: Homo sapiens

<400> SEQUENCE: 45

Met Ile Thr Phe Leu Pro Ile Ile Phe Ser Ile Leu Val Val Val Thr
1               5                   10                  15

Phe Val Ile Gly Asn Phe Ala Asn Gly Phe Ile Ala Leu Val Asn Ser
                20                  25                  30

Thr Glu Trp Val Lys Arg Gln Lys Ile Ser Phe Ala Asp Gln Ile Val
            35                  40                  45

Thr Ala Leu Ala Val Ser Arg Val Gly Leu Leu Trp Val Leu Leu Leu
50                  55                  60

Asn Trp Tyr Ser Thr Val Leu Asn Pro Ala Phe Cys Ser Val Glu Leu
65                  70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
            100                 105                 110

Phe Ser Asn Leu Ile Phe Leu Arg Leu Lys Arg Arg Val Lys Ser Val
        115                 120                 125

Ile Leu Val Val Leu Leu Gly Pro Leu Leu Phe Leu Ala Cys His Leu
130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205

Met Gln Leu His Gly Lys Gly Ser Gln Asp Pro Ser Thr Lys Val His
        210                 215                 220

Ile Lys Val Leu Gln Thr Val Ile Ser Phe Phe Leu Leu Arg Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270
```

```
Ser Ala His Pro Phe Ile Leu Ile Trp Gly Asn Lys Lys Leu Lys Gln
        275                 280                 285

Thr Tyr Leu Ser Val Leu Trp Gln Met Arg Tyr
        290                 295
```

<210> SEQ ID NO 46
<211> LENGTH: 309
<212> TYPE: PRT
<213> ORGANISM: Homo sapiens

<400> SEQUENCE: 46

```
Met Ile Thr Phe Leu Pro Ile Ile Phe Ser Ile Leu Ile Val Val Thr
1               5                   10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Val Leu
    50                  55                  60

Asn Trp Tyr Ala Thr Glu Leu Asn Pro Ala Phe Asn Ser Ile Glu Val
65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Met Lys Val His
    210                 215                 220

Ile Lys Ala Leu Gln Thr Val Thr Ser Phe Leu Leu Leu Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305
```

<210> SEQ ID NO 47
<211> LENGTH: 319
<212> TYPE: PRT

<213> ORGANISM: Homo sapiens

<400> SEQUENCE: 47

Met Ile Thr Phe Leu Pro Ile Ile Phe Ser Ile Leu Ile Val Val Ile
1               5                   10                  15

Phe Val Ile Gly Asn Phe Ala Asn Gly Phe Ile Ala Leu Val Asn Ser
            20                  25                  30

Ile Glu Trp Val Lys Arg Gln Lys Ile Ser Phe Val Asp Gln Ile Leu
        35                  40                  45

Thr Ala Leu Ala Val Ser Arg Val Gly Leu Leu Trp Val Leu Leu Leu
    50                  55                  60

His Trp Tyr Ala Thr Gln Leu Asn Pro Ala Phe Tyr Ser Val Glu Val
65                  70                  75                  80

Arg Ile Thr Ala Tyr Asn Val Trp Ala Val Thr Asn His Phe Ser Ser
                85                  90                  95

Trp Leu Ala Thr Ser Leu Ser Met Phe Tyr Leu Leu Arg Ile Ala Asn
            100                 105                 110

Phe Ser Asn Leu Ile Phe Leu Arg Ile Lys Arg Arg Val Lys Ser Val
        115                 120                 125

Val Leu Val Ile Leu Leu Gly Pro Leu Leu Phe Leu Val Cys His Leu
130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
290                 295                 300

Ser Leu Arg Leu His Arg Phe Thr Arg Ala Ala Leu Cys Lys Gly
305                 310                 315

<210> SEQ ID NO 48
<211> LENGTH: 299
<212> TYPE: PRT
<213> ORGANISM: Homo sapiens

<400> SEQUENCE: 48

Met Met Cys Phe Leu Leu Ile Ile Ser Ser Ile Leu Val Val Phe Ala
1               5                   10                  15

Phe Val Leu Gly Asn Val Ala Asn Gly Phe Ile Ala Leu Val Asn Val
            20                  25                  30

Ile Asp Trp Val Asn Thr Arg Lys Ile Ser Ser Ala Glu Gln Ile Leu

```
            35                  40                  45
Thr Ala Leu Val Val Ser Arg Ile Gly Leu Leu Trp Val Met Leu Phe
 50                  55                  60

Leu Trp Tyr Ala Thr Val Phe Asn Ser Ala Leu Tyr Gly Leu Glu Val
 65                  70                  75                  80

Arg Ile Val Ala Ser Asn Ala Trp Ala Val Thr Asn His Phe Ser Met
                 85                  90                  95

Trp Leu Ala Ala Ser Leu Ser Ile Phe Cys Leu Leu Lys Ile Ala Asn
                100                 105                 110

Phe Ser Asn Leu Ile Ser Leu His Leu Lys Lys Arg Ile Lys Ser Val
            115                 120                 125

Val Leu Val Ile Leu Leu Gly Pro Leu Val Phe Leu Ile Cys Asn Leu
        130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr Arg
    290                 295

<210> SEQ ID NO 49
<211> LENGTH: 309
<212> TYPE: PRT
<213> ORGANISM: Homo sapiens

<400> SEQUENCE: 49

Met Met Ser Phe Leu His Ile Val Phe Ser Ile Leu Val Val Val Ala
 1               5                  10                  15

Phe Ile Leu Gly Asn Phe Ala Asn Gly Phe Ile Ala Leu Ile Asn Phe
                20                  25                  30

Ile Ala Trp Val Lys Arg Gln Lys Ile Ser Ser Ala Asp Gln Ile Ile
            35                  40                  45

Ala Ala Leu Ala Val Ser Arg Val Gly Leu Leu Trp Val Ile Leu Leu
 50                  55                  60

His Trp Tyr Ser Thr Val Leu Asn Pro Thr Ser Ser Asn Leu Lys Val
 65                  70                  75                  80

Ile Ile Phe Ile Ser Asn Ala Trp Ala Val Thr Asn His Phe Ser Ile
                 85                  90                  95

Trp Leu Ala Thr Ser Leu Ser Ile Phe Tyr Leu Leu Lys Ile Val Asn
                100                 105                 110
```

-continued

Phe Ser Arg Leu Ile Phe His His Leu Lys Arg Lys Ala Lys Ser Val
        115                 120                 125

Val Leu Val Ile Val Leu Gly Ser Leu Phe Phe Leu Val Cys His Leu
    130                 135                 140

Val Met Lys His Thr Tyr Ile Asn Val Trp Thr Glu Glu Cys Glu Gly
145                 150                 155                 160

Asn Val Thr Trp Lys Ile Lys Leu Arg Asn Ala Met His Leu Ser Asn
                165                 170                 175

Leu Thr Val Ala Met Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Ile His
    210                 215                 220

Ile Lys Ala Leu Gln Thr Val Thr Ser Phe Leu Ile Leu Leu Ala Ile
225                 230                 235                 240

Tyr Phe Leu Cys Leu Ile Ile Ser Phe Trp Asn Phe Lys Met Arg Pro
                245                 250                 255

Lys Glu Ile Val Leu Met Leu Cys Gln Ala Phe Gly Ile Ile Tyr Pro
            260                 265                 270

Ser Phe His Ser Phe Ile Leu Ile Trp Gly Asn Lys Thr Leu Lys Gln
        275                 280                 285

Thr Phe Leu Ser Val Leu Trp Gln Val Thr Cys Trp Ala Lys Gly Gln
    290                 295                 300

Asn Gln Ser Thr Pro
305

<210> SEQ ID NO 50
<211> LENGTH: 299
<212> TYPE: PRT
<213> ORGANISM: Homo sapiens

<400> SEQUENCE: 50

Met Ile Thr Phe Leu Tyr Ile Phe Phe Ser Ile Leu Ile Met Val Leu
1               5                   10                  15

Phe Val Leu Gly Asn Phe Ala Asn Gly Phe Ile Ala Leu Val Asn Phe
            20                  25                  30

Ile Asp Trp Val Lys Arg Lys Lys Ile Ser Ser Ala Asp Gln Ile Leu
        35                  40                  45

Thr Ala Leu Ala Val Ser Arg Ile Gly Leu Leu Trp Ala Leu Leu Leu
    50                  55                  60

Asn Trp Tyr Leu Thr Val Leu Asn Pro Ala Phe Tyr Ser Val Glu Leu
65                  70                  75                  80

Arg Ile Thr Ser Tyr Asn Ala Trp Val Val Thr Asn His Phe Ser Met
                85                  90                  95

Trp Leu Ala Ala Asn Leu Ser Ile Phe Tyr Leu Leu Lys Ile Ala Asn
            100                 105                 110

Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
    130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

```
Leu Thr Val Thr Thr Leu Trp Ser Phe Ile Pro Phe Thr Leu Ser Leu
            180                 185                 190

Ile Ser Phe Leu Met Leu Ile Cys Ser Leu Tyr Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
                260                 265                 270

Ala Phe Asp Ser Phe Ile Leu Ile Trp Arg Thr Lys Lys Leu Lys His
                275                 280                 285

Thr Phe Leu Leu Ile Leu Cys Gln Ile Arg Cys
    290                 295
```

<210> SEQ ID NO 51
<211> LENGTH: 314
<212> TYPE: PRT
<213> ORGANISM: Homo sapiens

<400> SEQUENCE: 51

```
Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
        35                  40                  45

Thr Cys Leu Ala Ile Ser Thr Ile Gly Gln Leu Leu Val Ile Leu Phe
50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175

Lys Leu Ser Ile Leu Lys Thr Leu Leu Ser Leu Thr Ser Phe Ile Pro
            180                 185                 190

Phe Ser Leu Phe Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
    210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Gly Ile
```

```
                    245                 250                 255
Phe Phe Met Leu Trp Asn Asn Lys Tyr Ile Lys Phe Val Met Leu Ala
                260                 265                 270

Leu Asn Ala Phe Pro Ser Cys His Ser Phe Ile Leu Ile Leu Gly Asn
            275                 280                 285

Ser Lys Leu Arg Gln Thr Ala Val Arg Leu Leu Trp His Leu Arg Asn
290                 295                 300

Tyr Thr Lys Thr Pro Asn Ala Leu Pro Leu
305                 310

<210> SEQ ID NO 52
<211> LENGTH: 318
<212> TYPE: PRT
<213> ORGANISM: Homo sapiens

<400> SEQUENCE: 52

Met Asn Gly Asp His Met Val Leu Gly Ser Val Thr Asp Lys Lys
1               5                   10                  15

Ala Ile Ile Leu Val Thr Ile Leu Leu Leu Arg Leu Val Ala Ile
                20                  25                  30

Ala Gly Asn Gly Phe Ile Thr Ala Ala Leu Gly Val Glu Trp Val Leu
            35                  40                  45

Arg Arg Met Leu Leu Pro Cys Asp Lys Leu Leu Val Ser Leu Gly Ala
50                  55                  60

Ser Arg Phe Cys Leu Gln Ser Val Val Met Gly Lys Thr Ile Tyr Val
65                  70                  75                  80

Phe Leu His Pro Met Ala Phe Pro Tyr Asn Pro Val Leu Gln Phe Leu
                85                  90                  95

Ala Phe Gln Trp Asp Phe Leu Asn Ala Ala Thr Leu Trp Ser Ser Thr
            100                 105                 110

Trp Leu Ser Val Phe Tyr Cys Val Lys Ile Ala Thr Phe Thr His Pro
        115                 120                 125

Val Phe Phe Trp Leu Lys His Lys Leu Ser Gly Trp Leu Pro Trp Met
130                 135                 140

Leu Phe Ser Ser Val Gly Leu Ser Ser Phe Thr Thr Ile Leu Phe Phe
145                 150                 155                 160

Ile Gly Asn His Arg Met Tyr Gln Asn Tyr Leu Arg Asn His Leu Gln
                165                 170                 175

Pro Trp Asn Val Thr Gly Asp Ser Ile Arg Ser Tyr Cys Glu Lys Phe
            180                 185                 190

Tyr Leu Phe Pro Leu Lys Met Ile Thr Trp Thr Met Pro Thr Ala Val
        195                 200                 205

Phe Phe Ile Cys Met Ile Leu Leu Ile Thr Ser Leu Gly Arg His Arg
210                 215                 220

Lys Lys Ala Leu Leu Thr Thr Ser Gly Phe Arg Glu Pro Ser Val Gln
225                 230                 235                 240

Ala His Ile Lys Ala Leu Leu Ala Leu Leu Ser Phe Ala Met Leu Phe
                245                 250                 255

Ile Ser Tyr Phe Leu Ser Leu Val Phe Ser Ala Ala Gly Ile Phe Pro
            260                 265                 270

Pro Leu Asp Phe Lys Phe Trp Val Trp Glu Ser Val Ile Tyr Leu Cys
        275                 280                 285

Ala Ala Val His Pro Ile Ile Leu Leu Phe Ser Asn Cys Arg Leu Arg
290                 295                 300
```

Ala Val Leu Lys Ser Arg Arg Ser Arg Cys Gly Thr Pro
305                 310                 315

<210> SEQ ID NO 53
<211> LENGTH: 236
<212> TYPE: PRT
<213> ORGANISM: Mus musculus

<400> SEQUENCE: 53

Met Ala Arg Ser Thr Trp Gly Cys Cys Trp Cys Thr Lys Thr Ala Ala
1               5                   10                  15

Arg Asp Asn Arg Lys Lys Arg Lys Gly Gly Ser Gly Lys Ser Thr Lys
            20                  25                  30

Met Arg His Gly Val Gly Tyr Ser Asp Arg Arg Ala Arg Tyr Asn Val
        35                  40                  45

Ser Met Ala Met Asp Ala Met Asp Arg Ser Arg Asp Ser Lys His Ala
    50                  55                  60

Ser Val Met Thr Asp Tyr Lys Val Ser Thr Lys Tyr Ala Val Ala Met
65                  70                  75                  80

Tyr Trp Arg Asp Ala Gly Arg Ala Cys Tyr Arg Arg His Asp Ser
                85                  90                  95

Ala Val Tyr Tyr Ser His Arg Ser Asp Ser Tyr Thr Ala Asp Val Arg
            100                 105                 110

Ser Arg Met Thr Thr Gly Asn Tyr Cys Ser Val Lys Lys Thr Lys Arg
        115                 120                 125

Val Asp Val Gly Gly Arg Ser Arg Arg Lys Trp His Cys Asn Val Ala
    130                 135                 140

Tyr Ala Ser Ser Tyr Asp Cys Asn Asp Asn Arg Met Ser Ala Ser Thr
145                 150                 155                 160

Trp Lys Ser Thr Ser Val Asn Lys Thr Asp Lys His Thr Ser His
                165                 170                 175

Ala Thr Tyr Ser Gly Arg Arg Asp Ala Ala Lys Ser Asp Met Tyr
            180                 185                 190

Ala Arg Val Tyr Ala Ser Cys Ala Asp Gly Gly Arg Lys Gly Ser Arg
        195                 200                 205

Ala Arg Arg Ala His Thr Cys Ala Thr Asp Thr Ser Val Arg Ser Val
    210                 215                 220

Lys Asp Val Arg Asp Ser Val Ala Arg Tyr Asp Asn
225                 230                 235

<210> SEQ ID NO 54
<211> LENGTH: 333
<212> TYPE: PRT
<213> ORGANISM: Homo sapiens

<400> SEQUENCE: 54

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Pro Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

-continued

```
Phe Gln Lys Leu Ser Glu Pro Leu Asn His Ser Tyr Gln Ala Ile Ile
                 85                  90                  95
Met Leu Trp Met Ile Ala Asn Gln Ala Asn Leu Trp Leu Ala Ala Cys
            100                 105                 110
Leu Ser Leu Leu Tyr Cys Ser Lys Leu Ile Arg Phe Ser His Thr Phe
        115                 120                 125
Leu Ile Cys Leu Ala Ser Trp Val Ser Arg Lys Ile Ser Gln Met Leu
    130                 135                 140
Leu Gly Ile Ile Leu Cys Ser Cys Ile Cys Thr Val Leu Cys Val Trp
145                 150                 155                 160
Cys Phe Phe Ser Arg Pro His Phe Thr Val Thr Thr Val Leu Phe Met
                165                 170                 175
Asn Asn Asn Thr Arg Leu Asn Trp Gln Ile Lys Asp Leu Asn Leu Phe
            180                 185                 190
Tyr Ser Phe Leu Phe Cys Tyr Leu Trp Ser Val Pro Pro Phe Leu Leu
        195                 200                 205
Phe Leu Val Ser Ser Gly Met Leu Thr Val Ser Leu Gly Arg His Met
    210                 215                 220
Arg Thr Met Lys Val Tyr Thr Arg Asn Ser Arg Asp Pro Ser Leu Glu
225                 230                 235                 240
Ala His Ile Lys Ala Leu Lys Ser Leu Val Ser Phe Phe Cys Phe Phe
                245                 250                 255
Val Ile Ser Ser Cys Ala Ala Phe Ile Ser Val Pro Leu Leu Ile Leu
            260                 265                 270
Trp Arg Asp Lys Ile Gly Val Met Val Cys Val Gly Ile Met Ala Ala
        275                 280                 285
Cys Pro Ser Gly His Ala Ala Val Leu Ile Ser Gly Asn Ala Lys Leu
    290                 295                 300
Arg Arg Ala Val Met Thr Ile Leu Leu Trp Ala Gln Ser Ser Leu Lys
305                 310                 315                 320
Val Arg Ala Asp His Lys Ala Asp Ser Arg Thr Leu Cys
                325                 330
```

ASSAYS FOR IDENTIFYING COMPOUNDS THAT MODULATE BITTER TASTE

CROSS REFERENCE TO RELATED APPLICATIONS

This application is the National Phase entry under 35 USC §371 of PCT/US12/61400, filed Oct. 22, 2012, which claims priority to U.S. Provisional Application 61/549,693, filed Oct. 20, 2011, which applications are incorporated herein by reference in their entirety.

SEQUENCE LISTING

The Sequence Listing associated with this application is provided in text format in lieu of a paper copy, and is hereby incorporated by reference into the specification. The name of the text file containing the Sequence Listing is 002298-0027-301-Sequence-Listing.txt. The text file is 110,076 bytes in size, was created on Apr. 17, 2014, and is being submitted electronically via EFS Web.

FIELD OF THE INVENTION

The present invention relates to assays for identifying bitter taste modulators.

BACKGROUND OF THE INVENTION

The sense of taste, e.g., in human, can detect at least five traditional tastes: sweet, sour, salty, bitter, and umami (savory). Many nutritious substances including vegetables, foods, food ingredients and nutrients comprise bitter tastants and/or have a bitter taste. In addition, many pharmaceutical substances important to maintain or improve health comprise bitter tastants and/or have a bitter taste. While certain food products and consumer products have desirable bitter tastes, including coffee, beer and dark chocolate, in many contexts, consumers dislike such bitter tastes. For example, many consumers dislike the perception of certain bitter tastants and/or bitter taste and will avoid food or pharmaceutical products with an undesirable bitter tastant or bitter taste in favor of food and pharmaceutical products that have reduced levels of undesirable bitter tastants or that have reduced or that completely lack bitter taste. This aversion to products containing undesirable bitter tastants and/or having undesirable bitter taste may be caused by perception of bitter tastants and/or bitter taste mediated by activation of bitter taste receptors present in the oral cavity and/or in the gastrointestinal tract. In many cases, consumer dislike of bitter tastants and/or bitter taste prevents or hampers improvement of the nutritive quality and safety of foods as desired levels of nutrients or preservatives comprising bitter tastants and/or having bitter taste cannot be used. Also, dislike of or aversion to the bitter tastants or bitter taste of some pharmaceutical agents negatively impacts compliance with prescribed regimens for their use.

For instance, several additives, preservatives, emulsifiers and foodstuffs used in the production of food products comprise bitter tastants and/or have a bitter taste. While these additives, preservatives, emulsifiers and foodstuffs may affect the taste of a food product, they may also be important for improving the shelf life, nutritive quality, or texture of the food product. For example, the increasing trend of hypertension and cardiovascular disease has been attributed, in part, to the high sodium intake of the Western diet. Accordingly, substitution of sodium chloride with another salty tasting compound is desirable. The most common sodium chloride substitute is potassium chloride, which, to a portion of the population, is perceived as possessing a bitter taste in addition to its salty taste. The bitter taste of potassium chloride limits the extent to which it may be used to replace sodium chloride in foods without causing undesired bitter taste for the portion of the population sensitive to it.

Another common food additive, sodium lactate, has a broad antimicrobial action, is effective at inhibiting spoilage, and growth of pathogenic bacteria, and is commonly used in food products (e.g., meat and poultry products) to extend shelf life and increase food safety. Due to its sodium content, however, sodium lactate, can be undesirable as a preservative. Potassium lactate, which has similar antimicrobial properties, has been used in lieu of sodium lactate. However, potassium lactate is also associated with a bitter taste which limits the extent to which it may be used to replace sodium lactate in foods without causing undesired bitter taste.

In addition, the increasing incidence of obesity and diabetes has been attributed, in part, to the high sugar intake of many diets. Accordingly, substitution of sugar with another sweet tasting compound is desirable. Artificial and natural sugar substitutes that may be used to reduce sugar in foods are often associated with bitter taste which again limit the extent to which these may be used to replace sugar in foods without causing adverse bitter taste. For example, a common sugar substitute is Acesulfame K, which also has a bitter taste in addition to its sweet taste.

Without being limited by theory, bitter, sweet, and umami tastants and compounds typically elicit a taste response via G-protein coupled receptors, while salty and sour tastants and compounds are typically hypothesized to elicit a taste response via ion channels. Bitter taste receptors belong to the TAS2R (also referred to as T2R) family of G-protein coupled receptors that induce intracellular calcium concentration changes in response to a bitter tastant. TAS2R receptors act via gustducin, a taste-specific G-protein. There are at least twenty-five different members of the TAS2R family, suggesting that the perception of bitter taste is complex, involving several different tastant-receptor interactions. Some of the TAS2R members, e.g., TAS2R60, are orphan receptors, which have not had a ligand identified. Compounds capable of modulating the activation and/or signaling of bitter taste receptors in the oral cavity and/or the gastrointestinal tract could be effective to allow desired usage levels of bitter tastants or bitter tasting substances in food and pharmaceutical products without resulting in consumer dislike of such products due to perception of the increased levels of bitter tastants or bitter tastes. In some instances, blockers or modulators of bitter taste receptors and bitter taste may reduce the perception of bitter tastants and/or bitter taste via the bitter taste receptors and/or taste transduction signaling machinery present in the oral cavity and/or the gastrointestinal tract.

Traditionally in food preparation and pharmaceuticals, bitter taste was masked using sweeteners and other tastants, including salt. In some cases, however, this is undesirable or insufficient because it can alter, mask, or interfere with other tastes/flavors/impressions (e.g., non bitter tastes or desired bitter tastes) in the food product. Additionally, this approach has rarely been able to completely mask the bitter taste present in such food products or pharmaceuticals. For that reason, compounds which reduce bitter taste instead of, or in addition to, masking agents are preferred.

It is, therefore, desirable to provide assays to identify compounds that may be added to food products, consumer products and pharmaceuticals comprising bitter tastants or having a bitter taste to eliminate, modulate or reduce the perception of the bitter tastants or bitter taste or to reduce the corresponding activation of the bitter taste receptors in the oral cavity and/or the gastrointestinal tract. Similarly, it is desirable to identify compounds that do not activate other bitter taste receptors (i.e., compounds having off-target affects).

SUMMARY OF THE INVENTION

The present invention is based on applicants' discovery, disclosed herein, of agonists for the TAS2R receptors TAS2R1, TAS2R4, TAS2R9, TAS2R13, TAS2R14, TAS2R16, TAS2R44, TAS2R46, and TAS2R60. The assignment of agonists to these receptors makes assays for identifying compounds that modulate bitter taste possible. For example, the present invention provides methods of identifying compounds that inhibit the bitter taste due to these agonists. The present invention also provides methods of identifying compounds that selectively inhibit the bitter taste due to these agonists. The present invention further provides methods of identifying compounds that mimic the bitter taste due these agonists. The present invention also provides methods of identifying compounds that enhance the bitter taste due to these agonists.

Methods of Identifying Compounds that Inhibit Bitter Taste

One aspect of the present invention provides methods for identifying compounds that inhibit the bitter taste due to KCl. In some embodiments, the method comprises providing a first cell and a second cell, wherein the first and second cell each express one or more bitter taste receptors selected from the group consisting of: TAS2R4, TAS2R9, TAS2R13, TAS2R14, TAS2R44 and TAS2R60, wherein the first and second cell express the same one or more bitter taste receptors; contacting the first cell with a tastant that activates one or more of TAS2R4, TAS2R9, TAS2R13, TAS2R14, TAS2R44 and TAS2R60; contacting the second cell with a test compound and the tastant; assaying the first and second cells for bitter taste receptor activation; and comparing the bitter taste receptor activation of the first cell to the bitter taste receptor activation of the second cell, wherein the test compound is an inhibitor of bitter taste due to KCl if the bitter taste receptor activity of the second cell is less than the bitter taste receptor activity of the first cell.

In some embodiments, the method comprises providing a cell that expresses one or more bitter taste receptors selected from the group consisting of: TAS2R4, TAS2R9, TAS2R13, TAS2R14, TAS2R44 and TAS2R60; contacting the cell with a tastant that activates one or more of TAS2R4, TAS2R9, TAS2R13, TAS2R14, TAS2R44 and TAS2R60; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an inhibitor of bitter taste due to KCl if the bitter taste receptor activity of the second assay is less than the bitter taste receptor activity of the first assay.

Another aspect of the present invention provides methods for identifying compounds that inhibit the bitter taste due to potassium lactate. In some embodiments, the method comprises providing a first cell and a second cell, wherein the first and second cell each express one or more bitter taste receptors selected from the group consisting of: TAS2R4, TAS2R9, TAS2R13, TAS2R14, TAS2R44, TAS2R46 and TAS2R60, wherein the first and second cell express the same one or more bitter taste receptors; contacting the first cell with a tastant that activates one or more of TAS2R4, TAS2R9, TAS2R13, TAS2R14, TAS2R44, TAS2R46 and TAS2R60; contacting the second cell with a test compound and the tastant; assaying the first and second cells for bitter taste receptor activation; and comparing the bitter taste receptor activation of the first cell to the bitter taste receptor activation of the second cell, wherein the test compound is an inhibitor of bitter taste due to potassium lactate if the bitter taste receptor activity of the second cell is less than the bitter taste receptor activity of the first cell.

In some embodiments, the method comprises providing a cell that expresses one or more bitter taste receptors selected from the group consisting of: TAS2R4, TAS2R9, TAS2R13, TAS2R14, TAS2R44, TAS2R46 and TAS2R60; contacting the cell with a tastant that activates one or more of TAS2R4, TAS2R9, TAS2R13, TAS2R14, TAS2R44, TAS2R46 and TAS2R60; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an inhibitor of bitter taste due to potassium lactate if the bitter taste receptor activity of the second assay is less than the bitter taste receptor activity of the first assay.

Another aspect of the present invention provides methods for identifying compounds that inhibit the bitter taste due to Acesulfame K. In some embodiments, the method comprises providing a first cell and a second cell, wherein the first and second cell each express one or more bitter taste receptors selected from the group consisting of: TAS2R1, TAS2R4, TAS2R9, TAS2R13, TAS2R14, TAS2R16, and TAS2R44, wherein the first and second cell express the same one or more bitter taste receptors; contacting the first cell with a tastant that activates one or more of TAS2R1, TAS2R4, TAS2R9, TAS2R13, TAS2R14, TAS2R16, and TAS2R44; contacting the second cell with a test compound and the tastant; assaying the first and second cells for bitter taste receptor activation; and comparing the bitter taste receptor activation of the first cell to the bitter taste receptor activation of the second cell, wherein the test compound is an inhibitor of bitter taste due to Acesulfame K if the bitter taste receptor activity of the second cell is less than the bitter taste receptor activity of the first cell.

In some embodiments, the method comprises providing a cell that expresses one or more bitter taste receptors selected from the group consisting of: TAS2R1, TAS2R4, TAS2R9, TAS2R13, TAS2R14, TAS2R16, and TAS2R44; contacting the cell with a tastant that activates one or more of TAS2R1, TAS2R4, TAS2R9, TAS2R13, TAS2R14, TAS2R16, and TAS2R44; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an inhibitor of bitter taste due to Acesulfame K if the bitter taste receptor activity of the second assay is less than the bitter taste receptor activity of the first assay.

In some embodiments, the tastant is KCl, potassium lactate, Acesulfame K or a universal bitter compound. In some embodiments, the universal bitter compound is denatonium benzoate or denatonium saccharide.

In some embodiments, the bitter taste receptor is complexed to a G protein. In some embodiments, the G protein is a $G_q$ protein, an alpha transducin or an alpha gustducin. In some embodiments, the $G_q$ protein is a $G_{\alpha 15}$ protein.

In some embodiments, bitter taste receptor activity is determined by measuring intracellular calcium concentration. In some embodiments, intracellular calcium concentration is determined using a calcium-sensitive fluorescent dye, such as Fluo-4 or Calcium-3 dye.

In some embodiments, the cells of the method are present in in vitro cell lines. In some embodiments, the cells are present in panels of in vitro cell lines.

Methods of Identifying Compounds that Selectively Inhibit Bitter Taste

One aspect of the present invention provides methods for identifying compounds that selectively inhibit the bitter taste due to KCl. In some embodiments, the method comprises providing a first and a second panel of cell lines in which each panel comprises cell lines that express one or more bitter taste receptors selected from the group consisting of: TAS2R4, TAS2R9, TAS2R13, TAS2R14, TAS2R44 and TAS2R60 and each receptor is expressed in at least one cell line and each panel contains the same cell lines; contacting each cell line in the first panel with a tastant that activates at least two of TAS2R4, TAS2R9, TAS2R13, TAS2R14, TAS2R44 and TAS2R60; contacting each cell line in the second panel with a test compound and the tastant; assaying each cell line in the first and second panels for bitter taste receptor activation; and comparing the bitter taste receptor activation of each cell line in the first panel to the bitter taste receptor activation of the corresponding cell line in the second panel, wherein the test compound is an selective inhibitor of bitter taste due to KCl if the bitter taste receptor activity of at least two of the group selected from TAS2R4, TAS2R9, TAS2R13, TAS2R14, TAS2R44 and TAS2R60 is less in the second panel compared to the first panel. In some embodiments, if the bitter taste receptor activity is less in at least three of the cell lines of the second panel, wherein the cell lines are selected from TAS2R4, TAS2R9, TAS2R13, TAS2R14, TAS2R44 and TAS2R60, then the test compound selectively inhibits bitter taste due to KCl. In some embodiments, if the bitter taste receptor activity is less in at least four of the cell lines of the second panel, wherein the cell lines are selected from TAS2R4, TAS2R9, TAS2R13, TAS2R14, TAS2R44 and TAS2R60, then the test compound selectively inhibits bitter taste due to KCl. In some embodiments, if the bitter taste receptor activity is less in at least five of the cell lines of the second panel, wherein the cell lines are selected from TAS2R4, TAS2R9, TAS2R13, TAS2R14, TAS2R44 and TAS2R60, then the test compound selectively inhibits bitter taste due to KCl. In some embodiments, if the bitter taste receptor activity is less in the second panel for each of the TAS2R4, TAS2R9, TAS2R13, TAS2R14, TAS2R44 and TAS2R60 cell lines, then the test compound selectively inhibits bitter taste due to KCl. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter receptor activity in the second panel compared to the first panel. In some embodiments, each cell line of the first panel is washed after the assay for bitter taste receptor activation to provide the second panel of cell lines.

Another aspect of the present invention provides methods for identifying compounds that selectively inhibit the bitter taste due to potassium lactate. In some embodiments, the method comprises providing a first and a second panel of cell lines in which panel comprises cell lines that express one or more bitter taste receptors selected from the group consisting of: TAS2R4, TAS2R9, TAS2R13, TAS2R14, TAS2R44, TAS2R46 and TAS2R60 and each receptor is expressed in at least one cell line and each panel contains the same cell lines; contacting each cell line in the first panel with a tastant that activates at least two of TAS2R4, TAS2R9, TAS2R13, TAS2R14, TAS2R44, TAS2R46 and TAS2R60; contacting each cell line in the second panel with a test compound and the tastant; assaying each cell line in the first and second panels for bitter taste receptor activation; and comparing the bitter taste receptor activation of each cell line in the first panel to the bitter taste receptor activation of the corresponding cell line in the second panel, wherein the test compound is an selective inhibitor of bitter taste due to potassium lactate if the bitter taste receptor activity of at least two of the group selected from TAS2R4, TAS2R9, TAS2R13, TAS2R14, TAS2R44, TAS2R46 and TAS2R60 is less in the second panel compared to the first panel. In some embodiments, if the bitter taste receptor activity is less in at least three of the cell lines of the second panel, wherein the cell lines are selected from TAS2R4, TAS2R9, TAS2R13, TAS2R14, TAS2R44, TAS2R46 and TAS2R60, then the test compound selectively inhibits bitter taste due to potassium lactate. In some embodiments, if the bitter taste receptor activity is less in at least four of the cell lines of the second panel, wherein the cell lines are selected from TAS2R4, TAS2R9, TAS2R13, TAS2R14, TAS2R44, TAS2R46 and TAS2R60, then the test compound selectively inhibits bitter taste due to potassium lactate. In some embodiments, if the bitter taste receptor activity is less in at least five of the cell lines of the second panel, wherein the cell lines are selected from TAS2R4, TAS2R9, TAS2R13, TAS2R14, TAS2R44, TAS2R46 and TAS2R60, then the test compound selectively inhibits bitter taste due to potassium lactate. In some embodiments, if the bitter taste receptor activity is less in at least six of the cell lines of the second panel, wherein the cell lines are selected from TAS2R4, TAS2R9, TAS2R13, TAS2R14, TAS2R44, TAS2R46 and TAS2R60, then the test compound selectively inhibits bitter taste due to potassium lactate. In some embodiments, if the bitter taste receptor activity is less in the second panel for each of the TAS2R4, TAS2R9, TAS2R13, TAS2R14, TAS2R44, TAS2R46 and TAS2R60 cell lines, then the test compound selectively inhibits bitter taste due to potassium lactate. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter receptor activity in the second panel compared to the first panel. In some embodiments, each cell line of the first panel is washed after the assay for bitter taste receptor activation to provide the second panel of cell lines.

Another aspect of the present invention provides methods for identifying compounds that selectively inhibit the bitter taste due to Acesulfame K. In some embodiments, the method comprises providing a first and a second panel of cell lines in which panel comprises cell lines that express one or more bitter taste receptors selected from the group consisting of: TAS2R1, TAS2R4, TAS2R9, TAS2R13, TAS2R14, TAS2R16, and TAS2R44 and each receptor is expressed in at least one cell line and each panel contains the same cell lines; contacting each cell line in the first panel with a tastant that activates at least two of TAS2R1, TAS2R4, TAS2R9, TAS2R13, TAS2R14, TAS2R16, and TAS2R44; contacting each cell line in the second panel with a test compound and the tastant; assaying each cell line in the first and second panels for bitter taste receptor activation; and comparing the bitter taste receptor activation of each cell line in the first panel to the bitter taste receptor activation of the corresponding cell line in the second panel, wherein the test compound is an selective inhibitor of bitter taste due to Acesulfame K if the bitter taste receptor activity of at least two of the group selected from TAS2R1, TAS2R4, TAS2R9, TAS2R13, TAS2R14, TAS2R16, and TAS2R44 is less in the second panel compared to the first panel. In some embodiments, if the bitter taste receptor activity is less in at least three of the cell lines of the second panel, wherein the cell lines are selected from TAS2R1, TAS2R4, TAS2R9, TAS2R13, TAS2R14, TAS2R16, and TAS2R44, then the test compound selectively inhibits bitter taste due to Acesulfame K. In some embodiments, if the bitter taste receptor activity is less in at least four of the cell lines of the second panel, wherein the cell lines are selected from TAS2R1, TAS2R4, TAS2R9, TAS2R13, TAS2R14, TAS2R16, and TAS2R44, then the test compound selectively inhibits bitter taste due to Acesulfame K. In some embodiments, if the bitter taste receptor activity is less in at least five of the cell lines of the second panel, wherein the cell lines are selected from TAS2R1, TAS2R4, TAS2R9, TAS2R13, TAS2R14, TAS2R16, and TAS2R44, then the test compound selectively inhibits bitter taste due to Acesulfame K. In some embodiments, if the bitter taste receptor activity is less in at least six of the cell lines of the second panel, wherein the cell lines are selected from TAS2R1, TAS2R4, TAS2R9, TAS2R13, TAS2R14, TAS2R16, and TAS2R44, then the test compound selectively inhibits bitter taste due to Acesulfame K. In some embodiments, if the bitter taste receptor activity is less in the second panel for each of the TAS2R1, TAS2R4, TAS2R9, TAS2R13, TAS2R14, TAS2R16, and TAS2R44 cell lines, then the test compound selectively inhibits bitter taste due to Acesulfame K. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter receptor activity in the second panel compared to the first panel. In some embodiments, each cell line of the first panel is washed after the assay for bitter taste receptor activation to provide the second panel of cell lines.

In some embodiments, the tastant is KCl, potassium lactate, Acesulfame K or a universal bitter compound. In some embodiments, the universal bitter compound is denatonium benzoate or denatonium saccharide.

In some embodiments, the bitter taste receptor is complexed to a G protein. In some embodiments, the G protein is a $G_q$ protein, an alpha transducin or an alpha gustducin. In some embodiments, the $G_q$ protein is a $G_{\alpha 15}$ protein.

In some embodiments, bitter taste receptor activity is determined by measuring intracellular calcium concentration. In some embodiments, intracellular calcium concentration is determined using a calcium-sensitive fluorescent dye, such as Fluo-4 or Calcium-3 dye.

In some embodiments, the cells of the method are present in in vitro cell lines. In some embodiments, the cells are present in panels of in vitro cell lines.

Methods of Identifying Compounds that Mimic Bitter Taste

One aspect of the present invention provides methods for identifying compounds that mimic bitter taste due to KCl. In some embodiments, the method comprises providing a first and a second panel of cell lines in which panel comprises cell lines that expresses one or more bitter taste receptors selected from the group consisting of: TAS2R4, TAS2R9, TAS2R13, TAS2R14, TAS2R44 and TAS2R60 and each receptor is expressed in at least one cell line and each panel contains the same cell lines; contacting each cell line in the first panel with a negative control; contacting each cell line in the second panel with a test compound; assaying each cell line in the first and second panels for bitter taste receptor activation; and comparing the bitter taste receptor activation of each cell line in the first panel to the bitter taste receptor activation of the corresponding cell line in the second panel, wherein the test compound mimics bitter taste due to KCl if the test compound induces TAS2R4, TAS2R9, TAS2R13, TAS2R14, TAS2R44 and TAS2R60 bitter taste receptor activity in the second panel compared to the first panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter receptor activity in the second panel compared to the first panel. In some embodiments, each cell line of the first panel is washed after the assay for bitter taste receptor activation to provide the second panel of cell lines. In some embodiments, the negative control is the assay buffer before addition of the test compound.

Another aspect of the present invention provides methods for identifying compounds that mimic bitter taste due to potassium lactate. In some embodiments, the method comprises providing a first and a second panel of cell lines in which panel comprises cell lines that expresses one or more bitter taste receptors selected from the group consisting of: TAS2R4, TAS2R9, TAS2R13, TAS2R14, TAS2R44, TAS2R46 and TAS2R60 and each receptor is expressed in at least one cell line and each panel contains the same cell lines; contacting each cell line in the first panel with a negative control; contacting each cell line in the second panel with a test compound; assaying each cell line in the first and second panels for bitter taste receptor activation; and comparing the bitter taste receptor activation of each cell line in the first panel to the bitter taste receptor activation of the corresponding cell line in the second panel, wherein the test compound mimics bitter taste due to potassium lactate if the test compound induces TAS2R4, TAS2R9, TAS2R13, TAS2R14, TAS2R44, TAS2R46 and TAS2R60 bitter taste receptor activity in the second panel compared to the first panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter receptor activity in the second panel compared to the first panel. In some embodiments, each cell line of the first panel is washed after the assay for bitter taste receptor activation to provide the second panel of cell lines. In some embodiments, the negative control is the assay buffer before addition of the test compound.

Another aspect of the present invention provides methods for identifying compounds that mimic bitter taste due to Acesulfame K. In some embodiments, the method comprises providing a first and a second panel of cell lines in which panel comprises cell lines that expresses one or more bitter taste receptors selected from the group consisting of: TAS2R1, TAS2R4, TAS2R9, TAS2R13, TAS2R14, TAS2R16, and TAS2R44 and each receptor is expressed in at least one cell line and each panel contains the same cell lines; contacting each cell line in the first panel with a negative control; contacting each cell line in the second panel with a test compound; assaying each cell line in the first and second panels for bitter taste receptor activation; and comparing the bitter taste receptor activation of each cell line in the first panel to the bitter taste receptor activation of the corresponding cell line in the second panel, wherein the test compound mimics bitter taste due to Acesulfame K if the test compound induces TAS2R1, TAS2R4, TAS2R9, TAS2R13, TAS2R14, TAS2R16, and TAS2R44 bitter taste receptor activity in the second panel compared to the first panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. In some embodiments, the test compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter receptor activity in the second panel compared to the first panel. In some embodiments, each cell line of the first panel is washed after the assay for bitter taste receptor activation to provide the second panel of cell lines. In some embodiments, the negative control is the assay buffer before addition of the test compound.

In some embodiments, the bitter taste receptor is complexed to a G protein. In some embodiments, the G protein is a $G_q$ protein, an alpha transducin or an alpha gustducin. In some embodiments, the $G_q$ protein is a $G_{\alpha 15}$ protein.

In some embodiments, bitter taste receptor activity is determined by measuring intracellular calcium concentration. In some embodiments, intracellular calcium concentration is determined using a calcium-sensitive fluorescent dye, such as Fluo-4 or Calcium-3 dye.

In some embodiments, the cells of the method are present in in vitro cell lines. In some embodiments, the cells are present in panels of in vitro cell lines.

Methods of Identifying Compounds That Enhance Bitter Taste

One aspect of the present invention provides methods for identifying compounds that enhance the bitter taste due to KCl. In some embodiments, the method comprises providing a first cell and a second cell that each express one or more bitter taste receptors selected from the group consisting of: TAS2R4, TAS2R9, TAS2R13, TAS2R14, TAS2R44 and TAS2R60; contacting the first cell with a tastant that activates one or more of TAS2R4, TAS2R9, TAS2R13, TAS2R14, TAS2R44 and TAS2R60; contacting the second cell with a test compound and the tastant; assaying the first and second cells for bitter taste receptor activation; and comparing the bitter taste receptor activation of the first cell to the bitter taste receptor activation of the second cell, wherein the test compound is an enhancer of bitter taste due to KCl if the bitter taste receptor activity of the second cell is more than the bitter taste receptor activity of the first cell. In some embodiments, the method comprises providing a cell that expresses one or more bitter taste receptors selected from the group consisting of: TAS2R4, TAS2R9, TAS2R13, TAS2R14, TAS2R44 and TAS2R60; contacting the cell with a tastant that activates one or more of TAS2R4, TAS2R9, TAS2R13, TAS2R14, TAS2R44 and TAS2R60; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an enhancer of bitter taste due to KCl if the bitter taste receptor activity of the second assay is more than the bitter taste receptor activity of the first assay.

Another aspect of the present invention provides methods for identifying compounds that enhance the bitter taste due to potassium lactate. In some embodiments, the method comprises providing a first cell and a second cell that each express one or more bitter taste receptors selected from the group consisting of: TAS2R4, TAS2R9, TAS2R13, TAS2R14, TAS2R44, TAS2R46 and TAS2R60; contacting the first cell with a tastant that activates one or more of TAS2R4, TAS2R9, TAS2R13, TAS2R14, TAS2R44, TAS2R46 and TAS2R60; contacting the second cell with a test compound and the tastant; assaying the first and second cells for bitter taste receptor activation; and comparing the bitter taste receptor activation of the first cell to the bitter taste receptor activation of the second cell, wherein the test compound is an enhancer of bitter taste due to potassium lactate if the bitter taste receptor activity of the second cell is more than the bitter taste receptor activity of the first cell. In some embodiments, the method comprises providing a cell that expresses one or more bitter taste receptors selected from the group consisting of: TAS2R4, TAS2R9, TAS2R13, TAS2R14, TAS2R44, TAS2R46 and TAS2R60; contacting the cell with a tastant that activates one or more of TAS2R4, TAS2R9, TAS2R13, TAS2R14, TAS2R44, TAS2R46 and TAS2R60; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an enhancer of bitter taste due to potassium lactate if the bitter taste receptor activity of the second assay is more than the bitter taste receptor activity of the first assay.

Another aspect of the present invention provides methods for identifying compounds that enhance the bitter taste due to Acesulfame K. In some embodiments, the method comprises providing a first cell and a second cell that each express one or more bitter taste receptors selected from the group consisting of: TAS2R1, TAS2R4, TAS2R9, TAS2R13, TAS2R14, TAS2R16, and TAS2R44; contacting the first cell with a tastant that activates one or more of TAS2R1, TAS2R4, TAS2R9, TAS2R13, TAS2R14, TAS2R16, and TAS2R44; contacting the second cell with a test compound and the tastant; assaying the first and second cells for bitter taste receptor activation; and comparing the bitter taste receptor activation of the first cell to the bitter taste receptor activation of the second cell, wherein the test compound is an enhancer of bitter taste due to Acesulfame K if the bitter taste receptor activity of the second cell is more than the bitter taste receptor activity of the first cell. In some embodiments, the method comprises providing a cell that expresses one or more bitter taste receptors selected from the group consisting of: TAS2R1, TAS2R4, TAS2R9, TAS2R13, TAS2R14, TAS2R16, and TAS2R44; contacting the cell with a tastant that activates one or more of TAS2R1, TAS2R4, TAS2R9, TAS2R13, TAS2R14, TAS2R16, and TAS2R44; performing a first assay for bitter taste receptor activation; washing the cell; contacting the cell with a test compound and the tastant; performing a second assay for bitter taste receptor activation; and comparing the bitter taste receptor activation of the first assay to the bitter taste receptor activation of the second assay, wherein the test compound is an enhancer of bitter taste due to Acesulfame K if the bitter taste receptor activity of the second assay is more than the bitter taste receptor activity of the first assay.

In some embodiments, the tastant is KCl, potassium lactate, Acesulfame K or a universal bitter compound. In some embodiments, the universal bitter compound is denatonium benzoate or denatonium saccharide.

In some embodiments, the bitter taste receptor is complexed to a G protein. In some embodiments, the G protein is a $G_q$ protein, an alpha transducin or an alpha gustducin. In some embodiments, the $G_q$ protein is a $G_{\alpha 15}$ protein.

In some embodiments, bitter taste receptor activity is determined by measuring intracellular calcium concentration. In some embodiments, intracellular calcium concentration is determined using a calcium-sensitive fluorescent dye, such as Fluo-4 or Calcium-3 dye.

In some embodiments, the cells of the method are present in in vitro cell lines. In some embodiments, the cells are present in panels of in vitro cell lines.

Methods of Determining Whether Bitter Tastants are Present in a Composition

One aspect of the present invention provides methods for determining if KCl is present in a composition. In some embodiments, the method comprises providing a first and a second panel of cell lines in which each cell line expresses one or more bitter taste receptors selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 and each receptor is expressed in at least one cell line and each panel contains the same cell lines; contacting each cell line in the first panel with a negative control; contacting each cell line in the second panel with a composition; assaying each cell line in the first and second panels for bitter taste receptor activation; and comparing the bitter taste receptor activation of each cell line in the first panel to the bitter taste receptor activation of the corresponding cell line in the second panel, wherein KCl is present in the composition if the composition induces TAS2R4, TAS2R9, TAS2R13, TAS2R14, TAS2R44 and TAS2R60 bitter taste receptor activity in the second panel compared to the first panel and does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel. In some embodiments, each cell line of the first panel is washed after the assay for bitter taste receptor activation to provide the second panel of cell lines. In some embodiments, the negative control is the assay buffer before addition of the composition.

Another aspect of the present invention provides methods for determining if potassium lactate is present in a composition. In some embodiments, the method comprises providing a first and a second panel of cell lines in which each cell line expresses one or more bitter taste receptors selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 and each receptor is expressed in at least one cell line and each panel contains the same cell lines; contacting each cell line in the first panel with a negative control; contacting each cell line in the second panel with a composition; assaying each cell line in the first and second panels for bitter taste receptor activation; and comparing the bitter taste receptor activation of each cell line in the first panel to the bitter taste receptor activation of the corresponding cell line in the second panel, wherein potassium lactate is present in the composition if the composition induces TAS2R4, TAS2R9, TAS2R13, TAS2R14, TAS2R44, TAS2R46 and TAS2R60 bitter taste receptor activity in the second panel compared to the first panel and does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel. In some embodiments, each cell line of the first panel is washed after the assay for bitter taste receptor activation to provide the second panel of cell lines. In some embodiments, the negative control is the assay buffer before addition of the composition.

Another aspect of the present invention provides methods for determining if Acesulfame K is present in a composition. In some embodiments, the method comprises providing a first and a second panel of cell lines in which each cell line expresses one or more bitter taste receptors selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 and each receptor is expressed in at least one cell line and each panel contains the same cell lines; contacting each cell line in the first panel with a negative control; contacting each cell line in the second panel with a composition; assaying each cell line in the first and second panels for bitter taste receptor activation; and comparing the bitter taste receptor activation of each cell line in the first panel to the bitter taste receptor activation of the corresponding cell line in the second panel, wherein Acesulfame K is present in the composition if the composition induces TAS2R1, TAS2R4, TAS2R9, TAS2R13, TAS2R14, TAS2R16, and TAS2R44 bitter taste receptor activity in the second panel compared to the first panel and does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity in the second panel compared to the first panel. In some embodiments, each cell line of the first panel is washed after the assay for bitter taste receptor activation to provide the second panel of cell lines. In some embodiments, the negative control is the assay buffer before addition of the composition.

In some embodiments, the composition is an extract from a food product. In some embodiments, the composition comprises a pharmaceutically active ingredient.

In some embodiments, the bitter taste receptor is complexed to a G protein. In some embodiments, the G protein is a $G_q$ protein, an alpha transducin or an alpha gustducin. In some embodiments, the $G_q$ protein is a $G_{\alpha 15}$ protein.

In some embodiments, bitter taste receptor activity is determined by measuring intracellular calcium concentration. In some embodiments, intracellular calcium concentration is determined using a calcium-sensitive fluorescent dye, such as Fluo-4 or Calcium-3 dye.

In some embodiments, the cells of the method are present in in vitro cell lines. In some embodiments, the cells are present in panels of in vitro cell lines.

Particular embodiments of the invention are set forth in the following numbered paragraphs:

1. A method for identifying a compound that inhibits the bitter taste due to KCl comprising:
    a) providing a first and a second cell,
        wherein each cell expresses one or more bitter taste receptors independently selected from the group consisting of: TAS2R4, TAS2R9, TAS2R13, TAS2R14, TAS2R44 and TAS2R60 bitter taste receptors and
        wherein each cell expresses the same one or more bitter taste receptors;
    b) contacting said first cell with a tastant,
        wherein the tastant activates one or more of TAS2R4, TAS2R9, TAS2R13, TAS2R14, TAS2R44 and TAS2R60 bitter taste receptors;
    c) contacting said second cell with a test compound and the tastant;
    d) assaying said first and second cells for bitter taste receptor activation; and
    e) comparing the bitter taste receptor activation of said first cell to the bitter taste receptor activation of said second cell,
        wherein the test compound is an inhibitor of bitter taste due to KCl if bitter taste receptor activity of said second cell is less than the bitter taste receptor activity of said first cell.

2. A method for identifying a compound that inhibits the bitter taste due to potassium lactate comprising:
    a) providing a first and a second cell,
        wherein each cell expresses one or more bitter taste receptors independently selected from the group consisting of: TAS2R4, TAS2R9, TAS2R13, TAS2R14, TAS2R44, TAS2R46 and TAS2R60 bitter taste receptors and
        wherein each cell expresses the same one or more bitter taste receptors;
    b) contacting said first cell with a tastant,
        wherein the tastant activates one or more of TAS2R4, TAS2R9, TAS2R13, TAS2R14, TAS2R44, TAS2R46 and TAS2R60 bitter taste receptors;
    c) contacting said second cell with a test compound and the tastant;
    d) assaying said first and second cells for bitter taste receptor activation; and
    e) comparing the bitter taste receptor activation of said first cell to the bitter taste receptor activation of said second cell,
        wherein the test compound is an inhibitor of bitter taste due to potassium lactate if bitter taste receptor activity of said second cell is less than the bitter taste receptor activity of said first cell.

3. The method of any one of paragraphs 1-2, wherein the tastant is KCl, potassium lactate, or a universal bitter compound.

4. The method of any one of paragraphs 1-3, wherein the bitter taste receptor is complexed to a G protein.

5. The method according to paragraph 4, wherein said G protein is a $G_q$ protein, an alpha transducin or an alpha gustducin.

6. The method according to paragraph 5, wherein the $G_q$ protein is a $G_{\alpha 15}$ protein.

7. The method according to any one of paragraphs 1-6, wherein bitter taste receptor activity is determined by measuring intracellular calcium concentration.

8. The method according to paragraph 7, wherein the concentration of intracellular calcium is determined using a calcium-sensitive fluorescent dye.

9. The method according to paragraph 8, wherein the calcium-sensitive fluorescent dye is Fluo-4 or Calcium-3 dye.

10. The method according to any one of paragraphs 1-9, wherein said first and second cells are present in in vitro cell lines.

11. The method according to any one of paragraphs 1-9, wherein said first and second cells are present in panels of in vitro cell lines.

12. The method according to any one of paragraphs 1-11, wherein the universal bitter compound is denatonium benzoate or denatonium saccharide.

13. A method for identifying a compound that selectively inhibits the bitter taste due to KCl comprising:
    a) providing a first and second panel of cell lines,
        wherein each cell line comprises cells that express a bitter taste receptor selected from the group consisting of: TAS2R4, TAS2R9, TAS2R13, TAS2R14, TAS2R44 and TAS2R60 bitter taste receptor,
        wherein each receptor is expressed in at least one cell line, and
        wherein the first and second panels comprise the same cell lines;
    b) contacting each cell line in the first panel with a tastant,
        wherein the tastant activates at least two of the group selected from TAS2R4, TAS2R9, TAS2R13, TAS2R14, TAS2R44 and TAS2R60;
    c) contacting each cell line in the second panel with a test compound and the tastant;
    d) assaying each cell line for bitter taste receptor activation;
        wherein, the test compound is an selective inhibitor of bitter taste due to KCl if the bitter taste receptor activity of at least two of the group selected from TAS2R4, TAS2R9, TAS2R13, TAS2R14, TAS2R44 and TAS2R60 is less in the second panel compared to the first panel.

14. The method of paragraph 13, wherein the bitter taste receptor activity of at least three of the group selected from TAS2R4, TAS2R9, TAS2R13, TAS2R14, TAS2R44 and TAS2R60 is less in the second panel compared to the first panel.

15. The method of paragraph 13, wherein the bitter taste receptor activity of at least four of the group selected from TAS2R4, TAS2R9, TAS2R13, TAS2R14, TAS2R44 and TAS2R60 is less in the second panel compared to the first panel.

16. The method of paragraph 13, wherein the bitter taste receptor activity of at least five of the group selected from TAS2R4, TAS2R9, TAS2R13, TAS2R14, TAS2R44 and TAS2R60 is less in the second panel compared to the first panel.

17. The method of paragraph 13, wherein the bitter taste receptor of activity of TAS2R4, TAS2R9, TAS2R13, TAS2R14, TAS2R44 and TAS2R60 is less in the second panel compared to the first panel.

18. The method according to any one of paragraphs 13-17, wherein each panel comprises cell lines that express a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines.

19. The method according to paragraph 18, wherein the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel.

20. A method for identifying a compound that selectively inhibits the bitter taste due to potassium lactate comprising:
a) providing a first and second panel of cell lines,
wherein each cell line comprises cells that express a bitter taste receptor selected from the group consisting of: TAS2R4, TAS2R9, TAS2R13, TAS2R14, TAS2R44, TAS2R46 and TAS2R60 bitter taste receptor,
wherein each receptor is expressed in at least one cell line, and
wherein the first and second panels comprise the same cell lines;
b) contacting each cell line in the first panel with a tastant,
wherein the tastant activates at least two of the group selected from TAS2R4, TAS2R9, TAS2R13, TAS2R14, TAS2R44, TAS2R46 and TAS2R60;
c) contacting each cell line in the second panel with a test compound and the tastant;
d) assaying each cell line for bitter taste receptor activation;
wherein, the test compound is an selective inhibitor of bitter taste due to potassium lactate if the bitter taste receptor activity of at least two of the group selected from TAS2R4, TAS2R9, TAS2R13, TAS2R14, TAS2R44, TAS2R46 and TAS2R60 is less in the second panel compared to the first panel.

21. The method of paragraph 20, wherein the bitter taste receptor activity of at least three of the group selected from TAS2R4, TAS2R9, TAS2R13, TAS2R14, TAS2R44, TAS2R46 and TAS2R60 is less in the second panel compared to the first panel.

22. The method of paragraph 20, wherein the bitter taste receptor activity of at least four of the group selected from TAS2R4, TAS2R9, TAS2R13, TAS2R14, TAS2R44, TAS2R46 and TAS2R60 is less in the second panel compared to the first panel.

23. The method of paragraph 20, wherein the bitter taste receptor activity of at least five of the group selected from TAS2R4, TAS2R9, TAS2R13, TAS2R14, TAS2R44, TAS2R46 and TAS2R60 is less in the second panel compared to the first panel.

24. The method of paragraph 20, wherein the bitter taste receptor activity of at least six of the group selected from TAS2R4, TAS2R9, TAS2R13, TAS2R14, TAS2R44, TAS2R46 and TAS2R60 is less in the second panel compared to the first panel.

25. The method of paragraph 13, wherein the bitter taste receptor of activity of TAS2R4, TAS2R9, TAS2R13, TAS2R14, TAS2R44, TAS2R46 and TAS2R60 is less in the second panel compared to the first panel.

26. The method according to any one of paragraphs 20-25, wherein each panel comprises cell lines that express a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines.

27. The method according to paragraph 26, wherein the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel.

28. The method of any one of paragraphs 13-27, wherein the tastant is KCl, potassium lactate, or a universal bitter compound.

29. The method of any one of paragraphs 13-28, wherein the bitter taste receptors are complexed to a G protein.

30. The method according to paragraph 29, wherein the G protein is a $G_q$ protein, an alpha transducin or an alpha gustducin.

31. The method according to paragraph 30, wherein the $G_q$ protein is a $G_{\alpha 15}$ protein.

32. The method according to any one of paragraphs 28-31, wherein bitter taste receptor activity is determined by measuring intracellular calcium concentration.

33. The method according to paragraph 32, wherein the concentration of intracellular calcium is determined using a calcium-sensitive fluorescent dye.

34. The method according to paragraph 33, wherein the calcium-sensitive fluorescent dye is Fluo-4 or Calcium-3 dye.

35. The method according to any one of paragraphs 28-34, wherein the universal bitter compound is denatonium benzoate or denatonium saccharide.

36. The method according to any one of paragraphs 13-34, wherein the cell lines from the first panel are washed after the bitter taste receptor activation assay to provide the second panel of cell lines.

37. A method for identifying a compound that enhances the bitter taste due to KCl comprising:
a) providing a first and a second cell,
wherein each cell expresses one or more bitter taste receptors independently selected from the group consisting of: TAS2R4, TAS2R9, TAS2R13, TAS2R14, TAS2R44 and TAS2R60 bitter taste receptors;
b) contacting said first cell with a tastant,
wherein the tastant activates one or more of TAS2R4, TAS2R9, TAS2R13, TAS2R14, TAS2R44 and TAS2R60 bitter taste receptors;
c) contacting said second cell with a test compound and the tastant;
d) assaying said first and second cells for bitter taste receptor activation; and
e) comparing the bitter taste receptor activation of said first cell to the bitter taste receptor activation of said second cell,
wherein the test compound enhances bitter taste due to KCl if bitter taste receptor activity of said second cell is more than the bitter taste receptor activity of said first cell.

38. A method for identifying a compound that enhances the bitter taste due to potassium lactate comprising:
a) providing a first and a second cell,
wherein each cell expresses one or more bitter taste receptors independently selected from the group consisting of: TAS2R4, TAS2R9, TAS2R13, TAS2R14, TAS2R44, TAS2R46 and TAS2R60 bitter taste receptor;
b) contacting said first cell with a tastant,
wherein the tastant activates one or more of TAS2R4, TAS2R9, TAS2R13, TAS2R14, TAS2R44, TAS2R46 and TAS2R60 bitter taste receptors;
c) contacting said second cell with a test compound and the tastant;
d) assaying said first and second cells for bitter taste receptor activation; and
e) comparing the bitter taste receptor activation of said first cell to the bitter taste receptor activation of said second cell,
wherein the test compound enhances bitter taste due to potassium lactate if bitter taste receptor activity of said second cell is more than the bitter taste receptor activity of said first cell.

39. The method of any one of paragraphs 37-38, wherein the tastant is KCl, potassium lactate, or a universal bitter compound.

40. The method of any one of paragraphs 37-39, wherein the bitter taste receptor is complexed to a G protein.

41. The method according to paragraph 40, wherein the G protein is a $G_q$ protein, an alpha transducin or an alpha gustducin.

42. The method according to paragraph 41, wherein the $G_q$ protein is a $G_{\alpha 15}$ protein.

43. The method according to any one of paragraphs 37-42, wherein bitter taste receptor activity is determined by measuring intracellular calcium concentration.

44. The method according to paragraph 43, wherein the concentration of intracellular calcium is determined using a calcium-sensitive fluorescent dye.

45. The method according to paragraph 44, wherein the calcium-sensitive fluorescent dye is Fluo-4 or Calcium-3 dye.

46. The method according to any one of paragraphs 37-45, wherein the cell is present in an in vitro cell line.

47. The method according to any one of paragraphs 37-45, wherein the cell is present in a panel of in vitro cell lines.

48. The method according to any one of paragraphs 39-47, wherein the universal bitter compound is denatonium benzoate or denatonium saccharide.

49. The method according to any one of paragraphs 37-48, wherein the first cell is washed after the bitter taste receptor activation assay to provide the second cell.

50. A method for identifying a compound that inhibits the bitter taste due to KCl comprising:
a) providing a cell,
wherein the cell expresses one or more bitter taste receptors selected from the group consisting of: TAS2R4, TAS2R9, TAS2R13, TAS2R14, TAS2R44 and TAS2R60 bitter taste receptors;
b) contacting said cell with a tastant,
wherein the tastant activates one or more of TAS2R4, TAS2R9, TAS2R13, TAS2R14, TAS2R44 and TAS2R60 bitter taste receptors;
c) assaying said cell for bitter taste receptor activation;
d) washing said cell;
e) contacting said cell with a test compound and the tastant;
f) assaying said cell for bitter taste receptor activation; and
g) comparing the bitter taste receptor activation of said cell in step (c) to the bitter taste receptor activation of said cell in step (f),
wherein the test compound is an inhibitor of bitter taste due to KCl if bitter taste receptor activity in step (f) is less than the bitter taste receptor activity in step (c).

51. A method for identifying a compound that inhibits the bitter taste due to potassium lactate comprising:
a) providing a cell,
wherein the cell expresses one or more bitter taste receptors selected from the group consisting of: TAS2R4, TAS2R9, TAS2R13, TAS2R14, TAS2R44, TAS2R46 and TAS2R60 bitter taste receptors;
b) contacting said cell with a tastant,
wherein the tastant activates one or more of TAS2R4, TAS2R9, TAS2R13, TAS2R14, TAS2R44, TAS2R46 and TAS2R60 bitter taste receptors;
c) assaying said cell for bitter taste receptor activation;
d) washing said cell;
e) contacting said cell with a test compound and the tastant;
f) assaying said cell for bitter taste receptor activation; and
g) comparing the bitter taste receptor activation of said cell in step (c) to the bitter taste receptor activation of said cell in step (f),
wherein the test compound is an inhibitor of bitter taste due to potassium lactate if bitter taste receptor activity in step (f) is less than the bitter taste receptor activity in step (c).

52. The method of any one of paragraphs 50-51, wherein the tastant is KCl, potassium lactate, or a universal bitter compound.

53. The method of any one of paragraphs 50-52, wherein the bitter taste receptor is complexed to a G protein.

54. The method according to paragraph 53, wherein said G protein is a $G_q$ protein, an alpha transducin or an alpha gustducin.

55. The method according to paragraph 54, wherein the $G_q$ protein is a $G_{\alpha 15}$ protein.

56. The method according to any one of paragraphs 50-55, wherein bitter taste receptor activity is determined by measuring intracellular calcium concentration.

57. The method according to paragraph 56, wherein the concentration of intracellular calcium is determined using a calcium-sensitive fluorescent dye.

58. The method according to paragraph 57, wherein the calcium-sensitive fluorescent dye is Fluo-4 or Calcium-3 dye.

59. The method according to any one of paragraphs 50-58, wherein the cell is present in an in vitro cell line.

60. The method according to any one of paragraphs 50-58, wherein the cell is present in a panel of in vitro cell lines.

61. The method according to any one of paragraphs 52-60, wherein the universal bitter compound is denatonium benzoate or denatonium saccharide.

BRIEF DESCRIPTION OF THE DRAWINGS

FIG. 2 demonstrates that six receptors showed a robust functional response to KCl (20 mM), indicating that these six receptors are specifically tuned to detect KCl. None of the remaining nineteen receptors provided a functional response above threshold (40%).

FIG. 3 provides (A) the dose-response curve of KCl signaling in response to addition of KCl in cell lines expressing KCl-specific receptors, and (B) the dose-response curve of KCl signaling in response to addition of buffer in cell lines expressing KCl-specific receptors. Y-axis represents fluorescence (RFU). The X-axis represents log KCl-Concentration (M) in (A). The X-axis in (B), which had no KCl added, reflects the log KCl-Concentration (M) in (A).

FIG. 4 demonstrates that seven receptors showed a robust functional response to potassium lactate (20 mM), indicating that these seven receptors are specifically tuned to detect potassium lactate. None of the remaining eighteen receptors provided a functional response above threshold (40%).

FIG. 5 demonstrates that seven receptors showed a robust functional response to Acesulfame K (20 mM), indicating that these seven receptors are specifically tuned to detect Acesulfame K. None of the remaining eighteen receptors provided a functional response above threshold (40%).

FIG. 6 demonstrates the functional reactivity of all twenty-five bitter cell lines to KCl, potassium lactate, and Acesulfame K.

DETAILED DESCRIPTION OF THE INVENTION

Figure 1:
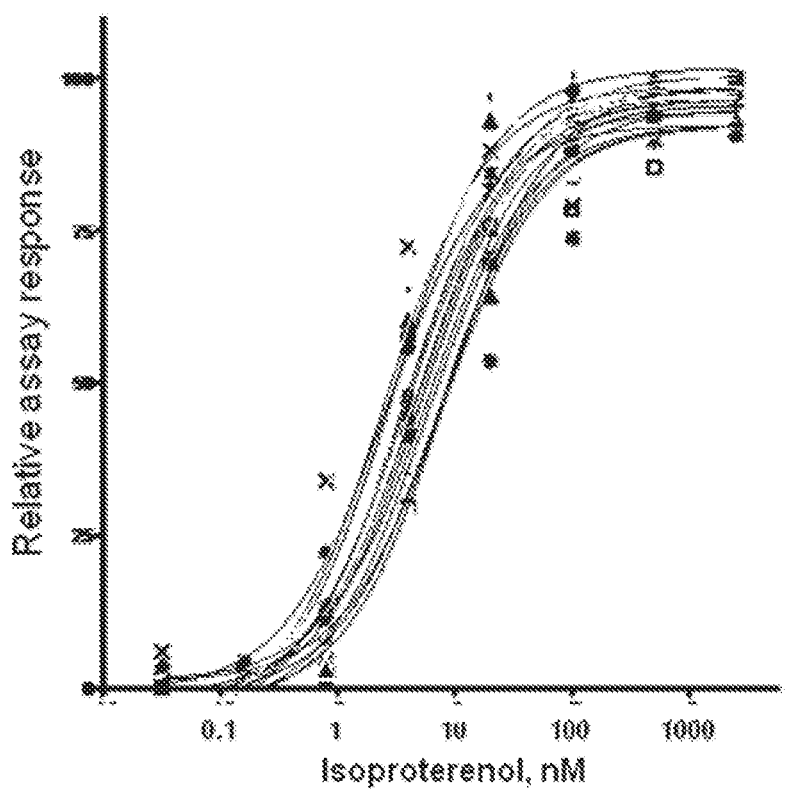
FIG. 1 demonstrates that the response of all twenty-five bitter cell lines to the endogenous receptor agonist isoproterenol is highly uniform across all lines. The percent response (Y-axis) was plotted as a function of isoproterenol concentration (X-axis), and the results were curve-fitted to calculate an $EC_{50}$ value (concentration of half-maximal receptor activation). For all twenty-five cell lines, the $EC_{50}$ value was approximately 4.9±0.41 nM.

In order that the invention described herein may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety for all purposes.

Throughout this specification, the word "comprise" or variations such as "comprises" or "comprising" will be understood to imply the inclusion of a stated integer or groups of integers but not the exclusion of any other integer or group of integers. Unless otherwise required by context, singular terms shall include pluralities and plural terms shall include the singular. The terms "or more" and "at least" are used interchangeably, herein. For example, "two or more" and "at least two" may be used interchangeably. Similarly, the terms "is less" or "is greater" are used interchangeably, herein. For example, "A is less than B" and "B is greater than A" may be used interchangeably.

The terms "agonist," "potentiator" or "activator" refer to a compound or substance that increases bitter taste receptor activity, resulting in a change in the amount or distribution of an intracellular molecule or the activity of an enzyme which is part of the intracellular signaling pathway for the bitter taste receptor. Examples of the intracellular molecule include, but are not limited to, free calcium, cyclic adenosine monophosphate (cAMP), inositol mono-, di- or triphosphate. Examples of the enzyme include, but are not limited to, adenylate cyclase, phospholipase-C, G-protein coupled receptor kinase.

The terms "antagonist," "inhibitor" or "blocker" refer to a compound or substance that decreases bitter taste receptor activity, resulting in a change in the amount or distribution of an intracellular molecule or the activity of an enzyme which is part of the intracellular signaling pathway for the bitter taste receptor. Examples of the intracellular molecule include, but are not limited to, free calcium, cyclic adenosine monophosphate (cAMP), inositol mono-, di- or triphosphate. Examples of the enzyme include, but are not limited to, adenylate cyclase, phospholipase-C, G-protein coupled receptor kinase. As used herein, an inhibitor, antagonist or blocker may act upon all or upon a specific subset of bitter taste receptors. The inhibitor, antagonist or blocker may decrease the activity of a TAS2R receptor by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99% or 100%.

The terms "artificial sweetener" and "sugar substitute" refer to a food additive that confers a sweet taste but has less caloric energy than sugar. In some instances, the caloric energy of the "artificial sweetener" or "sugar substitute" is negligible.

The term "bitter" or "bitter taste" as used herein refers to the perception or gustatory sensation resulting following the detection of a bitter tastant. The following attributes may contribute to bitter taste: astringent, bitter-astringent, metallic, bitter-metallic, as well as off-tastes, aftertastes and undesirable tastes including but not limited to freezer-burn and card-board taste, and/or any combinations of these. It is noted that, in the art, the term "off-taste" is often synonymous with "bitter taste." Without being limited by theory, the diversity of bitter tastes may reflect the large number of bitter taste receptors and the differential detection of bitter tastants by these receptors. Bitter taste as used herein includes activation of a bitter taste receptor by a bitter tastant. Bitter taste as used herein also includes activation of a bitter taste receptor by a bitter tastant followed by downstream signaling. Bitter taste as used herein also includes activation of a signaling pathway after stimulation by a bitter tastant. Bitter taste as used herein further includes perception resulting from signaling following the detection of a bitter tastant by a bitter taste receptor. Bitter taste as used herein further includes perception resulting from signaling following contacting a bitter taste receptor with a bitter tastant. Bitter taste can be perceived in the brain.

The term "bitter taste receptor" refers to a receptor, typically a cell surface receptor, to which a bitter tastant can bind. Bitter taste receptors may be present in the oral cavity, and/or extra-oral tissues, e.g., in taste-like, hormone producing cells throughout the gastrointestinal tract, including the stomach, intestines, and colon. Bitter receptors can also be present in vitro, such as in an assay, including but not limited to a cell based assay or a binding assay.

The term "bitter tastant," "bitter ligand," or "bitter compound" refers to a compound that activates or that can be detected by a bitter taste receptor and/or confers the perception of a bitter taste in a subject. A "bitter tastant" also refers to a multiplicity of compounds that combine to activate or be detected by a bitter taste receptor and/or confer the perception of a bitter taste in a subject. A "bitter tastant" further refers to a compound that is enzymatically modified upon ingestion by a subject to activate or be detected by a bitter taste receptor and/or confer the perception of a bitter taste in a subject. Because the perception of bitter taste may vary from individual to individual, some individuals may describe a "bitter tastant" as a compound which confers a different kind of bitter taste compared to the kind of bitter taste perceived for the same compound by other individuals. The term bitter tastant also refers to a compound which confers a bitter taste.

The term "cell line" or "clonal cell line" refers to a population of cells that are all progeny of a single original cell. As used herein, cell lines are maintained in vitro in cell culture and may be frozen in aliquots to establish banks of clonal cells.

The term "consumer product" refers to health and beauty products for the personal use and/or consumption by a subject. Consumer products may be present in any form including, but not limited to, liquids, solids, semi-solids, tablets, capsules, lozenges, strips, powders, gels, gums, pastes, slurries, syrups, aerosols and sprays. Non-limiting examples of consumer products include nutriceuticals, nutritional supplements, lipsticks, lip balms, soaps, shampoos, gums, adhesives (e.g., dental adhesives), toothpastes, oral analgesics, breath fresheners, mouthwashes, tooth whiteners, and other dentifrices.

The term "contacting" refers to any interaction between an antagonist, an agonist, a modulator, a tastant or a test compound with a polypeptide (e.g., a TAS2R receptor) or a host cell expressing a polypeptide, whereby any of the at least two components can be independently of each other in a liquid phase, for example in solution, or in suspension or can be bound to a solid phase, for example, in the form of an essentially planar surface or in the form of particles, pearls or the like. The polypeptide may be TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, or TAS2R60. Similarly, the host cell may express TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, TAS2R60, or a combination thereof.

The term "diet" collectively refers to the food products and/or beverages consumed by a subject. A subject's "diet" also includes any consumer products or pharmaceutical compositions the subject ingests.

The term "edible composition" refers to a composition suitable for consumption, typically via the oral cavity (although consumption may occur via non-oral means such as inhalation). Edible compositions may be present in any form including, but not limited to, liquids, solids, semi-solids, tablets, lozenges, powders, gels, gums, pastes, slurries, syrups, aerosols and sprays. As used herein, edible compositions include food products, pharmaceutical compositions, and consumer products. The term edible compositions also refers to, for example, dietary and nutritional supplements. As used herein, edible compositions also include compositions that are placed within the oral cavity but not swallowed, including professional dental products, such as dental treatments, fillings, packing materials, molds and polishes. The term "comestible" refers to similar compositions and is generally used as a synonym to the term "edible."

The term "effective amount" refers to an amount sufficient to produce a desired property or result. For example, an effective amount of a compound used in an assay of the present invention is an amount capable of reducing the perception of bitter taste associated with a bitter tastant. Typically, an effective amount of a compound used in an assay of the present invention is an amount capable of inhibiting the activation of a bitter taste receptor by a bitter tastant. Alternatively, an effective amount of a compound used in an assay of the present invention is an amount capable of activating a bitter taste receptor in the absence of another bitter tastant.

The term "flavor modifier" refers to a compound or a mixture of compounds that, when added to an edible composition, such as a food product, modifies (e.g., masks, eliminates, decreases, reduces, or enhances the perception of) a flavor (e.g., sweet, salty, umami, sour, or bitter taste) present in the edible composition.

The phrase "functional bitter taste receptor" refers to a bitter taste receptor that responds to a known activator or a known inhibitor in substantially the same way as the bitter taste receptor in a cell that normally expresses the bitter taste receptor without engineering. Bitter taste receptor behavior can be determined by, for example, physiological activities and pharmacological responses. Physiological activities include, but are not limited to, the sense of bitter taste. Pharmacological responses include, but are not limited to, a change in the amount or distribution of an intracellular molecule or the activity of an enzyme which is part of the intracellular signaling pathway for the bitter taste receptor when a bitter taste receptor is contacted with a modulator. For example, a pharmacological response may include an increase in intracellular free calcium when the bitter taste receptor is activated, or a decrease in intracellular free calcium when the bitter taste receptor is blocked.

The term "modulator" refers to a compound or substance that alters the structure, conformation, biochemical or biophysical properties or functionality of a bitter taste receptor, either positively or negatively. The modulator can be a bitter taste receptor agonist (potentiator or activator) or antagonist (inhibitor or blocker), including partial agonists or antagonists, selective agonists or antagonists and inverse agonists, and can be an allosteric modulator. A substance or compound is a modulator even if its modulating activity changes under different conditions or concentrations or with respect to different forms of bitter taste receptors, e.g., naturally occurring form vs. mutant form, and different naturally-occurring allelic variants of a bitter taste receptor (e.g., due to polymorphism). As used herein, a modulator may affect the activity of a bitter taste receptor, the response of a bitter taste receptor to another regulatory compound or the selectivity of a bitter taste receptor. A modulator may also change the ability of another modulator to affect the function of a bitter taste receptor. A modulator may act upon all or upon a specific subset of bitter taste receptors. Modulators include, but are not limited to, potentiators, activators, inhibitors, agonists, antagonists and blockers.

As used herein, the term "native" protein (e.g., bitter taste receptor) refers to a protein that does not have a heterologous amino acid sequence appended or inserted to it. For example, "native bitter taste receptor" used herein includes bitter taste receptors that do not have a tag sequence that is expressed on the polypeptide level. By referring to bitter taste receptors as native, applicants do not intend to exclude bitter taste receptor variants that comprise an amino acid substitution, mutation or deletion, or variants that are fragments or spliced forms of naturally occurring, or previously known receptor proteins.

The term "off-target effects" refers to the unintended modulation, activation or inhibition of an untargeted taste receptor. For example, a bitter taste modulator exhibits off-target effects if it is intended to modulate the activity of a particular subset of bitter taste receptors, and it also modulates other bitter taste receptors or the activity of other taste receptors, such as sweet taste receptors and umami taste receptors. Similarly, if a taste modulator is intended to modulate the bitter taste due to a bitter tastant, the taste modulator exhibits off-target effects if it modulates the taste due to another tastant or if it confers a taste on its own. Off-target effects of bitter taste modulators can result in the activation or inhibition of salty, sweet, sour, umami and/or other bitter tastes.

The terms "parts per million" and "ppm" are used in the food industry to refer to a low concentration of a solution. For example, one gram of solute in 1000 ml of solvent has a concentration of 1000 ppm and one thousandth of a gram (0.001 g) of solute in 1000 ml of solvent has a concentration of one ppm. Accordingly, a concentration of one milligram per liter (i.e. 1 mg/L) is equal to 1 ppm.

The phrase "percent identical" or "percent identity" in connection with amino acid and/or nucleic acid sequences refers to the similarity between at least two different sequences. This percent identity can be determined by standard alignment algorithms, for example, the Basic Local Alignment Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) that has been incorporated into the ALIGN program (version 2.0), using a PAM120 weight residue table, a gap length penalty of 12 and a gap penalty of 4. The percent identity is usually calculated by comparing sequences of similar length. Protein analysis software matches similar sequences using measures of similarity assigned to various substitutions, deletions and other modifications, including conservative amino acid substitutions. For instance, the GCG Wisconsin Package (Accelrys, Inc.) contains programs such as "Gap" and "Bestfit" that can be used with default parameters to determine sequence identity between closely related polypeptides, such as homologous polypeptides from different species of organisms or between a wild type protein and a mutation thereof. See, e.g., GCG Version 6.1. Polypeptide sequences also can be compared using FASTA using default or recommended parameters. A program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). The length of polypeptide sequences compared for identity will generally be at least about 16 amino acid residues, usually at least about 20 residues, more usually at least about 24 residues, typically at least about 28 residues, and preferably more than about 35 residues. The length of a DNA sequence compared for identity will generally be at least about 48 nucleic acid residues, usually at least about 60 nucleic acid residues, more usually at least about 72 nucleic acid residues, typically at least about 84 nucleic acid residues, and preferably more than about 105 nucleic acid residues.

The terms "perception of a bitter taste," "perception of saltiness," "perception of a flavor" and similar terms, refer to the awareness of a subject of a particular taste or flavor.

The term "selective bitter taste modulator" refers to a compound that modulates the bitter taste due to a specific bitter tastant without modulating any other tastants or conferring its own taste. For example, a compound that selectively inhibits bitter taste due to KCl decreases bitter taste due to KCl without increasing or decreasing the taste due to another tastant, including other bitter tastants. In some embodiments selective bitter taste modulators are agonists or antagonists for a particular bitter taste receptor or a particular subset of bitter taste receptors. For example, a compound that selectively inhibits bitter taste due to KCl antagonizes the bitter taste receptor activity of one or more of TAS2R4, TAS2R9, TAS2R13, TAS2R14, TAS2R44 and TAS2R60 without activating or inhibiting any other taste receptor, including other bitter taste receptors.

The term "stable" or "stably expressing" is meant to distinguish the cells and cell lines of the invention from cells with transient expression as the terms "stable expression" and "transient expression" would be understood by a person of skill in the art.

The term "stringent conditions" or "stringent hybridization conditions" describe temperature and salt conditions for hybridizing one or more nucleic acid probes to a nucleic acid sample and washing off probes that have not bound specifically to target nucleic acids in the sample. Stringent conditions are known to those skilled in the art and can be found in Current Protocols in Molecular Biology, John Wiley & Sons, N.Y. (1989), 6.3.1-6.3.6. Aqueous and nonaqueous methods are described in that reference and either can be used. An example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. Stringent conditions include hybridization in 0.5M sodium phosphate, 7% SDS at 65° C., followed by at least one wash at 0.2×SSC, 1% SDS at 65° C.

The term "subject" refers to a mammal. In preferred embodiments, the subject is human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

The term "sweet flavor" refers to the taste elicited by, for example, sugars. Non-limiting examples of compositions eliciting a sweet flavor include glucose, sucrose, fructose, saccharin, cyclamate, aspartame, Acesulfame potassium, sucralose, alitame, and neotame. The amount of sweet flavor or the sweetness of a composition can be determined by, e.g., taste testing.

The term "universal bitter compound" refers to a compound that activates all twenty-five bitter taste receptors. Non-limiting examples of universal bitter compounds include denatonium benzoate and denatonium saccharide.

The present invention provides assays for identifying compounds that modulate bitter taste. For example, the present invention provides methods of identifying compounds that inhibit the bitter taste due to KCl, potassium lactate or Acesulfame K. The present invention also provides methods of identifying compounds that selectively inhibit the bitter taste due to KCl, potassium lactate, or Acesulfame K. The present invention further provides methods of identifying compounds that mimic the bitter taste due to KCl, potassium lactate, or Acesulfame K. The present invention also provides methods of identifying compounds that enhance the bitter taste due to KCl, potassium lactate or Acesulfame K. The present invention additionally provides methods for determining if KCl, potassium lactate or Acesulfame K are present in a composition.

Cells and Cell Lines Expressing Bitter Taste Receptors

The present invention relates to in vitro assays utilizing cells and cell lines that express or have been engineered to express one or more bitter taste receptors. In some embodiments, the cells or cell lines of the invention express one or more functional bitter taste receptors.

According to one embodiment of the invention, the cells and cell lines are transfected with a nucleic acid encoding a bitter taste receptor. In other embodiments, the cells and cell lines endogenously express a bitter taste receptor. In some embodiments the cells and cell lines are transfected with a nucleic acid encoding an allelic variant (i.e., a polymorphism) of a bitter taste receptor, or a mutant bitter taste receptor. The cell lines of the invention may stably express the introduced bitter taste receptor. In another embodiment, the cells and cell lines have a bitter taste receptor activated for expression by gene activation. In some embodiments, the bitter taste receptor is a native bitter taste receptor.

In a particular embodiment, the cells and cell lines express an endogenous bitter taste receptor as a result of engineered gene activation, i.e., activation of the expression of an endogenous gene, wherein the activation does not naturally occur in a cell without proper treatment. Engineered gene activation may turn on the expression of an endogenous bitter taste receptor, for example, where the endogenous bitter taste receptor is not expressed in the cell line without the proper treatment. Alternatively, engineered gene activation may result in increased expression level of the endogenous bitter taste receptor, for example, where the expression level of the endogenous gene in the cell line is undesirably low without the proper treatment, for example, not sufficient for functional assay of the bitter taste receptor in the cell line. Alternatively, engineered gene activation may be used to over-express an endogenous bitter taste receptor, for example, for isolating the endogenous bitter taste receptor from the cell line. Engineered gene activation can be achieved by a number of means known to those skilled in the art. For example, one or more transcription factors or transactivators of transcription of a gene can be over-expressed or induced to express by, e.g., introducing nucleic acids expressing the transcription factors or transactivators into a cell under the control of a constitutive or inducible promoter. If the endogenous gene is known to be under the control of an inducible promoter, expression can be induced by exposing the cell to a known inducer of the gene. In addition, a nucleic acid encoding the endogenous gene itself can be introduced into a cell to obtain an increased level of expression of the gene due to increased copy number in the genome. Furthermore, certain known inhibitors of the expression of an endogenous gene that are expressed by the cell can be knocked down or even knocked out in the cell using techniques well known in the art, e.g., RNAi, thereby increasing the expression of the endogenous gene.

In some embodiments, cells and cell lines stably express one or more bitter taste receptors. In some embodiments, the expressed bitter taste receptors increase intracellular free calcium upon activation by an agonist. In some embodiments, a potentiator, agonist or activator can be a small molecule, a chemical moiety, a polypeptide, an antibody, or a food extract. In other embodiments, the expressed bitter taste receptors decrease intracellular free calcium upon inhibition by an antagonist. In some embodiments, an inhibitor, antagonist or blocker can be a small molecule, a chemical moiety, a polypeptide, an antibody, or a food extract. A potentiator, agonist, activator, inhibitor, antagonist or blocker may act upon all or upon a specific subset of bitter taste receptors.

According to the invention, the bitter taste receptor expressed by a cell or cell line can be from any mammal, including rat, mouse, rabbit, goat, dog, cow, pig or primate. In a preferred embodiment, the bitter taste receptor is human bitter taste receptor.

In some embodiments, a cell or cell line of the invention may comprise: a nucleotide sequence (SEQ ID NO:2) that encodes a human TAS2R1; a nucleotide sequence (SEQ ID NO:3) that encodes a human TAS2R3; a nucleotide sequence (SEQ ID NO:4) that encodes a human TAS2R4; a nucleotide sequence (SEQ ID NO:5) that encodes a human TAS2R5; a nucleotide sequence (SEQ ID NO:6) that encodes a human TAS2R7; a nucleotide sequence (SEQ ID NO:7) that encodes a human TAS2R8; a nucleotide sequence (SEQ ID NO:8) that encodes a human TAS2R9; a nucleotide sequence (SEQ ID NO:9) that encodes a human TAS2R10; a nucleotide sequence (SEQ ID NO:10) that encodes a human TAS2R13; a nucleotide sequence (SEQ ID NO:11) that encodes a human TAS2R14; a nucleotide sequence (SEQ ID NO:12) that encodes a human TAS2R16; a nucleotide sequence (SEQ ID NO:13) that encodes a human TAS2R38; a nucleotide sequence (SEQ ID NO:14) that encodes a human TAS2R39; a nucleotide sequence (SEQ ID NO:15) that encodes a human TAS2R40; a nucleotide sequence (SEQ ID NO:16) that encodes a human TAS2R41; a nucleotide sequence (SEQ ID NO:17) that encodes a human TAS2R43; a nucleotide sequence (SEQ ID NO:18) that encodes a human TAS2R44; a nucleotide sequence (SEQ ID NO:19) that encodes a human TAS2R45; a nucleotide sequence (SEQ ID NO:20) that encodes a human TAS2R46; a nucleotide sequence (SEQ ID NO:21) that encodes a human TAS2R47; a nucleotide sequence (SEQ ID NO:22) that encodes a human TAS2R48; a nucleotide sequence (SEQ ID NO:23) that encodes a human TAS2R49; a nucleotide sequence (SEQ ID NO:24) that encodes a human TAS2R50; a nucleotide sequence (SEQ ID NO:25) that encodes a human TAS2R55; a nucleotide sequence (SEQ ID NO:26) that encodes a human TAS2R60; or any combination thereof. In some embodiments, the cell or cell line comprises a nucleotide sequence selected from the group consisting of a nucleotide sequence having 80%, 85%, 90%, 95%, 98%, or 99% sequence identity to any one of SEQ ID NOs: 2-26. In some embodiments, the cell or cell line comprises a nucleotide sequence selected from the group consisting of a nucleotide sequence having 95% sequence identity to any one of SEQ ID NOs: 2-26. In some embodiments, the cell or cell line comprises a nucleotide sequence selected from the group consisting of a nucleotide sequence having 80%, 85%, 90%, 95%, 98%, or 99% sequence identity to any one of SEQ ID NOs: 2-26, wherein the nucleotide sequence encodes a polypeptide having TAS2R activity. In some embodiments, the cell or cell line comprises a nucleotide sequence selected from the group consisting of a nucleotide sequence having 95% sequence identity to any one of SEQ ID NOs: 2-26, wherein the nucleotide sequence encodes a polypeptide having TAS2R activity. In some embodiments, the cell or cell line comprises a nucleotide sequence selected from the group consisting of a nucleotide sequence that hybridizes under stringent conditions to any one of SEQ ID NOs: 2-26. In some embodiments, the cell or cell line comprises a nucleotide sequence selected from the group consisting of a nucleotide sequence that comprises the mature form of any one of SEQ ID NOs: 2-26. In some embodiments, the cell or cell line comprises a nucleotide sequence selected from the group consisting of a nucleotide sequence that is a variant of any one of SEQ ID NOs: 2-26. In some embodiments, the cell or cell line comprises a nucleotide sequence selected from the group consisting of a nucleotide sequence that is a fragment of any one of SEQ ID NOs: 2-26. In some embodiments, the cell or cell line comprises a nucleotide sequence selected from the group consisting of a nucleotide sequence proteolytic cleavage product of any one of SEQ ID NOs: 2-26. In some embodiments, the cell or cell line comprises a nucleotide sequence selected from the group consisting of a nucleotide sequence that is an ortholog of any one of SEQ ID NOs: 2-26. Such orthologs are well-known in the art. In some embodiments, the nucleotide sequence has five or fewer, four or fewer, three or fewer, two or fewer, or one or fewer conservative substitutions compared to any one of SEQ ID NO: 2-26.

In some embodiments, a cell or cell line of the invention may comprise a polynucleotide sequence encoding human TAS2R1 (SEQ ID NO: 28); human TAS2R3 (SEQ ID NO:29); human TAS2R4 (SEQ ID NO: 30); human TAS2R5 (SEQ ID NO:31); human TAS2R7 (SEQ ID NO:32); human TAS2R8 (SEQ ID NO:33); human TAS2R9 (SEQ ID NO:34); human TAS2R10 (SEQ ID NO:35); human TAS2R13 (SEQ ID NO:36); human TAS2R14 (SEQ ID NO:37); human TAS2R16 (SEQ ID NO:38); human TAS2R38 (SEQ ID NO:39); human TAS2R39 (SEQ ID NO:40); human TAS2R40 (SEQ ID NO:41); human TAS2R41 (SEQ ID NO:42); human TAS2R43 (SEQ ID NO:43); human TAS2R44 (SEQ ID NO:44); human TAS2R45 (SEQ ID NO:45); human TAS2R46 (SEQ ID NO:46); human TAS2R47 (SEQ ID NO:47); human TAS2R48 (SEQ ID NO:48); human TAS2R49 (SEQ ID NO:49); human TAS2R50 (SEQ ID NO:50); human TAS2R55 (SEQ ID NO:51); human TAS2R60 (SEQ ID NO:52); or any combination thereof. In some embodiments, the cell or cell line comprises a nucleotide sequence selected from the group consisting of a nucleotide sequence having 80%, 85%, 90%, 95%, 98%, or 99% sequence identity to the nucleotide sequence encoding any one of SEQ ID NOs: 28-52. In some embodiments, the cell or cell line comprises a nucleotide sequence selected from the group consisting of a nucleotide sequence having 95% sequence identity to the nucleotide sequence encoding any one of SEQ ID NOs: 28-52. In some embodiments, the cell or cell line comprises a nucleotide sequence selected from the group consisting of a nucleotide sequence having 80%, 85%, 90%, 95%, 98%, or 99% sequence identity to the nucleotide sequence encoding any one of SEQ ID NOs: 28-52, wherein the nucleotide sequence encodes a polypeptide having TAS2R activity. In some embodiments, the cell or cell line comprises a nucleotide sequence selected from the group consisting of a nucleotide sequence having 95% sequence identity to the nucleotide sequence encoding any one of SEQ ID NOs: 28-52, wherein the nucleotide sequence encodes a polypeptide having TAS2R activity. In some embodiments, the cell or cell line comprises a nucleotide sequence selected from the group consisting of a nucleotide sequence that hybridizes under stringent conditions to the nucleotide sequence encoding any one of SEQ ID NOs: 28-52. In some embodiments, the cell or cell line comprises a nucleotide sequence selected from the group consisting of a nucleotide sequence that encodes the mature form of any one of SEQ ID NOs: 28-52. In some embodiments, the cell or cell line comprises a nucleotide sequence selected from the group consisting of a nucleotide sequence that is a variant of the nucleotide sequence encoding any one of SEQ ID NOs: 28-52. In some embodiments, the cell or cell line comprises a nucleotide sequence selected from the group consisting of a nucleotide sequence that is a fragment of the nucleotide sequence encoding any one of SEQ ID NOs: 28-52. In some embodiments, the cell or cell line comprises a nucleotide sequence selected from the group consisting of a nucleotide sequence proteolytic cleavage product of the nucleotide sequence encoding any one of SEQ ID NOs: 28-52. In some embodiments, the cell or cell line comprises a nucleotide sequence selected from the group consisting of a nucleotide sequence that is an ortholog of the nucleotide sequence encoding any one of SEQ ID NOs: 28-52. Such orthologs are well-known in the art. In some embodiments, the nucleotide sequence encodes a TAS2R receptor that has five or fewer, four or fewer, three or fewer, two or fewer, or one or fewer conservative amino acid substitutions compared to any one of SEQ ID NO: 28-52.

In some embodiments, a cell or cell line of the invention may comprise a human TAS2R1 (SEQ ID NO: 28); human TAS2R3 (SEQ ID NO:29); human TAS2R4 (SEQ ID NO: 30); human TAS2R5 (SEQ ID NO:31); human TAS2R7 (SEQ ID NO:32); human TAS2R8 (SEQ ID NO:33); human TAS2R9 (SEQ ID NO:34); human TAS2R10 (SEQ ID NO:35); human TAS2R13 (SEQ ID NO:36); human TAS2R14 (SEQ ID NO:37); human TAS2R16 (SEQ ID NO:38); human TAS2R38 (SEQ ID NO:39); human TAS2R39 (SEQ ID NO:40); human TAS2R40 (SEQ ID NO:41); human TAS2R41 (SEQ ID NO:42); human TAS2R43 (SEQ ID NO:43); human TAS2R44 (SEQ ID NO:44); human TAS2R45 (SEQ ID NO:45); human TAS2R46 (SEQ ID NO:46); human TAS2R47 (SEQ ID NO:47); human TAS2R48 (SEQ ID NO:48); human TAS2R49 (SEQ ID NO:49); human TAS2R50 (SEQ ID NO:50); human TAS2R55 (SEQ ID NO:51); human TAS2R60 (SEQ ID NO:52); or any combination thereof. In some embodiments, the cell or cell line comprises a TAS2R receptor selected from the group consisting of an amino acid sequence having 80%, 85%, 90%, 95%, 98% or 99% sequence identity to any one of SEQ ID NOs: 28-52. In some embodiments, the cell or cell line comprises a TAS2R receptor selected from the group consisting of an amino acid sequence having 95% sequence identity to any one of SEQ ID NOs: 28-52. In some embodiments, the cell or cell line comprises a TAS2R receptor selected from the group consisting of an amino acid sequence having 80%, 85%, 90%, 95%, 98% or 99% sequence identity to any one of SEQ ID NOs: 28-52, wherein the TAS2R receptor has TAS2R receptor activity. In some embodiments, the cell or cell line comprises a TAS2R receptor selected from the group consisting of an amino acid sequence having 95% sequence identity to any one of SEQ ID NOs: 28-52, wherein the TAS2R receptor has TAS2R receptor activity. In some embodiments, the cell or cell line comprises a TAS2R receptor selected from the group consisting of the mature form of any one of SEQ ID NOs: 28-52. In some embodiments, the cell or cell line comprises a TAS2R receptor selected from the group consisting of a variant of any one of SEQ ID NOs: 28-52. In some embodiments, the cell or cell line comprises a TAS2R receptor selected from the group consisting of a fragment of any one of SEQ ID NOs: 28-52. In some embodiments, the cell or cell line comprises a TAS2R receptor selected from the group consisting of a proteolytic cleavage product of any one of SEQ ID NOs: 28-52. In some embodiments, the cell or cell line comprises a TAS2R receptor selected from the group consisting of an ortholog of any one of SEQ ID NOs: 28-52. Such orthologs are well-known in the art. In some embodiments, the TAS2R receptor has five or fewer, four or fewer, three or fewer, two or fewer, or one or fewer conservative amino acid substitutions compared to any one of SEQ ID NO: 28-52.

Nucleic acids encoding bitter taste receptors can be DNA, synthetic DNA, genomic DNA cDNA, RNA, double-stranded DNA, or single-stranded DNA. In some embodiments, the nucleic acids comprise one or more mutations, as compared to the nucleic acid sequences encoding wild type bitter taste receptors, that may or may not result in an amino acid substitution. In some other embodiments, the nucleic acids comprise one or more naturally-occurring allelic variants, as compared to the most frequently occurring nucleic acid sequences encoding a certain bitter taste receptor in a given population. Naturally-occurring allelic variants include different amino acid sequences of a same bitter taste receptor that are naturally-occurring, e.g., those observed in a given population due to allelic variation or polymorphism. In some embodiments, the nucleic acid encoding the bitter taste receptor is a fragment. In some embodiments the fragment encodes a polypeptide that has TAS2R activity. In some embodiments, the fragment comprises at least 30, at least 40, at least 50, at least 60, at least 80, at least 100, at least 125, at least 150, at least 175, at least 200, at least 250, at least 300, at least 400, at least 500, at least 600, at least 700, at least 800, at least 850, or at least 900 nucleotides of SEQ ID NO: 2-26.

Polymorphism is a common phenomenon in the human genome. Polymorphisms occurring within or near the bitter taste receptor genes may affect their expression or change their function by, e.g., up-regulating or down-regulating their expression levels or by changing their amino acid sequences. Appendix Table 1 shows reference numbers for unique polymorphisms, including single nucleotide polymorphisms ("SNPs") related to human TAS2R genes, position of the SNPs in each reference sequence, and description of the SNPs. The reference numbers are searchable in the Single Nucleotide Polymorphism database ("dbSNP") of the National Center for Biotechnology Information ("NCBI"; Bethesda, Md.).

Allelic variations of human bitter taste receptor genes resulting in coding sequence diversity have been studied and documented. See, e.g., Ueda et al., "Identification of coding single-nucleotide polymorphisms in human taste receptor genes involving bitter tasting", Biochem Biophys Res Commun 285:147-151, 2001; Wooding et al., "Natural selection and molecular evolution in PTC, a bitter-taste receptor gene," Am. J. Hum, Genet. 74:637-646, 2004; and Kim et al., "Worldwide haplotype diversity and coding sequence variation at human bitter taste receptor loci", Human Mutation 26:199-204, 2005. Appendix Table 2 is a list of natural variations in the coding sequences of different human bitter taste receptors. The human bitter taste receptors, SEQ ID NOS of their coding sequences, and the protein sequences are listed in the first three columns. The nucleotide changes and their positions within each coding sequence as identified by their SEQ ID NOS are indicated in the columns under "Nucleotide change" and "Position of nucleotide change," respectively. The amino acid changes within each bitter taste receptor as identified by their SEQ ID NOS are indicated in the column under "Description" using single-letter abbreviations. Their positions with reference to each corresponding SEQ ID NO are indicated in the column under "Position of amino acid change." In addition, the "Description" column also contains identifiers of those variations that are searchable in dbSNP of NCBI. "Feature identifiers" are unique and stable feature identifiers assigned to some of the variations by the UniProt Protein Knowledgebase hosted by the European Bioinformatics Institute (Cambridge, United Kingdom). They are searchable within UniProt. "NA" denotes no feature identifiers assigned by UniProt yet.

Variation in human taste is a well-known phenomenon. Without wishing to be bound by theory, the variation of bitter taste may be related to polymorphisms of the bitter taste receptors. For example, polymorphisms in the hTAS2R38, a receptor for phenylthiocarbamide (PTC), has been linked to the ability to detect propylthiouracil (PROP) (Kim et al., "Positional cloning of the human quantitative trait locus underlying taste sensitivity to phenylthiocarbamide", Science 299:1221-1225, 2003; Wooding et al., 2004). There are three common polymorphisms in the TAS2R38 gene-A49P, V262A, and 1296V-which combine to form two common haplotypes and several other very rare haplotypes. The two common haplotypes are AVI (often called "nontaster") and PAV (often called "taster"). Varying combinations of these haplotypes will yield homozygotes-PAV/PAV and AVI/AVI- and heterozygote PAV/AVI. These genotypes can account for up to 85% of the variation in PTC tasting ability: people possessing two copies of the PAV polymorphism report PTC to be bitterer than TAS2R38 heterozygotes, and people possessing two copies of the AVI/AVI polymorphism often report PTC as being essentially tasteless. These polymorphisms are hypothesized to affect taste by altering G-protein-binding domains. In some embodiments, a cell or cell line of the invention may comprise a polynucleotide sequence encoding human PAV TAS2R38 (SEQ ID NO: 54). In some embodiments, a cell or cell line of the invention may comprise a human PAV TAS2R38 (SEQ ID NO: 54).

Additionally, a subset of the population, who are very sensitive to the bitterness of the natural plant compounds aloin and aristolochic acid, have inherited certain polymorphisms in the hTAS2R43 gene. People who do not possess this allele do not taste these compounds at low concentrations. The hTAS2R43 sensitivity allele also makes people more sensitive to the bitterness of saccharin. Further, certain hTAS2R44 alleles, which are closely related to hTAS2R43 sensitivity alleles, also make people more sensitive to the bitterness of saccharin. Some subsets of the population do not possess certain hTAS2R genes, contributing to taste variation between individuals. Polymorphisms in bitter genes have also been linked to increased risk of disease, e.g., diabetes (TAS2R9) and alcoholism (TAS2R16). Assays utilizing cells and cell lines stably expressing a heterologous naturally-occurring bitter taste receptor, or an allelic variant or polymorph thereof, or a mutant form thereof having one or more mutations (e.g., random mutations or site-specific mutations) that are not naturally-occurring, are all within the scope of the present invention.

The cells and cell lines comprising a bitter taste receptor, a mutant form thereof, or a naturally-occurring allelic variant thereof, can be used to identify modulators of bitter taste receptor function, including modulators that are specific for a particular bitter taste receptor mutant form or naturally-occurring allelic variant. The cells and cell lines can thus be used to obtain information about the properties, activities and roles of individual native or mutant forms or naturally-occurring allelic variants of bitter taste receptors and to identify bitter taste receptor modulators with activity for a particular native or mutant form or naturally-occurring allelic variant or for a subset of native or mutant forms or naturally-occurring allelic variants. These modulators are useful as therapeutics that target differentially modified bitter taste receptor forms in disease states or tissues. Because the polymorphism of bitter taste receptors in vivo, for example, may contribute to an undesired activity or disease state, cells and cell lines of this invention also can be used to screen for modulators for therapeutic use where alteration of the response of a mutant form or naturally-occurring allelic variant may be desired. The cells and cell lines are also useful to identify modulators that have activity with only subset of native or mutant forms or naturally-occurring allelic variants of a bitter taste receptor.

Host cells used to produce a cell or cell line may express in their native state one or more endogenous bitter taste receptor or lack expression of any bitter taste receptor. In the case where the cell or cell line expresses one or more of its own bitter taste receptors, also referred to as "endogenous" bitter taste receptors, the heterologous bitter taste receptor can be the same as one of the cell or cell line's endogenous bitter taste receptor(s). For example, a nucleic acid encoding an bitter taste receptor endogenous to a cell or cell line may be introduced into the cell or the cell line to increase the copy number of the gene encoding the bitter taste receptor in the cell or the cell line so that the bitter taste receptor is expressed at a higher level in the cell or cell line than without the introduced nucleic acid. The host cell may be a primary, germ, or stem cell, including an embryonic stem cell. The host cell may also be an immortalized cell. Primary or immortalized host cells may be derived from mesoderm, ectoderm or endoderm layers of eukaryotic organisms. The host cell may be endothelial, epidermal, mesenchymal, neural, renal, hepatic, hematopoietic, or immune cells. For example, the host cells may be intestinal crypt or villi cells, clara cells, colon cells, intestinal cells, goblet cells, enterochromafin cells, enteroendocrine cells. The host cells may be eukaryotic, prokaryotic, mammalian, human, primate, bovine, porcine, feline, rodent, marsupial, murine or other cells. The host cells may also be non-mammalian, such as yeast, insect, fungus, plant, lower eukaryotes and prokaryotes. Such host cells may provide backgrounds that are more divergent for testing bitter taste receptor modulators with a greater likelihood for the absence of expression products provided by the cell that may interact with the target. In preferred embodiments, the host cell is a mammalian cell. Examples of host cells that may be used to produce a cell or cell line of the invention include but are not limited to: human embryonic kidney 293T cells, established neuronal cell lines, pheochromocytomas, neuroblastomas fibroblasts, rhabdomyosarcomas, dorsal root ganglion cells, NSO cells, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171), L-cells, HEK-293 (ATCC CRL1573) and PC12 (ATCC CRL-1721), HEK293T (ATCC CRL-11268), RBL (ATCC CRL-1378), SH-SY5Y (ATCC CRL-2266), MDCK (ATCC CCL-34), SJ-RH30 (ATCC CRL-2061), HepG2 (ATCC HB-8065), ND7/23 (ECACC 92090903), CHO (ECACC 85050302), Vero (ATCC CCL 81), Caco-2 (ATCC HTB 37), K562 (ATCC CCL 243), Jurkat (ATCC TIB-152), Per.C6 (Crucell, Leiden, The Netherlands), Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), T84 (ATCC CCL 248), or any established cell line (polarized or nonpolarized) or any cell line available from repositories such as American Type Culture Collection (ATCC, 10801 University Blvd. Manassas, Va. 20110-2209 USA) or European Collection of Cell Cultures (ECACC, Salisbury Wiltshire SP4 0JG England).

As will be appreciated by those of skill in the art, any vector that is suitable for use with the host cell may be used to introduce a nucleic acid encoding a TAS2R receptor into the host cell. The vectors comprising the various TAS2R receptors may be the same type or may be of different types. Examples of vectors that may be used to introduce the TAS2R receptor encoding nucleic acids into host cells include but are not limited to plasmids, viruses, including retroviruses and lentiviruses, cosmids, artificial chromosomes and may include for example, Pcmv-Script, pcDNA3.1 Hygro, pcDNA3.1neo, pcDNA3.1puro, pSV2neo, pIRES puro, pSV2 zeo, pFN11A (BIND) Flexi®, pGL4.31, pFC14A (HaloTag® 7) CMV Flexi®, pFC14K (HaloTag® 7) CMV Flexi®, pFN24A (HaloTag® 7) CMVd3 Flexi®, pFN24K (HaloTag® 7) CMVd3 Flexi®, HaloTag™ pHT2, pACT, pAdVAntage™, pALTER®-MAX, pBIND, pCAT®3-Basic, pCAT®3-Control, pCAT®3-Enhancer, pCAT®3-Promoter, pCI, pCMVTNT™, pG5luc, pSI, pTARGET™, pTNT™, pF12A RM Flexi®, pF12K RM Flexi®, pReg neo, pYES2/GS, pAd/CMV/V5-DEST Gateway® Vector, pAd/PL-DEST™ Gateway®, Vector, Gateway®, pDEST™, 27 Vector, Gateway®, pEF-DEST51 Vector, Gateway®, pcDNA™-DEST47 vector, pCMV/Bsd Vector, pEF6/His A, B, & c, pcDNA™6.2-DEST, pLenti6/TR, pLP-AcGFP1-C, pLPS-AcGFP1-N, pLP-IRESneo, pLP-TRE2, pLP-RevTRE, pLP-LNCX, pLP-CMV-HA, pLP-CMV-Myc, pLP-RetroQ, pLP-CMVneo. In some embodiments, the vectors comprise expression control sequences such as constitutive or conditional promoters. One of ordinary skill in the art will be able to select the appropriate sequences. For example, suitable promoters include but are not limited to CMV, TK, SV40 and EF-1α. In some embodiments, the promoters are inducible, temperature regulated, tissue specific, repressible, heat-shock, developmental, cell lineage specific, eukaryotic, prokaryotic or temporal promoters or a combination or recombination of unmodified or mutagenized, randomized, shuffled sequences of any one or more of the above. In other embodiments, TAS2R receptors are expressed by gene activation, wherein an exogenous promoter is inserted in a host cell's genome by homologous recombination to drive expression of a TAS2R receptor gene that is not normally expressed in that host cell. In some embodiments the gene encoding a TAS2R receptor is episomal. Nucleic acids encoding TAS2R receptor are preferably constitutively expressed.

Nucleic acids comprising a sequence encoding a TAS2 receptor, or the sequence of a component of the TAS2R signaling pathway, and optionally a nucleic acid encoding a selectable marker may be introduced into selected host cells by well known methods. The methods include but not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery. Examples of transfection reagents are GENEPORTER, GENEPORTER2, LIPOFECTAMINE, LIPOFECTAMINE 2000, FUGENE 6, FUGENE HD, TFX-10, TFX-20, TFX-50, OLIGOFECTAMINE, TRANSFAST, TRANSFECTAM, GENESHUTTLE, TROJENE, GENESILENCER, X-TREMEGENE, PERFECTIN, CYTOFECTIN, SIPORT, UNIFECTOR, SIFECTOR, TRANSIT-LT1, TRANSIT-LT2, TRANSIT-EXPRESS, IFECT, RNAI SHUTTLE, METAFECTENE, LYOVEC, LIPOTAXI, GENEERASER, GENEJUICE, CYTOPURE, JETSI, JET-PEI, MEGAFECTIN, POLYFECT, TRANSMESSANGER, RNAiFECT, SUPERFECT, EFFECTENE, TF-PEI-KIT, CLONFECTIN, AND METAFECTINE.

In another aspect, cells and cell lines expresses a G protein. There are two families of G proteins, heterotrimeric G proteins and monomeric G proteins. Heterotrimeric G proteins are activated by G protein coupled receptors ("GPCRs"), and include three subunits: $G_\alpha$, $G_\beta$ and $G_\gamma$. As used herein, the term G protein includes any one of these subunits, for example a $G_\alpha$, or any combination thereof, as well as a heterotrimeric G protein with all three subunits. In the inactive state, $G_\alpha$, $G_\beta$ and $G_\gamma$ form a trimer. The β and γ subunits are closely bound to one another and are referred to as the beta-gamma complex. $G_\alpha$ separates from $G_{\beta\gamma}$ after ligand binding to the GPCR. The $G_{\beta\gamma}$ complex is released from the $G_a$, subunit after its GDP-GTP exchange. The $G_{\beta\gamma}$ complex can activate other second messengers or gate ion channels. The four families of G alpha include: $G_\beta$ (stimulatory) which increase cAMP synthesis by activating adenylate cyclase; $G_i$ (inhibitory) that inhibits adenylate cyclase; the $G_{12/13}$ family regulates various cell movement processes (i.e. cytoskeleton, cell junctions); and $G_q$, which stimulates calcium signaling and phospholipase C. The monomeric G proteins are homologous to the a subunit of the heterotrimeric G proteins. Any G protein may be expressed in the cells or cell lines of the invention, including, but not limited to, transducin (e.g., GNAT1, GNAT2, and guanine nucleotide-binding protein G(t)), gustducin (e.g., GNAT3 guanine nucleotide binding protein and α transducin 3), human GNA15 (guanine nucleotide binding protein (G protein) α15 (Gq class; synonym GNA16) and mouse Gα15, and their chimera proteins, e.g. Gα15-GNA15 (also known as Gα15-Gα16). In a preferred embodiment, the G protein is mouse Gα15 (SEQ ID NO:53). In another preferred embodiment, the G protein is human GNA15 (SEQ ID NO:1) or is a human G protein encoded by a nucleic acid comprising SEQ ID NO:27. The G protein may also be any mammalian G protein, such as, but not limited to, any mammalian G protein listed in Appendix Table 3. The G protein stably expressed by the cell can be endogenous to the cell. Alternatively, the stable expression of the G protein may be a result of stable transfection of a nucleic acid encoding the G protein into the cell. Cells stably expressing a heterologous G protein are known in the art, e.g., HEK293/Gα15 cells (Chandrashekar et al., "T2R5 function as bitter taste receptors", Cell 100:703-711, 2000; Bufe et al., "The human TAS2R16 receptor mediates bitter taste in response to β-glucopyranosides", Na Genet. 32:397-401). In other embodiments, a nucleic acid encoding a G protein and a nucleic acid encoding a bitter taste receptor can be transfected consecutively into a host cell, with either the nucleic acid encoding the G protein transfected first or the nucleic acid encoding the bitter taste receptor transfected first. In other embodiments, a nucleic acid encoding a G protein and a nucleic acid encoding a bitter taste receptor can be co-transfected into a host cell on the same or different vectors. Accordingly, selection of cells stably expressing both the G protein and the bitter taste receptor, can likewise be carried out consecutively or simultaneously. The cells or cell lines that may be used to stably express a G protein are the same as those that may be used to stably express a bitter taste receptor, as explained above.

In some embodiments of the invention, cells or cell lines of the invention co-express other proteins with the bitter taste receptor(s). In a preferred embodiment, the other protein is at least one other taste receptor, such as a sweet (TAS1R2/TAS1R3) receptor or an umami (TAS1R1/TAS1R3) receptor. In some embodiments, the cell line panels of the invention include cell lines that express bitter receptors and cell lines that express other taste receptors, such as a sweet (TAS1R2/TAS1R3) receptor or an umami (TAS1R1/TAS1R3) receptor. Proteins that are co-expressed with bitter taste receptors may be expressed by any mechanism, such as, but not limited to, endogenously in the host cell or heterologously from a vector.

Also, in other embodiments of the invention, more than one type of bitter taste receptor may be stably expressed in a cell or cell line.

Also according to the invention, cells and cell lines that express a form of a naturally occurring bitter taste receptor or a naturally-occurring allelic variant thereof, as well as cells and cell lines that express a mutant form of bitter taste receptor, can be characterized for intracellular free calcium levels. In some embodiments, the cells and cell lines of the invention express bitter taste receptor with "physiologically relevant" activity. As used herein, physiological relevance refers to a property of a cell or cell line expressing a bitter taste receptor whereby the bitter taste receptor causes an increase in intracellular free calcium as a naturally occurring bitter taste receptor of the same type would when activated, and responds to modulators in the same ways that naturally occurring bitter taste receptors of the same type would respond when modulated by the same compounds. Bitter taste receptor-expressing cells and cell lines of this invention, including some mutant forms of bitter taste receptor and some naturally-occurring allelic variants of bitter taste receptors, preferably demonstrate comparable function to cells that normally express native bitter taste receptor in a suitable assay, such as an assay measuring intracellular free calcium. Such assays are known to those skilled in the art (Nahorski, "Pharmacology of intracellular signaling pathways," Brit. J. Pharm. 147: S38-S45, 2000)). Such comparisons are used to determine a cell or cell line's physiological relevance. "Sip and spit" taste tests using a panel of trained taste testers also may be used to further validate bitter taste receptor physiological relevance in cells and cell lines of the invention. The results of sip and spit taste tests using modulators identified via screening of native or mutant forms of a bitter taste receptor or a naturally-occurring allelic variant thereof can be used to validate the physiological relevance of these different forms.

In some embodiments, the cells and cell lines respond to modulators and increase intracellular free calcium with physiological range $EC_{50}$ or $IC_{50}$ values for bitter taste receptors. As used herein, $EC_{50}$ refers to the concentration of a compound or substance required to induce a half-maximal activating response in the cell or cell line. As used herein, $IC_{50}$ refers to the concentration of a compound or substance required to induce a half-maximal inhibitory response in the cell or cell line. $EC_{50}$ and $IC_{50}$ values may be determined using techniques that are well-known in the art, for example, a dose-response curve that correlates the concentration of a compound or substance to the response of the bitter taste receptor-expressing cell line.

To make bitter taste receptor expressing cells and cell lines, one can use, for example, the technology described in U.S. Pat. No. 6,692,965 and International Patent Publication WO/2005/079462. Both of these documents are incorporated herein by reference in their entirety for all purposes. This technology provides real-time assessment of millions of cells such that any desired number of clones (from hundreds to thousands of clones) may be selected. Using cell sorting techniques, such as flow cytometric cell sorting (e.g., with a FACS machine) or magnetic cell sorting (e.g., with a MACS machine), one cell per well may be automatically deposited with high statistical confidence in a culture vessel (such as a 96 well culture plate). The speed and automation of the technology allows multigene cell lines to be readily isolated. To make bitter taste receptor expressing cells and cell lines, one can also use, for example, the technology described in International Patent Publications WO 2009/102569 and WO 2010/088633. Both of these documents are incorporated herein by reference in their entirety for all purposes. This technology provides automated methods of generating cells and cell lines matched for physiological properties. Such methods may be used to generate panels of cell lines suitable for high-throughput screening of potential bitter taste receptor modulators.

Using the technology, the RNA sequence for each bitter taste receptor may be detected using a signaling probe, also referred to as a molecular beacon or fluorogenic probe. In some embodiments, the molecular beacon recognizes a target tag sequence as described above. In another embodiment, the molecular beacon recognizes a sequence within the bitter taste receptor coding sequence itself. Signaling probes may be directed against the RNA tag or bitter taste receptor coding sequence by designing the probes to include a portion that is complementary to the RNA sequence of the tag or the bitter taste receptor coding sequence, respectively. These same techniques may be used to detect the RNA sequence for a G protein, if used.

Methods of Identifying Compounds That Modulate Bitter Taste

One aspect, the invention provides methods of identifying compounds that modulate bitter taste. In some embodiments, the method is an in vitro cell-based assay to, e.g., screen for bitter taste receptor modulators; assess bitterness of substances; produce protein for crystallography and binding studies; and investigate compound selectivity and dosing, receptor/compound binding kinetic and stability, and effects of receptor expression on cellular physiology (e.g., electrophysiology, protein trafficking, protein folding, and protein regulation).

In some embodiments, the in vitro cell-based assays utilize the bitter taste receptor expressing cells and cell lines discussed above. Cells and cell lines expressing various combinations of bitter taste receptors can be used separately or together to identify bitter taste receptor modulators, including those specific for a particular bitter taste receptor or a mutant form or a naturally-occurring allelic variant of bitter taste receptor and to obtain information about the activities of individual forms.

Modulators include any substance or compound that alters an activity of a bitter taste receptor or a mutant form or a naturally-occurring allelic variant thereof. The modulator can be a bitter taste receptor agonist (potentiator or activator) or antagonist (inhibitor or blocker), including partial agonists or antagonists, selective agonists or antagonists and inverse agonists, and can be an allosteric modulator. A substance or compound is a modulator even if its modulating activity changes under different conditions or concentrations or with respect to different forms (e.g., mutant forms and naturally-occurring allelic variants) of bitter taste receptor. In other aspects, a modulator may change the ability of another modulator to affect the function of a bitter taste receptor. For example, a modulator of a form of bitter taste receptor that is not inhibited by an antagonist may render that form of bitter taste receptor susceptible to inhibition by the antagonist.

Cells and cell lines may be used to identify the roles of different forms of bitter taste receptors in different bitter taste receptors pathologies by correlating the identity of in vivo forms of bitter taste receptor with the identify of known forms of bitter taste receptors based on their response to various modulators. This allows selection of disease- or tissue-specific bitter taste receptor modulators for highly targeted treatment of such bitter taste receptor-related pathologies or other physiological conditions. For example, because many naturally occurring bitter compounds are toxic, bitter taste receptors may serve as warning sensors against the ingestion of toxic food compounds. Bitter taste receptors expressed in the gastrointestinal mucosa might participate in the functional detection of nutrients and harmful substances in the lumen and prepare the gut to absorb them or initiate a protective response. They might also participate in the control of food intake through the activation of gut-brain neural pathways. Accordingly, bitter taste receptor modulators identified using the cell lines and methods of the present invention may be used to regulate nutrient uptake in a number of contexts, e.g., to control the appetite and/or reduce nutrient uptake in the gut of the obese, or to control the hunger feeling and/or to increase the uptake of nutrients and/or energy from food in the malnourished. Bitter taste receptor modulators may also be useful in identifying bitter compounds, further characterizing the specific chemical or structural motifs or key residues of bitter taste receptors that influence their binding properties, identifying bitter taste receptors that are broadly, moderately or selectively tuned for ligand binding, defining groups and subgroups of bitter taste receptors based on their binding profiles, deorphaning orphan bitter taste receptors, using such data for molecular modeling or drug design for bitter taste receptors, and determining in which tissues various bitter taste receptors are active.

To identify a bitter taste receptor modulator, bitter taste receptor expressing cell or cell line may be exposed to a test compound under conditions in which the bitter taste receptor would be expected to be functional and then detect a statistically significant change (e.g., $p<0.05$) in bitter taste receptor activity compared to a suitable control, e.g., cells that are not exposed to the test compound. Positive and/or negative controls using known agonists or antagonists and/or cells expressing different bitter taste receptor or mutant forms or naturally-occurring allelic variants thereof may also be used. In some embodiments, the bitter taste receptor activity to be detected and/or measured is change in intracellular free calcium levels. One of ordinary skill in the art would understand that various assay parameters may be optimized, e.g., signal to noise ratio.

In a further aspect, the invention provides a method of identifying ligands for orphan bitter taste receptors, i.e. the invention provides a method of deorphaning bitter taste receptors. A cell or cell line expressing a bitter taste receptor with no known modulator may be screened using a compound or extract library to generate an expression profile for the receptor. Optionally, receptors with similar profiles (if any) are grouped together and screened with known bitter compounds to a ligand(s) that binds a receptor(s). Once a ligand is identified, the results may be further verified with taste tests. Optionally, the cells and cell lines stably express native (i.e. untagged) bitter taste receptors so the ligands identified using this method are accurate and relevant.

In some embodiments, one or more cells or cell lines, including collections of cell lines, are exposed to a test compound. In some embodiments, one or more cells or cell lines, including collections of cell lines, are exposed to a plurality of test compounds, for example, a library of test compounds. A library of test compounds can be screened using the cell lines of the invention to identify one or more modulators. The test compounds can be chemical moieties including small molecules, polypeptides, peptides, peptide mimetics, antibodies or antigen-binding portions thereof. In the case of antibodies, they may be non-human antibodies, chimeric antibodies, humanized antibodies, or fully human antibodies. The antibodies may be intact antibodies comprising a full complement of heavy and light chains or antigen-binding portions of any antibody, including antibody fragments (such as Fab, Fab', $F(ab')_2$, Fd, Fv, dAb and the like), single chain antibodies (scFv), single domain antibodies, all or an antigen-binding portion of a heavy chain or light chain variable region.

In some embodiments, one or more cells or cell lines, including collections of cell lines, are exposed to a test compound or a plurality of test compounds in the presence of a bitter tastant. In some embodiments, the bitter tastant is a "specific bitter tastant" that activates a subset of the bitter taste receptors. In some embodiments, the bitter tastant is a "universal bitter compound" that activates each bitter taste receptor. Non-limiting examples of universal bitter compounds include denatonium benzoate or denatonium saccharide. A test compound that decreases the induction of bitter taste receptor activity by a bitter tastant is an inhibitor of that bitter tastant. A test compound that increases the induction of bitter taste receptor activity by a bitter tastant is an enhancer of that bitter tastant.

Some bitter taste modulators and test compounds may exhibit off-target effects. Preferably, the bitter taste modulator or test compound is a selective bitter taste modulator and does not exhibit off-target effects.

The in vitro assays of the invention may be performed using collections of cells or cell lines. In a preferred embodiment, the collection of cells or cell lines includes cells or cell lines expressing each of the 25 bitter taste receptors and/or variants thereof. Such a panel may be used to determine on-target versus off-target activity for a compound, or the role of the receptors in pure bitter versus related (i.e., astringent or metallic) tastes.

In some embodiments, large compound collections are tested for bitter taste receptor modulating activity in a cell-based, functional, high-throughput screen (HTS), e.g., using a 96 well, 384 well, 1536 well or higher plate format. In some embodiments, a test compound or multiple test compounds including a library of test compounds may be screened using more than one cell or cell line, including collections of cell lines, of the invention. If multiple cells or cell lines, each expressing a different naturally occurring or mutant bitter taste receptor molecule, are used, one can identify modulators that are effective on multiple bitter taste receptors or mutant forms or naturally-occurring allelic variants thereof or alternatively, modulators that are specific for a particular bitter taste receptor or a mutant form or naturally-occurring allelic variant thereof and that do not modulate other bitter taste receptors or other forms of the bitter taste receptor. In the case of a cell or cell line that expresses a human bitter taste receptor, the cells can be exposed to a test compound to identify a compound that modulates bitter taste receptor activity (either increasing or decreasing) for use in the treatment of disease or condition characterized by undesired bitter taste receptor activity, or the decrease or absence of desired bitter taste receptor activity.

In some embodiments, prior to exposure to a test compound, the cells or cell lines of the invention may be modified by pretreatment with, for example, enzymes, including mammalian or other animal enzymes, plant enzymes, bacterial enzymes, enzymes from lysed cells, protein modifying enzymes, lipid modifying enzymes, and enzymes in the oral cavity, gastrointestinal tract, stomach or saliva. Such enzymes can include, for example, kinases, proteases, phosphatases, glycosidases, oxidoreductases, transferases, hydrolases, lyases, isomerases, ligases and the like. Alternatively, the cells and cell lines may be exposed to the test compound first followed by treatment to identify compounds that alter the modification of the bitter taste receptor by the treatment.

Assays for identifying and measuring GPCR activation are well-known in the art. See, e.g., "G-protein coupled receptors (Signal Transduction Series)," CRC Press 1999; 1$^{st}$ Edition; Eds Haga and Berstein. Any suitable assay for detecting GPCR activation may be used in the methods of the invention to evaluate effect on the activation of bitter taste receptors by potential bitter taste receptor modulators. Examples of such assays include ion sensitive or membrane voltage fluorescent indicators. Under resting state, these dyes are membrane permeable such that exposure to cells allows them to enter cells based on the concentration gradient. Once inside, cellular enzymes convert the dyes into a membrane-impermeable form, trapping the dyes. The membrane impermeable form of the dye is, typically, also highly sensitive to, for example, free intracellular calcium such that calcium binding allows the dye to become fluorescent, when stimulated with lights of specific intensity or wavelengths. Thus, intracellular calcium release in response to GPCR activation may be measured using membrane-permeable dyes that bind to calcium. Such dyes include Indo-1, Fura-2, Fluo-3, Fluo-4, Rhod-2, Rhod-5N, Calcein, Calcein blue, cytoCalcein Violet, Quin-2, Quest Fluo-8H™, Quest Fluo-8L™, Quest Fluo 8™, Quest Rhod-4™ coelenterazine and Calcium-3. In particular embodiments, GPCR activation is measured using Fluo-4 or Calcium-3 fluorescence. In some embodiments, the assay buffer (i.e. load solution) does not include probenecid. Intracellular calcium levels can be measured by measuring the fluorescence from such dyes in response to calcium binding using, for example, fluorescence microscopy, flow cytometry, fluorescence spectroscopy and fluorescence microplate readers. Most fluorescent indicators derive from BAPTA chelators that incorporate a photo-induced-electron transfer system that responds to calcium. FLIPR® and FlexStation™ instruments of Molecular Devices Corp., FDSS of Hamamatsu Corp. and NOVOstar™ of BMG Technologies, for example, continuously monitor changes in intracellular calcium levels thereby providing a kinetic read-out of a receptor's activity in the form of a time-dependent fluorescent signal. Accordingly, these instruments enable high throughput measurement of calcium for GPCR research.

GPCR activity may also be evaluated by measuring adenylate cyclase activity, IP3/Ca$^{2+}$ signaling, phospholipase C/intracellular Ca$^{2+}$ signaling, GTPase activity, GTP binding, microphysiometer/biosensor assays (see, e.g., Hafner, 2000, Biosens. Bioelectron. 15: 149-158), arachinoid acid levels (see, e.g., Gijon et al., 2000, J. Biol. Chem., 275: 20146-20156), cAMP/cGMP levels (by radioimmunoassay or with binding proteins, see, e.g., Horton and Baxendale, 1995, Methods Mol. Biol. 41: 91-105), diacylglycerol (DAG) levels, inositol triphosphate (IP3) levels, protein kinase C activity, and/or MAP kinase activity.

Methods of Identifying Compounds That Modulate Bitter Taste Due to KCl

According to another aspect, the invention provides a method for identifying a compound that modulates the bitter taste due to KCl. In some embodiments, the method identifies a compound that modulates, inhibits or enhances activation of a bitter taste receptor by KCl. In some embodiments, the method identifies a compound that modulates, inhibits or enhances activation of a bitter taste receptor by KCl followed by downstream signaling. In some embodiments, the method identifies a compound that modulates, inhibits or enhances activation of a signaling pathway after stimulation by KCl. In some embodiments, the method identifies a compound that modulates, inhibits or enhances perception of bitter taste due to KCl. As shown in Example 2 below, KCl activates bitter taste receptors TAS2R4, TAS2R9, TAS2R13, TAS2R14, TAS2R44 and TAS2R60. Thus, a compound that modulates KCl's activation of one or more of the TAS2R4, TAS2R9, TAS2R13, TAS2R14, TAS2R44 and TAS2R60 bitter taste receptors should be a modulator of bitter taste due to KCl. In some embodiments, the compound inhibits KCl's activation of one or more of the TAS2R4, TAS2R9, TAS2R13, TAS2R14, TAS2R44 and TAS2R60 bitter taste receptors. In such embodiments, the compound is an inhibitor of bitter taste due to KCl. In some embodiments, the compound enhances KCl's activation of one or more of the TAS2R4, TAS2R9, TAS2R13, TAS2R14, TAS2R44 and TAS2R60 bitter taste receptors. In such embodiments, the compound is an enhancer of bitter taste due to KCl. In some embodiments, the compound activates of one or more of the TAS2R4, TAS2R9, TAS2R13, TAS2R14, TAS2R44 and TAS2R60 bitter taste receptors. In such embodiments, the compound mimics bitter taste due to KCl. In some embodiments, any of the methods of identifying compounds that modulate bitter taste disclosed above is performed using a tastant that activates one or more of the TAS2R4, TAS2R9, TAS2R13, TAS2R14, TAS2R44 and TAS2R60 bitter taste receptors. In some embodiments, the tastant is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In some embodiments, the test compound modulates, inhibits or enhances KCl-induced activation of two or more of TAS2R4, TAS2R9, TAS2R13, TAS2R14, TAS2R44 and TAS2R60. In some embodiments, the test compound modulates, inhibits or enhances KCl-induced activation of three or more of TAS2R4, TAS2R9, TAS2R13, TAS2R14, TAS2R44 and TAS2R60. In some embodiments, the test compound modulates, inhibits or enhances KCl-induced activation of four or more of TAS2R4, TAS2R9, TAS2R13, TAS2R14, TAS2R44 and TAS2R60. In some embodiments, the test compound modulates, inhibits or enhances KCl-induced activation of five or more of TAS2R4, TAS2R9, TAS2R13, TAS2R14, TAS2R44 and TAS2R60. In some embodiments, the test compound modulates, inhibits or enhances KCl-induced activation of each of TAS2R4, TAS2R9, TAS2R13, TAS2R14, TAS2R44 and TAS2R60.

In any of the methods of identifying compounds that modulate bitter taste due to KCl described in this section, the bitter taste receptors used in the methods may be complexed to a G-protein, as described above. Any G-protein describe above may be used. In some embodiments, the G-protein is a $G_q$ protein, an alpha transducin or an alpha gustducin. In some embodiments, the $G_q$ protein is a $G_{\alpha15}$ protein.

In any of the methods of identifying compounds that modulate bitter taste due to KCl described in this section, any assay described above may be used to measure bitter taste receptor activity. In some embodiments, the bitter taste receptor activity is determined by measuring intracellular calcium concentration. In some embodiments, intracellular calcium concentration is measured using a calcium-sensitive fluorescent dye. In some embodiments, the calcium-sensitive fluorescent dye is selected from Indo-1, Fura-2, Fluo-3, Fluo-4, Rhod-2, Rhod-5N, Calcein, Calcein blue, cytoCalcein Violet, Quin-2, Quest Fluo-8H™, Quest Fluo-8L™, Quest Fluo 8™, Quest Rhod-4™, coelenterazine and Calcium-3. In a particular embodiment, the calcium-sensitive fluorescent dye is Fluo-4 or Calcium-3.

In some embodiments, the method comprises providing one or more bitter taste receptor selected from TAS2R4, TAS2R9, TAS2R13, TAS2R14, TAS2R44 and TAS2R60; contacting the one or more bitter taste receptor with a tastant that activates the one or more bitter taste receptor; measuring the activity of the one or more bitter taste receptor; washing the one or more bitter taste receptor; contacting the one or more bitter taste receptor with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to KCl. If the activity of the one or more bitter taste receptor due to the tastant is greater than the activity of the one or more bitter taste receptor due to the tastant and the test compound, then the test compound inhibits bitter taste due to KCl. If the activity of the one or more bitter taste receptor due to the tastant is less than the activity of the one or more bitter taste receptor due to the tastant and the test compound, then the test compound enhances bitter taste due to KCl. The skilled worker would recognize that, in such embodiments, the testing order does not matter. The receptor may be contacted with the test compound either before or after washing. The tastant and test compound may be added sequentially or simultaneously, i.e., the one or more bitter taste receptor may be contacted with the test compound prior to, at the same time as or subsequent to contacting the one or more bitter taste receptor with the tastant.

In some embodiments, the method comprises providing a first one or more bitter taste receptor and a second one or more bitter taste receptor, each selected from TAS2R4, TAS2R9, TAS2R13, TAS2R14, TAS2R44 and TAS2R60; contacting the first one or more bitter taste receptor with a tastant that activates the one or more bitter taste receptor; measuring the activity of the first one or more bitter taste receptor; contacting the second one or more bitter taste receptor with the tastant and a test compound; and measuring the second one or more bitter taste receptor activity. If the activity of the first one or more bitter taste receptor differs from the activity of the second one or more bitter taste receptor, then the test compound modulates bitter taste due to KCl. If the activity of the first one or more bitter taste receptor is greater than the activity of the second one or more bitter taste receptor, then the test compound inhibits bitter taste due to KCl. If the activity of the first one or more bitter taste receptor is less than the activity of the second one or more bitter taste receptor, then the test compound enhances bitter taste due to KCl. In some embodiments, the first one more bitter taste receptor is washed after measurement of activity to provide the second one or more bitter taste receptor. The tastant and test compound may be added sequentially or simultaneously, i.e., the second one or more bitter taste receptor may be contacted with the test compound prior to, at the same time as or subsequent to contacting the second one or more bitter taste receptor with the tastant.

In some embodiments, the method comprises providing a cell expressing one or more bitter taste receptor, wherein the one or more bitter taste receptor is selected from TAS2R4, TAS2R9, TAS2R13, TAS2R14, TAS2R44 and TAS2R60; contacting the cell with a tastant that activates one or more bitter taste receptor; measuring the activity of the one or more bitter taste receptor; washing the cell; contacting the cell with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to KCl. If the activity of the one or more bitter taste receptor due to the tastant is greater than the activity of the one or more bitter taste receptor due to the tastant and the test compound, then the test compound inhibits bitter taste due to KCl. If the activity of the one or more bitter taste receptor due to the tastant is less than the activity of the one or more bitter taste receptor due to the tastant and the test compound, then the test compound enhances bitter taste due to KCl. In some embodiments, the cell is present in an in vitro cell line. In some embodiments, the cell is present in a panel of in vitro cell lines. The skilled worker would recognize that, in such embodiments, the testing order does not matter. The cell may be contacted with the test compound either before or after washing. The tastant and test compound may be added sequentially or simultaneously, i.e., the cell may be contacted with the test compound prior to, at the same time as or subsequent to contacting the cell with the tastant.

In some embodiments, the method comprises providing a first cell expressing one or more bitter taste receptor and a second cell expressing one or more bitter taste receptor, wherein the one or more bitter taste receptor is selected from TAS2R4, TAS2R9, TAS2R13, TAS2R14, TAS2R44 and TAS2R60; contacting the first cell with a tastant that activates one or more bitter taste receptor; measuring the bitter taste receptor activity of the first cell; contacting the second cell with the tastant and a test compound; and measuring the bitter taste receptor activity of the second cell. If the bitter taste receptor activity of the first cell differs from the bitter taste receptor activity of the second cell, then the test compound modulates bitter taste due to KCl. If the bitter taste receptor activity of the first cell is greater than the bitter taste receptor activity of the second cell, then the test compound inhibits bitter taste due to KCl. If the bitter taste receptor activity of the first cell is less than the bitter taste receptor activity of the second cell, then the test compound enhances bitter taste due to KCl. In some embodiments, the first and second cells are present in in vitro cell lines. In some embodiments, the first and second cells are present in one or more panels of in vitro cell lines. In some embodiments, the first cell is washed after measuring the bitter taste receptor activity to provide the second cell. The tastant and test compound may be added sequentially or simultaneously, i.e., the second cell may be contacted with the test compound prior to, at the same time as or subsequent to contacting the second cell with the tastant.

In some embodiments, the method further comprises providing a third cell expressing one or more bitter taste receptor and a fourth cell expressing one or more bitter taste receptor, wherein the one or more bitter taste receptor is selected from TAS2R4, TAS2R9, TAS2R13, TAS2R14, TAS2R44 and TAS2R60; wherein the one or more bitter taste receptor in the third and fourth cell are the same; and wherein the one or more bitter taster receptor in the third and fourth cell are different from the bitter taste receptor in the first and second cells. In some embodiments, the method further comprises providing a fifth cell expressing one or more bitter taste receptor and a sixth cell expressing one or more bitter taste receptor, wherein the one or more bitter taste receptor is selected from TAS2R4, TAS2R9, TAS2R13, TAS2R14, TAS2R44 and TAS2R60; wherein the one or more bitter taste receptor in the fifth and sixth cell are the same; and wherein the one or more bitter taster receptor in the fifth and sixth cell are different from the bitter taste receptor in the first, second, third and fourth cells. In some embodiments, the method further comprises providing a seventh cell expressing one or more bitter taste receptor and an eighth cell expressing one or more bitter taste receptor, wherein the one or more bitter taste receptor is selected from TAS2R4, TAS2R9, TAS2R13, TAS2R14, TAS2R44 and TAS2R60; wherein the one or more bitter taste receptor in the seventh and eighth cell are the same; and wherein the one or more bitter taster receptor in the seventh and eighth cell are different from the bitter taste receptor in the first, second, third, fourth, fifth, and sixth cells. In some embodiments, the method further comprises providing a ninth cell expressing one or more bitter taste receptor and a tenth cell expressing one or more bitter taste receptor, wherein the one or more bitter taste receptor is selected from TAS2R4, TAS2R9, TAS2R13, TAS2R14, TAS2R44 and TAS2R60; wherein the one or more bitter taste receptor in the ninth and tenth cell are the same; and wherein the one or more bitter taster receptor in the ninth and tenth cell are different from the bitter taste receptor in the first, second, third, fourth, fifth, sixth, seventh and eighth cells. In some embodiments, the method further comprises providing an eleventh cell expressing one or more bitter taste receptor and a twelfth cell expressing one or more bitter taste receptor, wherein the one or more bitter taste receptor is selected from TAS2R4, TAS2R9, TAS2R13, TAS2R14, TAS2R44 and TAS2R60; wherein the one or more bitter taste receptor in the eleventh and twelfth cell are the same; and wherein the one or more bitter taster receptor in the eleventh and twelfth cell are different from the bitter taste receptor in the first, second, third, fourth, fifth, sixth, seventh, eighth, ninth and tenth cells. In such embodiments, the method comprises contacting the third, fifth, seventh, ninth, and/or eleventh cell with a tastant that activates one or more bitter taste receptor; measuring the bitter taste receptor activity of the third, fifth, seventh, ninth, and/or eleventh cell; contacting the fourth, sixth, eighth, tenth and/or twelfth cell with the tastant and a test compound; and measuring the bitter taste receptor activity of the fourth, sixth, eighth, tenth and/or twelfth cell. If the bitter taste receptor activity of the third, fifth, seventh, ninth, and/or eleventh cell differs from the bitter taste receptor activity of the fourth, sixth, eighth, tenth and/or twelfth cell, respectively, then the test compound modulates bitter taste due to KCl. If the bitter taste receptor activity of the fourth, sixth, eighth, tenth and/or twelfth cell is less than the bitter taste receptor activity of the third, fifth, seventh, ninth, and/or eleventh cell, respectively, then the test compound inhibits bitter taste due to KCl. If the bitter taste receptor activity of the fourth, sixth, eighth, tenth and/or twelfth cell is greater than the bitter taste receptor activity of the third, fifth, seventh, ninth, and/or eleventh cell, respectively, then the test compound enhances bitter taste due to KCl. In some embodiments, the third, fourth, fifth, sixth, seventh, eighth, ninth, tenth, eleventh and/or twelfth cells are present in in vitro cell lines. In some embodiments, the third, fourth, fifth, sixth, seventh, eighth, ninth, tenth, eleventh and/or twelfth cells are present in one or more panels of in vitro cell lines. In some embodiments, the third, fifth, seventh, ninth, and/or eleventh cell is washed after measuring the bitter taste receptor activity to provide the fourth, sixth, eighth, tenth and/or twelfth cell, respectively. The tastant and test compound may be added sequentially or simultaneously, i.e., the fourth, sixth, eighth, tenth and/or twelfth cell may be contacted with the test compound prior to, at the same time as or subsequent to contacting the fourth, sixth, eighth, tenth and/or twelfth cell with the tastant.

In some embodiments, the method comprises providing a panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line; contacting each cell line with a tastant that activates four or more of the group selected from TAS2R4, TAS2R9, TAS2R13, TAS2R14, TAS2R44 and TAS2R60; measuring the bitter taste receptor activity of each cell line; washing each cell line; contacting each cell line with the tastant and a test compound; and measuring bitter taste receptor activity of each cell line. If the bitter taste receptor activity of four or more of the cell lines selected from TAS2R4, TAS2R9, TAS2R13, TAS2R14, TAS2R44 and TAS2R60 differs when contacted with the tastant compared to when contacted with the tastant and the test compound, then the test compound selectively modulates bitter taste due to KCl. In some embodiments, the bitter taste receptor activity differs in five or more of the cell lines selected from TAS2R4, TAS2R9, TAS2R13, TAS2R14, TAS2R44 and TAS2R60. In some embodiments, the bitter taste receptor activity differs in the TAS2R4, TAS2R9, TAS2R13, TAS2R14, TAS2R44 and TAS2R60 cell lines. If the bitter taste receptor activity of four or more cell lines selected from TAS2R4, TAS2R9, TAS2R13, TAS2R14, TAS2R44 and TAS2R60 is greater when contacted with the tastant compared to when contacted with the tastant and the test compound, then the test compound selectively inhibits bitter taste due to KCl. In some embodiments, the bitter taste receptor activity is greater in five or more of the cell lines selected from TAS2R4, TAS2R9, TAS2R13, TAS2R14, TAS2R44 and TAS2R60. In some embodiments, the bitter taste receptor activity is greater in the TAS2R4, TAS2R9, TAS2R13, TAS2R14, TAS2R44 and TAS2R60 cell lines. If the bitter taste receptor activity of four or more cell lines selected from TAS2R4, TAS2R9, TAS2R13, TAS2R14, TAS2R44 and TAS2R60 is less when contacted with the tastant compared to when contacted with the tastant and the test compound, then the test compound selectively enhances bitter taste due to KCl. In some embodiments, the bitter taste receptor activity is less in five or more of the cell lines selected from TAS2R4, TAS2R9, TAS2R13, TAS2R14, TAS2R44 and TAS2R60. In some embodiments, the bitter taste receptor activity is less in the TAS2R4, TAS2R9, TAS2R13, TAS2R14, TAS2R44 and TAS2R60 cell lines. In some embodiments, the test compound selectively modulates, inhibits or activates bitter taste due to KCl if the compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting the each cell line with the tastant.

In some embodiments, the method comprises providing a panel of cell lines, wherein the panel comprises cell lines that express a bitter taste receptor selected from the group consisting of: TAS2R4, TAS2R9, TAS2R13, TAS2R14, TAS2R44 and TAS2R60, wherein each receptor is expressed in at least one cell line; contacting each cell line with a tastant that activates at least two of the group selected from TAS2R4, TAS2R9, TAS2R13, TAS2R14, TAS2R44 and TAS2R60; measuring the bitter taste receptor activity of each cell line; washing each cell line; contacting each cell line with the tastant and a test compound; and measuring bitter taste receptor activity of each cell line. In some embodiments, each cell line in the panel expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line. If the bitter taste receptor activity at least two of the cell lines selected from TAS2R4, TAS2R9, TAS2R13, TAS2R14, TAS2R44 and TAS2R60 differs when contacted with the tastant compared to when contacted with the tastant and the test compound, then the test compound selectively modulates bitter taste due to KCl. In some embodiments, if the bitter taste receptor activity differs in at least three of the cell lines selected from TAS2R4, TAS2R9, TAS2R13, TAS2R14, TAS2R44 and TAS2R60 then the test compound selectively modulates bitter taste due to KCl. In some embodiments, if the bitter taste receptor activity differs in at least four of the cell lines selected from TAS2R4, TAS2R9, TAS2R13, TAS2R14, TAS2R44 and TAS2R60, then the test compound selectively modulates bitter taste due to KCl. In some embodiments, if the bitter taste receptor activity differs in at least five of the cell lines selected from TAS2R4, TAS2R9, TAS2R13, TAS2R14, TAS2R44 and TAS2R60 then the test compound selectively modulates bitter taste due to KCl. In some embodiments, if the bitter taste receptor activity differs in each of the TAS2R4, TAS2R9, TAS2R13, TAS2R14, TAS2R44 and TAS2R60 cell lines then the test compound selectively modulates bitter taste due to KCl. If the bitter taste receptor activity of at least two cell lines selected from TAS2R4, TAS2R9, TAS2R13, TAS2R14, TAS2R44 and TAS2R60 is greater when contacted with the tastant compared to when contacted with the tastant and the test compound, then the test compound selectively inhibits bitter taste due to KCl. In some embodiments, if the bitter taste receptor activity is greater in at least three of the cell lines selected from TAS2R4, TAS2R9, TAS2R13, TAS2R14, TAS2R44 and TAS2R60, then the test compound selectively inhibits bitter taste due to KCl. In some embodiments, if the bitter taste receptor activity is greater in at least four of the cell lines selected from TAS2R4, TAS2R9, TAS2R13, TAS2R14, TAS2R44 and TAS2R60, then the test compound selectively inhibits bitter taste due to KCl. In some embodiments, if the bitter taste receptor activity is greater in at least five of the cell lines selected from TAS2R4, TAS2R9, TAS2R13, TAS2R14, TAS2R44 and TAS2R60, then the test compound selectively inhibits bitter taste due to KCl. In some embodiments, if the bitter taste receptor activity is greater in each of the TAS2R4, TAS2R9, TAS2R13, TAS2R14, TAS2R44 and TAS2R60 cell lines, then the test compound selectively inhibits bitter taste due to KCl. If the bitter taste receptor activity of at least two cell lines selected from TAS2R4, TAS2R9, TAS2R13, TAS2R14, TAS2R44 and TAS2R60 is less when contacted with the tastant compared to when contacted with the tastant and the test compound, then the test compound selectively enhances bitter taste due to KCl. In some embodiments, if the bitter taste receptor activity is less in at least three of the cell lines selected from TAS2R4, TAS2R9, TAS2R13, TAS2R14, TAS2R44 and TAS2R60, then the test compound selectively enhances bitter taste due to KCl. In some embodiments, if the bitter taste receptor activity is less in at least four of the cell lines selected from TAS2R4, TAS2R9, TAS2R13, TAS2R14, TAS2R44 and TAS2R60, then the test compound selectively enhances bitter taste due to KCl. In some embodiments, if the bitter taste receptor activity is less in at least five of the cell lines selected from TAS2R4, TAS2R9, TAS2R13, TAS2R14, TAS2R44 and TAS2R60, then the test compound selectively enhances bitter taste due to KCl. In some embodiments, if the bitter taste receptor activity is less in each of the TAS2R4, TAS2R9, TAS2R13, TAS2R14, TAS2R44 and TAS2R60 cell lines, then the test compound selectively enhances bitter taste due to KCl. In some embodiments, the test compound selectively modulates, inhibits or activates bitter taste due to KCl if the compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting each cell line with the tastant.

In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a tastant that activates four or more of the group selected from TAS2R4, TAS2R9, TAS2R13, TAS2R14, TAS2R44 and TAS2R60; measuring the bitter taste receptor activity of each cell line in the first panel; contacting each cell line in the second panel with the tastant and a test compound; and measuring the bitter taste receptor activity of each cell line in the second panel. If the bitter taste receptor activity of four or more of the cell lines selected from TAS2R4, TAS2R9, TAS2R13, TAS2R14, TAS2R44 and TAS2R60 differs in the first panel compared to the second panel, then the test compound selectively modulates bitter taste due to KCl. In some embodiments, the bitter taste receptor activity differs in five or more of the cell lines selected from TAS2R4, TAS2R9, TAS2R13, TAS2R14, TAS2R44 and TAS2R60. In some embodiments, the bitter taste receptor activity differs in the TAS2R4, TAS2R9, TAS2R13, TAS2R14, TAS2R44 and TAS2R60 cell lines. If the bitter taste receptor activity of four or more cell lines selected from TAS2R4, TAS2R9, TAS2R13, TAS2R14, TAS2R44 and TAS2R60 is greater in the first panel compared to the second panel, then the test compound selectively inhibits bitter taste due to KCl. In some embodiments, the bitter taste receptor activity is greater in five or more of the cell lines selected from TAS2R4, TAS2R9, TAS2R13, TAS2R14, TAS2R44 and TAS2R60. In some embodiments, the bitter taste receptor activity is greater in the TAS2R4, TAS2R9, TAS2R13, TAS2R14, TAS2R44 and TAS2R60 cell lines. If the bitter taste receptor activity of four or more cell lines selected from TAS2R4, TAS2R9, TAS2R13, TAS2R14, TAS2R44 and TAS2R60 is less in the first panel compared to the second panel, then the test compound selectively enhances bitter taste due to KCl. In some embodiments, the bitter taste receptor activity is less in five or more of the cell lines selected from TAS2R4, TAS2R9, TAS2R13, TAS2R14, TAS2R44 and TAS2R60. In some embodiments, the bitter taste receptor activity is less in the TAS2R4, TAS2R9, TAS2R13, TAS2R14, TAS2R44 and TAS2R60 cell lines. In some embodiments, the test compound selectively modulates, inhibits or activates bitter taste due to KCl if the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., the each cell line in the second panel may be contacted with the test compound prior to, at the same time as or subsequent to contacting each cell line in the second panel with the tastant.

In some embodiments, the method comprises providing a first panel of cell lines and a second panel of cell lines, wherein each panel comprises cell lines that express a bitter taste receptor selected from the group consisting of: TAS2R4, TAS2R9, TAS2R13, TAS2R14, TAS2R44 and TAS2R60 bitter taste receptor, wherein each receptor is expressed in at least one cell line, and wherein the first and second panels comprise the same cell lines; contacting each cell line in the first panel with a tastant that activates at least two of the group selected from TAS2R4, TAS2R9, TAS2R13, TAS2R14, TAS2R44 and TAS2R60; measuring the bitter taste receptor activity of each cell line in the first panel; contacting each cell line in the second panel with the tastant and a test compound; and measuring the bitter taste receptor activity of each cell line in the second panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. If the bitter taste receptor activity of at least two of the cell lines selected from TAS2R4, TAS2R9, TAS2R13, TAS2R14, TAS2R44 and TAS2R60 differs in the first panel compared to the second panel, then the test compound selectively modulates bitter taste due to KCl. In some embodiments, if the bitter taste receptor activity differs in at least three of the cell lines selected from TAS2R4, TAS2R9, TAS2R13, TAS2R14, TAS2R44 and TAS2R60, then the test compound selectively modulates bitter taste due to KCl. In some embodiments, if the bitter taste receptor activity differs in at least four of the cell lines selected from TAS2R4, TAS2R9, TAS2R13, TAS2R14, TAS2R44 and TAS2R60, then the test compound selectively modulates bitter taste due to KCl. In some embodiments, if the bitter taste receptor activity differs in at least five of the cell lines selected from TAS2R4, TAS2R9, TAS2R13, TAS2R14, TAS2R44 and TAS2R60, then the test compound selectively modulates bitter taste due to KCl. In some embodiments, if the bitter taste receptor activity differs in each of the TAS2R4, TAS2R9, TAS2R13, TAS2R14, TAS2R44 and TAS2R60 cell lines, then the test compound selectively modulates bitter taste due to KCl. If the bitter taste receptor activity of at least two cell lines selected from TAS2R4, TAS2R9, TAS2R13, TAS2R14, TAS2R44 and TAS2R60 is greater in the first panel compared to the second panel, then the test compound selectively inhibits bitter taste due to KCl. In some embodiments, if the bitter taste receptor activity of at least three cell lines selected from TAS2R4, TAS2R9, TAS2R13, TAS2R14, TAS2R44 and TAS2R60 is greater in the first panel compared to the second panel, then the test compound selectively inhibits bitter taste due to KCl. In some embodiments, if the bitter taste receptor activity of at least four cell lines selected from TAS2R4, TAS2R9, TAS2R13, TAS2R14, TAS2R44 and TAS2R60 is greater in the first panel compared to the second panel, then the test compound selectively inhibits bitter taste due to KCl. In some embodiments, if the bitter taste receptor activity of at least five cell lines selected from TAS2R4, TAS2R9, TAS2R13, TAS2R14, TAS2R44 and TAS2R60 is greater in the first panel compared to the second panel, then the test compound selectively inhibits bitter taste due to KCl. In some embodiments, if the bitter taste receptor activity in each of the TAS2R4, TAS2R9, TAS2R13, TAS2R14, TAS2R44 and TAS2R60 cell lines is greater in the first panel compared to the second panel, then the test compound selectively inhibits bitter taste due to KCl. If the bitter taste receptor activity of at least two cell lines selected from TAS2R4, TAS2R9, TAS2R13, TAS2R14, TAS2R44 and TAS2R60 is less in the first panel compared to the second panel, then the test compound selectively enhances bitter taste due to KCl. In some embodiments, if the bitter taste receptor activity of at least three cell lines selected from TAS2R4, TAS2R9, TAS2R13, TAS2R14, TAS2R44 and TAS2R60 is less in the first panel compared to the second panel, then the test compound selectively enhances bitter taste due to KCl. In some embodiments, if the bitter taste receptor activity of at least four cell lines selected from TAS2R4, TAS2R9, TAS2R13, TAS2R14, TAS2R44 and TAS2R60 is less in the first panel compared to the second panel, then the test compound selectively enhances bitter taste due to KCl. In some embodiments, if the bitter taste receptor activity of at least five cell lines selected from TAS2R4, TAS2R9, TAS2R13, TAS2R14, TAS2R44 and TAS2R60 is less in the first panel compared to the second panel, then the test compound selectively enhances bitter taste due to KCl. In some embodiments, if the bitter taste receptor activity in each of the TAS2R4, TAS2R9, TAS2R13, TAS2R14, TAS2R44 and TAS2R60 cell lines is less in the first panel compared to the second panel, then the test compound selectively enhances bitter taste due to KCl. In some embodiments, the test compound selectively modulates, inhibits or activates bitter taste due to KCl if the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., each cell line in the second panel may be contacted with the test compound prior to, at the same time as or subsequent to contacting each cell line in the second panel with the tastant.

In some embodiments, the tastant utilized in any of the above methods of identifying modulators of bitter taste due to KCl is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In another aspect, the invention provides a method of identifying a compound that mimics the bitter taste due to KCl. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with a test compound; and measuring the bitter taste receptor activity of each cell line in the second panel. If the test compound induces bitter taste receptor activity of TAS2R4, TAS2R9, TAS2R13, TAS2R14, TAS2R44 and TAS2R60, then the test compound mimics bitter taste due to KCl. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the test compound.

In another aspect, the invention provides a method for determining if KCl is present in a composition. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with the composition; and measuring the bitter taste receptor activity of each cell line in the second panel. KCl is present in the composition if the composition induces TAS2R4, TAS2R9, TAS2R13, TAS2R14, TAS2R44 and TAS2R60 bitter taste receptor activity in the second panel compared to the first panel and does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, and TAS2R55 bitter taste receptor activity in the second panel compared to the first panel. In some embodiments, the composition is an extract from a food product. In some embodiments, the composition comprises a pharmaceutically active ingredient. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the composition.

In some embodiments, the method comprises contacting the tastant and tastant plus test compound with two or more different bitter taste receptors selected from TAS2R4, TAS2R9, TAS2R13, TAS2R14, TAS2R44 and TAS2R60. In some embodiments, the method comprises contacting the tastant and tastant plus test compound with two or more cells each expressing a different bitter taste receptor selected from TAS2R4, TAS2R9, TAS2R13, TAS2R14, TAS2R44 and TAS2R60. In some embodiments, the method comprises contacting the tastant and tastant plus test compound with three or more different taste receptors selected from TAS2R4, TAS2R9, TAS2R13, TAS2R14, TAS2R44 and TAS2R60. In some embodiments, the method comprises contacting the tastant and tastant plus test compound with three or more cells each expressing a different bitter taste receptor selected from TAS2R4, TAS2R9, TAS2R13, TAS2R14, TAS2R44 and TAS2R60. In some embodiments, the method comprises contacting the tastant and tastant plus test compound with four or more different taste receptors selected from TAS2R4, TAS2R9, TAS2R13, TAS2R14, TAS2R44 and TAS2R60. In some embodiments, the method comprises contacting the tastant and tastant plus test compound with four or more cells each expressing a different bitter taste receptor selected from TAS2R4, TAS2R9, TAS2R13, TAS2R14, TAS2R44 and TAS2R60. In some embodiments, the method comprises contacting the tastant and tastant plus test compound with five or more different taste receptors selected from TAS2R4, TAS2R9, TAS2R13, TAS2R14, TAS2R44 and TAS2R60. In some embodiments, the method comprises contacting the tastant and tastant plus test compound with five or more cells each expressing a different bitter taste receptor selected from TAS2R4, TAS2R9, TAS2R13, TAS2R14, TAS2R44 and TAS2R60. In some embodiments, the method comprises contacting the tastant and tastant plus test compound with six or more different taste receptors selected from TAS2R4, TAS2R9, TAS2R13, TAS2R14, TAS2R44 and TAS2R60. In some embodiments, the method comprises contacting the tastant and tastant plus test compound with six or more cells each expressing a different bitter taste receptor selected from TAS2R4, TAS2R9, TAS2R13, TAS2R14, TAS2R44 and TAS2R60.

In some embodiments wherein the method of identifying a compound that modulates, inhibits, enhances or mimics bitter flavor due to KCl comprises contacting TAS2R44 or a cell expressing TAS2R44 with a tastant or a test compound, the method also comprises contacting at least one additional bitter taste receptor or a cell expressing at least one additional bitter taste receptor with the tastant or test compound, wherein the at least one additional bitter taste receptor is selected from TAS2R4, TAS2R9, TAS2R13, TAS2R14, and TAS2R60.

In some embodiments, the method further comprises admixing the test compound that modulates, inhibits, enhances or mimic bitter taste due to KCl with foodstuffs, any foodstuff precursor material or any additive employed in the production of foodstuffs. In some embodiments, the foodstuff is for human consumption. In some embodiments, the foodstuff is for animal consumption, such as pet or livestock consumption. In some embodiments, the method further comprises admixing the test compound that modulates, inhibits, enhances or mimic bitter taste due to KCl with an active agent in a pharmaceutically acceptable form.

Methods of Identifying Compounds That Modulate Bitter Taste Due to Potassium Lactate According to another aspect, the invention provides a method for identifying a compound that modulates the bitter taste due to potassium lactate. In some embodiments, the method identifies a compound that modulates, inhibits or enhances activation of a bitter taste receptor by potassium lactate. In some embodiments, the method identifies a compound that modulates, inhibits or enhances activation of a bitter taste receptor by potassium lactate followed by downstream signaling. In some embodiments, the method identifies a compound that modulates, inhibits or enhances activation of a signaling pathway after stimulation by potassium lactate. In some embodiments, the method identifies a compound that modulates, inhibits or enhances perception of bitter taste due to potassium lactate. As shown in Example 3 below, potassium lactate activates bitter taste receptors TAS2R4, TAS2R9, TAS2R13, TAS2R14, TAS2R44, TAS2R46 and TAS2R60. Thus, a compound that modulates potassium lactate's activation of one or more of the TAS2R4, TAS2R9, TAS2R13, TAS2R14, TAS2R44, TAS2R46 and TAS2R60 bitter taste receptors should be a modulator of bitter taste due to potassium lactate. In some embodiments, the compound inhibits potassium lactate's activation of one or more of the TAS2R4, TAS2R9, TAS2R13, TAS2R14, TAS2R44, TAS2R46 and TAS2R60 bitter taste receptors. In such embodiments, the compound is an inhibitor of bitter taste due to potassium lactate. In some embodiments, the compound enhances potassium lactate's activation of one or more of the TAS2R4, TAS2R9, TAS2R13, TAS2R14, TAS2R44, TAS2R46 and TAS2R60 bitter taste receptors. In such embodiments, the compound is an enhancer of bitter taste due to potassium lactate. In some embodiments, the compound activates of one or more of the TAS2R4, TAS2R9, TAS2R13, TAS2R14, TAS2R44, TAS2R46 and TAS2R60 bitter taste receptors. In such embodiments, the compound mimics bitter taste due to potassium lactate. In some embodiments, any of the methods of identifying compounds that modulate bitter taste disclosed above is performed using a tastant that activates one or more of the TAS2R4, TAS2R9, TAS2R13, TAS2R14, TAS2R44, TAS2R46 and TAS2R60 bitter taste receptors. In some embodiments, the tastant is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In some embodiments, the test compound modulates, inhibits or enhances potassium lactate-induced activation of two or more of TAS2R4, TAS2R9, TAS2R13, TAS2R14, TAS2R44, TAS2R46 and TAS2R60. In some embodiments, the test compound modulates, inhibits or enhances potassium lactate-induced activation of three or more of TAS2R4, TAS2R9, TAS2R13, TAS2R14, TAS2R44, TAS2R46 and TAS2R60. In some embodiments, the test compound modulates, inhibits or enhances potassium lactate-induced activation of four or more of TAS2R4, TAS2R9, TAS2R13, TAS2R14, TAS2R44, TAS2R46 and TAS2R60. In some embodiments, the test compound modulates, inhibits or enhances potassium lactate-induced activation of five or more of TAS2R4, TAS2R9, TAS2R13, TAS2R14, TAS2R44, TAS2R46 and TAS2R60. In some embodiments, the test compound modulates, inhibits or enhances potassium lactate-induced activation of six or more of TAS2R4, TAS2R9, TAS2R13, TAS2R14, TAS2R44, TAS2R46 and TAS2R60. In some embodiments, the test compound modulates, inhibits or enhances potassium lactate-induced activation of each of TAS2R4, TAS2R9, TAS2R13, TAS2R14, TAS2R44, TAS2R46 and TAS2R60.

In any of the methods of identifying compounds that modulate bitter taste due to potassium lactate described in this section, the bitter taste receptors used in the methods may be complexed to a G-protein, as described above. Any G-protein describe above may be used. In some embodiments, the G-protein is a $G_q$ protein, an alpha transducin or an alpha gustducin. In some embodiments, the $G_q$ protein is a $G_{\alpha 15}$ protein.

In any of the methods of identifying compounds that modulate bitter taste due to potassium lactate described in this section, any assay described above may be used to measure bitter taste receptor activity. In some embodiments, the bitter taste receptor activity is determined by measuring intracellular calcium concentration. In some embodiments, intracellular calcium concentration is measured using a calcium-sensitive fluorescent dye. In some embodiments, the calcium-sensitive fluorescent dye is selected from Indo-1, Fura-2, Fluo-3, Fluo-4, Rhod-2, Rhod-5N, Calcein, Calcein blue, cytoCalcein Violet, Quin-2, Quest Fluo-8H™, Quest Fluo-8L™, Quest Fluo 8™, Quest Rhod-4™, coelenterazine and Calcium-3. In a particular embodiment, the calcium-sensitive fluorescent dye is Fluo-4 or Calcium-3.

In some embodiments, the method comprises providing one or more bitter taste receptor selected from TAS2R4, TAS2R9, TAS2R13, TAS2R14, TAS2R44, TAS2R46 and TAS2R60; contacting the one or more bitter taste receptor with a tastant that activates the one or more bitter taste receptor; measuring the activity of the one or more bitter taste receptor; washing the one or more bitter taste receptor; contacting the one or more bitter taste receptor with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to potassium lactate. If the activity of the one or more bitter taste receptor due to the tastant is greater than the activity of the one or more bitter taste receptor due to the tastant and the test compound, then the test compound inhibits bitter taste due to potassium lactate. If the activity of the one or more bitter taste receptor due to the tastant is less than the activity of the one or more bitter taste receptor due to the tastant and the test compound, then the test compound enhances bitter taste due to potassium lactate. The skilled worker would recognize that, in such embodiments, the testing order does not matter. The receptor may be contacted with the test compound either before or after washing. The tastant and test compound may be added sequentially or simultaneously, i.e., the one or more bitter taste receptor may be contacted with the test compound prior to, at the same time as or subsequent to contacting the one or more bitter taste receptor with the tastant.

In some embodiments, the method comprises providing a first one or more bitter taste receptor and a second one or more bitter taste receptor, each selected from TAS2R4, TAS2R9, TAS2R13, TAS2R14, TAS2R44, TAS2R46 and TAS2R60; contacting the first one or more bitter taste receptor with a tastant that activates the one or more bitter taste receptor; measuring the activity of the first one or more bitter taste receptor; contacting the second one or more bitter taste receptor with the tastant and a test compound; and measuring the second one or more bitter taste receptor activity. If the activity of the first one or more bitter taste receptor differs from the activity of the second one or more bitter taste receptor, then the test compound modulates bitter taste due to potassium lactate. If the activity of the first one or more bitter taste receptor is greater than the activity of the second one or more bitter taste receptor, then the test compound inhibits bitter taste due to potassium lactate. If the activity of the first one or more bitter taste receptor is less than the activity of the second one or more bitter taste receptor, then the test compound enhances bitter taste due to potassium lactate. In some embodiments, the first one more bitter taste receptor is washed after measurement of activity to provide the second one or more bitter taste receptor. The tastant and test compound may be added sequentially or simultaneously, i.e., the second one or more bitter taste receptor may be contacted with the test compound prior to, at the same time as or subsequent to contacting the second one or more bitter taste receptor with the tastant.

In some embodiments, the method comprises providing a cell expressing one or more bitter taste receptor, wherein the one or more bitter taste receptor is selected from TAS2R4, TAS2R9, TAS2R13, TAS2R14, TAS2R44, TAS2R46 and TAS2R60; contacting the cell with a tastant that activates one or more bitter taste receptor; measuring the activity of the one or more bitter taste receptor; washing the cell; contacting the cell with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to potassium lactate. If the activity of the one or more bitter taste receptor due to the tastant is greater than the activity of the one or more bitter taste receptor due to the tastant and the test compound, then the test compound inhibits bitter taste due to potassium lactate. If the activity of the one or more bitter taste receptor due to the tastant is less than the activity of the one or more bitter taste receptor due to the tastant and the test compound, then the test compound enhances bitter taste due to potassium lactate. In some embodiments, the cell is present in an in vitro cell line. In some embodiments, the cell is present in a panel of in vitro cell lines. The skilled worker would recognize that, in such embodiments, the testing order does not matter. The cell may be contacted with the test compound either before or after washing. The tastant and test compound may be added sequentially or simultaneously, i.e., the cell may be contacted with the test compound prior to, at the same time as or subsequent to contacting the cell with the tastant.

In some embodiments, the method comprises providing a first cell expressing one or more bitter taste receptor and a second cell expressing one or more bitter taste receptor, wherein the one or more bitter taste receptor is selected from TAS2R4, TAS2R9, TAS2R13, TAS2R14, TAS2R44, TAS2R46 and TAS2R60; contacting the first cell with a tastant that activates one or more bitter taste receptor; measuring the bitter taste receptor activity of the first cell; contacting the second cell with the tastant and a test compound; and measuring the bitter taste receptor activity of the second cell. If the bitter taste receptor activity of the first cell differs from the bitter taste receptor activity of the second cell, then the test compound modulates bitter taste due to potassium lactate. If the bitter taste receptor activity of the first cell is greater than the bitter taste receptor activity of the second cell, then the test compound inhibits bitter taste due to potassium lactate. If the bitter taste receptor activity of the first cell is less than the bitter taste receptor activity of the second cell, then the test compound enhances bitter taste due to potassium lactate. In some embodiments, the first and second cells are present in in vitro cell lines. In some embodiments, the first and second cells are present in one or more panels of in vitro cell lines. In some embodiments, the first cell is washed after measuring the bitter taste receptor activity to provide the second cell. The tastant and test compound may be added sequentially or simultaneously, i.e., the second cell may be contacted with the test compound prior to, at the same time as or subsequent to contacting the second cell with the tastant.

In some embodiments, the method further comprises providing a third cell expressing one or more bitter taste receptor and a fourth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the third and fourth cell are the same; and wherein the one or more bitter taster receptor in the third and fourth cell are different from the bitter taste receptor in the first and second cells. In some embodiments, the method further comprises providing a fifth cell expressing one or more bitter taste receptor and a sixth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the fifth and sixth cell are the same; and wherein the one or more bitter taster receptor in the fifth and sixth cell are different from the bitter taste receptor in the first, second, third and fourth cells. In some embodiments, the method further comprises providing a seventh cell expressing one or more bitter taste receptor and an eighth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the seventh and eighth cell are the same; and wherein the one or more bitter taster receptor in the seventh and eighth cell are different from the bitter taste receptor in the first, second, third, fourth, fifth, and sixth cells. In some embodiments, the method further comprises providing a ninth cell expressing one or more bitter taste receptor and a tenth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the ninth and tenth cell are the same; and wherein the one or more bitter taster receptor in the ninth and tenth cell are different from the bitter taste receptor in the first, second, third, fourth, fifth, sixth, seventh and eighth cells. In some embodiments, the method further comprises providing an eleventh cell expressing one or more bitter taste receptor and a twelfth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the eleventh and twelfth cell are the same; and wherein the one or more bitter taster receptor in the eleventh and twelfth cell are different from the bitter taste receptor in the first, second, third, fourth, fifth, sixth, seventh, eighth, ninth and tenth cells. In some embodiments, the method further comprises providing an thirteenth cell expressing one or more bitter taste receptor and a fourteenth cell expressing one or more bitter taste receptor, wherein the one or more bitter taste receptor is selected from TAS2R4, TAS2R9, TAS2R13, TAS2R14, TAS2R44, TAS2R46 and TAS2R60; wherein the one or more bitter taste receptor in the thirteenth and fourteenth cell are the same; and wherein the one or more bitter taster receptor in the thirteenth and fourteenth cell are different from the bitter taste receptor in the first, second, third, fourth, fifth, sixth, seventh, eighth, ninth, tenth, eleventh and twelfth cells. In such embodiments, the method comprises contacting the third, fifth, seventh, ninth, eleventh and/or thirteenth cell with a tastant that activates one or more bitter taste receptor; measuring the bitter taste receptor activity of the third, fifth, seventh, ninth, eleventh and/or thirteenth cell; contacting the fourth, sixth, eighth, tenth, twelfth and/or fourteenth cell with the tastant and a test compound; and measuring the bitter taste receptor activity of the fourth, sixth, eighth, tenth, twelfth and/or fourteenth cell. If the bitter taste receptor activity of the third, fifth, seventh, ninth, eleventh and/or thirteenth cell differs from the bitter taste receptor activity of the fourth, sixth, eighth, tenth, twelfth and/or fourteenth cell, respectively, then the test compound modulates bitter taste due to potassium lactate. If the bitter taste receptor activity of the fourth, sixth, eighth, tenth, twelfth and/or fourteenth cell is less than the bitter taste receptor activity of the third, fifth, seventh, ninth, eleventh and/or thirteenth cell, respectively, then the test compound inhibits bitter taste due to potassium lactate. If the bitter taste receptor activity of the fourth, sixth, eighth, tenth, twelfth and/or fourteenth cell is greater than the bitter taste receptor activity of the third, fifth, seventh, ninth, eleventh and/or thirteenth cell, respectively, then the test compound enhances bitter taste due to potassium lactate. In some embodiments, the third, fourth, fifth, sixth, seventh, eighth, ninth, tenth, eleventh, twelfth, thirteenth, and/or fourteenth cells are present in in vitro cell lines. In some embodiments, the third, fourth, fifth, sixth, seventh, eighth, ninth, tenth, eleventh, twelfth, thirteenth, and/or fourteenth are present in one or more panels of in vitro cell lines. In some embodiments, the third, fifth, seventh, ninth, eleventh and/or thirteenth cell is washed after measuring the bitter taste receptor activity to provide the fourth, sixth, eighth, tenth, twelfth and/or fourteenth cell, respectively. The tastant and test compound may be added sequentially or simultaneously, i.e., the fourth, sixth, eighth, tenth, twelfth and/or fourteenth cell may be contacted with the test compound prior to, at the same time as or subsequent to contacting the fourth, sixth, eighth, tenth, twelfth, and/or fourteenth cell with the tastant.

In some embodiments, the method comprises providing a panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line; contacting each cell line with a tastant that activates four or more of the group selected from TAS2R4, TAS2R9, TAS2R13, TAS2R14, TAS2R44, TAS2R46 and TAS2R60; measuring the bitter taste receptor activity of each cell line; washing each cell line; contacting each cell line with the tastant and a test compound; and measuring bitter taste receptor activity of each cell line. If the bitter taste receptor activity of four or more of the cell lines selected from TAS2R4, TAS2R9, TAS2R13, TAS2R14, TAS2R44, TAS2R46 and TAS2R60 differs when contacted with the tastant compared to when contacted with the tastant and the test compound, then the test compound selectively modulates bitter taste due to potassium lactate. In some embodiments, the bitter taste receptor activity differs in five or more of the cell lines selected from TAS2R4, TAS2R9, TAS2R13, TAS2R14, TAS2R44, TAS2R46 and TAS2R60. In some embodiments, the bitter taste receptor activity differs in six or more of the cell lines selected from TAS2R4, TAS2R9, TAS2R13, TAS2R14, TAS2R44, TAS2R46 and TAS2R60. In some embodiments, the bitter taste receptor activity differs in the TAS2R4, TAS2R9, TAS2R13, TAS2R14, TAS2R44, TAS2R46 and TAS2R60 cell lines. If the bitter taste receptor activity of four or more cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, the bitter taste receptor activity is greater in five or more of the cell lines selected from TAS2R4, TAS2R9, TAS2R13, TAS2R14, TAS2R44, TAS2R46 and TAS2R60. In some embodiments, the bitter taste receptor activity is greater in six or more of the cell lines selected from TAS2R4, TAS2R9, TAS2R13, TAS2R14, TAS2R44, TAS2R46 and TAS2R60. In some embodiments, the bitter taste receptor activity is greater in the TAS2R4, TAS2R9, TAS2R13, TAS2R14, TAS2R44, TAS2R46 and TAS2R60 cell lines. If the bitter taste receptor activity of four or more cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, the bitter taste receptor activity is less in five or more of the cell lines selected from TAS2R4, TAS2R9, TAS2R13, TAS2R14, TAS2R44, TAS2R46 and TAS2R60. In some embodiments, the bitter taste receptor activity is less in the TAS2R4, TAS2R9, TAS2R13, TAS2R14, TAS2R44, TAS2R46 and TAS2R60 cell lines. In some embodiments, the test compound selectively modulates, inhibits or activates bitter taste due to potassium lactate if the compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting each cell line with the tastant.

In some embodiments, the method comprises providing a panel of cell lines, wherein the panel comprises cell lines that express a bitter taste receptor selected from the group consisting of: TAS2R4, TAS2R9, TAS2R13, TAS2R14, TAS2R44, TAS2R46 and TAS2R60 wherein each receptor is expressed in at least one cell line; contacting each cell line with a tastant that activates at least two of the group selected from TAS2R4, TAS2R9, TAS2R13, TAS2R14, TAS2R44, TAS2R46 and TAS2R60; measuring the bitter taste receptor activity of each cell line; washing each cell line; contacting each cell line with the tastant and a test compound; and measuring bitter taste receptor activity of each cell line. In some embodiments, each cell line in the panel expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line. If the bitter taste receptor activity at least two of the cell lines selected from TAS2R4, TAS2R9, TAS2R13, TAS2R14, TAS2R44, TAS2R46 and TAS2R60 differs when contacted with the tastant compared to when contacted with the tastant and the test compound, then the test compound selectively modulates bitter taste due to potassium lactate. In some embodiments, if the bitter taste receptor activity differs in at least three of the cell lines selected from TAS2R4, TAS2R9, TAS2R13, TAS2R14, TAS2R44, TAS2R46 and TAS2R60 then the test compound selectively modulates bitter taste due to potassium lactate. In some embodiments, if the bitter taste receptor activity differs in at least four of the cell lines selected from TAS2R4, TAS2R9, TAS2R13, TAS2R14, TAS2R44, TAS2R46 and TAS2R60, then the test compound selectively modulates bitter taste due to potassium lactate. In some embodiments, if the bitter taste receptor activity differs in at least five of the cell lines selected from TAS2R4, TAS2R9, TAS2R13, TAS2R14, TAS2R44, TAS2R46 and TAS2R60 then the test compound selectively modulates bitter taste due to potassium lactate. In some embodiments, if the bitter taste receptor activity differs in at least six of the cell lines selected from TAS2R4, TAS2R9, TAS2R13, TAS2R14, TAS2R44, TAS2R46 and TAS2R60 then the test compound selectively modulates bitter taste due to potassium lactate. In some embodiments, if the bitter taste receptor activity differs in each of the TAS2R4, TAS2R9, TAS2R13, TAS2R14, TAS2R44, TAS2R46 and TAS2R60 cell lines then the test compound selectively modulates bitter taste due to potassium lactate. If the bitter taste receptor activity of at least two cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, if the bitter taste receptor activity of at least three cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, if the bitter taste receptor activity of at least four cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, if the bitter taste receptor activity of at least five cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, if the bitter taste receptor activity of at least six cell lines selected from TAS2R4, TAS2R9, TAS2R13, TAS2R14, TAS2R44, TAS2R46 and TAS2R60 is greater when contacted with the tastant compared to when contacted with the tastant and the test compound, then the test compound selectively inhibits bitter taste due to potassium lactate. In some embodiments, if the bitter taste receptor activity in each of the TAS2R4, TAS2R9, TAS2R13, TAS2R14, TAS2R44, TAS2R46 and TAS2R60 cell lines is greater when contacted with the tastant compared to when contacted with the tastant and the test compound, then the test compound selectively inhibits bitter taste due to potassium lactate. If the bitter taste receptor activity of at least two cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, if the bitter taste receptor activity of at least three cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, if the bitter taste receptor activity of at least four cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, if the bitter taste receptor activity of at least five cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, if the bitter taste receptor activity of at least six cell lines selected from TAS2R4, TAS2R9, TAS2R13, TAS2R14, TAS2R44, TAS2R46 and TAS2R60 is less when contacted with the tastant compared to when contacted with the tastant and the test compound, then the test compound selectively enhances bitter taste due to potassium lactate. In some embodiments, if the bitter taste receptor activity in each of the TAS2R4, TAS2R9, TAS2R13, TAS2R14, TAS2R44, TAS2R46 and TAS2R60 cell lines is less when contacted with the tastant compared to when contacted with the tastant and the test compound, then the test compound selectively enhances bitter taste due to potassium lactate. In some embodiments, the test compound selectively modulates, inhibits or activates bitter taste due to potassium lactate if the compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting each cell line with the tastant.

In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a tastant that activates four or more of the group selected from TAS2R4, TAS2R9, TAS2R13, TAS2R14, TAS2R44, TAS2R46 and TAS2R60; measuring the bitter taste receptor activity of each cell line in the first panel; contacting each cell line in the second panel with the tastant and a test compound; and measuring the bitter taste receptor activity of each cell line in the second panel. If the bitter taste receptor activity of four or more of the cell lines selected from TAS2R4, TAS2R9, TAS2R13, TAS2R14, TAS2R44, TAS2R46 and TAS2R60 differs in the first panel compared to the second panel, then the test compound selectively modulates bitter taste due to potassium lactate. In some embodiments, the bitter taste receptor activity differs in five or more of the cell lines selected from TAS2R4, TAS2R9, TAS2R13, TAS2R14, TAS2R44, TAS2R46 and TAS2R60. In some embodiments, the bitter taste receptor activity differs in six or more of the cell lines selected from TAS2R4, TAS2R9, TAS2R13, TAS2R14, TAS2R44, TAS2R46 and TAS2R60. In some embodiments, the bitter taste receptor activity differs in the TAS2R4, TAS2R9, TAS2R13, TAS2R14, TAS2R44, TAS2R46 and TAS2R60 cell lines. If the bitter taste receptor activity of four or more cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, the bitter taste receptor activity is greater in five or more of the cell lines selected from TAS2R4, TAS2R9, TAS2R13, TAS2R14, TAS2R44, TAS2R46 and TAS2R60. In some embodiments, the bitter taste receptor activity is greater in six or more of the cell lines selected from TAS2R4, TAS2R9, TAS2R13, TAS2R14, TAS2R44, TAS2R46 and TAS2R60. In some embodiments, the bitter taste receptor activity is greater in the TAS2R4, TAS2R9, TAS2R13, TAS2R14, TAS2R44, TAS2R46 and TAS2R60 cell lines. If the bitter taste receptor activity of four or more cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, the bitter taste receptor activity is less in five or more of the cell lines selected from TAS2R4, TAS2R9, TAS2R13, TAS2R14, TAS2R44, TAS2R46 and TAS2R60. In some embodiments, the bitter taste receptor activity is less in six or more of the cell lines selected from TAS2R4, TAS2R9, TAS2R13, TAS2R14, TAS2R44, TAS2R46 and TAS2R60. In some embodiments, the bitter taste receptor activity is less in the TAS2R4, TAS2R9, TAS2R13, TAS2R14, TAS2R44, TAS2R46 and TAS2R60 cell lines. In some embodiments, the test compound selectively modulates, inhibits or activates bitter taste due to potassium lactate if the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., each cell line of the second panel may be contacted with the test compound prior to, at the same time as or subsequent to contacting each cell line of the second panel with the tastant.

In some embodiments, the method comprises providing a first panel of cell lines and a second panel of cell lines, wherein each panel comprises cell lines that express a bitter taste receptor selected from the group consisting of: TAS2R4, TAS2R9, TAS2R13, TAS2R14, TAS2R44, TAS2R46 and TAS2R60 bitter taste receptor, wherein each receptor is expressed in at least one cell line, and wherein the first and second panels comprise the same cell lines; contacting each cell line in the first panel with a tastant that activates at least two of the group selected from TAS2R4, TAS2R9, TAS2R13, TAS2R14, TAS2R44, TAS2R46 and TAS2R60; measuring the bitter taste receptor activity of each cell line in the first panel; contacting each cell line in the second panel with the tastant and a test compound; and measuring the bitter taste receptor activity of each cell line in the second panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. If the bitter taste receptor activity of at least two of the cell lines selected from TAS2R4, TAS2R9, TAS2R13, TAS2R14, TAS2R44, TAS2R46 and TAS2R60 differs in the first panel compared to the second panel, then the test compound selectively modulates bitter taste due to potassium lactate. In some embodiments, if the bitter taste receptor activity of at least three of the cell lines selected from TAS2R4, TAS2R9, TAS2R13, TAS2R14, TAS2R44, TAS2R46 and TAS2R60 differs in the first panel compared to the second panel, then the test compound selectively modulates bitter taste due to potassium lactate. In some embodiments, if the bitter taste receptor activity of at least four of the cell lines selected from TAS2R4, TAS2R9, TAS2R13, TAS2R14, TAS2R44, TAS2R46 and TAS2R60 differs in the first panel compared to the second panel, then the test compound selectively modulates bitter taste due to potassium lactate. In some embodiments, if the bitter taste receptor activity differs in at least five of the cell lines selected from TAS2R4, TAS2R9, TAS2R13, TAS2R14, TAS2R44, TAS2R46 and TAS2R60, then the test compound selectively modulates bitter taste due to potassium lactate. In some embodiments, if the bitter taste receptor activity differs in at least six of the cell lines selected from TAS2R4, TAS2R9, TAS2R13, TAS2R14, TAS2R44, TAS2R46 and TAS2R60, then the test compound selectively modulates bitter taste due to potassium lactate. In some embodiments, if the bitter taste receptor activity differs in each of the TAS2R4, TAS2R9, TAS2R13, TAS2R14, TAS2R44, TAS2R46 and TAS2R60 cell lines, then the test compound selectively modulates bitter taste due to potassium lactate. If the bitter taste receptor activity of at least two cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, if the bitter taste receptor activity of at least three cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, if the bitter taste receptor activity of at least four cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, if the bitter taste receptor activity of at least five cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, if the bitter taste receptor activity of at least six cell lines selected from TAS2R4, TAS2R9, TAS2R13, TAS2R14, TAS2R44, TAS2R46 and TAS2R60 is greater in the first panel compared to the second panel, then the test compound selectively inhibits bitter taste due to potassium lactate. In some embodiments, if the bitter taste receptor activity in each of the TAS2R4, TAS2R9, TAS2R13, TAS2R14, TAS2R44, TAS2R46 and TAS2R60 cell lines is greater in the first panel compared to the second panel, then the test compound selectively inhibits bitter taste due to potassium lactate. If the bitter taste receptor activity of at least two cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, if the bitter taste receptor activity of at least three cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, if the bitter taste receptor activity of at least four cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, if the bitter taste receptor activity of at least five cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, if the bitter taste receptor activity of at least six cell lines selected from TAS2R4, TAS2R9, TAS2R13, TAS2R14, TAS2R44, TAS2R46 and TAS2R60 is less in the first panel compared to the second panel, then the test compound selectively enhances bitter taste due to potassium lactate. In some embodiments, if the bitter taste receptor activity in each of the TAS2R4, TAS2R9, TAS2R13, TAS2R14, TAS2R44, TAS2R46 and TAS2R60 cell lines is less in the first panel compared to the second panel, then the test compound selectively enhances bitter taste due to potassium lactate. In some embodiments, the test compound selectively modulates, inhibits or activates bitter taste due to potassium lactate if the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., each cell line of the second panel may be contacted with the test compound prior to, at the same time as or subsequent to contacting each cell line of the second panel with the tastant.

In some embodiments, the tastant utilized in any of the above methods of identifying modulators of bitter taste due to potassium lactate is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In another aspect, the invention provides a method of identifying a compound that mimics the bitter taste due to potassium lactate. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with a test compound; and measuring the bitter taste receptor activity of each cell line in the second panel. If the test compound induces bitter taste receptor activity of TAS2R4, TAS2R9, TAS2R13, TAS2R14, TAS2R44, TAS2R46 and TAS2R60, then the test compound mimics bitter taste due to potassium lactate. In some embodiments, the test compound does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the test compound.

In another aspect, the invention provides a method for determining if potassium lactate is present in a composition. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with the composition; and measuring the bitter taste receptor activity of each cell line in the second panel. Potassium lactate is present in the composition if the composition induces TAS2R4, TAS2R9, TAS2R13, TAS2R14, TAS2R44, TAS2R46 and TAS2R60 bitter taste receptor activity in the second panel compared to the first panel and does not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity in the second panel compared to the first panel. In some embodiments, the composition is an extract from a food product. In some embodiments, the composition comprises a pharmaceutically active ingredient. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the composition.

In some embodiments, the method comprises contacting the tastant and tastant plus test compound with two or more different bitter taste receptors selected from TAS2R4, TAS2R9, TAS2R13, TAS2R14, TAS2R44, TAS2R46 and TAS2R60. In some embodiments, the method comprises contacting the tastant and tastant plus test compound with two or more cells each expressing a different bitter taste receptor selected from TAS2R4, TAS2R9, TAS2R13, TAS2R14, TAS2R44, TAS2R46 and TAS2R60. In some embodiments, the method comprises contacting the tastant and tastant plus test compound with three or more different taste receptors selected from TAS2R4, TAS2R9, TAS2R13, TAS2R14, TAS2R44, TAS2R46 and TAS2R60. In some embodiments, the method comprises contacting the tastant and tastant plus test compound with three or more cells each expressing a different bitter taste receptor selected from TAS2R4, TAS2R9, TAS2R13, TAS2R14, TAS2R44, TAS2R46 and TAS2R60. In some embodiments, the method comprises contacting the tastant and tastant plus test compound with four or more different taste receptors selected from TAS2R4, TAS2R9, TAS2R13, TAS2R14, TAS2R44, TAS2R46 and TAS2R60. In some embodiments, the method comprises contacting the tastant and tastant plus test compound with four or more cells each expressing a different bitter taste receptor selected from TAS2R4, TAS2R9, TAS2R13, TAS2R14, TAS2R44, TAS2R46 and TAS2R60. In some embodiments, the method comprises contacting the tastant and tastant plus test compound with five or more different taste receptors selected from TAS2R4, TAS2R9, TAS2R13, TAS2R14, TAS2R44, TAS2R46 and TAS2R60. In some embodiments, the method comprises contacting the tastant and tastant plus test compound with five or more cells each expressing a different bitter taste receptor selected from TAS2R4, TAS2R9, TAS2R13, TAS2R14, TAS2R44, TAS2R46 and TAS2R60. In some embodiments, the method comprises contacting the tastant and tastant plus test compound with six or more different taste receptors selected from TAS2R4, TAS2R9, TAS2R13, TAS2R14, TAS2R44, TAS2R46 and TAS2R60. In some embodiments, the method comprises contacting the tastant and tastant plus test compound with six or more cells each expressing a different bitter taste receptor selected from TAS2R4, TAS2R9, TAS2R13, TAS2R14, TAS2R44, TAS2R46 and TAS2R60. In some embodiments, the method comprises contacting the tastant and tastant plus test compound with seven or more different taste receptors selected from TAS2R4, TAS2R9, TAS2R13, TAS2R14, TAS2R44, TAS2R46 and TAS2R60. In some embodiments, the method comprises contacting the tastant and tastant plus test compound with seven or more cells each expressing a different bitter taste receptor selected from TAS2R4, TAS2R9, TAS2R13, TAS2R14, TAS2R44, TAS2R46 and TAS2R60.

In some embodiments wherein the method of identifying a compound that modulates, inhibits, enhances or mimics bitter flavor due to potassium lactate comprises contacting TAS2R44 or a cell expressing TAS2R44 with a tastant or a test compound, the method also comprises contacting at least one additional bitter taste receptor or a cell expressing at least one additional bitter taste receptor with the tastant or test compound, wherein the at least one additional bitter taste receptor is selected from TAS2R4, TAS2R9, TAS2R13, TAS2R14, TAS2R46 and TAS2R60.

In some embodiments, the method further comprises admixing the test compound that modulates, inhibits, enhances or mimic bitter taste due to potassium lactate with foodstuffs, any foodstuff precursor material or any additive employed in the production of foodstuffs. In some embodiments, the foodstuff is for human consumption. In some embodiments, the foodstuff is for animal consumption, such as pet or livestock consumption. In some embodiments, the method further comprises admixing the test compound that modulates, inhibits, enhances or mimic bitter taste due to potassium lactate with an active agent in a pharmaceutically acceptable form.

Methods of Identifying Compounds That Modulate Bitter Taste Due to Acesulfame K

According to another aspect, the invention provides a method for identifying a compound that modulates the bitter taste due to Acesulfame K. In some embodiments, the method identifies a compound that modulates, inhibits or enhances activation of a bitter taste receptor by Acesulfame K. In some embodiments, the method identifies a compound that modulates, inhibits or enhances activation of a bitter taste receptor by Acesulfame K followed by downstream signaling. In some embodiments, the method identifies a compound that modulates, inhibits or enhances activation of a signaling pathway after stimulation by Acesulfame K. In some embodiments, the method identifies a compound that modulates, inhibits or enhances perception of bitter taste due to Acesulfame K. As shown in Example 4 below, Acesulfame K activates bitter taste receptors TAS2R1, TAS2R4, TAS2R9, TAS2R13, TAS2R14, TAS2R16, and TAS2R44. Thus, a compound that modulates Acesulfame K's activation of one or more of the TAS2R1, TAS2R4, TAS2R9, TAS2R13, TAS2R14, TAS2R16, and TAS2R44 bitter taste receptors should be a modulator of bitter taste due to Acesulfame K. In some embodiments, the compound inhibits Acesulfame K's activation of one or more of the TAS2R1, TAS2R4, TAS2R9, TAS2R13, TAS2R14, TAS2R16, and TAS2R44 bitter taste receptors. In such embodiments, the compound is an inhibitor of bitter taste due to Acesulfame K. In some embodiments, the compound enhances Acesulfame K's activation of one or more of the TAS2R1, TAS2R4, TAS2R9, TAS2R13, TAS2R14, TAS2R16, and TAS2R44 bitter taste receptors. In such embodiments, the compound is an enhancer of bitter taste due to Acesulfame K. In some embodiments, the compound activates one or more of the TAS2R1, TAS2R4, TAS2R9, TAS2R13, TAS2R14, TAS2R16, and TAS2R44 bitter taste receptors. In such embodiments, the compound mimics bitter taste due to Acesulfame K. In some embodiments, any of the methods of identifying compounds that modulate bitter taste disclosed above is performed using a tastant that activates one or more of the TAS2R1, TAS2R4, TAS2R9, TAS2R13, TAS2R14, TAS2R16, and TAS2R44 bitter taste receptors. In some embodiments, the tastant is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In some embodiments, the test compound modulates, inhibits or enhances Acesulfame K-induced activation of two or more of TAS2R1, TAS2R4, TAS2R9, TAS2R13, TAS2R14, TAS2R16, and TAS2R44. In some embodiments, the test compound modulates, inhibits or enhances Acesulfame K-induced activation of three or more of TAS2R1, TAS2R4, TAS2R9, TAS2R13, TAS2R14, TAS2R16, and TAS2R44. In some embodiments, the test compound modulates, inhibits or enhances Acesulfame K-induced activation of four or more of TAS2R1, TAS2R4, TAS2R9, TAS2R13, TAS2R14, TAS2R16, and TAS2R44. In some embodiments, the test compound modulates, inhibits or enhances Acesulfame K-induced activation of five or more of TAS2R1, TAS2R4, TAS2R9, TAS2R13, TAS2R14, TAS2R16, and TAS2R44. In some embodiments, the test compound modulates, inhibits or enhances Acesulfame K-induced activation of six or more of TAS2R1, TAS2R4, TAS2R9, TAS2R13, TAS2R14, TAS2R16, and TAS2R44. In some embodiments, the test compound modulates, inhibits or enhances Acesulfame K-induced activation of each of TAS2R1, TAS2R4, TAS2R9, TAS2R13, TAS2R14, TAS2R16, and TAS2R44.

In any of the methods of identifying compounds that modulate bitter taste due to Acesulfame K described in this section, the bitter taste receptors used in the methods may be complexed to a G-protein, as described above. Any G-protein describe above may be used. In some embodiments, the G-protein is a $G_q$ protein, an alpha transducin or an alpha gustducin. In some embodiments, the $G_q$ protein is a $G_{\alpha15}$ protein.

In any of the methods of identifying compounds that modulate bitter taste due to Acesulfame K described in this section, any assay described above may be used to measure bitter taste receptor activity. In some embodiments, the bitter taste receptor activity is determined by measuring intracellular calcium concentration. In some embodiments, intracellular calcium concentration is measured using a calcium-sensitive fluorescent dye. In some embodiments, the calcium-sensitive fluorescent dye is selected from Indo-1, Fura-2, Fluo-3, Fluo-4, Rhod-2, Rhod-5N, Calcein, Calcein blue, cytoCalcein Violet, Quin-2, Quest Fluo-8H™, Quest Fluo-8L™, Quest Fluo 8™, Quest Rhod-4™, coelenterazine and Calcium-3. In a particular embodiment, the calcium-sensitive fluorescent dye is Fluo-4 or Calcium-3.

In some embodiments, the method comprises providing one or more bitter taste receptor selected from TAS2R1, TAS2R4, TAS2R9, TAS2R13, TAS2R14, TAS2R16, and TAS2R44; contacting the one or more bitter taste receptor with a tastant that activates the one or more bitter taste receptor; measuring the activity of the one or more bitter taste receptor; washing the one or more bitter taste receptor; contacting the one or more bitter taste receptor with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to Acesulfame K. If the activity of the one or more bitter taste receptor due to the tastant is greater than the activity of the one or more bitter taste receptor due to the tastant and the test compound, then the test compound inhibits bitter taste due to Acesulfame K. If the activity of the one or more bitter taste receptor due to the tastant is less than the activity of the one or more bitter taste receptor due to the tastant and the test compound, then the test compound enhances bitter taste due to Acesulfame K. The skilled worker would recognize that, in such embodiments, the testing order does not matter. The receptor may be contacted with the test compound either before or after washing. The tastant and test compound may be added sequentially or simultaneously, i.e., the one or more bitter taste receptor may be contacted with the test compound prior to, at the same time as or subsequent to contacting the one or more bitter taste receptor with the tastant.

In some embodiments, the method comprises providing a first one or more bitter taste receptor and a second one or more bitter taste receptor, each selected from TAS2R1, TAS2R4, TAS2R9, TAS2R13, TAS2R14, TAS2R16, and TAS2R44; contacting the first one or more bitter taste receptor with a tastant that activates the one or more bitter taste receptor; measuring the activity of the first one or more bitter taste receptor; contacting the second one or more bitter taste receptor with the tastant and a test compound; and measuring the second one or more bitter taste receptor activity. If the activity of the first one or more bitter taste receptor differs from the activity of the second one or more bitter taste receptor, then the test compound modulates bitter taste due to Acesulfame K. If the activity of the first one or more bitter taste receptor is greater than the activity of the second one or more bitter taste receptor, then the test compound inhibits bitter taste due to Acesulfame K. If the activity of the first one or more bitter taste receptor is less than the activity of the second one or more bitter taste receptor, then the test compound enhances bitter taste due to Acesulfame K. In some embodiments, the first one more bitter taste receptor is washed after measurement of activity to provide the second one or more bitter taste receptor. The tastant and test compound may be added sequentially or simultaneously, i.e., the second one or more bitter taste receptor may be contacted with the test compound prior to, at the same time as or subsequent to contacting the second one or more bitter taste receptor with the tastant.

In some embodiments, the method comprises providing a cell expressing one or more bitter taste receptor, wherein the one or more bitter taste receptor is selected from TAS2R1, TAS2R4, TAS2R9, TAS2R13, TAS2R14, TAS2R16, and TAS2R44; contacting the cell with a tastant that activates one or more bitter taste receptor; measuring the activity of the one or more bitter taste receptor; washing the cell; contacting the cell with the tastant and a test compound; and measuring activity of the one or more bitter taste receptor. If the activity of the one or more bitter taste receptor due to the tastant differs from the activity of the one or more bitter taste receptor due to the tastant and the test compound, then the test compound modulates bitter taste due to Acesulfame K. If the activity of the one or more bitter taste receptor due to the tastant is greater than the activity of the one or more bitter taste receptor due to the tastant and the test compound, then the test compound inhibits bitter taste due to Acesulfame K. If the activity of the one or more bitter taste receptor due to the tastant is less than the activity of the one or more bitter taste receptor due to the tastant and the test compound, then the test compound enhances bitter taste due to Acesulfame K. In some embodiments, the cell is present in an in vitro cell line. In some embodiments, the cell is present in a panel of in vitro cell lines. The skilled worker would recognize that, in such embodiments, the testing order does not matter. The cell may be contacted with the test compound either before or after washing. The tastant and test compound may be added sequentially or simultaneously, i.e., the cell may be contacted with the test compound prior to, at the same time as or subsequent to contacting the cell with the tastant.

In some embodiments, the method comprises providing a first cell expressing one or more bitter taste receptor and a second cell expressing one or more bitter taste receptor, wherein the one or more bitter taste receptor is selected from TAS2R1, TAS2R4, TAS2R9, TAS2R13, TAS2R14, TAS2R16, and TAS2R44; contacting the first cell with a tastant that activates one or more bitter taste receptor; measuring the bitter taste receptor activity of the first cell; contacting the second cell with the tastant and a test compound; and measuring the bitter taste receptor activity of the second cell. If the bitter taste receptor activity of the first cell differs from the bitter taste receptor activity of the second cell, then the test compound modulates bitter taste due to Acesulfame K. If the bitter taste receptor activity of the first cell is greater than the bitter taste receptor activity of the second cell, then the test compound inhibits bitter taste due to Acesulfame K. If the bitter taste receptor activity of the first cell is less than the bitter taste receptor activity of the second cell, then the test compound enhances bitter taste due to Acesulfame K. In some embodiments, the first and second cells are present in in vitro cell lines. In some embodiments, the first and second cells are present in one or more panels of in vitro cell lines. In some embodiments, the first cell is washed after measuring the bitter taste receptor activity to provide the second cell. The tastant and test compound may be added sequentially or simultaneously, i.e., the second cell may be contacted with the test compound prior to, at the same time as or subsequent to contacting the second cell with the tastant.

In some embodiments, the method further comprises providing a third cell expressing one or more bitter taste receptor and a fourth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the third and fourth cell are the same; and wherein the one or more bitter taster receptor in the third and fourth cell are different from the bitter taste receptor in the first and second cells. In some embodiments, the method further comprises providing a fifth cell expressing one or more bitter taste receptor and a sixth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the fifth and sixth cell are the same; and wherein the one or more bitter taster receptor in the fifth and sixth cell are different from the bitter taste receptor in the first, second, third and fourth cells. In some embodiments, the method further comprises providing a seventh cell expressing one or more bitter taste receptor and an eighth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the seventh and eighth cell are the same; and wherein the one or more bitter taster receptor in the seventh and eighth cell are different from the bitter taste receptor in the first, second, third, fourth, fifth, and sixth cells. In some embodiments, the method further comprises providing a ninth cell expressing one or more bitter taste receptor and a tenth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the ninth and tenth cell are the same; and wherein the one or more bitter taster receptor in the ninth and tenth cell are different from the bitter taste receptor in the first, second, third, fourth, fifth, sixth, seventh and eighth cells. In some embodiments, the method further comprises providing an eleventh cell expressing one or more bitter taste receptor and a twelfth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the eleventh and twelfth cell are the same; and wherein the one or more bitter taster receptor in the eleventh and twelfth cell are different from the bitter taste receptor in the first, second, third, fourth, fifth, sixth, seventh, eighth, ninth and tenth cells. In some embodiments, the method further comprises providing an thirteenth cell expressing one or more bitter taste receptor and a fourteenth cell expressing one or more bitter taste receptor, wherein the one or more bitter taste receptor is selected from TAS2R1, TAS2R4, TAS2R9, TAS2R13, TAS2R14, TAS2R16, and TAS2R44; wherein the one or more bitter taste receptor in the thirteenth and fourteenth cell are the same; and wherein the one or more bitter taster receptor in the thirteenth and fourteenth cell are different from the bitter taste receptor in the first, second, third, fourth, fifth, sixth, seventh, eighth, ninth, tenth, eleventh and twelfth cells. In such embodiments, the method comprises contacting the third, fifth, seventh, ninth, eleventh and/or thirteenth cell with a tastant that activates one or more bitter taste receptor; measuring the bitter taste receptor activity of the third, fifth, seventh, ninth, eleventh and/or thirteenth cell; contacting the fourth, sixth, eighth, tenth, twelfth and/or fourteenth cell with the tastant and a test compound; and measuring the bitter taste receptor activity of the fourth, sixth, eighth, tenth, twelfth and/or fourteenth cell. If the bitter taste receptor activity of the third, fifth, seventh, ninth, eleventh and/or thirteenth cell differs from the bitter taste receptor activity of the fourth, sixth, eighth, tenth, twelfth and/or fourteenth cell, respectively, then the test compound modulates bitter taste due to Acesulfame K. If the bitter taste receptor activity of the fourth, sixth, eighth, tenth, twelfth and/or fourteenth cell is less than the bitter taste receptor activity of the third, fifth, seventh, ninth, eleventh and/or thirteenth cell, respectively, then the test compound inhibits bitter taste due to Acesulfame K. If the bitter taste receptor activity of the fourth, sixth, eighth, tenth, twelfth and/or fourteenth cell is greater than the bitter taste receptor activity of the third, fifth, seventh, ninth, eleventh and/or thirteenth cell, respectively, then the test compound enhances bitter taste due to Acesulfame K. In some embodiments, the third, fourth, fifth, sixth, seventh, eighth, ninth, tenth, eleventh, twelfth, thirteenth, and/or fourteenth cells are present in in vitro cell lines. In some embodiments, the third, fourth, fifth, sixth, seventh, eighth, ninth, tenth, eleventh, twelfth, thirteenth, and/or fourteenth are present in one or more panels of in vitro cell lines. In some embodiments, the third, fifth, seventh, ninth, eleventh and/or thirteenth cell is washed after measuring the bitter taste receptor activity to provide the fourth, sixth, eighth, tenth, twelfth and/or fourteenth cell, respectively. The tastant and test compound may be added sequentially or simultaneously, i.e., the fourth, sixth, eighth, tenth, twelfth and/or fourteenth cell may be contacted with the test compound prior to, at the same time as or subsequent to contacting the fourth, sixth, eighth, tenth, twelfth and/or fourteenth cell with the tastant.

In some embodiments, the method comprises providing a panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line; contacting each cell line with a tastant that activates four or more of the group selected from TAS2R1, TAS2R4, TAS2R9, TAS2R13, TAS2R14, TAS2R16, and TAS2R44; measuring the bitter taste receptor activity of each cell line; washing each cell line; contacting each cell line with the tastant and a test compound; and measuring bitter taste receptor activity of each cell line. If the bitter taste receptor activity of four or more of the cell lines selected from TAS2R1, TAS2R4, TAS2R9, TAS2R13, TAS2R14, TAS2R16, and TAS2R44 differs when contacted with the tastant compared to when contacted with the tastant and the test compound, then the test compound selectively modulates bitter taste due to Acesulfame K. In some embodiments, the bitter taste receptor activity differs in five or more of the cell lines selected from TAS2R1, TAS2R4, TAS2R9, TAS2R13, TAS2R14, TAS2R16, and TAS2R44. In some embodiments, the bitter taste receptor activity differs in six or more of the cell lines selected from TAS2R1, TAS2R4, TAS2R9, TAS2R13, TAS2R14, TAS2R16, and TAS2R44. In some embodiments, the bitter taste receptor activity differs in the TAS2R1, TAS2R4, TAS2R9, TAS2R13, TAS2R14, TAS2R16, and TAS2R44 cell lines. If the bitter taste receptor activity of four or more cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, the bitter taste receptor activity is greater in five or more of the cell lines selected from TAS2R1, TAS2R4, TAS2R9, TAS2R13, TAS2R14, TAS2R16, and TAS2R44. In some embodiments, the bitter taste receptor activity is greater in six or more of the cell lines selected from TAS2R1, TAS2R4, TAS2R9, TAS2R13, TAS2R14, TAS2R16, and TAS2R44. In some embodiments, the bitter taste receptor activity is greater in the TAS2R1, TAS2R4, TAS2R9, TAS2R13, TAS2R14, TAS2R16, and TAS2R44 cell lines. If the bitter taste receptor activity of four or more cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, the bitter taste receptor activity is less in five or more of the cell lines selected from TAS2R1, TAS2R4, TAS2R9, TAS2R13, TAS2R14, TAS2R16, and TAS2R44. In some embodiments, the bitter taste receptor activity is less in the TAS2R1, TAS2R4, TAS2R9, TAS2R13, TAS2R14, TAS2R16, and TAS2R44 cell lines. In some embodiments, the test compound selectively modulates, inhibits or activates bitter taste due to Acesulfame K if the compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting each cell line with the tastant.

In some embodiments, the method comprises providing a panel of cell lines, wherein the panel comprises cell lines that express a bitter taste receptor selected from the group consisting of: TAS2R1, TAS2R4, TAS2R9, TAS2R13, TAS2R14, TAS2R16, and TAS2R44, wherein each receptor is expressed in at least one cell line; contacting each cell line with a tastant that activates at least two of the group selected from TAS2R1, TAS2R4, TAS2R9, TAS2R13, TAS2R14, TAS2R16, and TAS2R44; measuring the bitter taste receptor activity of each cell line; washing each cell line; contacting each cell line with the tastant and a test compound; and measuring bitter taste receptor activity of each cell line. In some embodiments, each cell line in the panel expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line. If the bitter taste receptor activity at least two of the cell lines selected from TAS2R1, TAS2R4, TAS2R9, TAS2R13, TAS2R14, TAS2R16, and TAS2R44 differs when contacted with the tastant compared to when contacted with the tastant and the test compound, then the test compound selectively modulates bitter taste due to Acesulfame K. In some embodiments, if the bitter taste receptor activity differs in at least three of the cell lines selected from TAS2R1, TAS2R4, TAS2R9, TAS2R13, TAS2R14, TAS2R16, and TAS2R44 then the test compound selectively modulates bitter taste due to Acesulfame K. In some embodiments, if the bitter taste receptor activity differs in at least four of the cell lines selected from TAS2R1, TAS2R4, TAS2R9, TAS2R13, TAS2R14, TAS2R16, and TAS2R44, then the test compound selectively modulates bitter taste due to Acesulfame K. In some embodiments, if the bitter taste receptor activity differs in at least five of the cell lines selected from TAS2R1, TAS2R4, TAS2R9, TAS2R13, TAS2R14, TAS2R16, and TAS2R44 then the test compound selectively modulates bitter taste due to Acesulfame K. In some embodiments, if the bitter taste receptor activity differs in at least six of the cell lines selected from TAS2R1, TAS2R4, TAS2R9, TAS2R13, TAS2R14, TAS2R16, and TAS2R44 then the test compound selectively modulates bitter taste due to Acesulfame K. In some embodiments, if the bitter taste receptor activity differs in each of the TAS2R1, TAS2R4, TAS2R9, TAS2R13, TAS2R14, TAS2R16, and TAS2R44 cell lines then the test compound selectively modulates bitter taste due to Acesulfame K. If the bitter taste receptor activity of at least two cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, if the bitter taste receptor activity of at least three cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, if the bitter taste receptor activity of at least four cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, if the bitter taste receptor activity of at least five cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, if the bitter taste receptor activity of at least six cell lines selected from TAS2R1, TAS2R4, TAS2R9, TAS2R13, TAS2R14, TAS2R16, and TAS2R44 is greater when contacted with the tastant compared to when contacted with the tastant and the test compound, then the test compound selectively inhibits bitter taste due to Acesulfame K. In some embodiments, if the bitter taste receptor activity in each of the TAS2R1, TAS2R4, TAS2R9, TAS2R13, TAS2R14, TAS2R16, and TAS2R44 cell lines is greater when contacted with the tastant compared to when contacted with the tastant and the test compound, then the test compound selectively inhibits bitter taste due to Acesulfame K. If the bitter taste receptor activity of at least two cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, if the bitter taste receptor activity of at least three cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, if the bitter taste receptor activity of at least four cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, if the bitter taste receptor activity of at least five cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, if the bitter taste receptor activity of at least six cell lines selected from TAS2R1, TAS2R4, TAS2R9, TAS2R13, TAS2R14, TAS2R16, and TAS2R44 is less when contacted with the tastant compared to when contacted with the tastant and the test compound, then the test compound selectively enhances bitter taste due to Acesulfame K. In some embodiments, if the bitter taste receptor activity in each of the TAS2R1, TAS2R4, TAS2R9, TAS2R13, TAS2R14, TAS2R16, and TAS2R44 cell lines is less when contacted with the tastant compared to when contacted with the tastant and the test compound, then the test compound selectively enhances bitter taste due to Acesulfame K. In some embodiments, the test compound selectively modulates, inhibits or activates bitter taste due to Acesulfame K if the compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity. In some embodiments, the panel is a matched panel of in vitro cell lines. The skilled worker would recognize that, in such embodiments, the testing order does not matter. The cell lines may be contacted with the test compound either before or after washing. The tastant and test compound may be added sequentially or simultaneously, i.e., each cell line may be contacted with the test compound prior to, at the same time as or subsequent to contacting each cell line with the tastant.

In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a tastant that activates four or more of the group selected from TAS2R1, TAS2R4, TAS2R9, TAS2R13, TAS2R14, TAS2R16, and TAS2R44; measuring the bitter taste receptor activity of each cell line in the first panel; contacting each cell line in the second panel with the tastant and a test compound; and measuring the bitter taste receptor activity of each cell line in the second panel. If the bitter taste receptor activity of four or more of the cell lines selected from TAS2R1, TAS2R4, TAS2R9, TAS2R13, TAS2R14, TAS2R16, and TAS2R44 differs in the first panel compared to the second panel, then the test compound selectively modulates bitter taste due to Acesulfame K. In some embodiments, the bitter taste receptor activity differs in five or more of the cell lines selected from TAS2R1, TAS2R4, TAS2R9, TAS2R13, TAS2R14, TAS2R16, and TAS2R44. In some embodiments, the bitter taste receptor activity differs in six or more of the cell lines selected from TAS2R1, TAS2R4, TAS2R9, TAS2R13, TAS2R14, TAS2R16, and TAS2R44. In some embodiments, the bitter taste receptor activity differs in the TAS2R1, TAS2R4, TAS2R9, TAS2R13, TAS2R14, TAS2R16, and TAS2R44 cell lines. If the bitter taste receptor activity of four or more cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, the bitter taste receptor activity is greater in five or more of the cell lines selected from TAS2R1, TAS2R4, TAS2R9, TAS2R13, TAS2R14, TAS2R16, and TAS2R44. In some embodiments, the bitter taste receptor activity is greater in six or more of the cell lines selected from TAS2R1, TAS2R4, TAS2R9, TAS2R13, TAS2R14, TAS2R16, and TAS2R44. In some embodiments, the bitter taste receptor activity is greater in the TAS2R1, TAS2R4, TAS2R9, TAS2R13, TAS2R14, TAS2R16, and TAS2R44 cell lines. If the bitter taste receptor activity of four or more cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, the bitter taste receptor activity is less in five or more of the cell lines selected from TAS2R1, TAS2R4, TAS2R9, TAS2R13, TAS2R14, TAS2R16, and TAS2R44. In some embodiments, the bitter taste receptor activity is less in six or more of the cell lines selected from TAS2R1, TAS2R4, TAS2R9, TAS2R13, TAS2R14, TAS2R16, and TAS2R44. In some embodiments, the bitter taste receptor activity is less in the TAS2R1, TAS2R4, TAS2R9, TAS2R13, TAS2R14, TAS2R16, and TAS2R44 cell lines. In some embodiments, the test compound selectively modulates, inhibits or activates bitter taste due to Acesulfame K if the test compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., each cell line in the second panel may be contacted with the test compound prior to, at the same time as or subsequent to contacting each cell line in the second panel with the tastant.

In some embodiments, the method comprises providing a first panel of cell lines and a second panel of cell lines, wherein each panel comprises cell lines that express a bitter taste receptor selected from the group consisting of: TAS2R1, TAS2R4, TAS2R9, TAS2R13, TAS2R14, TAS2R16, and TAS2R44 bitter taste receptor, wherein each receptor is expressed in at least one cell line, and wherein the first and second panels comprise the same cell lines; contacting each cell line in the first panel with a tastant that activates at least two of the group selected from TAS2R1, TAS2R4, TAS2R9, TAS2R13, TAS2R14, TAS2R16, and TAS2R44; measuring the bitter taste receptor activity of each cell line in the first panel; contacting each cell line in the second panel with the tastant and a test compound; and measuring the bitter taste receptor activity of each cell line in the second panel. In some embodiments, each cell line in the first and second panels expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60, wherein each receptor is expressed in at least one cell line of each panel. If the bitter taste receptor activity of at least two of the cell lines selected from TAS2R1, TAS2R4, TAS2R9, TAS2R13, TAS2R14, TAS2R16, and TAS2R44 differs in the first panel compared to the second panel, then the test compound selectively modulates bitter taste due to Acesulfame K. In some embodiments, if the bitter taste receptor activity differs in at least three of the cell lines selected from TAS2R1, TAS2R4, TAS2R9, TAS2R13, TAS2R14, TAS2R16, and TAS2R44, then the test compound selectively modulates bitter taste due to Acesulfame K. In some embodiments, if the bitter taste receptor activity differs in at least four of the cell lines selected from TAS2R1, TAS2R4, TAS2R9, TAS2R13, TAS2R14, TAS2R16, and TAS2R44, then the test compound selectively modulates bitter taste due to Acesulfame K. In some embodiments, if the bitter taste receptor activity differs in at least five of the cell lines selected from TAS2R1, TAS2R4, TAS2R9, TAS2R13, TAS2R14, TAS2R16, and TAS2R44, then the test compound selectively modulates bitter taste due to Acesulfame K. In some embodiments, if the bitter taste receptor activity differs in at least six of the cell lines selected from TAS2R1, TAS2R4, TAS2R9, TAS2R13, TAS2R14, TAS2R16, and TAS2R44, then the test compound selectively modulates bitter taste due to Acesulfame K. In some embodiments, if the bitter taste receptor activity differs in each of the TAS2R1, TAS2R4, TAS2R9, TAS2R13, TAS2R14, TAS2R16, and TAS2R44 cell lines, then the test compound selectively modulates bitter taste due to Acesulfame K. If the bitter taste receptor activity of at least two cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, if the bitter taste receptor activity of at least three cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, if the bitter taste receptor activity of at least four cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, if the bitter taste receptor activity of at least five cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, if the bitter taste receptor activity of at least six cell lines selected from TAS2R1, TAS2R4, TAS2R9, TAS2R13, TAS2R14, TAS2R16, and TAS2R44 is greater in the first panel compared to the second panel, then the test compound selectively inhibits bitter taste due to Acesulfame K. In some embodiments, if the bitter taste receptor activity in each of the TAS2R1, TAS2R4, TAS2R9, TAS2R13, TAS2R14, TAS2R16, and TAS2R44 cell lines is greater in the first panel compared to the second panel, then the test compound selectively inhibits bitter taste due to Acesulfame K. If the bitter taste receptor activity of at least two cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, if the bitter taste receptor activity of at least three cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, if the bitter taste receptor activity of at least four cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, if the bitter taste receptor activity of at least five cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, if the bitter taste receptor activity of at least six cell lines selected from TAS2R1, TAS2R4, TAS2R9, TAS2R13, TAS2R14, TAS2R16, and TAS2R44 is less in the first panel compared to the second panel, then the test compound selectively enhances bitter taste due to Acesulfame K. In some embodiments, if the bitter taste receptor activity in each of the TAS2R1, TAS2R4, TAS2R9, TAS2R13, TAS2R14, TAS2R16, and TAS2R44 cell lines is less in the first panel compared to the second panel, then the test compound selectively enhances bitter taste due to Acesulfame K. In some embodiments, the test compound selectively modulates, inhibits or activates bitter taste due to Acesulfame K if the test compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. The tastant and test compound may be added sequentially or simultaneously, i.e., each cell line in the second panel may be contacted with the test compound prior to, at the same time as or subsequent to contacting each cell line in the second panel with the tastant.

In some embodiments, the tastant utilized in any of the above methods of identifying modulators of bitter taste due to Acesulfame K is selected from KCl, potassium lactate, Acesulfame K, and a universal bitter compound. In some embodiments, the universal bitter compound is denatonium benzoate or denatonium saccharide. In some embodiments, the concentration of the tastant is 5 mM, 10 mM, 15 mM, 20 mM, 25 mM, 30 mM, 35 mM, 40 mM, 45 mM or 50 mM. In some embodiments, the concentration of the tastant is about 5 mM, about 10 mM, about 15 mM, about 20 mM, about 25 mM, about 30 mM, about 35 mM, about 40 mM, about 45 mM or about 50 mM. In some embodiments, the concentration of the tastant is at least 5 mM, at least 10 mM, at least 15 mM, at least 20 mM, at least 25 mM, at least 30 mM, at least 35 mM, at least 40 mM, at least 45 mM or at least 50 mM. In some embodiments, the concentration of the tastant is at least about 5 mM, at least about 10 mM, at least about 15 mM, at least about 20 mM, at least about 25 mM, at least about 30 mM, at least about 35 mM, at least about 40 mM, at least about 45 mM or at least about 50 mM.

In another aspect, the invention provides a method of identifying a compound that mimics the bitter taste due to Acesulfame K. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with a test compound; and measuring the bitter taste receptor activity of each cell line in the second panel. If the test compound induces bitter taste receptor activity of TAS2R1, TAS2R4, TAS2R9, TAS2R13, TAS2R14, TAS2R16, and TAS2R44, then the test compound mimics bitter taste due to Acesulfame K. In some embodiments, the test compound does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity in the second panel compared to the first panel. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the test compound.

In another aspect, the invention provides a method for determining if Acesulfame K is present in a composition. In some embodiments, the method comprises providing a first panel of cell lines and a second panel of cell lines, wherein each cell line expresses a bitter taste receptor selected from the group consisting of: TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptor, wherein each receptor is expressed in at least one cell line, and wherein the first and second panels comprise the same cell lines; contacting each cell line in the first panel with a negative control; measuring the bitter taste receptor activity of each cell line in the first panel; contacting each cell line in the second panel with the composition; and measuring the bitter taste receptor activity of each cell line in the second panel. Acesulfame K is present in the composition if the composition induces TAS2R1, TAS2R4, TAS2R9, TAS2R13, TAS2R14, TAS2R16, and TAS2R44 bitter taste receptor activity in the second panel compared to the first panel and does not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, and TAS2R60 bitter taste receptor activity in the second panel compared to the first panel. In some embodiments, the composition is an extract from a food product. In some embodiments, the composition comprises a pharmaceutically active ingredient. In some embodiments, the first and second panels are matched panels of in vitro cell lines. In some embodiments, the first panel of cell lines is washed after it is measured for bitter taste receptor activity to provide the second panel of cell lines. In other words, the first and second panels of cell lines are the same, with a washing step between first measuring step and the second contacting step. The skilled worker would recognize that, in such embodiments, the testing order does not matter. The cell lines may be contacted with the test compound either before or after washing. In some embodiments, the negative control is the assay buffer before addition of the composition.

In some embodiments, the method comprises contacting the tastant and tastant plus test compound with two or more different bitter taste receptors selected from TAS2R1, TAS2R4, TAS2R9, TAS2R13, TAS2R14, TAS2R16, and TAS2R44. In some embodiments, the method comprises contacting the tastant and tastant plus test compound with two or more cells each expressing a different bitter taste receptor selected from TAS2R1, TAS2R4, TAS2R9, TAS2R13, TAS2R14, TAS2R16, and TAS2R44. In some embodiments, the method comprises contacting the tastant and tastant plus test compound with three or more different taste receptors selected from TAS2R1, TAS2R4, TAS2R9, TAS2R13, TAS2R14, TAS2R16, and TAS2R44. In some embodiments, the method comprises contacting the tastant and tastant plus test compound with three or more cells each expressing a different bitter taste receptor selected from TAS2R1, TAS2R4, TAS2R9, TAS2R13, TAS2R14, TAS2R16, and TAS2R44. In some embodiments, the method comprises contacting the tastant and tastant plus test compound with four or more different taste receptors selected from TAS2R1, TAS2R4, TAS2R9, TAS2R13, TAS2R14, TAS2R16, and TAS2R44. In some embodiments, the method comprises contacting the tastant and tastant plus test compound with four or more cells each expressing a different bitter taste receptor selected from TAS2R1, TAS2R4, TAS2R9, TAS2R13, TAS2R14, TAS2R16, and TAS2R44. In some embodiments, the method comprises contacting the tastant and tastant plus test compound with five or more different taste receptors selected from TAS2R1, TAS2R4, TAS2R9, TAS2R13, TAS2R14, TAS2R16, and TAS2R44. In some embodiments, the method comprises contacting the tastant and tastant plus test compound with five or more cells each expressing a different bitter taste receptor selected from TAS2R1, TAS2R4, TAS2R9, TAS2R13, TAS2R14, TAS2R16, and TAS2R44. In some embodiments, the method comprises contacting the tastant and tastant plus test compound with six or more different taste receptors selected from TAS2R1, TAS2R4, TAS2R9, TAS2R13, TAS2R14, TAS2R16, and TAS2R44. In some embodiments, the method comprises contacting the tastant and tastant plus test compound with six or more cells each expressing a different bitter taste receptor selected from TAS2R1, TAS2R4, TAS2R9, TAS2R13, TAS2R14, TAS2R16, and TAS2R44. In some embodiments, the method comprises contacting the tastant and tastant plus test compound with seven or more different taste receptors selected from TAS2R1, TAS2R4, TAS2R9, TAS2R13, TAS2R14, TAS2R16, and TAS2R44. In some embodiments, the method comprises contacting the tastant and tastant plus test compound with seven or more cells each expressing a different bitter taste receptor selected from TAS2R1, TAS2R4, TAS2R9, TAS2R13, TAS2R14, TAS2R16, and TAS2R44.

In some embodiments wherein the method of identifying a compound that modulates, inhibits, enhances or mimics bitter flavor due to Acesulfame K comprises contacting TAS2R44 or a cell expressing TAS2R44 with a tastant or a test compound, the method also comprises contacting at least one additional bitter taste receptor or a cell expressing at least one additional bitter taste receptor with the tastant or test compound, wherein the at least one additional bitter taste receptor is selected from TAS2R1, TAS2R4, TAS2R9, TAS2R13, TAS2R14, and TAS2R16.

In some embodiments, the method further comprises admixing the test compound that modulates, inhibits, enhances or mimic bitter taste due to Acesulfame K with foodstuffs, any foodstuff precursor material or any additive employed in the production of foodstuffs. In some embodiments, the foodstuff is for human consumption. In some embodiments, the foodstuff is for animal consumption, such as pet or livestock consumption. In some embodiments, the method further comprises admixing the test compound that modulates, inhibits, enhances or mimic bitter taste due to Acesulfame K with an active agent in a pharmaceutically acceptable form.

Panels of Cell Lines for Identifying Compounds that Modulate Bitter Taste

According to another aspect, the invention provides panels of cell lines for identifying a compound that modulates the bitter taste.

In some embodiments, the panel of cell lines is for identifying a compound that modulates the bitter taste due to KCl. In some embodiments, the panel comprises cell lines that express a bitter taste receptor selected from the group consisting of: TAS2R4, TAS2R9, TAS2R13, TAS2R14, TAS2R44 and TAS2R60. In some embodiments, each of TAS2R4, TAS2R9, TAS2R13, TAS2R14, TAS2R44 and TAS2R60 is expressed in at least one cell line in the panel. In some embodiments, the panel consists essentially of cell lines that express a bitter taste receptor selected from the group consisting of: TAS2R4, TAS2R9, TAS2R13, TAS2R14, TAS2R44 and TAS2R60. In some embodiments, the panel of cell lines further comprises a negative control cell line. In some embodiments, the negative control is a negative control for a method of identifying a compound that modulates the bitter taste due to KCl.

In some embodiments, the panel of cell lines is for identifying a compound that modulates the bitter taste due to potassium lactate. In some embodiments, the panel comprises cell lines that express a bitter taste receptor selected from the group consisting of: TAS2R4, TAS2R9, TAS2R13, TAS2R14, TAS2R44, TAS2R46 and TAS2R60. In some embodiments, each of TAS2R4, TAS2R9, TAS2R13, TAS2R14, TAS2R44, TAS2R46 and TAS2R60 is expressed in at least one cell line in the panel. In some embodiments, the panel consists essentially of cell lines that express a bitter taste receptor selected from the group consisting of: TAS2R4, TAS2R9, TAS2R13, TAS2R14, TAS2R44, TAS2R46 and TAS2R60. In some embodiments, the panel of cell lines further comprises a negative control cell line. In some embodiments, the negative control is a negative control for a method of identifying a compound that modulates the bitter taste due to potassium lactate.

In some embodiments, the panel of cell lines is for identifying a compound that modulates the bitter taste due to Acesulfame K In some embodiments, the panel comprises cell lines that express a bitter taste receptor selected from the group consisting of: TAS2R1, TAS2R4, TAS2R9, TAS2R13, TAS2R14, TAS2R16, and TAS2R44. In some embodiments, each of TAS2R1, TAS2R4, TAS2R9, TAS2R13, TAS2R14, TAS2R16, and TAS2R44 is expressed in at least one cell line in the panel. In some embodiments, the panel consists essentially of cell lines that express a bitter taste receptor selected from the group consisting of: TAS2R1, TAS2R4, TAS2R9, TAS2R13, TAS2R14, TAS2R16, and TAS2R44. In some embodiments, the panel of cell lines further comprises a negative control cell line. In some embodiments, the negative control is a negative control for a method of identifying a compound that modulates the bitter taste due to Acesulfame K.

EXAMPLES

In order that this invention be more fully understood, the following examples are set forth. These examples are for the purpose of illustration only and are not to be construed as limiting the scope of the invention in any way.

A panel of cell lines expressing each of the twenty-five bitter taste receptors was generated as described in International Patent Application Publication WO 2010/088633 (see, e.g., Example 26). Accordingly, each cell line of the panel expressed a human bitter taste receptor and mouse $G\alpha_{15}$ signaling protein.

Each of the Examples below utilized the following functional assay:

Day 1:
Stable cell lines were seeded onto black wall/clear bottom 96-well, plates (e.g., Corning, 3904). Approximately 40K cells were added per well and incubated at 37° C., 5% $CO_2$ overnight in cell growth media (DMEM (Sigma, D5796) supplemented with 10% Fetal Bovine Serum (Sigma, 5178), 2 mM Glutamine (Sigma, G7513)).

Day 2:
Growth media was discarded and cells were incubated at 37° C., 5% $CO_2$ for 60 minutes in 100 ul of load solution containing 1× Ca-3 dye (Molecular Devices, R8090), 1% DMSO in buffer containing 130 mM NaCl, 2 mM CaCl$_2$, 5 mM KCl, 1.2 mM MgCl$_2$, mM HEPES and 10 mM Glucose (pH 7.0). Probenecid was not included in the load solution.

Functional Assay:

After dye loading, cell plates were placed in a fluorescent plate reader (e.g., FDSS6000 (Hamamatsu, Japan)) and receptor stimulation was measured by adding 50 ul of 3× concentrated ligand/agonist stock. Fluorescence was monitored continuously for 10 s before agonist addition and for 100-250 s after stimulation with agonist.

Receptor Activation is defined as follows:

% Activation=[((Maximum signal fluorescence−Minimum signal fluorescence)−(Maximum control fluorescence−Minimum control fluorescence))/(Maximum buffer fluorescence−Minimum buffer fluorescence)]*100

Functional Response=[(Maximum signal fluorescence−Minimum signal fluorescence)−(Maximum control fluorescence−Minimum control fluorescence)]

Signal Fluorescence: refers to the change in fluorescence seen with addition of ligand Control fluorescence: refers to the change in fluorescence seen with addition of buffer (negative control)

Calcium signals from ligand and control were normalized to the basal fluorescence of the cells prior to the stimulation.

A concentration analysis was performed and EC$_{50}$ values were calculated by nonlinear regression using the formula: Y=Bottom+(Top-Bottom)/(1+10^((Log EC50-X)*Hill Slope)), X=log of dose or concentration, Y=Response (increasing as X increases), Top=maximum signal, Bottom=minimum signal. EC$_{50}$ (half maximal effective concentration) refers to the molar concentration of the agonist which produces 50% of the maximum possible effective response from that agonist.

Example 1

Verification of Functional Signaling in the Bitter Taste Receptor Panel

To confirm that each of the 25 bitter receptor cell lines functionally and stably express the G protein (Gα$_{15}$), the entire panel was tested, as described above, with increasing concentrations of isoproterenol, an agonist of β2-adrenergic receptor, which is endogenously expressed in the HEK293T host cell line. Isoproterenol is known to signal via Gα$_{15}$ signaling cascade to increase intracellular calcium levels.

As shown in FIG. 1, all twenty-five bitter taste receptor cell lines present in the panel uniformly respond to isoproterenol in a functional assay. For each of the twenty-five cell lines, the EC$_{50}$ value was approximately 4.9±0.41 nM, which is in close agreement with published literature values. The EC$_{50}$ values show remarkable reproducibility between the twenty-five clonal cell lines and confirm that the panel of bitter cell lines is useful for functional assays.

Example 2

Identification of the Bitter Taste Receptors That Respond to KCl

To identify the set of receptors that are sensitive to KCl and likely mediate bitter taste due to KCl, the entire panel of twenty-five bitter receptor expressing cell lines were independently and simultaneously exposed to 20 mM KCl. Bitter taste receptor activation was measured by changes in intracellular calcium using the fluorescent reporter system described above. As shown in FIG. 2, only six bitter taste receptor expressing cell lines out of the twenty-five strongly and specifically responded to KCl stimulation. KCl elicited a weak or background response in the other nineteen cell lines. KCl induced TAS2R4, TAS2R9, TAS2R13, TAS2R14, TAS2R44 and TAS2R60 bitter receptor activity (FIGS. 2 and 6). KCl did not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R46, TAS2R47, TAS2R48, TAS2R49, TAS2R50, or TAS2R55 bitter taste receptor activity (FIGS. 2 and 6). Heretofore, no ligand had been identified for TAS2R60, which has now been deorphaned.

To further characterize KCl-induced signaling by TAS2R4, TAS2R9, TAS2R13, TAS2R14, TAS2R44 and TAS2R60, a functional profile was created by measuring KCl's activation of each of the receptors by stimulating them with increasing concentrations of KCl and calculating EC$_{50}$ values as described above. As shown in FIG. 3, the EC$_{50}$ value for each cell line was approximately 5-15 mM. Due to the difference in the nature of the receptors and ligands, the dose-response curves in the TAS2R activity assays are not directly comparable to the dose-response curves in FIG. 1.

Example 3

Identification of the Bitter Taste Receptors that Respond to Potassium Lactate

To identify the set of receptors that are sensitive to potassium lactate and likely mediate bitter taste due to potassium lactate, the entire panel of twenty-five bitter receptor expressing cell lines were independently and simultaneously exposed to 20 mM potassium lactate. Bitter taste receptor activation was measured by changes in intracellular calcium using the fluorescent reporter system described above. As shown in FIG. 4, only seven bitter taste receptor expressing cell lines out of the twenty-five strongly and specifically responded to potassium lactate stimulation. Potassium lactate elicited a weak or background response in the other eighteen cell lines. Potassium lactate induced TAS2R4, TAS2R9, TAS2R13, TAS2R14, TAS2R44, TAS2R46 and TAS2R60 bitter receptor activity (FIGS. 4 and 6). Potassium lactate did not induce TAS2R1, TAS2R3, TAS2R5, TAS2R7, TAS2R8, TAS2R10, TAS2R16, TAS2R38, TAS2R39, TAS2R40, TAS2R41, TAS2R43, TAS2R45, TAS2R47, TAS2R48, TAS2R49, TAS2R50, and TAS2R55 bitter taste receptor activity (FIGS. 4 and 6). Heretofore, no ligand had been identified for TAS2R60, which has now been deorphaned.

Example 4

Identification of the Bitter Taste Receptors That Respond to Acesulfame K

To identify the set of receptors that are sensitive to Acesulfame K and likely mediate bitter taste due to Acesulfame K, the entire panel of twenty-five bitter receptor expressing cell lines were independently and simultaneously exposed to 20 mM Acesulfame K. Bitter taste receptor activation was measured by changes in intracellular calcium using the fluorescent reporter system described above. As shown in FIG. 5, only seven bitter taste receptor expressing cell lines out of the twenty-five strongly and specifically responded to Acesulfame K stimulation. Acesulfame K elicited a weak or background response in the other eighteen cell lines. Acesulfame K induced TAS2R1, TAS2R4, TAS2R9, TAS2R13, TAS2R14, TAS2R16, and TAS2R44 bitter receptor activity (FIGS. 5 and 6). Acesulfame K did not induce TAS2R3, TAS2R5, TAS2R7, TAS2R8, TAS2R10, TAS2R38, TAS2R39, TAS2R40, TAS2R41, TAS2R43, TAS2R45, TAS2R46, TAS2R47, TAS2R48, TAS2R49, TAS2R50, TAS2R55, or TAS2R60 bitter taste receptor activity (FIGS. 5 and 6).

```
                          SEQUENCE LISTING

Human GNA15
MARSLTWRCCPWCLTEDEKAAARVDQEINRILLEQKKQDRGELKLLLLGPGESGKSTFIKQM
RIIHGAGYSEEERKGFRPLVYQNIFVSMRAMIEAMERLQIPFSRPESKHHASLVMSQDPYKVTTFEKRY
AAAMQWLWRDAGIRACYERRREFHLLDSAVYYLSHLERITEEGYVPTAQDVLRSRMPTTGINEYCFSV
QKTNLRIVDVGGQKSERKKWIHCFENVIALIYLASLSEYDQCLEENNQENRMKESLALFGTILELPWFK
STSVILFLNKTDILEEKIPTSHLATYFPSFQGPKQDAEAAKRFILDMYTRMYTGCVDGPEGSKKGARSRR
LFSHYTCATDTQNIRKVFKDVRDSVLARYLDEINLL (SEQ ID NO: 1)

TAS2R1 CDS
ATGCTAGAGTCTCACCTCATTATCTATTTTCTTCTTGCAGTGATACAATTTCTTCTTGGGAT
TTTTCACAAATGGCATCATTGTGGTGGTGAATGGCATTGACTTGATCAAGCACAGAAAAATGGCTCC
GCTGGATCTCCTTCTTTCTTGTCTGGCAGTTTCTAGAATTTTTCTGCAGTTGTTCATCTTCTACGTTA
ATGTGATTGTTATCTTCTTCATAGAATTCATCATGTGTTCTGCGAATTGTGCAATTCTCTTATTTATA
AATGAATTGGAACTTTGGCTTGCCACATGGCTCGGCGTTTTCTATTGTGCCAAGGTTGCCAGCGTC
CGTCACCCACTCTTCATCTGGTTGAAGATGAGGATATCCAAGCTGGTCCCATGGATGATCCTGGGG
TCTCTGCTATATGTATCTATGATTTGTGTTTTCCATAGCAAATATGCAGGGTTTATGGTCCCATACT
TCCTAAGGAAATTTTTCTCCCAAAATGCCACAATTCAAAAAGAAGATACACTGGCTATACAGATTT
TCTCTTTTGTTGCTGAGTTCTCAGTGCCATTGCTTATCTTCCTTTTTGCTGTTTTGCTCTTGATTTTCT
CTCTGGGGAGGCACACCCGGCAAATGAGAAACACAGTGGCCGGCAGCAGGGTTCCTGGCAGGGGT
GCACCCATCAGCGCGTTGCTGTCTATCCTGTCCTTCCTGATCCTCTACTTCTCCCACTGCATGATAA
AAGTTTTTCTCTCTTCTCTAAAGTTTCACATCAGAAGGTTCATCTTTCTGTTCTTCATCCTTGTGATT
GGTGTATACCCTTCTGGACACTCTCTCATCTTAATTTTAGGAAATCCTAAATTGAAACAAAATGCA
AAAAAGTTCCTCCTCCACAGTAAGTGCTGTCAGTGA (SEQ ID NO: 2)

TAS2R3 CDS
ATGATGGGACTCACCGAGGGGGTGTTCCTGATTCTGTCTGGCACTCAGTTCACACTGGGA
ATTCTGGTCAATTGTTTCATTGAGTTGGTCAATGGTAGCAGCTGGTTCAAGACCAAGAGAATGTCT
TTGTCTGACTTCATCATCACCACCCTGGCACTCTTGAGGATCATTCTGCTGTGTATTATCTTGACTG
ATAGTTTTTTAATAGAATTCTCTCCCAACACACATGATTCAGGGATAATAATGCAAATTATTGATG
TTTCCTGGACATTTACAAACCATCTGAGCATTTGGCTTGCCACCTGTCTTGGTGTCCTCTACTGCCT
GAAAATCGCCAGTTTCTCTCACCCCACATTCCTCTGGCTCAAGTGGAGAGTTTCTAGGGTGATGGT
ATGGATGCTGTTGGGTGCACTGCTCTTATCCTGTGGTAGTACCGCATCTCTGATCAATGAGTTTAAG
CTCTATTCTGTCTTTAGGGGAATTGAGGCCACCAGGAATGTGACTGAACACTTCAGAAAGAAGAG
GAGTGAGTATTATCTGATCCATGTTCTTGGGACTCTGTGGTACCTGCCTCCCTTAATTGTGTCCCTG
GCCTCCTACTCTTTGCTCATCTTCTCCCTGGGGAGGCACACACGGCAGATGCTGCAAAATGGGACA
AGCTCCAGAGATCCAACCACTGAGGCCCACAAGAGGGCCATCAGAATCATCCTTTCCTTCTTCTTT
CTCTTCTTACTTTACTTTCTTGCTTTCTTAATTGCATCATTTGGTAATTTCCTACCAAAAACCAAGAT
GGCTAAGATGATTGGTGAAGTAATGACAATGTTTTATCCTGCTGGCCACTCATTTATTCTCATTCTG
GGGAACAGTAAGCTGAAGCAGACATTTGTAGTGATGCTCCGGTGTGAGTCTGGTCATCTGAAGCCT
GGATCCAAGGGACCCATTTTCTCTTAG (SEQ ID NO: 3)

TAS2R4 CDS
ATGCTTCGGTTATTCTATTTCTCTGCTATTATTGCCTCAGTTATTTTAAATTTTGTAGGAAT
CATTATGAATCTGTTTATTACAGTGGTCAATTGCAAAACTTGGGTCAAAAGCCATAGAATCTCCTC
TTCTGATAGGATTCTGTTCAGCCTGGGCATCACCAGGTTTCTTATGCTGGGACTATTTCTGGTGAAC
ACCATCTACTTCGTCTCTTCAAATACGGAAAGGTCAGTCTACCTGTCTGCTTTTTTTGTGTTGTGTTT
CATGTTTTTGGACTCGAGCAGTGTCTGGTTTGTGACCTTGCTCAATATCTTGTACTGTGTGAAGATT
ACTAACTTCCAACACTCAGTGTTTCTCCTGCTGAAGCGGAATATCTCCCCAAAGATCCCCAGGCTG
CTGCTGGCCTGTGTGCTGATTTCTGCTTTCACCACTTGCCTGTACATCACGCTTAGCCAGGCATCAC
CTTTTCCTGAACTTGTGACTACGAGAAATAACACATCATTTAATATCAGTGAGGGCATCTTGTCTTT
AGTGGTTTCTTTGGTCTTGAGCTCATCTCTCCAGTTCATCATTAATGTGACTTCTGCTTCCTTGCTAA
TACACTCCTTGAGGAGACATATACAGAAGATGCAGAAAAATGCCACTGGTTTCTGGAATCCCCAG
ACGGAAGCTCATGTAGGTGCTATGAAGCTGATGGTCTATTTCCTCATCCTCTACATTCCATATTCAG
TTGCTACCCTGGTCCAGTATCTCCCCTTTTATGCAGGGATGGATATGGGGACCAAATCCATTTGTCT
GATTTTTGCCACCCTTTACTCTCCAGGACATTCTGTTCTCATTATTATCACACATCCTAAACTGAAA
ACAACAGCAAAGAAGATTCTTTGTTTCAAAAAATAG (SEQ ID NO: 4)

TAS2R5 CDS
ATGCTGAGCGCTGGCCTAGGACTGCTGATGCTGGTGGCAGTGGTTGAATTTCTCATCGGTT
TAATTGGAAATGGAAGCCTGGTGGTCTGGAGTTTTAGAGAATGGATCAGAAAATTCAACTGGTCCT
CATATAACCTCATTATCCTGGGCCTGGCTGGCTGCCGATTTCTCCTGCAGTGGCTGATCATTTTGGA
CTTAAGCTTGTTTCCACTTTTCCAGAGCAGCCGTTGGCTTCGCTATCTTAGTATCTTCTGGGTCCTG
GTAAGCCAGGCCAGCTTATGGTTTGCCACCTTCCTCAGTGTCTTCTATTGCAAGAAGATCACGACC
TTCGATCGCCCGGCCTACTTGTGGCTGAAGCAGAGGGCCTATAACCTGAGTCTCTGGTGCCTTCTG
GGCTACTTTATAATCAATTTGTTACTTACAGTCCAAATTGGCTTAACATTCTATCATCCTCCCCAAG
GAAACAGCAGCATTCGGTATCCCTTTGAAAGCTGGCAGTACCTGTATGCATTTCAGCTCAATTCAG
GAAGTTATTTGCCTTTAGTGGTGTTTCTTGTTTCCTCTGGGATGTGATTGTCTCTTTGTATACACAC
CACAAGAAGATGAAGGTCCATTCAGCTGGTAGGAGGGATGTCCGGGCCAAGGCTCACATCACTGC
GCTGAAGTCCTTGGGCTGCTTCCTCTTACTTCACCTGGTTTATATCATGGCCAGCCCCTTCTCCATC
ACCTCCAAGACTTATCCTCCTGATCTCACCAGTGTCTTCATCGGGAGACACTCATGGCAGCCTATC
CTTCTCTTCATTCTCTCATATTGATCATGGGGATTCCTAGGGTGAAGCAGACTTGTCAGAAGATCCT
GTGGAAGACAGTGTGCTCGGAGATGCTGGGGCCCATGA (SEQ ID NO: 5)
```

SEQUENCE LISTING

```
TAS2R7 CDS
ATGGCAGATAAAGTGCAGACTACTTTATTGTTCTTAGCAGTTGGAGAGTTTTCAGTGGGGA
TCTTAGGGAATGCATTCATTGGATTGGTAAACTGCATGGATTGGGTCAAGAAGAGGAAAATTGCCT
CCATTGATTTAATCCTCACAAGTCTGGCCATATCCAGAATTTGTCTATTGTGCGTAATACTATTAGA
TTGTTTTATATTGGTGCTATATCCAGATGTCTATGCCACTGGTAAAGAAATGAGAATCATTGACTTC
TTCTGGACACTAACCAATCATTTAAGTATCTGGTTTGCAACCTGCCTCAGCATTTACTATTTCTTCA
AGATAGGTAATTTCTTTCACCCACTTTTCCTCTGGATGAAGTGGAGAATTGACAGGGTGATTTCCT
GGATTCTACTGGGGTGCGTGGTTCTCTCTGTGTTATTAGCCTTCCAGCCACTGAGAATTTGAACGC
TGATTTCAGGTTTTGTGTGAAGGCAAAGAGGAAAACAAACTTAACTTGGAGTTGCAGAGTAAATA
AAACTCAACATGCTTCTACCAAGTTATTTCTCAACCTGGCAACGCTGCTCCCCTTTTGTGTGCCT
AATGTCCTTTTTCCTCTTGATCCTCTCCCTGCGGAGACATATCAGGCGAATGCAGCTCAGTGCCACA
GGGTGCAGAGACCCCAGCACAGAAGCCCATGTGAGAGCCCTGAAAGCTGTCATTTCCTTCCTTCTC
CTCTTTATTGCCTACTATTTGTCCTTTCTCATTGCCACCTCCAGCTACTTTATGCCAGAGACGGAATT
AGCTGTGATTTTTGGTGAGTCCATAGCTCTAATCTACCCCTCAAGTCATTCATTTATCCTAATACTG
GGGAACAATAAATTAAGACATGCATCTCTAAAGGTGATTTGGAAAGTAATGTCTATTCTAAAAGG
AAGAAAATTCCAACAACATAAACAAATCTGA (SEQ ID NO: 6)

TAS2R8 CDS
ATGTTCAGTCCTGCAGATAACATCTTTATAATCCTAATAACTGGAGAATTCATACTAGGAA
TATTGGGGAATGGATACATTGCACTAGTCAACTGGATTGACTGGATTAAGAAGAAAAAGATTTCC
ACAGTTGACTACATCCTTACCAATTTAGTTATCGCCAGAATTTGTTTGATCAGTGTAATGGTTGTAA
ATGGCATTGTAATAGTACTGAACCCAGATGTTTATACAAAAAATAAACAACAGATAGTCATTTTA
CCTTCTGGACATTTGCCAACTACTTAAATATGTGGATTACCTACCCTGCTTAATGTCTTCTATTTTCT
GAAGATAGCCAGTTCCTCTCATCCACTTTTTCTCTGGCTGAAGTGGAAAATTGATATGGTGGTGCA
CTGGATCCTGCTGGGATGCTTTGCCATTTCCTTGTTGGTCAGCCTTATAGCAGCAATAGTACTGAGT
TGTGATTATAGGTTTCATGCAATTGCCAAACATAAAAGAAACATTACTGAAATGTTCCATGTGAGT
AAAATACCATACTTTGAACCCTTGACTCTCTTTAACCTGTTTGCAATTGTCCCATTTATTGTGTCAC
TGATATCATTTTTCCTTTTAGTAAGATCTTTATGGAGACATACCAAGCAAATAAAACTCTATGCTAC
CGGCAGTAGAGACCCCAGCACAGAAGTTCATGTGAGAGCCATTAAAACTATGACTTCATTTATCTT
CTTTTTTTCCTATACTATATTTCTTCTATTTTGATGACCTTTAGCTATCTTATGACAAAATACAAGT
TAGCTGTGGAGTTTGGAGAGATTGCAGCAATTCTCTACCCCTTGGGTCACTCACTTATTTTAATTGT
TTTAAATAATAAACTGAGGCAGACATTTGTCAGAATGCTGACATGTAGAAAAATTGCCTGCATGAT
ATGA (SEQ ID NO: 7)

TAS2R9 CDS
ATGCCAAGTGCAATAGAGGCAATATATATTATTTTAATTGCTGGTGAATTGACCATAGGG
ATTTGGGGAAATGGATTCATTGTACTAGTTAACTGCATTGACTGGCTCAAAAGAAGAGATATTTCC
TTGATTGACATCATCCTGATCAGCTTGGCCATCTCCAGAATCTGTCTGCTGTGTAATATCATTAG
ATGGCTTCTTTATGCTGCTCTTTCCAGGTACATATGGCAATAGCGTGCTAGTAAGCATTGTGAATGT
TGTCTGGACATTTGCCAATAATTCAAGTCTCTGGTTTACTTCTTGCCTCAGTATCTTCTATTTACTCA
AGATAGCCAATATATCGCACCCATTTTCTTCTGGCTGAAGCTAAAGATCAACAAGGTCATGCTTG
CGATTCTTCTGGGGTCCTTTCTTATCTCTTTAATTATTAGTGTTCCAAAGAATGATGATATGTGGTA
TCACCTTTTCAAAGTCAGTCATGAAGAAAACATTACTTGGAAATTCAAAGTGAGTAAAATTCCAGG
TACTTTCAAACAGTTAACCCTGAACCTGGGGGTGATGGTTCCCTTTATCCTTTGCCTGATCTCATTT
TTCTTGTTACTTTTCTCCCTAGTTAGACACACCAAGCAGATTCGACTGCATGCTACAGGGTTCAGAG
ACCCCAGTACGAGGCCCACATGAGGGCCATAAAGGCAGTGATCATCTTTCTGCTCCTCCTCATCG
TGTACTACCCAGTCTTTCTTGTTATGACCTCTAGCGCTCTGATTCCTCAGGGAAAATTAGTGTTGAT
GATTGGTGACATAGTAACTGTCATTTTCCCATCAAGCCATTCATTCATTCTAATTATGGGAAATAGC
AAGTTGAGGGAAGCTTTTCTGAAGATGTTAAGATTTGTGAAGTGTTTCCTTAGAAGAAGAAAGCCT
TTTGTTCCATAG (SEQ ID NO: 8)

TAS2R10 CDS
ATGCTACGTGTAGTGGAAGGCATCTTCATTTTTGTTGTAGTTAGTGAGTCAGTGTTTGGGG
TTTTGGGGAATGGATTTATTGGACTTGTAAACTGCATTGACTGTGCCAAGAATAAGTTATCTACGA
TTGGCTTTATTCTCACCGGCTTAGCTATTTCAAGAATTTTTCTGATATGGATAATAATTACAGATGG
ATTTATACAGATATTCTCTCCAAATATATATGCCTCCGGTAACCTAATTGAATATATTAGTTACTTT
TGGGTAATTGGTAATCAATCAAGTATGTGGTTTGCCACCAGCCTCAGCATCTTCTATTTCCTGAAG
ATAGCAAATTTTTCCAACTACATATTTCTCTGGTTGAAGAGCAGAACAAATATGGTTCTTCCCTTCA
TGATAGTATTCTTACTTATTTCATCGTTACTTAATTTTGCATACATTGCGAAGATTCTTAATGATTAT
AAAATGAAGAATGACACAGTCTGGGATCTCAACATGTATAAAAGTGAATACTTTATTAAACAGAT
TTTGCTAAATCTGGGAGTCATTTTCTTCTTTACACTATCCCTAATTACATGTATTTTTTAATCATTT
CCCTTTGGAGACACAACAGGCAGATGCAATCAAATGTGACAGGATTGAGAGACTCCAACACAGAA
GCTCATGTGAAGGCAATGAAAGTTTTGATATCTTTCATCATCCTCTTTATCTTGTATTTATAGGCA
TGGCCATAGAAATATCATGTTTTACTGTGCGAGAAAACAAACTGCTGCTTATGTTTGGAATGACAA
CCACAGCCATCTATCCCTGGGGTCACTCATTTATCTTAATTCTAGGAAACAGCAAGCTAAAGCAAG
CCTCTTTGAGGGTACTGCAGCAATTGAAGTGCTGTGAGAAAAGGAAAAATCTCAGAGTCACATAG
(SEQ ID NO: 9)

TAS2R13 CDS
ATGGAAAGTGCCCTGCCGAGTATCTTCACTCTTGTAATAATTGCAGAATTCATAATTGGGA
ATTTGAGCAATGGATTTATAGTACTGATCAACTGCATTGACTGGGTCAGTAAAAGAGAGCTGTCCT
CAGTCGATAAACTCCTCATTATCTTGGCAATCTCCAGAATTGGGCTGATCTGGGAAATATTAGTAA
GTTGGTTTTAGCTCTGCATTATCTAGCCATATTTGTGTCTGGAACAGGATTAAGAATTATGATTTT
TAGCTGGATAGTTTCTAATCACTTCAATCTCTGGCTTGCTACAATCTTCAGCATCTTTTATTTGCTCA
AAATAGCGAGTTTCTCTAGCCCTGCTTTTCTCTATTTGAAGTGGAGAGTAAACAAAGTGATTCTGA
TGATACTGCTAGGAACCTTGGTCTTCTTATTTTTTAAATCTGATACAAATAAACATGCATATAAAG
```

SEQUENCE LISTING

```
ACTGGCTGGACCGATATGAAAGAAACACAACTTGGAATTTCAGTATGAGTGACTTTGAAACATTTT
CAGTGTCGGTCAAATTCACTATGACTATGTTCAGTCTAACACCATTTACTGTGGCCTTCATCTCTTT
TCTCCTGTTAATTTTCTCCCTGCAGAAACATCTCCAGAAAATGCAACTCAATTACAAAGGACACAG
AGACCCCAGGACCAAGGTCCATACAAATGCCTTGAAAATTGTGATCTCATTCCTTTTATTCTATGCT
AGTTTCTTTCTATGTGTTCTCATATCATGGATTTCTGAGCTGTATCAGAACACAGTGATCTACATGC
TTTGTGAGACGATTGGAGTCTTCTCTCCTTCAAGCCACTCCTTTCTTCTGATTCTAGGAAACGCTAA
GTTAAGACAGGCCTTTCTTTTGGTGGCAGCTAAGGTATGGGCTAAACGATGA (SEQ ID NO: 10)

TAS2R14 CDS
ATGGGTGGTGTCATAAAGAGCATATTTACATTCGTTTTAATTGTGGAATTTATAATTGGAA
ATTTAGGAAATAGTTTCATAGCACTGGTGAACTGTATTGACTGGGTCAAGGGAAGAAAGATCTCTT
CGGTTGATCGGATCCTCACTGCTTTGGCAATCTCTCGAATTAGCCTGGTTTGGTTAATATTCGGAAG
CTGGTGTGTGTCTGTGTTTTCCCAGCTTATTTGCCACTGAAAAATGTTCAGAATGCTTACTAAT
ATCTGGACAGTGATCAATCATTTTAGTGTCGGTTAGCTACAGGCCTCGGTACTTTTTATTTTCTCA
AGATAGCCAATTTTTCTAACTCTATTTTTCTCTACCTAAAGTGGAGGGTTAAAAAGGTGGTTTTGGT
GCTGCTTCTTGTGACTTCGGTCTTCTTGTTTTTAAATATTGCACTGATAAACATCCATATAAATGCC
AGTATCAATGGATACAGAAGAAACAAGACTTGCAGTTCTGATTCAAGTAACTTTACACGATTTTCC
AGTCTTATTGTATTAACCAGCACTGTGTTCATTTTCATACCCTTTACTTTGTCCCTGGCAATGTTTCT
TCTCCTCATCTTCTCCATGTGGAAACATCGCAAGAAGATGCAGCACACTGTCAAAATATCCGGAGA
CGCCAGCACCAAAGCCCACAGAGGAGTTAAAAGTGTGATCACTTTCTTCCTACTCTATGCCATTTT
CTCTCTGTCTTTTTTCATATCAGTTTGGACCTCTGAAAGGTTGGAGGAAAATCTAATTATTCTTTCC
CAGGTGATGGGAATGGCTTATCCTTCATGTCACTCATGTGTTCTGATTCTTGGAAACAAGAAGCTG
AGACAGGCCTCTCTGTCAGTGCTACTGTGGCTGAGGTACATGTTCAAAGATGGGGAGCCCTCAGGT
CACAAAGAATTTAGAGAATCATCTTGA (SEQ ID NO: 11)

TAS2R16 CDS
ATGATACCCATCCAACTCACTGTCTTCTTCATGATCATCTATGTGCTTGAGTCCTTGACAAT
TATTGTGCAGAGCAGCCTAATTGTTGCAGTGCTGGGCAGAGATGGCTGCAAGTCAGAAGGCTGA
TGCCTGTGGACATGATTCTCATCAGCCTGGGCATCTCTCGCTTCTGTCTACAGTGGGCATCAATGCT
GAACAATTTTTGCTCCTATTTTAATTTGAATTATGTACTTTGCAACTTAACAATCACCTGGGAATTT
TTTAATATCCTTACATTCTGGTTAAACAGCTTGCTTACCGTGTTCTACTGCATCAAGGTCTCTTCTTT
CACCCATCACATCTTTCTCTGGCTGAGGTGGAGAATTTTGAGGTTGTTTCCCTGGATATTACTGGGT
TCTCTGATGATTACTTGTGTAACAATCATCCCTTCAGCTATTGGGAATTACATTCAAATTCAGTTAC
TCACCATGGAGCATCTACCAAGAAACAGCACTGTAACTGACAAACTTGAAAATTTTCATCAGTATC
AGTTCCAGGCTCATACAGTTGCATTGGTTATTCCTTTCATCCTGTTCCTGGCCTCCACCATCTTTCTC
ATGGCATCACTGACCAAGCAGATACAACATCATAGCACTGGTCACTGCAATCCAAGCATGAAAGC
GCGCTTCACTGCCCTGAGGTCCCTTGCCGTCTTATTTATTGTGTTTACCTCTTACTTTCTAACCATAC
TCATCACCATTATAGGTACTCTATTTGATAAGAGATGTTGGTTATGGGTCTGGGAAGCTTTTGTCTA
TGCTTTCATCTTAATGCATTCCACTTCACTGATGCTGAGCAGCCCTACGTTGAAAAGGATTCTAAA
GGGAAAGTGCTAG (SEQ ID NO: 12)

TAS2R38 CDS
ATGTTGACTCTAACTCGCATCCGCACTGTGTCCTATGAAGTCAGGAGTACATTTCTGTTCA
TTTCAGTCCTGGAGTTTGCAGTGGGGTTTCTGACCAATGCCTTCGTTTTCTTGGTGAATTTTTGGGA
TGTAGTGAAGAGGCAGGCACTGAGCAACAGTGATTGTGTGCTGCTGTCTCAGCATCAGCCGGT
TTTCCTGCATGGACTGCTGTTCCTGAGTGCTATCCAGCTTACCCACTTCCAGAAGTTGAGTGAACCA
CTGAACCACAGCTACCAAGCCATCATCATGCTATGGATGATTGCAAACCAAGCCAACCTCTGGCTT
GCTGCCTGCCTCAGCCTGCTTTACTGCTCCAAGCTCATCCGTTTCTCTCACACCTTCCTGATCTGCTT
GGCAAGCTGGGTCTCCAGGAAGATCTCCCAGATGCTCCTGGGTATTATTCTTTGCTCCTGCATCTGC
ACTGTCCTCTGTGTTTGGTGCTTTTTTAGCAGACCTCACTTCACAGTCACAACTGTGCTATTCATGA
ATAACAATACAAGGCTCAACTGGCAGATTAAAGATCTCAATTTATTTTATTCCTTTCTCTTCTGCTA
TCTGTGGTCTGTGCCTCCTTTCCTATTGTTTCGGTTTCTTCTGGGATGCTGACTGTCTCCCTGGGAA
GGCACATGAGGACAATGAAGGTCTATACCAGAAACTCTCGTGACCCCAGCCTGGAGGCCCACATT
AAAGCCCTCAAGTCTCTTGTCTCCTTTTTCTGCTTCTTTGTGATATCATCCTGTGCTGCCTTCATCTC
TGTGCCCCTACTGATTCTGTGGCGCGACAAAATAGGGGTGATGGTTTGTGTTGGGATAATGGCAGC
TTGTCCCTCGGGCATGCAGCCATCCTGATCTCAGGCAATGCCAAGTTGAGGAGAGCTGTGATGAC
CATTCTGCTCTGGGCTCAGAGCAGCCTGAAGGTAAGAGCCGACCACAAGGCAGATTCCCGGACAC
TGTGCTGA (SEQ ID NO: 13)

TAS2R39 CDS
ATGCTAGGGAGATGTTTTCCTCCAGACACCAAAGAGAAGCAACAGCTCAGAATGACTAAA
CTCTGCGATCCTGCAGAAAGTGAATTGTCGCCATTTCTCATCACCTTAATTTTAGCAGTTTTACTTG
CTGAATACCTCATTGGTATCATTGCAAATGGTTTCATCATGGCTATACATGCAGCTGAATGGGTTC
AAAATAAGGCAGTTTCCACAAGTGGCAGGATCCTGGTTTTCCTGAGTGTATCCAGAATAGCTCTCC
AAAGCCTCATGATGTTAGAAATTACCATCAGCTCAACCTCCCTAAGTTTTTATTCTGAAGACGCTG
TATATTATGCATTCAAAATAAGTTTTATATTCTTAAATTTTTGTAGCCTGTGGTTTGCTGCCTGGCTC
AGTTTCTTCTACTTTGTGAAGATTGCCAATTTCTCCTACCCCCTTTCCTCAAACTGAGGTGGAGAA
TTACTGGATTGATACCCTGGCTTCTGTGGCTGTCCGTGTTTATTTCCTTCAGTCACAGCATGTTCTG
CATCAACATCTGCACTGTGTATTGTAACAATTCTTTCCCTATCCACTCCTCCAACTCCACTAAGAAA
ACATACTTGTCTGAGATCAATGTGGTCGGTCTGGCTTTTTCTTTAACCTGGGGATTGTGACTCCTC
TGATCATGTTCATCCTGACAGCCACCCTGCTGATCCTCTCTCAAGAGACACACCCTACACATGG
GAAGCAATGCCACAGGGTCCAACGACCCCAGCATGGAGGCTCACATGGGGGCCATCAAAGCTATC
AGCTACTTTCTCATTCTCTACATTTTCAATGCAGTTGCTCTGTTTATCTACCTGTCCAACATGTTTGA
CATCAACAGTCTGTGGAATAATTTGTGCCAGATCATCATGGCTGCCTACCCTGCCAGCCACTCAAT
TCTACTGATTCAAGATAACCCTGGGCTGAGAAGAGCCTGGAGCGGCTTCAGCTTCGACTTCATCTT
TACCCAAAAGAGTGGACTCTGA (SEQ ID NO: 14)
```

SEQUENCE LISTING

TAS2R40 CDS
ATGGCAACGGTGAACACAGATGCCACAGATAAAGACATATCCAAGTTCAAGGTCACCTTC
ACTTTGGTGGTCTCCGGAATAGAGTGCATCACTGGCATCCTTGGGAGTGGCTTCATCACGGCCATC
TATGGGGCTGAGTGGGCCAGGGGCAAAACACTCCCCACTGGTGACCGCATTATGTTGATGCTGAG
CTTTTCCAGGCTCTTGCTACAGATTTGGATGATGCTGGAGAACATTTTCAGTCTGCTATTCCGAATT
GTTTATAACCAAAACTCAGTGTATATCCTCTTCAAAGTCATCACTGTCTTTCTGAACCATTCCAATC
TCTGGTTTGCTGCCTGGCTCAAAGTCTTCTATTGTCTTAGAATTGCAAACTTCAATCATCCTTTGTTC
TTCCTGATGAAGAGGAAAATCATAGTGCTGATGCCTTGGCTTCTCAGGCTGTCAGTGTTGGTTTCCT
TAAGCTTCAGCTTTCCTCTCGAGAGATGTCTTCAATGTGTATGTGAATAGCTCCATTCCTATCCC
CTCCTCCAACTCCACGGAGAAGAAGTACTTCTCTGAGACCAATATGGTCAACCTGGTATTTTTCTA
TAACATGGGGATCTTCGTTCCTCTGATCATGTTCATCCTGGCAGCCACCCTGCTGATCCTCTCTCTC
AAGAGACACACCCTACACATGGGAAGCAATGCCACAGGGTCCAGGGACCCCAGCATGAAGGCTC
ACATAGGGGCCATCAAAGCCACCAGCTACTTTCTCATCCTCTACATTTTCAATGCAATTGCTCTATT
TCTTTCCACGTCCAACATCTTTGACACTTACAGTTCCTGGAATATTTTGTGCAAGATCATCATGGCT
GCCTACCCTGCCGGCCACTCAGTACAACTGATCTTGGGCAACCCTGGGCTGAGAAGAGCCTGGAA
GCGGTTTCAGCACCAAGTTCCTCTTTACCTAAAAGGGCAGACTCTGTGA (SEQ ID NO: 15)

tAS2R41 CDS
ATGCAAGCAGCACTGACGGCCTTCTTCGTGTTGCTCTTTAGCCTGCTGAGTCTTCTGGGGA
TTGCAGCGAATGGCTTCATTGTGCTGGTGCTGGGCAGGGAGTGGCTGCGATATGGCAGGTTGCTGC
CCTTGGATATGATCCTCATTAGCTTGGGTGCCTCCCGCTTCTGCCTGCAGTTGGTTGGGACGGTGCA
CAACTTCTACTACTCTGCCCAGAAGGTCGAGTACTCTGGGGGTCTCGGCCGACAGTTCTTCCATCT
ACACTGGCACTTCCTGAACTCAGCCACCTTCTGGTTTTGCAGCTGGCTCAGTGTCCTGTTCTGTGTG
AAGATTGCTAACATCACACACTCCACCTTCCTGTGGCTGGAAGTGGAGGTTCCCAGGGTGGGTGCCC
TGGCTCCTGTTGGGCTCTGTCCTGATCTCCTTCATCATAACCCTGCTGTTTTTTTGGGTGAACTACCC
TGTATATCAAGAATTTTTAATTAGAAAATTTTCTGGGAACATGACCTACAAGTGGAATACAAGGAT
AGAAACATACTATTTCCCATCCCTGAAACTGGTCATCTGGTCAATTCCTTTTTCTGTTTTTCTGGTCT
CAATTATGCTGCTGATTAATTCTCTGAGGAGGCATACTCAGAGAATGCAGCACAACGGGCACAGC
CTGCAGGACCCCAGCACCCAGGCTCACACCAGAGCTCTGAAGTCCCTCATCTCCTTCCTCATTCTTT
ATGCTCTGTCCTTTCTGTCCCTGATCATTGATGCCGCAAAATTTATCTCCATGCAGAACGACTTTTA
CTGGCCATGGCAAATTGCAGTCTACCTGTGCATATCTGTCCATCCCTTCATCCTCATCTTCAGCAAC
CTCAAGCTTCGAAGCGTGTTCTCACAGCTCCTGTTGTTGGCAAGGGGCTTCTGGGTGGCCTGA
(SEQ ID NO: 16)

TAS2R43 CDS
ATGATAACTTTTCTGCCCATCATTTTTTCCAGTCTGGTAGTGGTTACATTTGTTATTGGAAA
TTTTGCTAATGGCTTCATAGCACTGGTAAATTCCATTGAGTGGTTCAAGAGACAAAAGATCTCCTT
TGCTGACCAAATTCTCACTGCTCTGGCGGTCTCCAGAGTTGGTTTGCTCTGGGTATTATTATTAAAC
TGGTATTCAACTGTGTTGAATCCAGCTTTTAATAGTGTAGAAGTAAGAACTACTGCTTATAATATCT
GGGCAGTGATCAACCATTTCAGCAACTGGCTTGCTACTACCCTCAGCATATTTTATTTGCTCAAGAT
TGCCAATTTCTCCAACTTTATTTTTCTTCACTTAAAGAGGAGAGTTAAGAGTGTCATTCTGGTGATG
TTGTTGGGGCCTTTGCTATTTTTGGCTTGTCATCTTTTTGTGATAAACATGAATGAGATTGTGCGGA
CAAAAGAATTTGAAGGAAACATGACTTGGAAGATCAAATTGAAGAGTGCAATGTACTTTTCAAAT
ATGACTGTAACCATGGTAGCAAACTTAGTACCCTTCACTCTGACCCTACTATCTTTTATGCTGTTAA
TCTGTTCTTTGTGTAAACATCTCAAGAAGATGCAGCTCCATGGTAAAGGATCTCAAGATCCCAGCA
CCAAGGTCCACATAAAAGCTTTGCAAACTGTGATCTCCTTCCTCTTGTTATGTGCCATTTACTTTCT
GTCCATAATGATATCAGTTTGGAGTTTTGGAAGTCTGGAAAACAAACCTGTCTTCATGTTCTGCAA
AGCTATTAGATTCAGCTATCCTTCAATCCACCCATTCATCCTGATTTGGGGAAACAAGAAGCTAAA
GCAGACTTTTCTTTCAGTTTTTTGGCAAATGAGGTACTGGGTGAAAGGAGAGAAGACTTCATCTCC
ATGA (SEQ ID NO: 17)

tAS2R44 CDS
ATGACAACTTTTATACCCATCATTTTTTCCAGTGTGGTAGTGGTTCTATTTGTTATTGGAAA
TTTTGCTAATGGCTTCATAGCATTGGTAAATTCCATTGAGCGGGTCAAGAGACAAAAGATCTCTTT
TGCTGACCAGATTCTCACTGCTCTGGCGGTCTCCAGAGTTGGTTTGCTCTGGGTATTATTATTAAAT
TGGTATTCAACTGTGTTTAATCCAGCTTTTTATAGTGTAGAAGTAAGAACTACTGCTTATAATGTCT
GGGCAGTAACCGGCCATTTCAGCAACTGGCTGCTACTAGCCTCAGCATATTTTATTTGCTCAAGA
TTGCCAATTTCTCCAACCTTATTTTTCTTCACTTAAAGAGGAGAGTTAAGAGTGTCATTCTGGTGAT
GCTGTTGGGGCCTTTACTATTTTTGGCTTGTCAACTTTTGTGATAAACATGAAGAGATTGTACGG
ACAAAAGAATATGAAGGAAACTTGACTTGGAAGATCAAATTGAGGAGTGCAGTGTACCTTTCAGA
TGCGACTGTAACCACGCTAGGAAACTTAGTGCCCTTCACTCTGACCCTGCTATGTTTTTTGCTGTTA
ATCTGTTCTCTGTGTAAACATCTCAAGAAGATGCAGCTCCATGGTAAAGGATCTCAAGATCCCAGC
ACCAAGGTCCACATAAAGCTTTGCAAACTGTGATCTTTTTCCTCTTGTTATGTGCCGTTTACTTTC
TGTCCATAATGATATCAGTTTGGAGTTTTGGGAGTCTGGAAAACAAACCTGTCTTCATGTTCTGCA
AAGCTATTAGATTCAGCTATCCTTCAATCCACCCATTCATCCTGATTTGGGGAAACAAGAAGCTAA
AGCAGACTTTTCTTTCAGTTTTGCGGCAAGTGAGGTACTGGGTGAAAGGAGAGAAGCCTTCATCTC
CATGA (SEQ ID NO: 18)

tAS2R45 CDS
ATGATAACTTTTCTGCCCATCATATTTTCCATTCAGTAGTGGTTACATTTGTTATTGGAAA
TTTTGCTAATGGCTTCATAGCGTTGGTAAATTCCACCGAGTGGTGTCAAGAGAGACAAAAGATCTCCTT
TGCTGACCAAATTGTCACTGCTCTGGCGGTCTCCAGAGTTGGTTTGCTCTGGGTGTTATTATTAAAT
TGGTATTCAACTGTGTTGAATCCAGCTTTTTGTAGTGTAGAATTAAGAACTACTGCTTATAATATCT
GGGCAGTAACCGGCCATTTCAGCAACTGGCCTGCTACTAGCCTCAGCATATTTTATTTGCTCAAGA
TTGCCAATTTCTCCAACCTTATTTTTCTTCGCTTAAAGAGGAGAGTTAAGAGTGTCATTCTGGTGAT
GCTGTTGGGGCCTTTGCTATTTTTGGCTTGTCATCTTTTTGTGGTAAACATGAATCAGATTGTATGG
ACAAAAGAATATGAAGGAAACATGACTTGGAAGATCAAATTGAGGCGTGCAATGTACCTTTCAGA

```
TACGACTGTAACCATGCTAGCAAACTTAGTACCCTTTACTGTAACCCTGATATCTTTTCTGCTGTTA
GTCTGTTCTCTGTGTAAACATCTCAAGAAGATGCACCTCCATGGCAAAGGATCTCAAGATCCCAGT
ACCAAGGTCCACATAAAAGTTTTGCAAACTGTGATCTCCTTCCTCTTGTTATGTGCCATTTACTTTG
TGTCTGTAATAATATCAGTTTGGAGTTTTAAGAATCTGGAAAACAAACCTGTCTTCATGTTCTGCCA
AGCTATTGGATTCAGCTGTTCTTCAGCCCACCCGTTCATCCTGATTTGGGGAAACAAGAAGCTAAA
GCAGACTTATCTTTCAGTTTTGTGGCAAATGAGGTACTGA (SEQ ID NO: 19)

TAS2R46 CDS
ATGATAACTTTTCTGCCCATCATTTTTTCCATTCTAATAGTGGTTACATTTGTGATTGGAAA
TTTTGCTAATGGCTTCATAGCATTGGTAAATTCCATTGAGTGGTTTAAGAGACAAAAGATCTCTTTT
GCTGACCAAATTCTCACTGCTCTGGCAGTCTCCAGAGTTGGTTTACTCTGGGTATTAGTATTAAATT
GGTATGCAACTGAGTTGAATCCAGCTTTTAACAGTATAGAAGTAAGAATTACTGCTTACAATGTCT
GGGCAGTAATCAACCATTTCAGCAACTGGCTTGCTACTAGCCTCAGCATATTTTATTTGCTCAAGA
TTGCCAATTTCTCCAACCTTATTTTTCTTCACTTAAAGAGGAGAGTTAAGAGTGTTGTTCTGGTGAT
ACTATTGGGGCTTTGCTATTTTTGGTTTGTCATCTTTTTGTGATAAACATGAATCAGATTATATGG
ACAAAAGAATATGAAGGAAACATGACTTGGAAGATCAAACTGAGGAGTGCAATGTACCTTTCAAA
TACAACGGTAACCATCCTAGCAAACTTAGTTCCCTTCACTCTGACCCTGATATCTTTTCTGCTGTTA
ATCTGTTCTCTGTGTAAACATCTCAAAAGATGCAGCTCCATGGCAAAGGATCTCAAGATCCCAGC
ATGAAGGTCCACATAAAAGCTTTGCAAACTGTGACCTCCTTCCTCTTGTTATGTGCCATTTACTTTC
TGTCCATAATCATGTCAGTTTGGAGTTTTGAGAGTCTGGAAAACAAACCTGTCTTCATGTTCTGCG
AAGCTATTGCATTCAGCTATCCTTCAACCCACCCATTCATCCTGATTTGGGGAAACAAGAAGCTAA
AGCAGACTTTTCTTTCAGTTTTGTGGCAAATGAGGTACTGA (SEQ ID NO: 20)

TAS2R47 CDS
ATGATAACTTTTCTGCCCATCATTTTTTCCATTCTAATAGTGGTTATATTTGTTATTGGAAA
TTTTGCTAATGGCTTCATAGCATTGGTAAATTCCATTGAGTGGGTCAAGAGACAAAAGATCTCCTT
TGTTGACCAAATTCTCACTGCTCTGGCGGTCTCCAGAGTTGGTTTGCTCTGGGTGTTATTACTACAT
TGGTATGCAACTCAGTTGAATCCAGCTTTTTATAGTGTAGAAGTAAGAATTACTGCTTATATGTCT
GGGCAGTAACCAACCATTTCAGCAGCTGGCTTGCTACTAGCCTCAGCATGTTTTATTTGCTCAGGA
TTGCCAATTTCTCCAACCTTATTTTTCTTCGCATAAAGAGGAGAGTTAAGAGTGTTGTTCTGGTGAT
ACTGTTGGGGCCTTTGCTATTTTTGGTTTGTCATCTTTTTGTGATAAACATGGATGAGACTGTATGG
ACAAAAGAATATGAAGGAAACGTGACTTGGAAGATCAAATTGAGGAGTGCAATGTACCATTCAAA
TATGACTCTAACCATGCTAGCAAACTTTGTACCCCTCACTCTGACCCTGATATCTTTTCTGCTGTTA
ATCTGTTCTCTGTGTAAACATCTCAAGAAGATGCAGCTCCATGGCAAAGGATCTCAAGATCCCAGC
ACCAAGGTCCACATAAAAGCTTTGCAAACTGTGACCTCCTTTCTTCGTTATGTGCCATTTACTTTC
TGTCCATGATCATATCAGTTTGTAATTTTGGGAGGCTGGAAAAGCAACCTGTCTTCATGTTCTGCCA
AGCTATTATATTCAGCTATCCTTCAACCCACCCATTCATCCTGATTTTGGGAAACAAGAAGCTAAA
GCAGATTTTTCTTTCAGTTTTGCGGCATGTGAGGTACTGGGTGAAAGACAGAAGCCTTCGTCTCCA
TAGATTCACAAGAGGGGCATTGTGTGTCTTCTGA (SEQ ID NO: 21)

TAS2R48 CDS
ATGATGTGTTTTCTGCTCATCATTTCATCAATTCTGGTAGTGTTTGCATTTGTTCTTGGAAA
TGTTGCCAATGGCTTCATAGCCCTAGTAAATGTCATTGACTGGGTTAACACACGAAAGATCCTC
AGCTGAGCAAATTCTCACTGCTCTGGTGGTCTCCAGAATTGGTTTACTCTGGGTCATGTTATTCCTT
TGGTATGCAACTGTGTTTAATTCTGCTTTATATGGTTTAGAAGTAAGAATTGTTGCTTCTAATGCCT
GGGCTGTAACGAACCATTTCAGCATGTGGCTTGCTGCTAGCCTCAGCATATTTTGTTTGCTCAAGAT
TGCCAATTTCTCCAACCTTATTTCTCCACCTAAAGAAGAGAATTAAGAGTGTTGTTCTGGTGATA
CTGTTGGGGCCCTTGGTATTTCTGATTTGTAATCTTGCTGTGATAACCATGGATGAGAGAGTGTGG
ACAAAAGAATATGAAGGAAATGTGACTTGGAAGATCAAATTGAGGAGTGCAATACACCTTTCAAG
CTTGACTGTAACTACTCTAGCAAACCTCATACCCTTTACTCTGAGCCTAATATGTTTTCTGCTGTTA
ATCTGTTCTCTTTGTAAACATCTCAAGAAGATGCGGCTCCATAGCAAAGGATCTCAAGATCCCAGC
ACCAAGGTCCATATAAAAGCTTTGCAAACTGTGACCTCCTTCCTCATGTTATTTGCCATTTACTTTC
TGTGTATAATCACATCAACTTGGAATCTTAGGACACAGCAGGCAAACTTGTACTCCTGCTTTGCC
AAACTGTTGCAATCATGTATCCTTCATTCCACTCATTCATCCTGATTATGGGAAGTAGGAAGCTAA
AACAGACCTTTCTTTCAGTTTTGTGGCAGATGACACGCTGA (SEQ ID NO: 22)

TAS2R49 CDS
ATGATGAGTTTTCTACACATTGTTTTTCCATTCTAGTAGTGGTTGCATTTATTCTTGGAAA
TTTTGCCAATGGCTTTATAGCACTGATAAATTTCATTGCCTGGGTCAAGAGACAAAAGATCTCCTC
AGCTGATCAAATTATTGCTGCTCTGGCAGTCTCCAGAGTTGGTTTGCTCTGGGTAATATTATTACAT
TGGTATTCAACTGTGTTGAATCCAACTTCATCTAATTTAAAAGTAATAATTTTTATTTCTAATGCCT
GGGCAGTAACCAATCATTTCAGCATCTGGCTTGCTACTAGCCTCAGCATATTTTATTTGCTCAAGAT
CGTCAATTTCTCCAGACTTATTTTTCATCACTTAAAAGGAAGGCTAAGAGTGTAGTTCTGGTGAT
AGTGTTGGGGTCTTTGTTCTTTTTGGTTTGTCACCTTGTGATGAAACACACGTATATAAATGTGTGG
ACAGAAGAATGTGAAGGAAACGTAACTTGGAAGATCAAACTGAGGAATGCAATGCACCTTTCCAA
CTTGACTGTAGCCATGCTAGCAAACTTGATACCATTCACTCTGACCCTGATATCTTTTCTGCTGTTA
ATCTACTCTCTGTGTAAACATCTCAAGAAGATGCAGCTCCATGGCAAAGGATCTCAAGATCCCAGC
ACCAAGATCCACATAAAAGCTCTGCAAACTGTGACCTCCTTCCTCATATTACTTGCCATTTACTTTC
TGTGTCTAATCATATCGTTTTGGAATTTTAAGATGCGACCAAAAGAATTGTCTTAATGCTTTGCCA
AGCTTTTGGAATCATATATCCATCATTCCACTCATTCATTCTGATTTGGGGAACAAGACGCTAAA
GCAGACCTTTCTTTCAGTTTTGTGGCAGGTGACTTGCTGGGCAAAAGGACAGAACCAGTCAACTCC
ATAG (SEQ ID NO: 23)

TAS2R50 CDS
ATGATAACTTTTCTATACATTTTTTTTTCAATTCTAATAATGGTTTTATTTGTTCTCGGAAA
CTTTGCCAATGGCTTCATAGCACTGGTAAATTTCATTGACTGGGTGAAGAGAAAAAAGATCTCCTC
AGCTGACCAAATTCTCACTGCTCTGGCGGTCTCCAGAATTGGTTTGCTCTGGGCATTATTATTAAAT
```

```
TGGTATTTAACTGTGTTGAATCCAGCTTTTTATAGTGTAGAATTAAGAATTACTTCTTATAATGCCT
GGGTTGTAACCAACCATTTCAGCATGTGGCTTGCTGCTAACCTCAGCATATTTTATTTGCTCAAGAT
TGCCAATTTCTCCAACCTTCTTTTTCTTCATTTAAAGAGGAGATTAGGAGTGTCATTCTGGTGATA
CTGTTGGGGACTTTGATATTTTTGGTTTGTCATCTTCTTGTGGCAAACATGGATGAGAGTATGTGGG
CAGAAGAATATGAAGGAAACATGACTGGGAAGATGAAATTGAGGAATACAGTACATCTTTCATAT
TTGACTGTAACTACCCTATGGAGCTTCATACCCTTTACTCTGTCCCTGATATCTTTTCTGATGCTAAT
CTGTTCTCTGTGTAAACATCTCAAGAAGATGCAGCTCCATGGAGAAGGATCGCAAGATCTCAGCAC
CAAGGTCCACATAAAAGCTTTGCAAACTCTGATCTCCTTCCTCTTGTTATGTGCCATTTTCTTTCTAT
TCCTAATCGTTTCGGTTTGGAGTCCTAGGAGGCTGCGGAATGACCCGGTTGTCATGGTTAGCAAGG
CTGTTGGAAACATATATCTTGCATTCGACTCATTCATCCTAATTTGGAGAACCAAGAAGCTAAAAC
ACACCTTTCTTTTGATTTTGTGTCAGATTAGGTGCTGA (SEQ ID NO: 24)

TAS2R55 CDS
ATGGCCACCGAATTGGACAAAATCTTTCTGATTCTGGCAATAGCAGAATTCATCATCAGC
ATGCTGGGGAATGTGTTCATTGGACTGGTAAACTGCTCTGAAGGGATCAAGAACCAAAAGGTCTT
CTCAGCTGACTTCATCCTCACCTGCTTGGCTATCTCCACAATTGGACAACTGTTGGTGATACTGTTT
GATTCATTTCTAGTGGGACTTGCTTCACATTTATATACCACATATAGACTAGGAAAAACTGTTATTA
TGCTTTGGCACATGACTAATCACTTGACAACCTGGCTTGCCACCTGCCTAAGCATTTTCTATTTCTT
TAAGATAGCCCACTTCCCCACTCCCTTTTCCTCTGGCTGAGGTGGAGGATGAACGGAATGATTGT
TATGCTTCTTATATTGTCTTTGTTCTTACTGATTTTTGACAGTTTAGTGCTAGAAATATTTATTGATA
TCTCACTCAATATAATAGATAAAAGTAATCTGACTTTATATTTAGATGAAAGTAAAACTCTCTTTG
ATAAACTCTCTATTTTAAAAACTCTTCTCAGCTTGACCAGTTTTATCCCCTTTTCTCTGTCCCTGACC
TCCTTGCTTTTTTTATTTCTGTCCTTGGTGAGACATACTAGAAATTTGAAGCTCAGTTCCTTGGGCTC
TAGAGACTCCAGCACAGAGGCCCATAGGAGGGCCATGAAAATGGTGATGTCTTTCCTTTTCCTCTT
CATAGTTCATTTTTTTTCCTTACAAGTGGCCAATTGGATATTTTTTATGTTGTGGAACAACAAGTAC
ATAAAGTTTGTCATGTTAGCCTTAAATGCCTTTCCCTCGTGCCACTCATTATTCTCATTCTGGGAA
ACAGCAAGCTGCGCAGACAGCTGTGAGGCTACTGTGGCATCTTAGGAACTATACAAAAACACCA
AATGCTTTACCTTTGTGA (SEQ ID NO: 25)

TAS2R60 CDS
ATGAATGGAGACCACATGGTTCTAGGATCTTCGGTGACTGACAAGAAGGCCATCATCTTG
GTTACCATTTTACTCCTTTTACGCCTGGTAGCAATAGCAGGCAATGGCTTCATCACTGCTGCTCTGG
GCGTGGAGTGGGTGCTACGAGAATGTTGTTGCCTTGTGATAAGTTATTGGTTAGCCTAGGGGCCT
CTCGCTTCTGTCTGCAGTCAGTGGTAATGGGTAAGACCATTTATGTTTTCTTGCATCCGATGGCCTT
CCCATACAACCCTGTACTGCAGTTTCTAGCTTTCCAGTGGGACTTCCTGAATGCTGCCACCTTATGG
TCCTCTACCTGGCTCAGTGTCTTCTATTGTGTGAAAATTGCTACCTTCACCCACCCTGTCTTCTTCTG
GCTAAAGCACAAGTTGTCTGGGTGGCTACCATGGATGCTCTTCAGCTCTGTAGGGCTCTCCAGCTT
CACCACCATTCTATTTTCATAGGCAACCACAGAATGTATCAGAACTATTTAAGGAACCATCTACA
ACCTTGGAATGTCACTGGCGATAGCATACGGAGCTACTGTGAGAAATTCTATCTCTTCCCTCTAAA
AATGATTACTTGGACAATGCCCACTGCTGTCTTTTTCATTTGCATGATTTTGCTCATCACATCTCTG
GGAAGACACAGGAAGAAGGCTCTCCTTACAACCTCAGGATTCCGAGAGCCCAGTGTGCAGGCACA
CATAAAGGCTCTGCTGGCTCTCCTCTCTTTTGCCATGCTCTTCATCTCATATTTCCTGTCACTGGTGT
TCAGTGCTGCAGGTATTTTCCACCTCTGGACTTTAAATTCTGGGTGTGGGAGTCAGTGATTTATCT
GTGTGCAGCAGTTCACCCCATCATTCTGCTCTTCAGCAACTGCAGGCTGAGAGCTGTGCTGAAGAG
TCGTCGTTCCTCAAGGTGTGGGACACCTTGA (SEQ ID NO: 26)

HUMAN GNA15 CDS
ATGGCCCGGTCCCTGACTTGGGGCTGCTGTCCCTGGTGCCTGACAGAGGAGGAGAAGACT
GCCGCCAGAATCGACCAGGAGATCAACAGGATTTTGTTGGAACAGAAAAAACAAGAGCGCGAGG
AATTGAAACTCCTGCTGTTGGGGCCTGGTGAGAGCGGGAAGAGTACGTTCATCAAGCAGATGCGC
ATCATTCACGGTGTGGGCTACTCGGAGGAGGACCGCAGAGCCTTCCGGCTGCTCATCTACCAGAAC
ATCTTCGTCTCCATGCAGGCCATGATAGATGCGATGGACCGGCTGCAGATCCCCTTCAGCAGGCCT
GACAGCAAGCAGCACGCCAGCCTAGTGATGACCCAGGACCCCTATAAAGTGAGCACATTCGAGAA
GCCATATGCAGTGGCCATGCAGTACCTGTGGCGGGACGCGGGCATCCGTGCATGCTACGAGCGAA
GGCGTGAATTCCACCTTCTGGACTCCGCGGTGTATTACCTGTCACACCTGGAGCGCATATCAGAGG
ACAGCTACATCCCCACTGCGCAAGACGTGCTGCGCAGTCGCATGCCCACCACAGGCATCAATGAG
TACTGCTTCTCCGTGAAGAAAACCAAACTGCGCATCGTGGATGTTGGTGGCCAGAGGTCAGACGG
TAGGAAATGGATTCACTGTTTCGAGAACGTGATTGCCCTCATCTACCTGGCCTCCCTGAGCGAGTA
TGACCAGTGCCTAGAGGAGAACGATCAGGAGAACCGCATGGAGGAGTCTCGCTCTGTTCAGCA
CGATCCTAGAGCTGCCCTGGTTCAAGAGCACCTCGGTCATCCTCTTCCTCAACAAGACGGACATCC
TGGAAGATAAGATTCACACCTCCCACCTGGCCACATACTTCCCCAGCTTCCAGGGACCCCGGCGAG
ACGCAGAGGCCGCCAAGAGCTTCATCTTGGACATGTATGCGCGCGTGTACGCGAGCTGCGCAGAG
CCCCAGGACGGTGGCAGGAAAGGCTCCCGCGCGCGCCGCTTCTTCGCACACTTCACCTGTGCCACG
GACACGCAAAGCGTCCGCAGCGTGTTCAAGGACGTGCGGGACTCGGTGCTGGCCCGGTACCTGGA
CGAGATCAACCTGCTGTGA (SEQ ID NO: 27)

TAS2R1
MLESHLIIYFLLAVIQFLLGIFTNGIIVVVNGIDLIKHRKMAPLDLLLSCLAVSRIFLQLFIFYVNV
IVIFFIEFIMCSANCAILLFINELELWLATWLGVFYCAKVASVRHPLFIWLKMRISKLVPWMILGSLLYVS
MICVFHSKYAGFMVPYFLRKFFSQNATIQKEDTLAIQIFSFVAEFSVPLLIFLFAVLLLIFSLGRHTRQMR
NTVAGSRVPGRGAPISALLSILSFLILYFSHCMIKVFLSSLKFHIRRFIFLFFILVIGIYPSGHSLILILGNPKL
KQNAKKFLLHSKCCQ (SEQ ID NO: 28)

TAS2R3
MMGLTEGVFLILSGTQFTLGILVNCFIELVNGSSWFKTKRMSLSDFIITTLALLRIILLCIILTDSF
LIEFSPNTHDSGIIMQIIDVSWTFTNHLSIWLATCLGVLYCLKIASFSHPTFLWLKWRVSRVMVWMLLG
ALLLSCGSTASLINEFKLYSVFRGIEATRNVTEHFRKKRSEYYLIHVLGTLWYLPPLIVSLASYSLLIFSLG
```

SEQUENCE LISTING

RHTRQMLQNGTSSRDPTTEAHKRAIRIILSFFFLFLLYFLAFLIASFGNFLPKTKMAKMIGEVMTMFYPA
GHSFILILGNSKLKQTFVVMLRCESGHLKPGSKGPIFS (SEQ ID NO: 29)

TAS2R4
MLRLFYFSAIIASVILNFVGIIMNLFITVVNCKTWVKSHRISSSDRILFSLGITRFLMLGLFLVNTI
YFVSSNTERSVYLSAFFVLCFMFLDSSSVWFVTLLNILYCVKITNFQHSVFLLLKRNISPKIPRLLLACVLI
SAFTTCLYITLSQASPPPELVTTRNNTSFNISEGILSLVVSLVLSSSLQFIINVTSASLLIHSLRRHIQKMQK
NATGFWNPQTEAHVGAMKLMVYFLILYIPYSVATLVQYLPFYAGMDMGTKSICLIFATLYSPGHSVLIII
THPKLKTTAKKILCFKK (SEQ ID NO: 30)

TAS2R5
MLSAGLGLLMLVAVVEFLIGLIGNGSLVVWSFREWIRKFNWSSYNLIILGLAGCRFLLQWLIIL
DLSLFPLFQSSRWLRYLSIFWVLVSQASLWFATFLSVFYCKKITTFDRPAYLWLKQRAYNLSLWCLLGY
FIINLLLTVQIGLTFYHPPQGNSSIRYPFESWQYLYAFQLNSGSYLPLVVFLVSSGMLIVSLYTHHKKMK
VHSAGRRDVRAKAHITALKSLGCFLLLHLVYIMASPFSITSKTYPPDLTSVFIWETLMAAYPSLHSLILIM
GIPRVKQTCQKILWKTVCARRCWGP (SEQ ID NO: 31)

TAS2R7
MADKVQTTLLFLAVGEFSVGILGNAFIGLVNCMDWVKKRKIASIDLILTSLAISRICLLCVILLD
CFILVLYPDVYATGKEMRIIDFFWTLTNHLSIWFATCLSIYYFFKIGNFFHPLFLWMKWRIDRVISWILLG
CVVLSVFISLPATENLNADFRFCVKAKRKTNLTWSCRVNKTQHASTKLFLNLATLLPFCVCLMSFFLLI
LSLRRHIRRMQLSATGCRDPSTEAHVRALKAVISFLLLFIAYYLSFLIATSSYFMPETELAVIFGESIALIY
PSSHSFILILGNNKLRHASLKVIWKVMSILKGRKFQQHKQI (SEQ ID NO: 32)

TAS2R8
MFSPADNIFIILITGEFILGILGNGYIALVNWIDWIKKKKISTVDYILTNLVIARICLISVMVVNGI
VIVLNPDVYTKNKQQIVIFTFWTFANYLNMWITTCLNVFYFLKIASSSHPLFLWLKWKIDMVVHWILLG
CFAISLLVSLIAAIVLSCDYRFHAIAKHKRNITEMFHVSKIPYFEPLTLFNLFAIVPFIVSLISFFLLVRSLW
RHTKQIKLYATGSRDPSTEVHVRAIKTMTSFIFFFFLYYISSILMTFSYLMTKYKLAVEFGEIAAILYPLG
HSLILIVLNNKLRQTFVRMLTCRKIACMI (SEQ ID NO: 33)

TAS2R9
MPSAIEAIYIILIAGELTIGIWGNGFIVLVNCIDWLKRRDISLIDIILISLAISRICLLCVISLDGFFML
LPPGTYGNSVLVSIVNVVWTFANNSSLWFTSCLSIFYLLKIANISHPFFFWKLKINKVMLAILLGSFLISL
IISVPKNDDMWYHLPKVSHEENITWKFKVSKIPGTFKQLTLNLGVMVPFILCLISFFLLLFSLVRHTKQIR
LHATGFRDPSTEAHMRAIKAVIIFLLLLIVYYPVFLVMTSSALIPQGKLVLMIGDIVTVIFPSSHSFILIMG
NSKLREAFLKMLRFVKCFLRRRKPFVP (SEQ ID NO: 34)

TAS2R10
MLRVVEGIFIFVVVSESVFGVLGNGFIGLVNCIDCAKNKLSTIGFILTGLAISRIFLIWIIITDGFIQI
FSPNIYASGNLIEYISYFWVIGNQSSMWFATSLSIFYFLKIANFSNYIFLWLKSRTNMVLPFMIVFLLISSL
LNFAYIAKILNDYKMKNDTVWDLNMYKSEYFIKQILLNLGVIFFFTLSLITCIFLIISLWRHNRQMQSNV
TGLRDSNTEAHVKAMKVLISFIILFILYFIGMAIEISCFTVRENKLLLMFGMTTTAIYPWGHSFILILGNSK
LKQASLRVLQQLKCCEK (SEQ ID NO: 35)

TAS2R13
MESALPSIFTLVIIAEFIIGNLSNGFIVLINCIDWVSKRELSSVDKLLIILAISRIGLIWEILVSWFLA
LHYLAIFVSGTGLRIMIFSWIVSNHFNLWLATIFSIFYLLKIASFSSPAFLYLKWRVNKVILMILLGTLVFL
FLNLIQINMHIKDWLDRYERNTTWNFSMSDFETFSVSVKFTMTMFSLTPFTVAFISFLLLIFSLQKHLQK
MQLNYKGHRDPRTKVHTNALKIVISFLLFYASFFLCVLISWISELYQNTVIYMLCETIGVFSPSSHSFLLIL
GNAKLRQAFLLVAAKVW (SEQ ID NO: 36)

TAS2R14
MGGVIKSIFTFVLIVEFIIGNLGNSFIALVNCIDWVKGRKISSVDRILTALAISRISLVWLIFGSWC
VSVFFPALFATEKMFRMLTNIWTVINHFSVWLATGLGTFYPLKIANFSNSIFLYLKWRVKKVVLVLLLV
TSVFLFLNIALINIHINASINGYRRNKTCSSDSSNFTRFSSLIVLTSTVFIFIPFTLSLAMFLLLIFSMWKHRK
KMQHTVKISGDASTKAHRGVKSVITFFLLYAIFSLSFFISVWTSERLEENLIILSQVMGMAYPSCHSCVLI
LGNKKLRQASLVLLWLRYMFKDGEPSGHKEFRESS (SEQ ID NO: 37)

TAS2R16
MIPIQLTVFFMIIYVLESLTIIVQSSLIVAVLGREWLQVRRLMPVDMILISLGISRFCLQWASMLN
NFCSYFPNLNYVLCNLTITWEFFNILTFWLNSLLTVFYCIKVSSFTHHIFLWLRWRILRLFPWILLGSLMIT
CVTIIPSAIGNYIQIQLLTMEHLPRNSTVTDKLENFHQYQFQAHTVALVIPFILFLASTIFLMASLTKQIQH
HSTGHCNPSMKARFTALRSLAVLFIVPTSYFLTILITIIGTLFDKRCWLWVWEAFVYAFILMHSTSLMLS
SPTLKRILKGKC (SEQ ID NO: 38)

TAS2R38
MLTLTRIRTVSYEVRSTFLFISVLEFAVGFLTNAFVFLVNFWDVVKRQALSNSDCVLLCLSISRL
FLHGLLFLSAIQLTHFQKLSEPLNHSYQAIIMLWMIANQANLWLAACLSLLYCSKLIRFSHTFLICLASW
VSRKISQMLLGIILCSCICTVLCVWCFFSRPHFTVTTVLFMNNNTRLNWQIKDLNLFYSFLFCYLWSVPP
FLLFLVSSGMLTVSLGRHMRTMKVYTRNSRDPSLEAHIKALKSLVSFFCFFVISSCAAFISVPLLILWRD
KIGVMVCVGIMAACPSGHAAILISGNAKLRRAVMTILLWAQSSLKVRADHKADSRTLC (SEQ ID NO: 39)

TAS2R39
MLGRCFPPDTKEKQQLRMTKLCDPAESELSPFLITLILAVLLAEYLIGIIANGFIMAIHAAEWVQ
NKAVSTSGRILVFLSVSRIALQSLMMLEITISSSTLSFYSEDAVYYAFKISFIFLNFCSLWFAAWLSFFYFV

```
KIANFSYPLFLKLRWRITGLIPWLLWLSVFISFSHSMFCINICTVYCNNSFPIHSSNSTKKTYLSEINVVGL
AFFFNLGIVTPLIMFILTATLLILSLKRHTLHMGSNATGSNDPSMEAHMGAIKAISYFLILYIFNAVALFIY
LSNMFDINSLWNNLCQIIMAAYPASHSILLIQDNPGLRRAWKRLQLRLHLYPKEWTL (SEQ ID
NO: 40)

TAS2R40
MATVNTDATDKDISKFKVTFTLVVSGIECITGILGSGFITAIYGAEWARGKTLPTGDRIMLMLS
FSRLLLQIWMMLENIFSLLFRIVYNQNSVYILFKVITVFLNHSNLWFAAWLKVFYCLRIANFNHPLFFLM
KRKIIVLMPWLLRLSVLVSLSFSPLSRDVFNVYVNSSIPIPSSNSTEKKYFSETNMVNLVFFYNMGIFVP
LIMFILAATLLILSLKRHTLHMGSNATGSRDPSMKAHIGAIKATSYFLILYIFNAIALFLSTSNIFDTYSSW
NILCKIIMAAYPAGHSVQLILGNPGLRRAWKRFQHQVPLYLKGQTL (SEQ ID NO: 41)

TAS2R41
MQAALTAFFVLLFSLLSLLGIAANGFIVLVLGREWLRYGRLLPLDMILISLGASRFCLQLVGTV
HNFYYSAQKVEYSGGLGRQFFHLHWHFLNSATFWFC SWLSVLFCVKIANITHSTFLWLKWRFLGWVP
WLLLGSVLISFIITLLFFWVNYPVYQEFLIRKFSGNMTYKWNTRIETYYFPSLKLVIWSIFFSVFLVSIMLL
INSLRRHTQRMQHNGHSLQDPSTQAHTRALKSLISFLILYALSFLSLIIDAAKFISMQNDFYWPWQIAVY
LCISVHPFILIFSNLKLRSVFSQLLLLARGFWVA (SEQ ID NO: 42)

TAS2R43
MITFLPIIFSSLVVVTFVIGNFANGFIALVNSIESFKRQKISFADQILTALAVSRVGLLWVLLLNW
YSTVLNPAFNSVEVRTTAYNIWAVINHFSNWLATTLSIFYLLKIANFSNFIFLHLKRRVKSVILVMLLGP
LLFLACHLFVINMNEIVRTKEFEGNMTWKIKLKSAMYFSNMTVTMVANLVPFTLTLLSFMLLICSLCKH
LKKMQLRGKGSQDPSTKVHIKALQTVISFLLLCAIYFLSIMISVWSFGSLENKPVFMFCKAIRFSYPSIHP
FILIWGNKKLKQTFLSVFWQMRYWVKGEKTSSP (SEQ ID NO: 43)

TAS2R44
MTTFIPIIFSSVVVVLFVIGNFANGFIALVNSIERVKRQKISFADQILTALAVSRVGLLWVLLLN
WYSTVFNPAFYSVEVRTTAYNVWAVTGHFSNWLATSLSIFYLLKIANFSNLIFLHLKRRVKSVILVMLL
GPLLFLACQLFVINMKEIVRTKEYEGNMTWKIKLRSAVYLSDATVTTLGNLVPFTLTLLCFLLLICSLCK
HLKKMQLHGKGSQDPSTKVHIKALQTVIFFLLLCAVYFLSIMISVWSFGSLENKPVFMFCKAIRFSYPSI
HPFILIWGNKKLKQTFLSVLRQVRYW (SEQ ID NO: 44)

TAS2R45
MITFLPIIFSILVVVTFVIGNFANGFIALVNSTEWVKRQKISFADQIVTALAVSRVGLLWVLLLN
WYSTVLNPAFCSVELRTTAYNIWAVTGHFSNWPATSLSIFYLLKIANFSNLIFLRLKRRVKSVILVVLLG
PLLFLACHLFVVNMNQIVWTKEYEGNMTWKIKLRRAMYLSDTTVTMLANLVPFTVTLISFLLLVCSLC
KHLKKMQLHGKGSQDPSTKVHIKVLQTVISFFLLRAIYFVSVIISVWSFKNLENKPVFMFCQAIGFSCSS
AHPFILIWGNKKLKQTYLSVLWQMRY (SEQ ID NO: 45)

TAS2R46
MITFLPIIFSILIVVTFVIGNFANGFIALVNSIEWFKRQKISFADQILTALAVSRVGLLWVLVLNW
YATELNPAFNSIEVRITAYNVWAVINHFSNWLATSLSIFYLLKIANFSNLIFLHLKRRVKSVVLVILLGPL
LFLVCHLFVINMNQIIWTKEYEGNMTWKIKLRSAMYLSNTTVTILANLVPFTLTLISFLLLICSLCKHLK
KMQLHGKGSQDPSMKVHIKALQTVTSFLLLCAIYFLSIIMSVWSFESLENKPVFMFCEAIAFSYPSTHPFI
LIWGNKKLKQTFLSVLWHVRYWVKGEKPSSS (SEQ ID NO: 46)

TAS2R47
MITFLPIIFSILIVVIFVIGNFANGFIALVNSIEWVKRQKISFVDQILTALAVSRVGLLWVLLLHW
YATQLNPAFYSVEVRITAYNVWAVTNHFSSWLATSLSMFYLLRIANFSNLIFLRIKRRVKSVVLVILLGP
LLFLVCHLFVINMDETVWTKEYEGNVTWKIKLRSAMYHSNMTLTMLANFVPLTLTLISFLLLICSLCKH
LKKMQLHGKGSQDPSTKVHIKALQTVTSFLLLCAIYFLSMIISVCNLGRLEKQPVFMFCQAIIFSYPSTHP
FILILGNKKLKQIFLSVLRHVRYWVKDRSLRLHRFTRAALCKG (SEQ ID NO: 47)

TAS2R48
MMCFLLIISSILVVFAFVLGNVANGFIALVNVIDWVNTRKISSAEQILTALVVSRIGLLWVMLFL
WYATVFNSALYGLEVRIVASNAWAVTNHFSMWLAASLSIFCLLKIANFSNLISLHLKKRIKSVVLVILL
GPLVFLICNLAVITMDERVWTKEYEGNVTWKIKLRNAIHLSSLTVTTLANLIPFTLSLICFLLLICSLCKH
LKKMRLHSKGSQDPSTKVHIKALQTVTSFLMLFAIYFLCIITSTWNLRTQQSKLVLLLCQTVAIMYPSFH
SFILIMGSRKLKQTFLSVLWQMTR (SEQ ID NO: 48)

TAS2R49
MMSFLHIVFSILVVVAFILGNFANGFIALINFIAWVKRQKISSADQIIAALAVSRVGLLWVILLH
WYSTVLNPTSSNLKVIIFISNAWAVTNHFSIWLATSLSIFYLLKIVNFSRLIFHHLKRKAKSVVLVIVLGSL
FFLVCHLVMKHTYINVWTEECEGNVTWKIKLRNAMHLSNLTVAMLANLIPFTLTLISFLLLIYSLCKHL
KKMQLHGKGSQDPSTKIHIKALQTVTSFLILLAIYFLCLIISFWNFKMRPKEIVLMLCQAFGIIYPSFHSFI
LIWGNKTLKQTFLSVLWQVTCWAKGQNQSTP (SEQ ID NO: 49)

TAS2R50
MITFLYIFFSILIMVLFVLGNFANGFIALVNFIDWVKRKKIS SADQILTALAVSRIGLLWALLLN
WYLTVLNPAFYSVELRITSYNAWVVTNHFSMWLAANLSIFYLLKIANFSNLLFLHLKRRVRSVILVILL
GTLIFLVCHLLVANMDESMWAEEYEGNMTGKMKLRNTVHLSYLTVTTLWSFIPFTLSLISFLMLICSLY
KHLKKMQLHGEGSQDLSTKVHIKALQTLISFLLLCAIFFLFIVSVWSPRRLRNDPVVMVSKAVGNIYL
AFDSFILIWRTKKLKHTFLLILCQIRC (SEQ ID NO: 50)
```

SEQUENCE LISTING

TAS2R55
MATELDKIFLILAIAEFIISMLGNVFIGLVNCSEGIKNQKVFSADFILTCLAISTIGQLLVILFDSFL
VGLASHLYTTYRLGKTVIMLWHMTNHLTTWLATCLSIFYFFKIAHFPHSLFLWLRWRMNGMIVMLLIL
SLFLLIFDSLVLEIFIDISLNIIDKSNLTLYLDESKTLYDKLSILKTLLSLTSFIPFSLFLTSLLFLFLSLVRHTR
NLKLSSLGSRDSSTEAHRRAMKMVMSFLFLFIVHFFSLQVANGIFFMLWNNKYIKFVMLALNAFPSCHS
FILILGNSKLRQTAVRLLWHLRNYTKTPNALPL (SEQ ID NO: 51)

TAS2R60
MNGDHMVLGSSVTDKKAIILVTILLLLRLVAIAGNGFITAALGVEWVLRRMLLPCDKLLVSLG
ASRFCLQSVVMGKTIYVFLHPMAFPYNPVLQFLAFQWDFLNAATLWSSTWLSVFYCVKIATFTHPVFF
WLKHKLSGWLPWMLFSSVGLSSFTTILFFIGNHRMYQNYLRNHLQPWNVTGDSIRSYCEKFYLFPLKM
ITWTMPTAVFFICMILLITSLGRHRKKALLTTSGFREPSVQAHIKALLALLSFAMLFISYFLSLVFSAAGIF
PPLDFKFWVWESVIYLCAAVHPIILLFSNCRLRAVLKSRRSSRCGTP (SEQ ID NO: 52)

Mouse Gna15 (Gα15)
MARSTWGCCWCTKTAARDNRKKRKGGSGKSTKMRHGVGYSDRRARYNVSMAMDAMDRS
RDSKHASVMTDYKVSTKYAVAMYWRDAGRACYRRRHDSAVYYSHRSDSYTADVRSRMTTGNYCSV
KKTKRVDVGGRSRRKWHCNVAYASSYDCNDNRMSASTWKSTSVNKTDDKHTSHATYSGRRDAAAK
SDMYARVYASCADGGRKGSRARRAHTCATDTSVRSVKDVRDSVARYDN (SEQ ID NO: 53)

TAS2R38 (PAV Haplotype)
MLTLTRIRTVSYEVRSTFLFISVLEFAVGFLTNAFVFLVNFWDVVKRQPLSNSDCVLLCLSISRL
FLHGLLFLSAIQLTHFQKLSEPLNHSYQAIIMLWMIANQANLWLAACLSLLYCSKLIRFSHTFLICLASW
VSRKISQMLLGIILCSCICTVLCVWCFFSRPHFTVTTVLFMNNNTRLNWQIKDLNLFYSFLFCYLWSVPP
FLLFLVSSGMLTVSLGRHMRTMKVYTRNSRDPSLEAHIKALKSLVSFFCFFVISSCAAFISVPLLILWRD
KIGVMVCVGIMAACPSGHAAVLISGNAKLRRAVMTILLWAQSSLKVRADHKADSRTLC
(SEQ ID NO: 54)

APPENDIX TABLE 1

Polymorphisms related to human bitter taste receptor genes

| Gene | Reference sequence number | Position in reference sequence | SNP |
|---|---|---|---|
| TAS2R1 | rs10543720 | pos = 401 | alleles = "—/CTATCTAT" |
| | rs2234228 | pos = 101 | alleles = "A/G" |
| | rs2234229 | pos = 101 | alleles = "C/T" |
| | rs2234230 | pos = 101 | alleles = "A/C" |
| | rs2234231 | pos = 101 | alleles = "C/T" |
| | rs2234232 | pos = 101 | alleles = "A/G" |
| | rs2234233 | pos = 301 | alleles = "C/T" |
| | rs2234234 | pos = 101 | alleles = "C/T" |
| | rs2234235 | pos = 301 | alleles = "C/T" |
| | rs34440745 | pos = 301 | alleles = "A/T" |
| | rs35186690 | pos = 301 | alleles = "—/G" |
| | rs35524938 | pos = 401 | alleles = "—/ATCT" |
| | rs36214451 | pos = 401 | alleles = "—/TATCTATC" |
| | rs41464 | pos = 201 | alleles = "A/G" |
| | rs41465 | pos = 201 | alleles = "A/G" |
| | rs41466 | pos = 301 | alleles = "A/G" |
| | rs41467 | pos = 301 | alleles = "G/T" |
| | rs41468 | pos = 301 | alleles = "C/T" |
| | rs41469 | pos = 301 | alleles = "A/G" |
| | rs41470 | pos = 201 | alleles = "A/G" |
| | rs56300050 | pos = 253 | alleles = "—/ATCT" |
| | rs57183738 | pos = 101 | alleles = "G/T" |
| | rs58046500 | pos = 101 | alleles = "C/T" |
| | rs58171988 | pos = 201 | alleles = "A/G" |
| TAS2R3 | rs11514837 | pos = 458 | alleles = "A/G" |
| | rs11763979 | pos = 501 | alleles = "G/T" |
| | rs11771020 | pos = 501 | alleles = "C/T" |
| | rs11771072 | pos = 201 | alleles = "A/C" |
| | rs12667706 | pos = 201 | alleles = "A/G" |
| | rs12703406 | pos = 277 | alleles = "A/G" |
| | rs13311828 | pos = 367 | alleles = "A/G" |
| | rs13311829 | pos = 367 | alleles = "C/G" |
| | rs13311831 | pos = 342 | alleles = "A/G" |
| | rs17162469 | pos = 101 | alleles = "A/G" |
| | rs17162471 | pos = 101 | alleles = "A/G" |
| | rs17162473 | pos = 101 | alleles = "A/G" |
| | rs17162483 | pos = 101 | alleles = "A/G" |
| | rs2270009 | pos = 301 | alleles = "C/T" |
| | rs28480612 | pos = 201 | alleles = "A/G" |
| | rs4726475 | pos = 609 | alleles = "C/T" |
| | rs56917574 | pos = 101 | alleles = "G/T" |
| | rs58640454 | pos = 101 | alleles = "A/G" |
| | rs60922375 | pos = 101 | alleles = "A/C" |
| | rs6962760 | pos = 301 | alleles = "C/T" |
| | rs6965618 | pos = 259 | alleles = "C/T" |
| | rs765007 | pos = 301 | alleles = "C/T" |
| | rs765008 | pos = 301 | alleles = "G/T" |
| | rs7793232 | pos = 714 | alleles = "A/G" |
| TAS2R4 | rs10485837 | pos = 101 | alleles = "A/G" |
| | rs2233990 | pos = 301 | alleles = "A/G" |
| | rs2233991 | pos = 101 | alleles = "C/T" |
| | rs2233992 | pos = 101 | alleles = "A/G" |
| | rs2233993 | pos = 101 | alleles = "A/G" |
| | rs2233994 | pos = 101 | alleles = "A/G" |
| | rs2233995 | pos = 301 | alleles = "A/G" |
| | rs2233996 | pos = 101 | alleles = "C/G" |
| | rs2233997 | pos = 101 | alleles = "A/C" |
| | rs2233998 | pos = 301 | alleles = "C/T" |
| | rs2233999 | pos = 101 | alleles = "A/T" |
| | rs2234000 | pos = 101 | alleles = "C/T" |
| | rs2234001 | pos = 301 | alleles = "C/G" |
| | rs2234002 | pos = 301 | alleles = "A/G" |
| | rs2234003 | pos = 101 | alleles = "A/G" |
| | rs33920115 | pos = 301 | alleles = "A/G" |
| | rs34855644 | pos = 301 | alleles = "—/T" |
| | rs3840580 | pos = 61 | alleles = "—/AA" |
| | rs57597591 | pos = 201 | alleles = "—/T" |
| | rs59513189 | pos = 201 | alleles = "G/T" |
| | rs61582517 | pos = 201 | alleles = "—/TGTAGATA" |
| TAS2R5 | rs10952507 | pos = 201 | alleles = "A/G" |
| | rs11761380 | pos = 301 | alleles = "A/C" |
| | rs11769235 | pos = 201 | alleles = "A/C" |
| | rs2227264 | pos = 301 | alleles = "G/T" |
| | rs2234004 | pos = 101 | alleles = "C/T" |
| | rs2234005 | pos = 101 | alleles = "A/G" |
| | rs2234006 | pos = 682 | alleles = "C/T" |

APPENDIX TABLE 1-continued

Polymorphisms related to human bitter taste receptor genes

| Gene | Reference sequence number | Position in reference sequence | SNP |
|---|---|---|---|
| | rs2234007 | pos = 494 | alleles = "A/G" |
| | rs2234008 | pos = 101 | alleles = "A/G" |
| | rs2234009 | pos = 101 | alleles = "C/T" |
| | rs2234010 | pos = 101 | alleles = "A/G" |
| | rs2234011 | pos = 101 | alleles = "C/T" |
| | rs2234012 | pos = 301 | alleles = "A/G" |
| | rs2234013 | pos = 101 | alleles = "A/G" |
| | rs2234014 | pos = 101 | alleles = "C/T" |
| | rs2234015 | pos = 301 | alleles = "A/G" |
| | rs2234016 | pos = 101 | alleles = "G/T" |
| | rs2234017 | pos = 201 | alleles = "C/G" |
| | rs2234018 | pos = 101 | alleles = "A/T" |
| | rs2234019 | pos = 101 | alleles = "A/G" |
| | rs2234020 | pos = 101 | alleles = "C/T" |
| | rs34529840 | pos = 301 | alleles = "—/C" |
| | rs3801001 | pos = 61 | alleles = "A/C" |
| | rs4726476 | pos = 201 | alleles = "C/G" |
| | rs60900504 | pos = 101 | alleles = "C/T" |
| | rs62477710 | pos = 251 | alleles = "C/T" |
| | rs62477711 | pos = 251 | alleles = "G/T" |
| TAS2R7 | rs10161483 | pos = 201 | alleles = "A/G" |
| | rs10772362 | pos = 501 | alleles = "C/T" |
| | rs11054041 | pos = 201 | alleles = "A/C" |
| | rs11838055 | pos = 301 | alleles = "A/G" |
| | rs2418107 | pos = 501 | alleles = "C/G" |
| | rs2588350 | pos = 301 | alleles = "C/T" |
| | rs34212148 | pos = 301 | alleles = "—/G" |
| | rs36067388 | pos = 301 | alleles = "—/G" |
| | rs3759251 | pos = 101 | alleles = "A/T" |
| | rs3759252 | pos = 61 | alleles = "A/C" |
| | rs619381 | pos = 519 | alleles = "C/T" |
| | rs7303054 | pos = 201 | alleles = "C/T" |
| TAS2R8 | rs12314840 | pos = 224 | alleles = "C/T" |
| | rs1548803 | pos = 780 | alleles = "C/T" |
| | rs1838344 | pos = 277 | alleles = "C/T" |
| | rs1838345 | pos = 322 | alleles = "A/G" |
| | rs2537817 | pos = 301 | alleles = "C/T" |
| | rs40313 | pos = 176 | alleles = "C/T" |
| | rs41324347 | pos = 65 | alleles = "G/T" |
| | rs60652912 | pos = 201 | alleles = "A/C" |
| | rs620878 | pos = 283 | alleles = "G/T" |
| | rs7972779 | pos = 424 | alleles = "C/T" |
| TAS2R9 | rs11054042 | pos = 201 | alleles = "C/G" |
| | rs11054043 | pos = 201 | alleles = "G/T" |
| | rs11054044 | pos = 201 | alleles = "C/G" |
| | rs11402198 | pos = 401 | alleles = "—/G" |
| | rs17207899 | pos = 101 | alleles = "G/T" |
| | rs17742870 | pos = 101 | alleles = "A/T" |
| | rs1838346 | pos = 301 | alleles = "A/G" |
| | rs2159903 | pos = 84 | alleles = "A/G" |
| | rs36044129 | pos = 301 | alleles = "—/T" |
| | rs3741845 | pos = 179 | alleles = "C/T" |
| | rs3944035 | pos = 100 | alleles = "A/G" |
| | rs40313 | pos = 176 | alleles = "C/T" |
| | rs60652912 | pos = 201 | alleles = "A/C" |
| | rs61320953 | pos = 201 | alleles = "—/T" |
| | rs655046 | pos = 301 | alleles = "A/G" |
| | rs667123 | pos = 301 | alleles = "A/G" |
| | rs667128 | pos = 201 | alleles = "C/T" |
| TAS2R10 | rs10845219 | pos = 301 | alleles = "C/T" |
| | rs12307411 | pos = 301 | alleles = "C/T" |
| | rs35370388 | pos = 301 | alleles = "—/TGTG" |
| | rs58719830 | pos = 225 | alleles = "—/TGTG" |
| | rs597468 | pos = 301 | alleles = "A/G" |
| | rs60832178 | pos = 101 | alleles = "C/T" |
| | rs61912242 | pos = 251 | alleles = "G/T" |
| | rs689118 | pos = 301 | alleles = "C/T" |
| TAS2R13 | rs1015442 | pos = 519 | alleles = "C/T" |
| | rs1015443 | pos = 946 | alleles = "A/C" |
| | rs10566346 | pos = 401 | alleles = "—/TG" |
| | rs10591343 | pos = 501 | alleles = "—/GT" |
| | rs10845238 | pos = 258 | alleles = "G/T" |
| | rs10845239 | pos = 346 | alleles = "A/T" |
| | rs10845240 | pos = 449 | alleles = "C/G" |
| | rs11054070 | pos = 2000 | alleles = "C/G" |
| | rs11054071 | pos = 201 | alleles = "C/G" |
| | rs11830286 | pos = 301 | alleles = "A/G" |
| | rs34885344 | pos = 301 | alleles = "C/T" |
| | rs35172210 | pos = 301 | alleles = "—/T" |
| | rs56987993 | pos = 101 | alleles = "C/G" |
| | rs7308212 | pos = 256 | alleles = "C/T" |
| | rs7968736 | pos = 201 | alleles = "A/T" |
| | rs7978678 | pos = 201 | alleles = "A/G" |
| TAS2R14 | rs10492104 | pos = 101 | alleles = "C/G" |
| | rs11610105 | pos = 201 | alleles = "A/G" |
| | rs16925868 | pos = 101 | alleles = "C/T" |
| | rs3033010 | pos = 501 | alleles = "—/C/CT/G" |
| | rs34789740 | pos = 301 | alleles = "A/G" |
| | rs35386049 | pos = 301 | alleles = "—/C" |
| | rs35405135 | pos = 301 | alleles = "—/T" |
| | rs35804287 | pos = 301 | alleles = "A/G" |
| | rs35926739 | pos = 301 | alleles = "—/T" |
| | rs3741843 | pos = 301 | alleles = "A/G" |
| | rs3851583 | pos = 501 | alleles = "A/G" |
| | rs3851584 | pos = 500 | alleles = "G/T" |
| | rs3851585 | pos = 501 | alleles = "C/G" |
| | rs3863321 | pos = 21 | alleles = "C/T" |
| | rs3936285 | pos = 537 | alleles = "A/T" |
| | rs4140968 | pos = 101 | alleles = "C/T" |
| | rs56393802 | pos = 241 | alleles = "—/TG" |
| | rs60186756 | pos = 201 | alleles = "—/T" |
| | rs60288130 | pos = 201 | alleles = "—/TT" |
| | rs61659284 | pos = 226 | alleles = "—/CTCT" |
| | rs7138535 | pos = 301 | alleles = "A/T" |
| | rs7487884 | pos = 239 | alleles = "C/T" |
| TAS2R16 | rs10487745 | pos = 101 | alleles = "A/C" |
| | rs1204014 | pos = 201 | alleles = "A/G" |
| | rs1357949 | pos = 497 | alleles = "A/G" |
| | rs1525489 | pos = 301 | alleles = "A/G" |
| | rs2233988 | pos = 301 | alleles = "C/T" |
| | rs2233989 | pos = 201 | alleles = "C/T" |
| | rs2692396 | pos = 301 | alleles = "C/G" |
| | rs28371571 | pos = 94 | alleles = "A/G" |
| | rs28371572 | pos = 114 | alleles = "C/G" |
| | rs28371573 | pos = 126 | alleles = "C/T" |
| | rs28371574 | pos = 133 | alleles = "A/G" |
| | rs28371575 | pos = 140 | alleles = "C/T" |
| | rs28371576 | pos = 136 | alleles = "C/T" |
| | rs28371577 | pos = 140 | alleles = "A/C" |
| | rs28371578 | pos = 138 | alleles = "A/G" |
| | rs28371579 | pos = 139 | alleles = "C/T" |
| | rs28371580 | pos = 139 | alleles = "A/G" |
| | rs28371581 | pos = 139 | alleles = "G/T" |
| | rs34032423 | pos = 301 | alleles = "—/CT" |
| | rs34215184 | pos = 301 | alleles = "A/C" |
| | rs34638781 | pos = 301 | alleles = "—/C" |
| | rs35947098 | pos = 301 | alleles = "C/T" |
| | rs58410964 | pos = 101 | alleles = "A/G" |
| | rs59108896 | pos = 101 | alleles = "G/T" |
| | rs59743922 | pos = 101 | alleles = "A/G" |
| | rs60714340 | pos = 101 | alleles = "C/T" |
| | rs6466849 | pos = 201 | alleles = "C/T" |
| | rs702423 | pos = 301 | alleles = "A/G" |
| | rs846664 | pos = 301 | alleles = "G/T" |
| | rs846665 | pos = 284 | alleles = "C/G" |
| | rs846666 | pos = 392 | alleles = "G/T" |
| | rs860170 | pos = 301 | alleles = "A/G" |
| | rs978739 | pos = 535 | alleles = "A/G" |
| TAS2R38 | rs10246939 | pos = 301 | alleles = "C/T" |
| | rs1726866 | pos = 301 | alleles = "C/T" |
| | rs35251805 | pos = 301 | alleles = "—/G" |
| | rs4613903 | pos = 301 | alleles = "G/T" |
| | rs61464348 | pos = 201 | alleles = "A/C" |
| | rs713598 | pos = 301 | alleles = "C/G" |
| TAS2R39 | rs10608369 | pos = 401 | alleles = "—/GT" |
| | rs34169190 | pos = 301 | alleles = "C/T" |
| | rs35474877 | pos = 301 | alleles = "A/G" |
| | rs4103817 | pos = 451 | alleles = "A/G" |

APPENDIX TABLE 1-continued

Polymorphisms related to human bitter taste receptor genes

| Gene | Reference sequence number | Position in reference sequence | SNP |
|---|---|---|---|
| | rs4726600 | pos = 301 | alleles = "A/G" |
| | rs56782833 | pos = 283 | alleles = "—/A" |
| | rs59031091 | pos = 201 | alleles = "C/G" |
| | rs6964922 | pos = 227 | alleles = "C/T" |
| TAS2R40 | rs10225801 | pos = 201 | alleles = "A/G" |
| | rs10260248 | pos = 301 | alleles = "A/C" |
| | rs17164164 | pos = 301 | alleles = "C/G" |
| TAS2R41 | rs10278721 | pos = 301 | alleles = "C/T" |
| | rs13243940 | pos = 501 | alleles = "A/T" |
| | rs13362832 | pos = 201 | alleles = "C/T" |
| | rs13362858 | pos = 301 | alleles = "C/G" |
| | rs1404634 | pos = 301 | alleles = "A/G" |
| | rs1404635 | pos = 301 | alleles = "A/G" |
| | rs1473653 | pos = 301 | alleles = "A/G" |
| | rs33922222 | pos = 401 | alleles = "—/C" |
| | rs34170633 | pos = 301 | alleles = "—/A" |
| | rs34281448 | pos = 301 | alleles = "—/A" |
| | rs34863914 | pos = 301 | alleles = "C/T" |
| | rs5888105 | pos = 401 | alleles = "—/G" |
| | rs5888106 | pos = 401 | alleles = "—/C" |
| | rs59826238 | pos = 101 | alleles = "C/T" |
| | rs60096100 | pos = 201 | alleles = "A/C" |
| | rs6947971 | pos = 5600 | alleles = "G/T" |
| | rs6949267 | pos = 526 | alleles = "C/G" |
| TAS2R43 | rs10556970 | pos = 401 | alleles = "—/AT" |
| | rs1965231 | pos = 265 | alleles = "C/T" |
| | rs34115566 | pos = 301 | alleles = "—/GT" |
| | rs35720106 | pos = 301 | alleles = "C/G" |
| TAS2R44 | rs10591850 | pos = 401 | alleles = "—/AAAT" |
| | rs10743938 | pos = 201 | alleles = "A/T" |
| | rs10772422 | pos = 501 | alleles = "C/T" |
| | rs10772423 | pos = 301 | alleles = "C/T" |
| | rs10845293 | pos = 301 | alleles = "A/G" |
| | rs10845294 | pos = 301 | alleles = "C/G" |
| | rs10845295 | pos = 201 | alleles = "A/G" |
| | rs10845296 | pos = 371 | alleles = "A/G" |
| | rs11522329 | pos = 301 | alleles = "A/G" |
| | rs11537117 | pos = 201 | alleles = "A/T" |
| | rs11537118 | pos = 218 | alleles = "A/G" |
| | rs11560815 | pos = 231 | alleles = "C/T" |
| | rs11612527 | pos = 301 | alleles = "A/T" |
| | rs12315036 | pos = 201 | alleles = "G/T" |
| | rs12318612 | pos = 301 | alleles = "C/G" |
| | rs12370363 | pos = 201 | alleles = "A/G" |
| | rs12819202 | pos = 301 | alleles = "C/T" |
| | rs1965230 | pos = 663 | alleles = "A/G" |
| | rs2418291 | pos = 501 | alleles = "C/T" |
| | rs2418292 | pos = 500 | alleles = "A/G" |
| | rs2418293 | pos = 500 | alleles = "C/T" |
| | rs2418294 | pos = 500 | alleles = "C/T" |
| | rs2418295 | pos = 500 | alleles = "C/G" |
| | rs2418296 | pos = 500 | alleles = "A/G" |
| | rs2418297 | pos = 500 | alleles = "C/T" |
| | rs2418298 | pos = 500 | alleles = "A/C" |
| | rs2418299 | pos = 500 | alleles = "A/T" |
| | rs2418300 | pos = 500 | alleles = "A/C" |
| | rs2418301 | pos = 500 | alleles = "C/T" |
| | rs28409955 | pos = 201 | alleles = "C/T" |
| | rs28679275 | pos = 201 | alleles = "C/T" |
| | rs2900583 | pos = 501 | alleles = "C/T" |
| | rs2900584 | pos = 501 | alleles = "C/T" |
| | rs2900585 | pos = 501 | alleles = "C/T" |
| | rs2952703 | pos = 201 | alleles = "G/T" |
| | rs33998340 | pos = 401 | alleles = "—/AGT" |
| | rs34066385 | pos = 401 | alleles = "—/ACAC" |
| | rs34763234 | pos = 301 | alleles = "A/G" |
| | rs35241999 | pos = 301 | alleles = "A/G" |
| | rs3759246 | pos = 61 | alleles = "C/G" |
| | rs3759247 | pos = 61 | alleles = "A/T" |
| | rs3983336 | pos = 500 | alleles = "A/G" |
| | rs3983337 | pos = 500 | alleles = "A/C" |
| | rs3983338 | pos = 500 | alleles = "A/C" |
| | rs3983339 | pos = 500 | alleles = "C/T" |
| | rs3983340 | pos = 500 | alleles = "C/T" |
| | rs3983341 | pos = 500 | alleles = "A/G" |
| | rs3983342 | pos = 500 | alleles = "G/T" |
| | rs3983343 | pos = 500 | alleles = "C/T" |
| | rs5024225 | pos = 401 | alleles = "A/T" |
| | rs56079155 | pos = 201 | alleles = "—/CA" |
| | rs56873588 | pos = 201 | alleles = "—/AATA" |
| | rs5796420 | pos = 401 | alleles = "—/ACAC" |
| | rs7952952 | pos = 301 | alleles = "A/G" |
| | rs7953498 | pos = 301 | alleles = "C/G" |
| TAS2R46 | rs11560816 | pos = 201 | alleles = "A/G" |
| | rs2244875 | pos = 500 | alleles = "C/T" |
| | rs2598002 | pos = 301 | alleles = "A/C" |
| | rs2599402 | pos = 201 | alleles = "A/G" |
| | rs2708378 | pos = 201 | alleles = "C/T" |
| | rs2708379 | pos = 201 | alleles = "A/G" |
| | rs2708380 | pos = 301 | alleles = "A/T" |
| | rs2708381 | pos = 301 | alleles = "A/G" |
| | rs2708382 | pos = 495 | alleles = "A/G" |
| | rs34033169 | pos = 301 | alleles = "—/G" |
| | rs34164014 | pos = 301 | alleles = "—/C" |
| | rs35602687 | pos = 301 | alleles = "—/C" |
| | rs35801645 | pos = 301 | alleles = "—/T" |
| | rs61912070 | pos = 251 | alleles = "G/T" |
| | rs62760561 | pos = 401 | alleles = "—/TCT" |
| | rs63450660 | pos = 401 | alleles = "—/T" |
| | rs7970996 | pos = 201 | alleles = "C/T" |
| TAS2R47 | rs10645657 | pos = 401 | alleles = "—/AC" |
| | rs1669404 | pos = 201 | alleles = "A/G" |
| | rs1669405 | pos = 201 | alleles = "G/T" |
| | rs1960613 | pos = 502 | alleles = "G/T" |
| | rs2218819 | pos = 37 | alleles = "C/T" |
| | rs2597924 | pos = 201 | alleles = "A/G" |
| | rs2597925 | pos = 201 | alleles = "A/G" |
| | rs2597926 | pos = 201 | alleles = "G/T" |
| | rs2597927 | pos = 201 | alleles = "G/T" |
| | rs2599396 | pos = 301 | alleles = "A/G" |
| | rs2599397 | pos = 301 | alleles = "C/G" |
| | rs2599404 | pos = 301 | alleles = "A/C" |
| | rs2600355 | pos = 301 | alleles = "G/T" |
| | rs2600356 | pos = 301 | alleles = "A/C" |
| | rs2600357 | pos = 301 | alleles = "C/T" |
| | rs2600358 | pos = 301 | alleles = "A/G" |
| | rs2708351 | pos = 201 | alleles = "G/T" |
| | rs2708371 | pos = 201 | alleles = "C/G" |
| | rs2708372 | pos = 201 | alleles = "C/T" |
| | rs2923236 | pos = 201 | alleles = "C/T" |
| | rs2952701 | pos = 201 | alleles = "C/T" |
| | rs2952702 | pos = 201 | alleles = "C/T" |
| | rs34383190 | pos = 401 | alleles = "—/TC" |
| | rs34570579 | pos = 301 | alleles = "—/C" |
| | rs34656404 | pos = 301 | alleles = "A/G" |
| | rs34960146 | pos = 301 | alleles = "—/C" |
| | rs35267335 | pos = 301 | alleles = "A/G" |
| | rs35413568 | pos = 301 | alleles = "—/C" |
| | rs35632581 | pos = 301 | alleles = "—/C" |
| | rs35884825 | pos = 401 | alleles = "—/AG" |
| | rs36109559 | pos = 301 | alleles = "—/A" |
| | rs36123978 | pos = 301 | alleles = "—/AG" |
| | rs3759244 | pos = 201 | alleles = "C/T" |
| | rs3759245 | pos = 201 | alleles = "C/T" |
| | rs3863323 | pos = 501 | alleles = "G/T" |
| | rs4092162 | pos = 91 | alleles = "A/G" |
| | rs4763238 | pos = 201 | alleles = "A/C" |
| | rs5796422 | pos = 401 | alleles = "—/AG" |
| | rs61928449 | pos = 251 | alleles = "A/C" |
| | rs7296647 | pos = 201 | alleles = "A/G" |
| | rs7313796 | pos = 201 | alleles = "A/C" |
| | rs7980677 | pos = 301 | alleles = "C/T" |
| | rs977473 | pos = 209 | alleles = "A/T" |
| | rs977474 | pos = 512 | alleles = "A/G" |
| TAS2R48 | rs10743937 | pos = 301 | alleles = "C/T" |
| | rs10772419 | pos = 301 | alleles = "A/C" |
| | rs10772420 | pos = 301 | alleles = "A/G" |
| | rs11054169 | pos = 335 | alleles = "A/G" |

APPENDIX TABLE 1-continued

Polymorphisms related to human bitter taste receptor genes

| Gene | Reference sequence number | Position in reference sequence | SNP |
|---|---|---|---|
| | rs11054170 | pos = 337 | alleles = "G/T" |
| | rs11054171 | pos = 356 | alleles = "A/G" |
| | rs12313469 | pos = 301 | alleles = "A/G" |
| | rs12424373 | pos = 301 | alleles = "G/T" |
| | rs12578654 | pos = 301 | alleles = "C/T" |
| | rs1868768 | pos = 301 | alleles = "A/C" |
| | rs1868769 | pos = 312 | alleles = "A/G" |
| | rs34254748 | pos = 301 | alleles = "—/G" |
| | rs35032794 | pos = 301 | alleles = "—/C" |
| | rs36057973 | pos = 301 | alleles = "—/G" |
| | rs3863330 | pos = 499 | alleles = "A/T" |
| | rs3863333 | pos = 301 | alleles = "G/T" |
| | rs4763235 | pos = 201 | alleles = "C/G" |
| | rs56985810 | pos = 201 | alleles = "C/T" |
| | rs60770813 | pos = 101 | alleles = "C/G" |
| | rs61624520 | pos = 201 | alleles = "—/T" |
| | rs7131800 | pos = 267 | alleles = "A/G" |
| | rs7961372 | pos = 201 | alleles = "A/C" |
| | rs9330646 | pos = 301 | alleles = "A/T" |
| | rs9777804 | pos = 301 | alleles = "C/G" |
| | rs9777906 | pos = 301 | alleles = "A/T" |
| TAS2R49 | rs10772407 | pos = 201 | alleles = "A/C" |
| | rs10845278 | pos = 356 | alleles = "C/T" |
| | rs10845279 | pos = 301 | alleles = "A/C" |
| | rs10845280 | pos = 301 | alleles = "A/G" |
| | rs10845281 | pos = 301 | alleles = "C/T" |
| | rs11054139 | pos = 501 | alleles = "C/T" |
| | rs11054140 | pos = 301 | alleles = "C/T" |
| | rs11054141 | pos = 261 | alleles = "C/T" |
| | rs11054142 | pos = 301 | alleles = "A/G" |
| | rs11054143 | pos = 301 | alleles = "C/T" |
| | rs12226919 | pos = 301 | alleles = "G/T" |
| | rs12226920 | pos = 301 | alleles = "G/T" |
| | rs12311429 | pos = 301 | alleles = "A/G" |
| | rs12311490 | pos = 301 | alleles = "A/G" |
| | rs12312963 | pos = 201 | alleles = "C/T" |
| | rs1450839 | pos = 301 | alleles = "A/G" |
| | rs1463237 | pos = 348 | alleles = "C/T" |
| | rs34365504 | pos = 301 | alleles = "—/T" |
| | rs34579433 | pos = 301 | alleles = "—/A" |
| | rs34813278 | pos = 301 | alleles = "—/A" |
| | rs34965724 | pos = 301 | alleles = "—/A" |
| | rs35021650 | pos = 301 | alleles = "—/C" |
| | rs35875890 | pos = 301 | alleles = "—/ATG" |
| | rs4388985 | pos = 401 | alleles = "A/G" |
| | rs4418898 | pos = 401 | alleles = "C/T" |
| | rs4506739 | pos = 401 | alleles = "A/G" |
| | rs4763604 | pos = 201 | alleles = "G/T" |
| | rs4763605 | pos = 201 | alleles = "A/G" |
| | rs58133495 | pos = 501 | alleles = "—/GAT" |
| | rs59686635 | pos = 101 | alleles = "A/C" |
| | rs61912291 | pos = 251 | alleles = "G/T" |
| | rs7135018 | pos = 251 | alleles = "C/T" |
| | rs7135941 | pos = 301 | alleles = "C/T" |
| | rs7301234 | pos = 301 | alleles = "A/G" |
| TAS2R50 | rs10772396 | pos = 362 | alleles = "C/T" |
| | rs10772397 | pos = 301 | alleles = "C/T" |
| | rs10772398 | pos = 201 | alleles = "C/T" |
| | rs10772399 | pos = 201 | alleles = "C/T" |
| | rs11054131 | pos = 201 | alleles = "C/G" |
| | rs11054132 | pos = 201 | alleles = "A/G" |
| | rs11054133 | pos = 201 | alleles = "C/T" |
| | rs11421487 | pos = 401 | alleles = "—/T" |
| | rs12426805 | pos = 301 | alleles = "A/G" |
| | rs1376251 | pos = 301 | alleles = "C/T" |
| | rs2167263 | pos = 245 | alleles = "C/G" |
| | rs35533340 | pos = 301 | alleles = "—/C/G" |
| | rs35633248 | pos = 301 | alleles = "—/T" |
| | rs35638884 | pos = 301 | alleles = "—/A" |
| | rs35852119 | pos = 301 | alleles = "—/T" |
| | rs35970171 | pos = 301 | alleles = "—/T" |
| | rs55748583 | pos = 201 | alleles = "C/T" |
| | rs58805611 | pos = 101 | alleles = "C/T" |
| TAS2R60 | rs10241042 | pos = 316 | alleles = "C/G" |
| | rs10241523 | pos = 316 | alleles = "A/C" |
| | rs11978402 | pos = 337 | alleles = "A/G" |
| | rs12534427 | pos = 301 | alleles = "C/G" |
| | rs12671578 | pos = 201 | alleles = "A/G" |
| | rs34328217 | pos = 301 | alleles = "—/C" |
| | rs34465195 | pos = 301 | alleles = "A/G" |
| | rs34910453 | pos = 301 | alleles = "C/T" |
| | rs35195910 | pos = 301 | alleles = "—/TCT" |
| | rs36004042 | pos = 301 | alleles = "—/G" |
| | rs4541818 | pos = 401 | alleles = "C/G" |
| | rs4595035 | pos = 301 | alleles = "C/T" |
| | rs58270521 | pos = 251 | alleles = "C/T" |

APPENDIX TABLE 2

Allelic variations in coding sequences of human bitter taste receptors

| Human bitter taste receptor | Nucleic Acid SEQ ID NO | Protein SEQ ID NO | Position of nucleotide change | Nucleotide change | Position of amino acid change | Description | Feature identifier |
|---|---|---|---|---|---|---|---|
| TAS2R1 | 2 | 28 | 332 | G → A | 111 | R → H: dbSNP rs41469. | VAR_020198 |
| | | | 422 | G → A | 141 | C → Y: dbSNP rs2234232. | VAR_053340 |
| | | | 616 | C → T | 206 | R → W: dbSNP rs2234233. | VAR_020199 |
| TAS2R3 | 3 | 29 | 349 | C → T | 117 | P → S | NA |
| TAS2R4 | 4 | 30 | 8 | G → A | 3 | R → Q: dbSNP rs2233995. | VAR_034535 |
| | | | 17 | A → C | 6 | Y → S: dbSNP rs2233997 | NA |
| | | | 20 | C → T | 7 | F → S: dbSNP rs2233998. | VAR_034536 |
| | | | 186 | T → A | 62 | F → L: dbSNP rs2233999. | VAR_053341 |
| | | | 221 | C → T | 74 | T → M: dbSNP rs2234000. | VAR_020200 |
| | | | 286 | G → C | 96 | V → L: dbSNP rs2234001. | VAR_020201 |

APPENDIX TABLE 2-continued

Allelic variations in coding sequences of human bitter taste receptors

| Human bitter taste receptor | Nucleic Acid SEQ ID NO | Protein SEQ ID NO | Position of nucleotide change | Nucleotide change | Position of amino acid change | Description | Feature identifier |
|---|---|---|---|---|---|---|---|
| | | | 512 | G → A | 171 | S → N: dbSNP rs2234002. | VAR_020202 |
| | | | 571 | A → G | 191 | I → V: dbSNP rs2234003. | VAR_053342 |
| TAS2R5 | 5 | 31 | 58 | G → A | 20 | G → S: dbSNP rs2234013. | VAR_053343 |
| | | | 77 | G → T | 26 | S → I: dbSNP rs2227264. | VAR_020203 |
| | | | 235 | C → T | 79 | R → C | NA |
| | | | 338 | C → T | 113 | P → L: dbSNP rs2234014. | VAR_034537 |
| | | | 500 | A → G | 167 | Y → C: dbSNP rs34529840. | VAR_034538 |
| | | | 638 | G → A | 213 | R → Q: dbSNP rs2234015. | VAR_024184 |
| | | | 881 | G → T | 294 | R → L: dbSNP rs2234016. | VAR_053344 |
| TAS2R7 | 6 | 32 | 254 | T → C | 85 | I → T | NA |
| | | | 538 | G → T | 180 | A → T | NA |
| | | | 640 | C → T | 214 | R → stop codon | NA |
| | | | 787 | A → T | 263 | T → S: dbSNP rs3759251. | VAR_021852 |
| | | | 788 | C → T | 263 | T → M | NA |
| | | | 912 | G → A | 304 | M → I: dbSNP rs619381. | VAR_024185 |
| TAS2R8 | 7 | 33 | 142 | C → T | 48 | L → F | NA |
| | | | 370 | T → G | 124 | W → G | NA |
| | | | 496 | A → G | 166 | R → G | NA |
| | | | 829 | T → C | 277 | Y → H | NA |
| | | | 922 | A → G | 308 | M → V: dbSNP rs2537817. | VAR_024186 |
| TAS2R9 | 8 | 34 | 201 | C → A | 67 | F → L | NA |
| | | | 381 | C → A | 127 | N → K | NA |
| | | | 450 | T → A | 150 | D → E | NA |
| | | | 508 | A → C | 170 | K → Q: dbSNP rs11054043. | VAR_053345 |
| | | | 560 | T → C | 187 | V → A: dbSNP rs3741845. | VAR_020204 |
| | | | 697 | G → A | 233 | A → T | NA |
| | | | 712 | C → G | 238 | L → V: dbSNP rs11054042. | VAR_053346 |
| | | | 867 | G → T | 289 | L → F | NA |
| | | | 880 | C → A | 294 | L → M | NA |
| TAS2R10 | 9 | 35 | 467 | T → C | 156 | M → T: dbSNP rs597468. | VAR_030009 |
| | | | 521 | A → C | 174 | K → T | NA |
| | | | 691 | T → C | 231 | S → P | NA |
| TAS2R13 | 10 | 36 | 446 | A → G | 149 | N → S | VAR_036432 |
| | | | 776 | A → G | 259 | N → S: dbSNP rs1015443. | VAR_021853 |
| TAS2R14 | 11 | 37 | 256 | A → G | 86 | T → A: dbSNP rs16925868. | VAR_053347 |
| | | | 589 | A → G | 197 | M → V | NA |
| TAS2R16 | 12 | 38 | 301 | G → A | 101 | V → M | NA |
| | | | 481 | C → T | 161 | P → S | NA |
| | | | 516 | T → G | 172 | N → K:. dbSNP rs846664. | VAR_034539 |
| | | | 665 | G → A | 222 | R → H: dbSNP rs860170. | VAR_020205 |
| TAS2R38 | 13 | 39 | 145 | G → C | 49 | A → P: dbSNP rs713598. | VAR_017860 |
| | | | 239 | A → G | 80 | H → R | NA |
| | | | 785 | C → T | 262 | A → V: dbSNP rs1726866. | VAR_017861 |
| | | | 820 | C → T | 274 | R → C | NA |
| | | | 886 | A → G | 296 | I → V: dbSNP rs10246939. | VAR_017862 |
| TAS2R39 | 14 | 40 | 578 | C → T | 193 | S → F: dbSNP rs35474877. | VAR_053348 |
| | | | 589 | A → G | 197 | K → E: dbSNP rs34169190. | VAR_053349 |
| TAS2R40 | 15 | 41 | 67 | G → C | 23 | V → L: dbSNP rs17164164. | VAR_053350 |

APPENDIX TABLE 2-continued

Allelic variations in coding sequences of human bitter taste receptors

| Human bitter taste receptor | Nucleic Acid SEQ ID NO | Protein SEQ ID NO | Position of nucleotide change | Nucleotide change | Position of amino acid change | Description | Feature identifier |
|---|---|---|---|---|---|---|---|
| | | | 560 | C → A | 187 | S → Y: dbSNP rs10260248. | VAR_053351 |
| | | | 817 | A → G | 273 | T → A | NA |
| | | | 871 | G → A | 291 | G → S | NA |
| TAS2R41 | 16 | 42 | 380 | C → T | 127 | P → L | NA |
| | | | 584 | T → A | 195 | V → D | NA |
| TAS2R43 | 17 | 43 | 599 | G → T | 200 | C → F | NA |
| | | | 635 | G → A | 212 | R → H | NA |
| | | | 889 | A → G | 297 | M → V | NA |
| | | | 916 | A → C | 306 | T → P | NA |
| TAs2R44 | 18 | 44 | 103 | C → T | 35 | R → W: dbSNP rs10845295. | VAR_030684 |
| | | | 484 | T → A | 162 | L → M: dbSNP rs10743938. | VAR_030685 |
| | | | 599 | G → A | 200 | C → Y | NA |
| | | | 649 | C → G | 217 | Q → E: dbSNP rs10845294. | VAR_030686 |
| | | | 656 | C → T | 219 | P → L | NA |
| | | | 680 | C → T | 227 | A → V: dbSNP rs10845293. | VAR_030687 |
| | | | 718 | G → A | 240 | V → I: dbSNP rs10772423. | VAR_030688 |
| | | | 827 | C → G | 276 | P → R | NA |
| | | | 843 | G → T | 281 | W → C | NA |
| TAS2R45 | 19 | 45 | 176 | T → G | 59 | L → R | NA |
| | | | 227 | A → G | 76 | Y → S | NA |
| | | | 394 | G → A | 132 | V → M | NA |
| | | | 630 | G → C | 210 | Q → H | NA |
| | | | 703 | T → C | 235 | F → L | NA |
| | | | 712 | T → C | 238 | C → R | NA |
| TAS2R46 | 20 | 46 | 106 | T → G | 36 | F → V | NA |
| | | | 682 | T → A | 228 | L → M | NA |
| | | | 749 | G → A | 250 | W → stop codon | NA |
| | | | 834 | C → G | 278 | I → M | NA |
| | | | 862 | C → T | 288 | Q → stop codon | NA |
| TAS2R47 | 21 | 47 | 521 | A → G | 174 | H → R | NA |
| | | | 577 | A → G | 193 | I → V | NA |
| | | | 756 | T → G | 252 | F → L | NA |
| TAS2R48 | 22 | 48 | 94 | G → A | 32 | V → I | NA |
| | | | 113 | C → A | 38 | T → K | NA |
| | | | 376 | A → C | 126 | K → Q: dbSNP rs12424373. | VAR_053354 |
| | | | 456 | A → T | 152 | R → S | NA |
| | | | 673 | A → G | 225 | I → V | NA |
| | | | 719 | T → C | 240 | I → T | NA |
| | | | 799 | G → C | 267 | V → L | NA |
| | | | 815 | C → T | 272 | P → L | NA |
| | | | 895 | C → T | 299 | R → C: dbSNP rs10772420 | VAR_053355 |
| TAS2R49 | 23 | 49 | 235 | A → G | 79 | K → E: dbSNP rs7135018. | VAR_053356 |
| | | | 421 | G → A | 141 | V → I | NA |
| | | | 429 | C → A | 143 | H → Q: dbSNP rs12226920. | VAR_053357 |
| | | | 442 | C → A | 148 | H → N: dbSNP rs12226919. | VAR_053358 |
| | | | 516 | G → A | 172 | M → I | NA |
| | | | 706 | A → G | 236 | I → V: dbSNP rs10845281. | VAR_053359 |
| | | | 755 | T → C | 252 | F → S: dbSNP rs10845280. | VAR_053360 |
| | | | 764 | G → T | 255 | R → L: dbSNP rs10845279. | VAR_053361 |
| | | | 808 | A → G | 270 | I → V | NA |
| TAS2R50 | 24 | 50 | 155 | C → T | 52 | A → V | NA |
| | | | 181 | G → T | 61 | A → S | NA |
| | | | 608 | G → A | 203 | C → Y: dbSNP rs1376251 | VAR_024187 |
| TAS2R55 | 25 | 51 | 524 | T → A | 175 | F → Y | NA |
| | | | 587 | T → C | 196 | F → S: dbSNP rs5020531. | VAR_053352 |

APPENDIX TABLE 2-continued

Allelic variations in coding sequences of human bitter taste receptors

| Human bitter taste receptor | Nucleic Acid SEQ ID NO | Protein SEQ ID NO | Position of nucleotide change | Nucleotide change | Position of amino acid change | Description | Feature identifier |
|---|---|---|---|---|---|---|---|
|  |  |  | 763 | G → T | 255 | G → W | NA |
|  |  |  | 794 | A → G | 265 | Y → C: dbSNP rs1451772. | VAR_053353 |
| TAS2R60 | 26 | 52 | 595 | A → T | 199 | M → L |  |

APPENDIX TABLE 3

Mammalian G proteins, their families and descriptions

| Class | Family/Subtype | Protein # (UniProt) | Description |
|---|---|---|---|
| G-alpha | $G_s$ |  |  |
|  | Gs | P04896 | Galpha-s-*Bos taurus* |
|  | Gs | P16052 | Galpha-s-*Cricetulus longicaudatus* |
|  | Gs | P63092 | Galpha-s-*Homo sapiens*-2 |
|  | Gs | P63091 | Galpha-s-*Canis familiaris* |
|  | Gs | P63093 | Galpha-s-*Mesocricetus auratus* |
|  | Gs | P63094 | Galpha-s-*Mus musculus*-2 |
|  | Gs | P63095 | Galpha-s-*Rattus norvegicus*-2 |
|  | Gs | P29797 | Galpha-s-*Sus scrofa* |
|  | Gs | O60726 | Galpha-s-*Homo sapiens*-4 |
|  | Gs | O75632 | Galpha-s-*Homo sapiens*-5 |
|  | Gs | O75633 | Galpha-s-*Homo sapiens*-6 |
|  | Gs | Q14433 | Galpha-s-*Homo sapiens*-7 |
|  | Gs | Q14455 | Galpha-s-*Homo sapiens* |
|  | Gs | Q8R4A8 | Galpha-s-*Cricetulus griseus* |
|  | Gs | Q9JJ33 | Galpha-s-*Mus musculus* |
|  | Gs | Q9JLG1 | Galpha-s-*Rattus norvegicus*-1 |
|  | Gs | Q5JWF2 | Galpha-s-*Homo sapiens*-3 |
|  | Golf | P38405 | Galpha-olf-*Homo sapiens*-2 |
|  | Golf | Q8CGK7 | Galpha-olf-*Mus musculus* |
|  | Golf | P38406 | Galpha-olf-*Rattus norvegicus* |
|  | Golf | Q86XU3 | Galpha-olf-*Homo sapiens*-1 |
|  | $G_{i/o}$ |  |  |
|  | Gi | Q29047 | Galpha-i-*Sus scrofa* |
|  | Gi1 | P38401 | Galpha-i1-*Cavia porcellus* |
|  | Gi1 | P50146 | Galpha-i1-*Gallus gallus* |
|  | Gi1 | P63096 | Galpha-i1-*Homo sapiens*-1 |
|  | Gi1 | P63097 | Galpha-i1-*Bos taurus* |
|  | Gi1 | P10824 | Galpha-i1-*Rattus norvegicus* |
|  | Gi1 | O43383 | Galpha-i1-*Homo sapiens*-2 |
|  | Gi1 | Q61018 | Galpha-i1-*Mus musculus* |
|  | Gi2 | P38400 | Galpha-i2-*Canis familiaris* |
|  | Gi2 | P38402 | Galpha-i2-*Cavia porcellus* |
|  | Gi2 | P50147 | Galpha-i2-*Gallus gallus* |
|  | Gi2 | P04899 | Galpha-i2-*Homo sapiens*-2 |
|  | Gi2 | P08752 | Galpha-i2-*Mus musculus*-2 |
|  | Gi2 | P04897 | Galpha-i2-*Rattus norvegicus* |
|  | Gi2 | Q7M3G8 | Galpha-i2-*Sus scrofa* |
|  | Gi2 | Q7M3G9 | Galpha-i2-*Bos taurus*-2 |
|  | Gi2 | Q7M3H0 | Galpha-i2-*Bos taurus*-1 |
|  | Gi2 | Q8JZT4 | Galpha-i2-*Mus musculus*-1 |
|  | Gi2 | Q96C71 | Galpha-i2-*Homo sapiens*-1 |
|  | Gi3 | P38403 | Galpha-i3-*Cavia porcellus* |
|  | Gi3 | Q60397 | Galpha-i3-*Cricetulus griseus* |
|  | Gi3 | P08754 | Galpha-i3-*Homo sapiens* |
|  | Gi3 | P08753 | Galpha-i3-*Rattus norvegicus* |
|  | Gi3 | Q9DC51 | Galpha-i3-*Mus musculus* |
|  | Go | P59215 | Galpha-o-*Rattus norvegicus* |
|  | Go | Q8N6I9 | Galpha-o-*Homo sapiens* |
|  | Go1 | P08239 | Galpha-o1-*Bos taurus* |
|  | Go1 | P59216 | Galpha-o1-*Cricetulus longicaudatus* |
|  | Go1 | P09471 | Galpha-o1-*Homo sapiens* |
|  | Go1 | P18872 | Galpha-o1-*Mus musculus* |
|  | Gz | P19086 | Galpha-z-*Homo sapiens*-2 |
|  | Gz | O70443 | Galpha-z-*Mus musculus* |
|  | Gz | P19627 | Galpha-z-*Rattus norvegicus* |
|  | Gz | Q8IY73 | Galpha-z-*Homo sapiens*-3 |
|  | Gz | Q8N652 | Galpha-z-*Homo sapiens*-1 |
|  | Gz | Q95LC0 | Galpha-z-*Sus scrofa* |
|  | Gt | Q16162 | Galpha-t-*Homo sapiens* |
|  | Gt | Q9D7B3 | Galpha-t-*Mus musculus* |
|  | Gt1 | P04695 | Galpha-t1-*Bos taurus* |
|  | Gt1 | Q28300 | Galpha-t1-*Canis familiaris* |
|  | Gt1 | P11488 | Galpha-t1-*Homo sapiens* |
|  | Gt1 | P20612 | Galpha-t1-*Mus musculus* |
|  | Gt2 | P04696 | Galpha-t2-*Bos taurus* |
|  | Gt2 | P19087 | Galpha-t2-*Homo sapiens* |
|  | Gt2 | P50149 | Galpha-t2-*Mus musculus*-2 |
|  | Gt2 | Q8BSY7 | Galpha-t2-*Mus musculus*-1 |
|  | Ggust | P29348 | Galpha-gust-*Rattus norvegicus* |
|  | $G_{q/11}$ |  |  |
|  | Gq | Q6NT27 | Galpha-q-*Homo sapiens*-2 |
|  | Gq | Q28294 | Galpha-q-*Canis familiaris* |
|  | Gq | P50148 | Galpha-q-*Homo sapiens*-1 |
|  | Gq | P21279 | Galpha-q-*Mus musculus* |
|  | Gq | P82471 | Galpha-q-*Rattus norvegicus* |
|  | G11 | Q71RI7 | Galpha-11-*Gallus gallus* |
|  | G11 | P38409 | Galpha-11-*Bos taurus* |
|  | G11 | P52206 | Galpha-11-*Canis familiaris* |
|  | G11 | P29992 | Galpha-11-*Homo sapiens* |
|  | G11 | P45645 | Galpha-11-*Meleagris gallopavo* |
|  | G11 | P21278 | Galpha-11-*Mus musculus*-2 |
|  | G11 | Q9JID2 | Galpha-11-*Rattus norvegicus* |
|  | G11 | Q8SPP3 | Galpha-11-*Macaca mulatta* |
|  | G11 | Q91X95 | Galpha-11-*Mus musculus*-1 |
|  | G14 | P38408 | Galpha-14-*Bos taurus* |
|  | G14 | O95837 | Galpha-14-*Homo sapiens* |
|  | G14 | P30677 | Galpha-14-*Mus musculus*-2 |
|  | G14 | Q8C3M7 | Galpha-14-*Mus musculus*-3 |
|  | G14 | Q8CBT5 | Galpha-14-*Mus musculus*-4 |
|  | G14 | Q8R2X9 | Galpha-14-*Mus musculus*-1 |
|  | G15 | P30678 | Galpha-15-*Mus musculus* |
|  | G15 | O88302 | Galpha-15-*Rattus norvegicus* |
|  | G16 | P30679 | Galpha-16-*Homo sapiens* |
|  | $G_{12/13}$ |  |  |
|  | G12 | Q03113 | Galpha-12-*Homo sapiens* |
|  | G12 | P27600 | Galpha-12-*Mus musculus* |
|  | G12 | Q63210 | Galpha-12-*Rattus norvegicus* |
|  | G13 | Q14344 | Galpha-13-*Homo sapiens* |
|  | G13 | P27601 | Galpha-13-*Mus musculus*-2 |
|  | G13 | Q8C5L2 | Galpha-13-*Mus musculus*-3 |
|  | G13 | Q9D034 | Galpha-13-*Mus musculus*-1 |
| G-beta | $B_{1-5}$ |  |  |
|  | B1 | Q6TMK6 | Gbeta-1-*Cricetulus griseus* |
|  | B1 | P62871 | Gbeta-1-*Bos taurus* |
|  | B1 | P62872 | Gbeta-1-*Canis familiaris* |
|  | B1 | P62873 | Gbeta-1-*Homo sapiens* |
|  | B1 | P62874 | Gbeta-1-*Mus musculus* |
|  | B1 | P54311 | Gbeta-1-*Rattus norvegicus*-2 |
|  | B1 | Q9QX36 | Gbeta-1-*Rattus norvegicus*-1 |
|  | B2 | P11017 | Gbeta-2-*Bos taurus* |

APPENDIX TABLE 3-continued

Mammalian G proteins, their families and descriptions

| Class | Family/Subtype | Protein # (UniProt) | Description |
|---|---|---|---|
| | B2 | P62879 | Gbeta-2-*Homo sapiens* |
| | B2 | P62880 | Gbeta-2-*Mus musculus* |
| | B2 | P54313 | Gbeta-2-*Rattus norvegicus*-2 |
| | B2 | Q9QX35 | Gbeta-2-*Rattus norvegicus*-1 |
| | B3 | P79147 | Gbeta-3-*Canis familiaris* |
| | B3 | P16520 | Gbeta-3-*Homo sapiens*-1 |
| | B3 | Q61011 | Gbeta-3-*Mus musculus* |
| | B3 | P52287 | Gbeta-3-*Rattus norvegicus* |
| | B3 | Q96B71 | Gbeta-3-*Homo sapiens*-2 |
| | B4 | Q9HAV0 | Gbeta-4-*Homo sapiens* |
| | B4 | P29387 | Gbeta-4-*Mus musculus* |
| | B4 | O35353 | Gbeta-4-*Rattus norvegicus* |
| | B5 | O14775 | Gbeta-5-*Homo sapiens*-2 |
| | B5 | P62881 | Gbeta-5-*Mus musculus*-2 |
| | B5 | P62882 | Gbeta-5-*Rattus norvegicus* |
| | B5 | Q60525 | Gbeta-5-*Mesocricetus auratus* |
| | B5 | Q96F32 | Gbeta-5-*Homo sapiens*-1 |
| | B5 | Q9CSQ0 | Gbeta-5-*Mus musculus*-3 |
| | B5 | Q9CU21 | Gbeta-5-*Mus musculus*-1 |
| | B$_{unclassified}$ | | |
| | B unclassified | Q61621 | unclassified_Gbeta-*Mus musculus*-1 |
| | B unclassified | Q8BMQ1 | unclassified_Gbeta-*Mus musculus*-2 |
| | B unclassified | Q9UFT3 | unclassified_Gbeta-*Homo sapiens* |
| G-gamma | γ$_{1-12}$ | | |
| | γ1 | Q8R1U6 | Ggamma-1-*Mus musculus* |
| | γ2 | P59768 | Ggamma-2-*Homo sapiens* |
| | γ2 | P63212 | Ggamma-2-*Bos taurus* |
| | γ2 | P63213 | Ggamma-2-*Mus musculus* |
| | γ2 | O35355 | Ggamma-2-*Rattus norvegicus* |
| | γ3 | P63214 | Ggamma-3-*Bos taurus* |
| | γ3 | P63215 | Ggamma-3-*Homo sapiens* |
| | γ3 | P63216 | Ggamma-3-*Mus musculus* |
| | γ3 | O35356 | Ggamma-3-*Rattus norvegicus* |
| | γ4 | P50150 | Ggamma-4-*Homo sapiens* |
| | γ4 | P50153 | Ggamma-4-*Mus musculus* |
| | γ4 | O35357 | Ggamma-4-*Rattus norvegicus* |
| | γ5 | P63217 | Ggamma-5-*Bos taurus* |
| | γ5 | P63218 | Ggamma-5-*Homo sapiens*-2 |
| | γ5 | Q80SZ7 | Ggamma-5-*Mus musculus* |
| | γ5 | P63219 | Ggamma-5-*Rattus norvegicus* |
| | γ5 | Q9Y3K8 | Ggamma-5-*Homo sapiens*-1 |
| | γ7 | P30671 | Ggamma-7-*Bos taurus* |
| | γ7 | O60262 | Ggamma-7-*Homo sapiens* |
| | γ7 | Q61016 | Ggamma-7-*Mus musculus* |
| | γ7 | P43425 | Ggamma-7-*Rattus norvegicus* |
| | γ8 | Q9UK08 | Ggamma-8-*Homo sapiens*-2 |
| | γ8 | P63078 | Ggamma-8-*Mus musculus*-2 |
| | γ8 | P63077 | Ggamma-8-*Rattus norvegicus* |
| | γ8 | P50154 | Ggamma-8-*Bos taurus* |
| | γ8 | O14610 | Ggamma-8-*Homo sapiens*-1 |
| | γ8 | Q61017 | Ggamma-8-*Mus musculus*-1 |
| | γ10 | P50151 | Ggamma-10-*Homo sapiens*-2 |
| | γ10 | O35358 | Ggamma-10-*Rattus norvegicus* |
| | γ10 | Q96BN9 | Ggamma-10-*Homo sapiens*-1 |
| | γ10 | Q9CXP8 | Ggamma-10-*Mus musculus* |
| | γ11 | P61952 | Ggamma-11-*Homo sapiens* |
| | γ11 | P61953 | Ggamma-11-*Mus musculus* |
| | γ11 | P61954 | Ggamma-11-*Rattus norvegicus* |
| | γ12 | Q28024 | Ggamma-12-*Bos taurus* |
| | γ12 | Q9UBI6 | Ggamma-12-*Homo sapiens* |
| | γ12 | Q9DAS9 | Ggamma-12-*Mus musculus* |
| | γ12 | O35359 | Ggamma-12-*Rattus norvegicus* |
| | γ13 | Q9P2W3 | Ggamma-13-*Homo sapiens* |
| | γ13 | Q9JMF3 | Ggamma-13-*Mus musculus* |
| | γt1 | P02698 | Ggamma-t1-*Bos taurus* |
| | γt1 | P63211 | Ggamma-t1-*Homo sapiens* |
| | γt1 | P63210 | Ggamma-t1-*Canis familiaris* |
| | γt1 | Q61012 | Ggamma-t1-*Mus musculus* |
| | γ$_{unclassified}$ | | |
| | γ unclassified | Q7M3H1 | unclassified_Ggamma-*Bos indicus* |

What is claimed:

1. A method for identifying a compound that inhibits the bitter taste due to KCl, comprising:
   a) providing a first and a second cell,
   wherein said first and second cell express one or more bitter taste receptors selected from the group consisting of: TAS2R4, TAS2R9, TAS2R13, TAS2R14, TAS2R44 and TAS2R60, wherein said first and second cell express the same one or more bitter taste receptors;
   b) contacting said first cell with a tastant,
   wherein the tastant activates the one or more bitter taste receptor;
   c) contacting said second cell with a test compound and the tastant;
   d) assaying said first and second cells for bitter taste receptor activation; and
   e) comparing the bitter taste receptor activation of said first cell to the bitter taste receptor activation of said second cell,
   wherein the test compound is an inhibitor of bitter taste due to KCl, if bitter taste receptor activity of said second cell is less than the bitter taste receptor activity of said first cell, and wherein the tastant is KCl.

2. The method of claim 1, wherein the bitter taste receptor is complexed to a G protein.

3. The method according to claim 2, wherein said G protein is a Gq protein, an alpha transducin or an alpha gustducin.

4. The method according to claim 3, wherein the Gq protein is a Gα15 protein.

5. The method according to any one of claims 1-4, wherein bitter taste receptor activity is determined by measuring intracellular calcium concentration.

6. The method according to claim 5, wherein the concentration of intracellular calcium is determined using a calcium-sensitive fluorescent dye.

7. The method according to claim 6, wherein the calcium-sensitive fluorescent dye is selected from the group consisting of Indo-1, Fura-2, Fluo-3, Fluo-4, Rhod-2, Rhod-5N, Calcein, Calcein blue, cytoCalcein Violet, Quin-2, Quest Fluo-8H™, Quest Fluo 8L™, Quest Fluo 8™, Quest Rhod-4™, coelenterazine and Calcium-3.

8. The method according to claim 1, wherein said first and second cells are present in in vitro cell lines.

9. The method according to claim 1, wherein said first and second cells are present in panels of in vitro cell lines.

10. A method for identifying a compound that selectively acts on receptors to inhibit the bitter taste due to KCl comprising:

a) providing a first and second panel of cell lines,
wherein each of said first and second panel comprises cell lines that express a bitter taste receptor selected from the group consisting of: TAS2R4, TAS2R9, TAS2R13, TAS2R14, TAS2R44 and TAS2R60;
wherein TAS2R4, TAS2R9, TAS2R13, TAS2R14, TAS2R44 and TAS2R60 are each expressed in at least one cell line, and
wherein the first and second panels comprise the same cell lines;
b) contacting each cell line in the first panel with a tastant, wherein the tastant activates at least two of the group selected from TAS2R4, TAS2R9, TAS2R13, TAS2R14, TAS2R44 and TAS2R60;
c) contacting each cell line in the second panel with a test compound and the tastant;
d) assaying each cell line for bitter taste receptor activation;
wherein, the test compound is a selective inhibitor of bitter taste due to KCl if the bitter taste receptor activity of at least two of the group selected from TAS2R4, TAS2R9, TAS2R13, TAS2R14, TAS2R44 and TAS2R60 is less in the second panel compared to the first panel, and wherein the tastant is KCl.

11. The method of claim 10, wherein the bitter taste receptor activity of at least three of the group selected from TAS2R4, TAS2R9, TAS2R13, TAS2R14, TAS2R44 and TAS2R60 is less in the second panel compared to the first panel.

12. The method of claim 10, wherein the bitter taste receptor activity of at least four of the group selected from TAS2R4, TAS2R9, TAS2R13, TAS2R14, TAS2R44 and TAS2R60 is less in the second panel compared to the first panel.

13. The method of claim 10, wherein the bitter taste receptor activity of at least five of the group selected from TAS2R4, TAS2R9, TAS2R13, TAS2R14, TAS2R44 and TAS2R60 is less in the second panel compared to the first panel.

14. The method of claim 10, wherein the bitter taste receptor activity of each member in the group selected from TAS2R4, TAS2R9, TAS2R13, TAS2R14, TAS2R44 and TAS2R60 is less in the second panel compared to the first panel.

15. The method of any one of claims 10-14, wherein the first and second panel comprise TAS2R1, TAS2R3, TAS2R4, TAS2R5, TAS2R7, TAS2R8, TAS2R9, TAS2R10, TAS2R13, TAS2R14, TAS2R16, TAS2R38, TAS2R39, TAS2R40, TAS2R41, TAS2R43, TAS2R44, TAS2R45, TAS2R46, TAS2R47, TAS2R48, TAS2R49, TAS2R50, TAS2R55, and TAS2R60 bitter taste receptors.

16. The method of claim 10, wherein the bitter taste receptor is complexed to a G protein.

17. The method according to claim 16, wherein said G protein is a Gq protein, an alpha transducin or an alpha gustducin.

18. The method according to claim 17, wherein the Gq protein is a Gα15 protein.

19. The method according to claim 10, wherein bitter taste receptor activity is determined by measuring intracellular calcium concentration.

20. The method according to claim 19, wherein the concentration of intracellular calcium is determined using a calcium-sensitive fluorescent dye.

21. The method according to claim 20, wherein the calcium-sensitive fluorescent dye is selected from the group consisting of Indo-1, Fura-2, Fluo-3, Fluo-4, Rhod-2, Rhod-5N, Calcein, Calcein blue, cytoCalcein Violet, Quin-2, Quest Fluo-8H™, Quest Fluo 8L™, Quest Fluo 8™, Quest Rhod-4™, coelenterazine and Calcium-3.

* * * * *